US007374760B2

(12) United States Patent
Zou

(10) Patent No.: US 7,374,760 B2
(45) Date of Patent: May 20, 2008

(54) METHODS AND COMPOSITIONS FOR NERVE REGENERATION

(75) Inventor: Yimin Zou, Chicago, IL (US)

(73) Assignee: The University of Chicago, Chicago, IL (US)

( * ) Notice: Subject to any disclaimer, the term of this patent is extended or adjusted under 35 U.S.C. 154(b) by 376 days.

(21) Appl. No.: 10/847,972

(22) Filed: May 17, 2004

(65) Prior Publication Data

US 2005/0049195 A1 Mar. 3, 2005

Related U.S. Application Data

(60) Provisional application No. 60/470,913, filed on May 15, 2003.

(51) Int. Cl.
*A61K 39/00* (2006.01)
*A61K 39/395* (2006.01)
*C12N 5/00* (2006.01)
*C12N 5/06* (2006.01)
*C12N 5/08* (2006.01)

(52) U.S. Cl. .............................. 424/143.1; 424/130.1; 424/139.1; 435/377

(58) Field of Classification Search ...................... None
See application file for complete search history.

(56) References Cited

U.S. PATENT DOCUMENTS

| 4,554,101 A | 11/1985 | Hopp |
| 4,797,368 A | 1/1989 | Carter et al. |
| 5,139,941 A | 8/1992 | Muzyczka et al. |

FOREIGN PATENT DOCUMENTS

| WO | WO 99/57248 A | 11/1999 |
| WO | WO 01/74856 A | 10/2001 |
| WO | WO01/88103 A | 11/2001 |
| WO | WO02/063959 A | 8/2002 |

OTHER PUBLICATIONS

Keeble et al., The International Journal of Biochemistry & Cell Biology, vol. 38, Issue 12, 2006, pp. 2011-2017.*
Aksentijevich, I. et al., "In Vitro and In Vivo Liposome-Mediated Gene Transfer Leads to Human *MDR1* Expression in Mouse Bone Marrow Progenitor Cells" *Hum. Gene Ther.* (1996) 7:1111-1122.
Altman, J. and Bayer, S., *The Development of the Rat Spinal Cord*, Springer-Verlag, Berlin-Heidelberg-New York-Tokyo (1984) 85:1-164 (Cover and Table of Contents).
Augsburger, A. et al., "BMPs as Mediators of Roof Plate Repulsion of Commissural Neurons," *Neuron* (1999) 24:127-141.
Borello, U. et al., "Differential expression of the Wnt putative receptors *Frizzled* during mouse somitogenesis," *Mech. Dev.* (1999) 89:173-177.
Boussif, O. et al., "A versatile vector for gene and oligonucleotide transfer into cells in culture and in vivo: Polyethylenimine," *Proc. Natl. Acad. Sci. USA* (1995) 92:7297-7301.

Bradley, R.S. and Brown, A.M.C., "The proto-oncogene *int*-1 encodes a secreted protein associated with the extracellular matrix," *EMBO J.* (1990) 9(5):1569-1575.
Bueno, D. and Heath, J.K., "Co-expression pattern analysis of *Fgf4*, *Fgf8* and *Shh* gene expression at diverse signalling centers during mouse development," *Int. J. Dev. Biol. Suppl.*(1996) 1:79S-80S.
Caley, I.J. et al., "Humoral, Mucosal, and Cellular Immunity in Response to a Human Immunodeficiency Virus Type 1 Immunogen Expressed by a Venezuelan Equine Encephalitis Virus Vaccine Vector," *J. Virology* (1997) 71(4):3031-3038.
Carbonelli, D.L., et al., "A plasmid vector for isolation of strong promoters in *Escherichia coli,*" *FEMS Microbiol. Lett.* (1999) 177:75-82.
Chen, C. and Okayama, H., "High-Efficiency Transformation of Mammalian Cells by Plasmid DNA," *Mol. Cell Biol.* (1987) 7(8):2745-2752.
Christiansen, J.H. et al., "Murine *Wnt*-11 and *Wnt*-12 have temporally and spatially restricted expression patterns during embryonic development," *Mech. Dev.* (1995) 51:341-350.
Cocea, L., "Duplication of a region in the multiple cloning site of a plasmid vector to enhance cloning-mediated addition of restriction sites to a DNA fragment," *Biotechniques* (1997) 23(5):814-816.
Coffin, J.M., "Retroviridae and Their Replication," Chapter 51 of *Virology*, Fields et al., eds., Raven Press, New York (1990) 1437-1500.
Couch, R.B. et al., "Immunization with types 4 and 7 adenovirus by selective infection of the intestinal tract,"*Am. Rev. Resp. Dis.* (1963) 88:394-403.
Davis, R.L. and Han, K-A., "Neuroanatomy: Mushrooming mushroom bodies," *Curr. Biol.* (1996) 6(2):146-148.
Dealy, C.N. et al., "*Wnt*-5a an *Wnt*-7a are expressed in the developing chick limb bud in a manner suggesting roles in pattern formation along the proximodistal and dorsoventral axes," *Mech. Dev.* (1993) 43:175-186.

(Continued)

*Primary Examiner*—David Romeo
*Assistant Examiner*—Daniel C Gamett
(74) *Attorney, Agent, or Firm*—Michael Best & Friedrich LLP

(57) ABSTRACT

Methods and compositions for modulating growth of a neuron with a Wnt, a Wnt-like substance, and/or a chemical compound affecting a Wnt signaling pathway are disclosed. Also disclosed are methods for identifying a substance that modulates growth of a neuron by obtaining a candidate substance and contacting the candidate substance with the neuron are disclosed and methods for modulating growth of a neuron in a subject using a Wnt, a Wnt-like substance, and/or a chemical compound affecting a Wnt signaling pathway. The Wnt, Wnt-like substance, and/or chemical compounds affecting a Wnt signaling pathway can be delivered to the subject using gene therapy techniques. Also disclosed are pharmaceutical compositions for modulating growth of a neuron in a mammal that include a Wnt or a Wnt-like substance. Methods and compositions for inhibiting growth of a neuron are also disclosed.

14 Claims, 6 Drawing Sheets

OTHER PUBLICATIONS

DeRossi, D., et al., "The Third Helix of the Antennapedia Homeodomain Translocates through Biological Membranes," *J. Biol. Chem.* (1994) 269(14):10444-10450.

Dickson, B.J., "Molecular Mechanisms of Axon Guidance," *Science* (2002) 298:1959-1964 plus Erratum, 1 page.

Ebens, A. et al., "Hepatocyte Growth Factor/Scatter Factor Is an Axonal Chemoattractant and a Neurotrophic Factor for Spinal Motor Neurons," *Neuron* (1996) 17:1157-1172.

Elliott, G. and O'Hare, P., "Intercellular Trafficking and Protein Delivery by a Herpesvirus Structural Protein," *Cell* (1997) 88:223-233.

Fan, C-M. et al., "A role for WNT proteins in induction of dermomyotome," *Dev. Biol.* (1997) 191:160-165.

Fechheimer, M. et al., "Transfection of mammalian cells with plasmid DNA by scrape loading and sonication loading," *Proc. Natl. Acad. Sci. USA* (1987) 84(23):8463-8467.

Felgner, P.L. et al., "Lipofection: A highly efficient, lipid-mediated DNA-transfection procedure," *Proc. Natl. Acad. Sci. USA* (1987) 84:7413-7417.

Finch, P.W. et al., "Purification and molecular cloning of a secreted, Frizzled-related antagonist of Wnt action," *Proc. Natl. Acad. Sci. USA* (1997) 94:6770-6775.

Fitzgerald, M.J.T., *Neuroanatomy Basic and Clinical* (1996) W.B. Sauders Company Ltd., London (Cover and Table of Contents).

Fraley, R.T. et al., "Entrapment of a bacterial plasmid in phospholipid vesicles: Potential for gene transfer," *Proc. Natl. Acad. Sci. USA* (1979) 76(7):3348-3352.

Francis, P.H. et al., " Bone morphogenetic proteins and a signalling pathway that controls patterning in the developing chick limb," *Development* (1994) 120:209-218.

Frazer, S.E., "Iontophoretic Dye Labeling of Embryonic Cells," *Methods in Cell Biology* (1996) Academic Press, Inc. 147-160.

Gabizon, A. et al., "Effect of liposome composition and other factors on the targeting of liposomes to experimental tumors: Biodistribution and imaging studies," *Cancer Res.* (1990) 50:6371-6378.

Gavin, B.J. et al., "Expression of multiple novel *Wnt-1/int-1*-related genes during fetal and adult mouse development," *Genes Dev.* (1990) 4:2319-2332.

Glorioso, J.C. et al., "HSV as a gene transfer vector for the nervous system," *Mol. Biotechnol.* (1995) 4:87-99.

Gopal, T.V., "Gene transfer method for transient gene expression, stable transformation, and cotransformation of suspension cell cultures," *Mol. Cell Biol.* (1985) 5(5):1188-1190.

Graham, F.L. and Van Der Eb, A.J., "A new technique for the assay of infectivity of human adenovirus 5 DNA," *Virology* (1973) 52:456-467.

Grunhaus, A. et al., "Association of vaccinia virus-expressed adenovirus E3-19K glycoprotein with class I MHC and its effects on virulence in a murine pneumonia model," *Virology* (1994) 200(2):535-546.

Halford, M.M. et al., "Ryk-deficient mice exhibit craniofacial defects associated with perturbed Eph receptor crosstalk," *Nat. Genet.* (2000) 25:414-418.

Hall, A.C. et al., "Axonal remodeling and synaptic differentiation in the cerebellum is regulated by WNT-7a signaling," *Cell* (2000) 100:525-535.

Harland, R. and Weintraub, H., "Translation of mRNA injected into *Xenopus* Oocytes is specifically inhibited by antisenses RNA," *J. Cell Biol.* (1985) 101:1094-1099.

Hofmann, C. et al., "Analysis of limb patterning in BMP-7-Deficient mice," *Dev. Genet.* (1996) 19:43-50.

Joosten, E.A.J. et al., "Embryonic form of N-CAM and development of the rat corticospinal tract; immuno-electron microscopical localization during spinal white matter ingrowth," *Dev. Brain Res.* (1996) 94:99-105.

Kamitori, K. et al., "Cell-type-specific expression of protein tyrosine kinase-related receptor RYK in the central nervous sytem of the rat," *Mol. Brain Res.* (2002) 104:255-266.

Keino-Masu, K. et al., "*Deleted in Colorectal Cancer (DCC)* encodes a netrin receptor," *Cell* (1996) 87:175-185.

Kennedy, T.E. et al., "Netrins are diffusible chemotropic factors for commissural axons in the embryonic spinal cord," *Cell* (1994) 78:425-435.

Kispert, A. et al., "Proteoglycans are required for maintenance of *Wnt-11* expression in the ureter tips," *Development* (1996) 122:3627-3637.

Klein, P.S. and Melton, D.A., "A molecular mechansim for the effect of lithium on development," *Proc. Natl. Acad. Sci. USA* (1996) 93:8455-8459.

Klingensmith, J. and Nusse, R., "Signaling by *wingless* in *Drosophila*," *Dev. Biol.* (1994) 166:396-414.

Kotin, R.M. et al., "Site-specific integration by adeno-associated virus," *Proc. Natl. Acad. Sci. USA* (1990) 87:2211-2215.

Krylova, O. et al., "WNT-3, Expressed by motoneurons, regulates terminal arborization of neurotrophin-3-responsive spinal sensory neurons," *Neuron* (2002) 35:1043-1056.

Kyte, J. and Doolittle, R.F., "A simple method for displaying the hydropathic character of a protein," *J. Mol. Biol.*(1982) 157:105-132.

Laughlin, C.A. et al., "Latent infection of KB cells with adeno-associated virus type 2," *J. Virol.* (1986) 60(2):515-524.

Lebkowski, J.S. et al., "Adeno-associated virus: a vector system for efficient introduction and integration of DNA into a variety of mammalian cell types," *Mol. Cell Biol.* (1988) 8(10):3988-3996.

Levenson, V.V. et al., "Internal ribosomal entry site-containing retroviral vectors with green fluorescent protein and drug resistance markers," *Hum. Gene Ther.* (1998) 9:1233-1236.

Liu, A. et al., "Zebrafish wnt4b expression in the floor plate is altered in sonic hedgehog and gli-2 mutants," *Mech. Dev.* (2000) 91:409-413.

Long, D. and Young, J., "Dexamphetamine treatment in stroke," *Q. J. Med.* (2003) 96:673-685.

Lucas, F.R. and Salinas, P.C., "WNT-7a induces axonal remodeling and increases synapsin I levels in cerebellar neurons," *Dev. Biol.* (1997) 192:31-44.

Lyuksyutova, A.I. et al., "Anterior-posterior guidance of commissural axons by Wnt-frizzled signaling," *Science* (2003) 302:1984-1988.

McCarty, D.M. et al., "Sequence required for coordinate induction of adeno-associated virus p19 and p40 promoters by rep protein," *J. Virol.* (1991) 65(6):2936-2945.

McLaughlin, S.K. et al., "Adeno-associated virus general transduction vectors: Analysis of proviral structures," *J. Virol.* (1988) 62(6):1963-1973.

McMahon, A.P., "The *Wnt* family of developmental regulators," *Trends Genet.* (1992) 8(7):236-242.

McMahon, A.P. and Bradley, A., "The *Wnt-1* (*int-1*) proto-oncogene is required for development of a large region of the mouse brain," *Cell* (1990) 62:1073-1085.

Miller, J.R., "The wnts," *Genome Biology* (2001) 3(1):3001.1-3001.15.

Morata, G. and Lawrence, P.A., "The development of *wingless*, a homeotic mutation of *drosophila*," *Dev. Biol.* (1977) 56:227-240.

Muzyczka, N., "Use of Adeno-associated virus as a general transduction vector for mammalian cells," *Curr. Top Mirobiol. Immunol.* (1992) 158:97-129.

Nagahara, H. et al., "Transduction of full-length TAT fusion proteins into mammalian cells: TAT-p27$^{Kip1}$ induces cell migration," *Nature Medicine* (1998) 4(12):1449-1452.

Nicolau, C. and Sene, C., "Liposome-mediated DNA transfer in eukaryotic cells. Dependence of the transfer efficiency upon the type of liposomes used and the host cell cycle stage," *Biochim. Biophys. Acta* (1982) 721:185-190.

Nusse, R. and Varmus, H.E., "*Wnt* Genes," *Cell* (1992) 69:1073-1087.

Papkoff, J. and Schryver, B., "Secreted *int-1* protein is associated with the cell surface," *Mol. Cell Biol.* (1990) 10(6):2723-2730.

Parr, B.A. et al., "Wnt7b regulates placental development in mice," *Dev. Biol.* (2001) 237:324-332.

Paxinos, G. *The Rat Nervous System*, 2nd Ed. Academic Press (1995) (Cover and Table of Contents).

Pelletier, J. and Sonenberg, N., "Internal initiation of translation of eukaryotic mRNA directed by a sequence derived from poliovirus RNA," *Nature* (1988) 334:320-325.

Pinson, K.I. et al., "An LDL-receptor-related protein mediates Wnt signalling in mice," *Nature* (2000) 407:535-538.

Potter, H. et al., "Enhancer-dependent expression of human κ immunoglobulin genes introduced into mouse pre-B lymphocytes by electroporation," *Proc. Natl. Acad. Sci. USA* (1984) 81:7161-7165.

Ramon, S. y Cajal, "La Retine des vertebres," *La Cellule* (1893) 9, 145 pages.

Rijsewijk, F. et al., "The *drosophila* homolog of the mouse mammary oncogene *int*-1 is identical to the segment polarity gene *wingless*," *Cell* (1987) 50:649-657.

Rippe, R.A. et al., "DNA-mediated gene transfer into adult rat hepatocytes in primary culture," *Mol. Cell Biol.* (1990) 10(2):689-695.

Roux, P. et al., "A versatile and potentially general approach to the targeting of specific cell types by retroviruses: application to the infection of human cells by means of major histocompatability complex class I and class II antigens by mouse ecotropic murine leukemia virus-derived viruses," *Proc. Natl. Acad. Sci. USA* (1989) 86:9079-9083.

Samulski, R.J. et al., "Targeted integration of adeno-associated virus (AAV) into human chromosome 19," *EMBO J.* (1991) 10(12):3941-3950.

Samulski, R.J. et al., "Helper-free stocks of recombinant adeno-associated viruses: normal integration does not require viral gene expression," *J. Virol* (1989) 63(9):3822-3828.

Saulnier, D.M.E. et al., "Essential function of Wnt-4 for tubulogenesis in the *Xenopus* pronephric kidney," *Dev. Biol.* (2002) 248:13-28.

Serafini, T. et al., "The netrins define a family of axon outgrowth-promoting proteins homologous to *C. elegans* UNC-6," *Cell* (1994) 78:409-424.

Serafini, T. et al., "Netrin-1 is required for commissural axon guidance in the developing vertebrate nervous sytem," *Cell* (1996) 87:1001-1014.

Shelling, A. and Smith, M.G., "Targeted integration of transfected and infected adeno-associated virus vectors containing the neomycin resistance gene," *Gene Therapy* (1994) 1:165-169.

Shirasaki, R. et al., "Change in chemoattractant responsiveness of developing axons at an intermediate target," *Science* (1998) 279:105-107.

Shu, W. et al., "Wnt7b regulates mesenchymal proliferation and vascular development in the lung," *Development* (2002) 129:4831-4842.

Sivasankaran, R. et al., "PKC mediates inhibitory effects of myelin and chonodroitin sulfate proteoglycans on axonal regeneration," *Nat. Neurosci.* (2004) 7(3)261-268.

Solodin, I. et al., "A novel series of amphiphilic imidazolinium compounds for in vitro and in vivo gene delivery," *Biochemistry*(1995) 34:13537-13544.

Tessier-Lavigne, M. et al., "Chemotropic guidance of developing axons in the mammalian central nervous sytem," *Nature* (1988) 336:775-778.

Tessier-Lavigne, M. and Goodman, C.S., "The molecular biology of axon guidance," *Science* (1996) 274:1123-1133.

Tessier-Lavigne, M., "Axon guidance by diffusible repellants and attractants," *Curr. Opin. Genet. Dev.* (1994) 4:596-601.

Thierry, A.R. et al., "Systemic gene therapy: biodistribution and long-term expression of a transgene in mice," *Proc. Natl. Sci. USA* (1995) 92:9742-9746.

Thomas, K.R. and Capecchi, M.R., "Targeted disruption of the murine *int*-1 proto-oncogene resulting in severe abnormalities in midbrain and cerebellar development," *Nature* (1990) 346:847-850.

Top, F.H. et al., "Immunization with live types 7 and 4 adenovirus vaccines. II. Antibody response and protective effect against acute respiratory disease due to adenovirus type 7," *J. Infect. Dis.* (1971) 124(2):155-160.

Tratschin, J-D. et al., "A human parvovirus, adeno-associated virus, as a eucaryotic vector: transient expression and encapsidation of the procaryotic gene for chloramphenicol acetyltransferase," *Mol. Cell Biol.* (1984) 4(10):2072-2081.

Tsukamoto, M. et al., "Gene transfer and expression in progeny after intravenous DNA injection into pregnant mice," *Nat. Genet.* (1995) 9(3):243-248.

Tur-Kaspa, R. et al., "Use of electroporation to introduce biologically active foreign genes into primary rat hepatocytes," *Mol. Cell Biol.* (1986) 6(2):716-718.

Ungar, A.R. et al., "*Wnt4* affects morphogenesis when misexpressed in the zebrafish embryo," *Mech. Dev.* (1995) 52:153-164.

Van 'T Veer, L.J. et al., "Molecular cloning and chromosomal assignment of the human homolog of *int*-1, a mouse gene implicated in mammary tumorigenesis," *Mol. Cell Biol.* (1984) 4(11):2532-2534.

Wagner, R.W. et al., "Antisense gene inhibition by oligoucleotides containing C-5 propyne pyrimidines," *Science* (1993) 260:1510-1513.

Wang, Y. et al., "*Frizzled-3* is required for the development of major fiber tracts in the rostral CNS," *J. Neurosci.* (2002) 22(19):8563-8573.

Wodarz, A. and Nusse, R., "Mechanisms of Wnt Signaling in Development," *Ann. Rev. Cell Dev. Biol.* (1998) 14:59-88.

Wu, G.Y. and Wu, C.H., "Evidence for targeted gene delivery to Hep G2 hepatoma cells in vitro," *Biochemistry* (1988) 27:887-892.

Wu, G.Y. and Wu, C.H., "Receptor-mediated in vitro gene transformation by a soluble DNA carrier system," *J. Biol. Chem.* (1987) 262(10) :4429-4432.

Yang, N-S. et al., "In vivo and in vitro gene transfer to mammalian somatic cells by particle bombardment," *Proc. Natl. Acad. Sci. USA* (1990) 87:9568-9572.

Yoshikawa, S. et al., "Wnt-mediated axon guidance via the *Drosophila* derailed receptor," *Nature* (2003) 422(6932):583-588.

Zakany, J. and DuBoule, D., "Correlation of expression of *Wnt-1* developing limbs with abnormalities in growth and skeletal patterning," *Nature* (1993) 362:546-549.

Zhu, N. et al., "Systemic gene expression after intravenous DNA delivery into adult mice," *Science* (1993) 261(5118):209-211.

Zou, Y. et al., "Squeezing axons out of the gray matter: a role for slit and semphorin proteins from midline and ventral spinal cord," *Cell* (2000) 102:363-375.

Zou, Y. et al., "CARP, a cardiac ankyrin repeat protein, is downstream in the *Nkx2-5* homeobox gene pathway," *Development* (1997) 124:793-804.

Mautes, A.E.M. et al., "Actual aspects of treatment strategies in spinal cord injury," *Eur. J. Trauma* (2002) 3:143-156.

Megason, S.G. and McMahon, A.P., "A mitogen gradient of dorsal midline Wnts organizes growth in the CNS," *Development* (2002) 129:2087-2098.

Song, H.J. et al., Database Biosis (2002) 1-2 (Database accession No. PREV200300268105).

\* cited by examiner

SEQUENCE LISTING

<160> NUMBER OF SEQ ID NOS: 85

<210> SEQ ID NO 1
<211> LENGTH: 2368
<212> TYPE: DNA
<213> ORGANISM: Homo sapiens
<220> FEATURE:
<221> NAME/KEY: CDS
<222> LOCATION: (199)..(1311)

<400> SEQUENCE: 1
gcggtgccgc ccgccgtggc cgcctcagcc caccagccgg gaccgcgagc catgctgtcc    60

-continued

```
gccgcccgcc cccagggttg ttaaagccag actgcgaact ctcgccactg ccgccaccgc      120
cgcgtcccgt cccaccgtcg cgggcaacaa ccaaagtcgc cgcaactgca gcacagagcg      180
ggcaaagcca ggcaggcc atg ggg ctc tgg gcg ctg ttg cct ggc tgg gtt       231
                    Met Gly Leu Trp Ala Leu Leu Pro Gly Trp Val
                     1               5                      10 tct gct acg ctg ctg ctg gcg ctg gcc gct ctg ccc gca gcc ctg gct       279
Ser Ala Thr Leu Leu Leu Ala Leu Ala Ala Leu Pro Ala Ala Leu Ala
            15                  20                  25 gcc aac agc agt ggc cga tgg tgg ggt att gtg aac gta gcc tcc tcc       327
Ala Asn Ser Ser Gly Arg Trp Trp Gly Ile Val Asn Val Ala Ser Ser
        30                  35                  40 acg aac ctg ctt aca gac tcc aag agt ctg caa ctg gta ctc gag ccc       375
Thr Asn Leu Leu Thr Asp Ser Lys Ser Leu Gln Leu Val Leu Glu Pro
    45                  50                  55 agt ctg cag ctg ttg agc cgc aaa cag cgg cgt ctg ata cgc caa aat       423
Ser Leu Gln Leu Leu Ser Arg Lys Gln Arg Arg Leu Ile Arg Gln Asn
60                  65                  70                  75 ccg ggg atc ctg cac agc gtg agt ggg ggg ctg cag agt gcc gtg cgc       471
Pro Gly Ile Leu His Ser Val Ser Gly Gly Leu Gln Ser Ala Val Arg
                80                  85                  90 gag tgc aag tgg cag ttc cgg aat cgc cgc tgg aac tgt ccc act gct       519
Glu Cys Lys Trp Gln Phe Arg Asn Arg Arg Trp Asn Cys Pro Thr Ala
            95                  100                 105 cca ggg ccc cac ctc ttc ggc aag atc gtc aac cga ggc tgt cga gaa       567
Pro Gly Pro His Leu Phe Gly Lys Ile Val Asn Arg Gly Cys Arg Glu
        110                 115                 120 acg gcg ttt atc ttc gct atc acc tcc gcc ggg gtc acc cat tcg gtg       615
Thr Ala Phe Ile Phe Ala Ile Thr Ser Ala Gly Val Thr His Ser Val
    125                 130                 135 gcg cgc tcc tgc tca gaa ggt tcc atc gaa tcc tgc acg tgt gac tac       663
Ala Arg Ser Cys Ser Glu Gly Ser Ile Glu Ser Cys Thr Cys Asp Tyr
140                 145                 150                 155 cgg cgg cgc ggc ccc ggg ggc ccc gac tgg cac tgg ggg ggc tgc agc       711
Arg Arg Arg Gly Pro Gly Gly Pro Asp Trp His Trp Gly Gly Cys Ser
                160                 165                 170 gac aac att gac ttc ggc cgc ctc ttc ggc cgg gag ttc gtg gac tcc       759
Asp Asn Ile Asp Phe Gly Arg Leu Phe Gly Arg Glu Phe Val Asp Ser
            175                 180                 185 ggg gag aag ggg cgg gac ctg cgc ttc ctc atg aac ctt cac aac aac       807
Gly Glu Lys Gly Arg Asp Leu Arg Phe Leu Met Asn Leu His Asn Asn
        190                 195                 200 gag gca ggc cgt acg acc gta ttc tcc gag atg cgc cag gag tgc aag       855
Glu Ala Gly Arg Thr Thr Val Phe Ser Glu Met Arg Gln Glu Cys Lys
    205                 210                 215 tgc cac ggg atg tcc ggc tca tgc acg gtg cgc acg tgc tgg atg cgg       903
Cys His Gly Met Ser Gly Ser Cys Thr Val Arg Thr Cys Trp Met Arg
220                 225                 230                 235 ctg ccc acg ctg cgc gcc gtg ggc gat gtg ctg cgc gac cgc ttc gac       951
Leu Pro Thr Leu Arg Ala Val Gly Asp Val Leu Arg Asp Arg Phe Asp
                240                 245                 250 ggc gcc tcg cgc gtc ctg tac ggc aac cgc ggc agc aac cgc gct tcg       999
Gly Ala Ser Arg Val Leu Tyr Gly Asn Arg Gly Ser Asn Arg Ala Ser
            255                 260                 265 cga gcg gag ctg ctg cgc ctg gag ccg gaa gac ccg gcc cac aaa ccg      1047
Arg Ala Glu Leu Leu Arg Leu Glu Pro Glu Asp Pro Ala His Lys Pro
        270                 275                 280 ccc tcc ccc cac gac ctc gtc tac ttc gag aaa tcg ccc aac ttc tgc      1095
Pro Ser Pro His Asp Leu Val Tyr Phe Glu Lys Ser Pro Asn Phe Cys
    285                 290                 295
```

-continued

```
acg tac agc gga cgc ctg ggc aca gca ggc acg gca ggg cgc gcc tgt      1143
Thr Tyr Ser Gly Arg Leu Gly Thr Ala Gly Thr Ala Gly Arg Ala Cys
300                 305                 310                 315 aac agc tcg tcg ccc gcg ctg gac ggc tgc gag ctg ctc tgc tgc ggc      1191
Asn Ser Ser Ser Pro Ala Leu Asp Gly Cys Glu Leu Leu Cys Cys Gly
            320                 325                 330 agg ggc cac cgc acg cgc acg cag cgc gtc acc gag cgc tgc aac tgc      1239
Arg Gly His Arg Thr Arg Thr Gln Arg Val Thr Glu Arg Cys Asn Cys
        335                 340                 345 acc ttc cac tgg tgc tgc cac gtc agc tgc cgc aac tgc acg cac acg      1287
Thr Phe His Trp Cys Cys His Val Ser Cys Arg Asn Cys Thr His Thr
    350                 355                 360 cgc gta ctg cac gag tgt ctg tga ggcgctgcgc ggactcgccc ccaggaaacg    1341
Arg Val Leu His Glu Cys Leu
    365                 370 ctctcctcga gccctccccc aaacagactc gctagcactc aagacccggt tattcgccca    1401
cccgagtacc tccagtcaca ctccccgcgg ttcatacgca tcccatctct cccacttcct    1461
cctacctggg gactcctcaa accacttgcc tggggcggca tgaaccctct tgccatcctg    1521
atggacctgc cccggaccta cctccctccc tctccgcggg agaccccttg ttgcactgcc    1581
ccctgcttgg ccaggaggtg agagaaggat gggtcccctc cgccatgggg tcggctcctg    1641
atggtgtcat tctgcctgct ccatcgcgcc agcgacctct ctgcctctct tcttcccctt    1701
tgtcctgcgt tttctccggg tcctcctaag tcccttccta ttctcctgcc atgggtgcag    1761
accctgaacc cacacctggg catcagggcc tttctcctcc ccacctgtag ctgaagcagg    1821
aggttacagg gcaaaagggc agctgtgatg atgtggaaat gaggttgggg gaaccagcag    1881
aaatgccccc attctcccag tctctgtcgt ggagccattg aacagctgtg agccatgcct    1941
ccctgggcca cctcctaccc cttcctgtcc tgcctcctca tcagtgtgta ataatttgc     2001 actgaaacgt ggatacagag ccacgagttt ggatgttgta ataaaaacta tttattgtgc    2061
tgggtcccag cctggtttgc aaagaccacc tccaacccaa cccatccct ctccactctt     2121 ctctcctttc tccctgcagc ctttttctggt ccctcttctc tcctcagttt tcaaagatg    2181 cgtttgcctc ctggaatcag tatttccttc cactgtagct attagcggct cctcgccccc    2241
accagtgtag catcttcctc tgcagaataa aatctctatt tttatcgatg acttggtggc    2301
ttttccttga atccagaaca caaccttgtt tgtggtgtcc cctatcctcc ccttttacca    2361
ctcccag                                                              2368
```

<210> SEQ ID NO 2
<211> LENGTH: 370
<212> TYPE: PRT
<213> ORGANISM: Homo sapiens

<400> SEQUENCE: 2

```
Met Gly Leu Trp Ala Leu Leu Pro Gly Trp Val Ser Ala Thr Leu Leu
1               5                   10                  15

Leu Ala Leu Ala Ala Leu Pro Ala Ala Leu Ala Ala Asn Ser Ser Gly
            20                  25                  30

Arg Trp Trp Gly Ile Val Asn Val Ala Ser Ser Thr Asn Leu Leu Thr
        35                  40                  45

Asp Ser Lys Ser Leu Gln Leu Val Glu Pro Ser Leu Gln Leu Leu
    50                  55                  60

Ser Arg Lys Gln Arg Arg Leu Ile Arg Gln Asn Pro Gly Ile Leu His
65                  70                  75                  80
```

```
Ser Val Ser Gly Gly Leu Gln Ser Ala Val Arg Glu Cys Lys Trp Gln
                85                  90                  95
Phe Arg Asn Arg Arg Trp Asn Cys Pro Thr Ala Pro Gly Pro His Leu
            100                 105                 110
Phe Gly Lys Ile Val Asn Arg Gly Cys Arg Glu Thr Ala Phe Ile Phe
        115                 120                 125
Ala Ile Thr Ser Ala Gly Val Thr His Ser Val Ala Arg Ser Cys Ser
    130                 135                 140
Glu Gly Ser Ile Glu Ser Cys Thr Cys Asp Tyr Arg Arg Arg Gly Pro
145                 150                 155                 160
Gly Gly Pro Asp Trp His Trp Gly Gly Cys Ser Asp Asn Ile Asp Phe
                165                 170                 175
Gly Arg Leu Phe Gly Arg Glu Phe Val Asp Ser Gly Glu Lys Gly Arg
            180                 185                 190
Asp Leu Arg Phe Leu Met Asn Leu His Asn Asn Glu Ala Gly Arg Thr
        195                 200                 205
Thr Val Phe Ser Glu Met Arg Gln Glu Cys Lys Cys His Gly Met Ser
    210                 215                 220
Gly Ser Cys Thr Val Arg Thr Cys Trp Met Arg Leu Pro Thr Leu Arg
225                 230                 235                 240
Ala Val Gly Asp Val Leu Arg Asp Arg Phe Asp Gly Ala Ser Arg Val
                245                 250                 255
Leu Tyr Gly Asn Arg Gly Ser Asn Arg Ala Ser Arg Ala Glu Leu Leu
            260                 265                 270
Arg Leu Glu Pro Glu Asp Pro Ala His Lys Pro Pro Ser Pro His Asp
        275                 280                 285
Leu Val Tyr Phe Glu Lys Ser Pro Asn Phe Cys Thr Tyr Ser Gly Arg
    290                 295                 300
Leu Gly Thr Ala Gly Thr Ala Gly Arg Ala Cys Asn Ser Ser Ser Pro
305                 310                 315                 320
Ala Leu Asp Gly Cys Glu Leu Leu Cys Cys Gly Arg Gly His Arg Thr
                325                 330                 335
Arg Thr Gln Arg Val Thr Glu Arg Cys Asn Cys Thr Phe His Trp Cys
            340                 345                 350
Cys His Val Ser Cys Arg Asn Cys Thr His Thr Arg Val Leu His Glu
        355                 360                 365
Cys Leu
    370

<210> SEQ ID NO 3
<211> LENGTH: 2102
<212> TYPE: DNA
<213> ORGANISM: Homo sapiens
<220> FEATURE:
<221> NAME/KEY: CDS
<222> LOCATION: (53)..(1135)

<400> SEQUENCE: 3
gcatggcgcc cgcacacgga gtctgacctg atgcagacgc aaggggggtta at atg aac      58
                                                          Met Asn
                                                            1 gcc cct ctc ggt gga atc tgg ctc tgg ctc cct ctg ctc ttg acc tgg       106
Ala Pro Leu Gly Gly Ile Trp Leu Trp Leu Pro Leu Leu Leu Thr Trp
        5                  10                  15 ctc acc ccc gag gtc aac tct tca tgg tgg tac atg aga gct aca ggt      154
Leu Thr Pro Glu Val Asn Ser Ser Trp Trp Tyr Met Arg Ala Thr Gly
```

-continued

```
                  20                  25                  30
ggc tcc tcc agg gtg atg tgc gat aat gtg cca ggc ctg gtg agc agc    202
Gly Ser Ser Arg Val Met Cys Asp Asn Val Pro Gly Leu Val Ser Ser
 35                  40                  45                  50 cag cgg cag ctg tgt cac cga cat cca gat gtg atg cgt gcc att agc    250
Gln Arg Gln Leu Cys His Arg His Pro Asp Val Met Arg Ala Ile Ser
                 55                  60                  65 cag ggc gtg gcc gag tgg aca gca gaa tgc cag cac cag ttc cgc cag    298
Gln Gly Val Ala Glu Trp Thr Ala Glu Cys Gln His Gln Phe Arg Gln
             70                  75                  80 cac cgc tgg aat tgc aac acc ctg gac agg gat cac agc ctt ttt ggc    346
His Arg Trp Asn Cys Asn Thr Leu Asp Arg Asp His Ser Leu Phe Gly
         85                  90                  95 agg gtc cta ctc cga agt agt cgg gaa tct gcc ttt gtt tat gcc atc    394
Arg Val Leu Leu Arg Ser Ser Arg Glu Ser Ala Phe Val Tyr Ala Ile
     100                 105                 110 tcc tca gct gga gtt gta ttt gcc atc acc agg gcc tgt agc caa gga    442
Ser Ser Ala Gly Val Val Phe Ala Ile Thr Arg Ala Cys Ser Gln Gly
 115                 120                 125                 130 gaa gta aaa tcc tgt tcc tgt gat cca aag aag atg gga agc gcc aag    490
Glu Val Lys Ser Cys Ser Cys Asp Pro Lys Lys Met Gly Ser Ala Lys
                 135                 140                 145 gac agc aaa ggc att ttt gat tgg ggt ggc tgc agt gat aac att gac    538
Asp Ser Lys Gly Ile Phe Asp Trp Gly Gly Cys Ser Asp Asn Ile Asp
             150                 155                 160 tat ggg atc aaa ttt gcc cgc gca ttt gtg gat gca aag gaa agg aaa    586
Tyr Gly Ile Lys Phe Ala Arg Ala Phe Val Asp Ala Lys Glu Arg Lys
         165                 170                 175 gga aag gat gcc aga gcc ctg atg aat ctt cac aac aac aga gct ggc    634
Gly Lys Asp Ala Arg Ala Leu Met Asn Leu His Asn Asn Arg Ala Gly
     180                 185                 190 agg aag gct gta aag cgg ttc ttg aaa caa gag tgc aag tgc cac ggg    682
Arg Lys Ala Val Lys Arg Phe Leu Lys Gln Glu Cys Lys Cys His Gly
 195                 200                 205                 210 gtg agc ggc tca tgt act ctc agg aca tgc tgg ctg gcc atg gcc gac    730
Val Ser Gly Ser Cys Thr Leu Arg Thr Cys Trp Leu Ala Met Ala Asp
                 215                 220                 225 ttc agg aaa acg ggc gat tat ctc tgg agg aag tac aat ggg gcc atc    778
Phe Arg Lys Thr Gly Asp Tyr Leu Trp Arg Lys Tyr Asn Gly Ala Ile
             230                 235                 240 cag gtg gtc atg aac cag gat ggc aca ggt ttc act gtg gct aac gag    826
Gln Val Val Met Asn Gln Asp Gly Thr Gly Phe Thr Val Ala Asn Glu
         245                 250                 255 agg ttt aag aag cca acg aaa aat gac ctc gtg tat ttt gag aat tct    874
Arg Phe Lys Lys Pro Thr Lys Asn Asp Leu Val Tyr Phe Glu Asn Ser
     260                 265                 270 cca gac tac tgt atc agg gac cga gag gca ggc tcc ctg ggt aca gca    922
Pro Asp Tyr Cys Ile Arg Asp Arg Glu Ala Gly Ser Leu Gly Thr Ala
 275                 280                 285                 290 ggc cgt gtg tgc aac ctg act tcc cgg ggc atg gac agc tgt gaa gtc    970
Gly Arg Val Cys Asn Leu Thr Ser Arg Gly Met Asp Ser Cys Glu Val
                 295                 300                 305 atg tgc tgt ggg aga ggc tac gac acc tcc cat gtc acc cgg atg acc   1018
Met Cys Cys Gly Arg Gly Tyr Asp Thr Ser His Val Thr Arg Met Thr
             310                 315                 320 aag tgt ggg tgt aag ttc cac tgg tgc tgc gcc gtg cgc tgt cag gac   1066
Lys Cys Gly Cys Lys Phe His Trp Cys Cys Ala Val Arg Cys Gln Asp
         325                 330                 335 tgc ctg gaa gct ctg gat gtg cac aca tgc aag gcc ccc aag aac gct   1114
Cys Leu Glu Ala Leu Asp Val His Thr Cys Lys Ala Pro Lys Asn Ala
```

-continued

```
Cys Leu Glu Ala Leu Asp Val His Thr Cys Lys Ala Pro Lys Asn Ala
        340                 345                 350 gac tgg aca acc gct aca tga ccccagcagg cgtcaccatc caccttccct      1165
Asp Trp Thr Thr Ala Thr
355                 360 tctacaagga ctccattgga tctgcaagaa cactggacct tgggttcttt ctgggggga   1225 tatttcctaa ggcatgtggc ctttatctca acggaagccc cctcttcctc cctgggggcc  1285
ccaggatggg ggggccacac gctgcaccta agcctaccc tattctatcc atctcctggt   1345
gttctgcagt catctcccct cctggcgagt tctctttgga aatagcatga caggctgttc  1405
agccgggagg gtggtgggcc cagaccactg tctccaccca ccttgacgtt tcttctttct  1465
agagcagttg gccaagcaga aaaaaagtg tctcaaagga gctttctcaa tgtcttccca   1525
caaatggtcc caattaagaa attccatact tctctcagat gggaacagta agaaagcag   1585 aatcaactgc ccctgactta actttaactt ttgaaaagac caagacttt gtctgatcaa    1645 gtggttttac agctaccacc cttaggggta attggtaatt acctggagaa gaatggcttt   1705
caataccctt ttaagtttaa aatgtgtatt tttcaaggca tttattgcca tattaaaatc   1765
tgatgtaaca aggtggggac gtgtgtcctt tggtactatg gtgtgttgta tctttgtaag   1825
agcaaaagcc tcagaaaggg attgctttgc attactgtcc ccttgatata aaaaatcttt   1885
agggaatgag agttccttct cacttagaat ctgaaggaa ttaaaagaa gatgaatggt    1945 ctggcaatat tctgtaacta ttgggtgaat atggtggaaa ataatttagt ggatggaata   2005
tcagaagtat atctgtacag atcaagaaaa aaagggagaa taaaattcct atctcatatt   2065
atgcatgtga cccaaaaaaa aaaaaaaaa aaaaaaa                           2102
```

```
<210> SEQ ID NO 4
<211> LENGTH: 360
<212> TYPE: PRT
<213> ORGANISM: Homo sapiens

<400> SEQUENCE: 4

Met Asn Ala Pro Leu Gly Gly Ile Trp Leu Trp Leu Pro Leu Leu Leu
1               5                   10                  15

Thr Trp Leu Thr Pro Glu Val Asn Ser Ser Trp Trp Tyr Met Arg Ala
            20                  25                  30

Thr Gly Gly Ser Ser Arg Val Met Cys Asp Asn Val Pro Gly Leu Val
        35                  40                  45

Ser Ser Gln Arg Gln Leu Cys His Arg His Pro Asp Val Met Arg Ala
    50                  55                  60

Ile Ser Gln Gly Val Ala Glu Trp Thr Ala Glu Cys Gln His Gln Phe
65                  70                  75                  80

Arg Gln His Arg Trp Asn Cys Asn Thr Leu Asp Arg Asp His Ser Leu
                85                  90                  95

Phe Gly Arg Val Leu Leu Arg Ser Ser Arg Glu Ser Ala Phe Val Tyr
            100                 105                 110

Ala Ile Ser Ser Ala Gly Val Val Phe Ala Ile Thr Arg Ala Cys Ser
        115                 120                 125

Gln Gly Glu Val Lys Ser Cys Ser Cys Asp Pro Lys Lys Met Gly Ser
    130                 135                 140

Ala Lys Asp Ser Lys Gly Ile Phe Asp Trp Gly Gly Cys Ser Asp Asn
145                 150                 155                 160

Ile Asp Tyr Gly Ile Lys Phe Ala Arg Ala Phe Val Asp Ala Lys Glu
                165                 170                 175
```

```
Arg Lys Gly Lys Asp Ala Arg Ala Leu Met Asn Leu His Asn Asn Arg
            180                 185                 190

Ala Gly Arg Lys Ala Val Lys Arg Phe Leu Lys Gln Glu Cys Lys Cys
        195                 200                 205

His Gly Val Ser Gly Ser Cys Thr Leu Arg Thr Cys Trp Leu Ala Met
    210                 215                 220

Ala Asp Phe Arg Lys Thr Gly Asp Tyr Leu Trp Arg Lys Tyr Asn Gly
225                 230                 235                 240

Ala Ile Gln Val Val Met Asn Gln Asp Gly Thr Gly Phe Thr Val Ala
                245                 250                 255

Asn Glu Arg Phe Lys Lys Pro Thr Lys Asn Asp Leu Val Tyr Phe Glu
            260                 265                 270

Asn Ser Pro Asp Tyr Cys Ile Arg Asp Arg Glu Ala Gly Ser Leu Gly
        275                 280                 285

Thr Ala Gly Arg Val Cys Asn Leu Thr Ser Arg Gly Met Asp Ser Cys
    290                 295                 300

Glu Val Met Cys Cys Gly Arg Gly Tyr Asp Thr Ser His Val Thr Arg
305                 310                 315                 320

Met Thr Lys Cys Gly Cys Lys Phe His Trp Cys Cys Ala Val Arg Cys
                325                 330                 335

Gln Asp Cys Leu Glu Ala Leu Asp Val His Thr Cys Lys Ala Pro Lys
            340                 345                 350

Asn Ala Asp Trp Thr Thr Ala Thr
        355                 360

<210> SEQ ID NO 5
<211> LENGTH: 1970
<212> TYPE: DNA
<213> ORGANISM: Homo sapiens
<220> FEATURE:
<221> NAME/KEY: CDS
<222> LOCATION: (20)..(1195)

<400> SEQUENCE: 5
cgggagtctt cggggagct atg ctg aga ccg ggt ggt gcg gag gaa gct gcg        52
                    Met Leu Arg Pro Gly Gly Ala Glu Glu Ala Ala
                      1               5                  10 cag ctc ccg ctt cgg cgc gcc agc gcc ccg gtc cct gtg ccg tcg ccc        100
Gln Leu Pro Leu Arg Arg Ala Ser Ala Pro Val Pro Val Pro Ser Pro
            15                  20                  25 gcg gcc ccc gac ggc tcc cgg gct tcg gcc cgc cta ggt ctt gcc tgc        148
Ala Ala Pro Asp Gly Ser Arg Ala Ser Ala Arg Leu Gly Leu Ala Cys
        30                  35                  40 ctt ctc ctg ctg ctg ctg acg ctg ccg gcc cgc gta gac acg tcc            196
Leu Leu Leu Leu Leu Leu Thr Leu Pro Ala Arg Val Asp Thr Ser
    45                  50                  55 tgg tgg tac att ggg gca ctg ggg gca cga gtg atc tgt gac aat atc        244
Trp Trp Tyr Ile Gly Ala Leu Gly Ala Arg Val Ile Cys Asp Asn Ile
60                  65                  70                  75 cct ggt ttg gtg agc cgg cag cgg cag ctg tgc cag cgt tac cca gac        292
Pro Gly Leu Val Ser Arg Gln Arg Gln Leu Cys Gln Arg Tyr Pro Asp
                80                  85                  90 atc atg cgt tca gtg ggc gag ggt gcc cga gaa tgg atc cga gag tgt        340
Ile Met Arg Ser Val Gly Glu Gly Ala Arg Glu Trp Ile Arg Glu Cys
            95                  100                 105 cag cac caa ttc cgc cac cac cgc tgg aac tgt acc acc ctg gac cgg        388
Gln His Gln Phe Arg His His Arg Trp Asn Cys Thr Thr Leu Asp Arg
        110                 115                 120
```

```
gac cac acc gtc ttt ggc cgt gtc atg ctc aga agt agc cga gag gca        436
Asp His Thr Val Phe Gly Arg Val Met Leu Arg Ser Ser Arg Glu Ala
    125                 130                 135 gct ttt gta tat gcc atc tca tca gca ggg gta gtc cac gct att act        484
Ala Phe Val Tyr Ala Ile Ser Ser Ala Gly Val Val His Ala Ile Thr
140                 145                 150                 155 cgc gcc tgt agc cag ggt gaa ctg agt gtg tgc agc tgt gac ccc tac        532
Arg Ala Cys Ser Gln Gly Glu Leu Ser Val Cys Ser Cys Asp Pro Tyr
                160                 165                 170 acc cgt ggc cga cac cat gac cag cgt ggg gac ttt gac tgg ggt ggc        580
Thr Arg Gly Arg His His Asp Gln Arg Gly Asp Phe Asp Trp Gly Gly
            175                 180                 185 tgc agt gac aac atc cac tac ggt gtc cgt ttt gcc aag gcc ttc gtg        628
Cys Ser Asp Asn Ile His Tyr Gly Val Arg Phe Ala Lys Ala Phe Val
        190                 195                 200 gat gcc aag gag aag agg ctt aag gat gcc cgg gcc ctc atg aac tta        676
Asp Ala Lys Glu Lys Arg Leu Lys Asp Ala Arg Ala Leu Met Asn Leu
    205                 210                 215 cat aat aac cgc tgt ggt cgc acg gct gtg cgg cgg ttt ctg aag ctg        724
His Asn Asn Arg Cys Gly Arg Thr Ala Val Arg Arg Phe Leu Lys Leu
220                 225                 230                 235 gag tgt aag tgc cat ggc gtg agt ggt tcc tgt act ctg cgc acc tgc        772
Glu Cys Lys Cys His Gly Val Ser Gly Ser Cys Thr Leu Arg Thr Cys
                240                 245                 250 tgg cgt gca ctc tca gat ttc cgc cgc aca ggt gat tac ctg cgg cga        820
Trp Arg Ala Leu Ser Asp Phe Arg Arg Thr Gly Asp Tyr Leu Arg Arg
            255                 260                 265 cgc tat gat ggg gct gtg cag gtg atg gcc acc caa gat ggt gcc aac        868
Arg Tyr Asp Gly Ala Val Gln Val Met Ala Thr Gln Asp Gly Ala Asn
        270                 275                 280 ttc acc gca gcc cgc caa ggc tat cgc cgt gcc acc cgg act gat ctt        916
Phe Thr Ala Ala Arg Gln Gly Tyr Arg Arg Ala Thr Arg Thr Asp Leu
    285                 290                 295 gtc tac ttt gac aac tct cca gat tac tgt gtc ttg gac aag gct gca        964
Val Tyr Phe Asp Asn Ser Pro Asp Tyr Cys Val Leu Asp Lys Ala Ala
300                 305                 310                 315 ggt tcc cta ggc act gca ggc cgt gtc tgc agc aag aca tca aaa gga       1012
Gly Ser Leu Gly Thr Ala Gly Arg Val Cys Ser Lys Thr Ser Lys Gly
                320                 325                 330 aca gac ggt tgt gaa atc atg tgc tgt ggc cga ggg tac gac aca act       1060
Thr Asp Gly Cys Glu Ile Met Cys Cys Gly Arg Gly Tyr Asp Thr Thr
            335                 340                 345 cga gtc acc cgt gtt acc cag tgt gag tgc aaa ttc cac tgg tgc tgt       1108
Arg Val Thr Arg Val Thr Gln Cys Glu Cys Lys Phe His Trp Cys Cys
        350                 355                 360 gct gta cgg tgc aag gaa tgc aga aat act gtg gac gtc cat act tgc       1156
Ala Val Arg Cys Lys Glu Cys Arg Asn Thr Val Asp Val His Thr Cys
    365                 370                 375 aaa gcc ccc aag aag gca gag tgg ctg gac cag acc tga acacacagat       1205
Lys Ala Pro Lys Lys Ala Glu Trp Leu Asp Gln Thr
380                 385                 390 acctcactca tccctccaat tcaagcctct caactcaaaa gcacaagatc cttgcatgca    1265
caccttcctc caccctccac cctgggctgc taccgcttct atttaaggat gtagagagta    1325
atccataggg accatggtgt cctggctggt tccttagccc tgggaaggag ttgtcagggg    1385
atataagaaa ctgtgcaagc tccctgattt cccgctctgg agatttgaag ggagagtaga    1445
agagataggg ggtctttaga gtgaaatgag ttgcactaaa gtacgtagtt gaggctcctt    1505
```

```
tttctttcc  tttgcaccag  cttcccgaca  cttcttggtg  tgcaagagga  agggtacctg     1565
tagagagctt  cttttttgttt ctacctggcc  aaagttagat  gggacaaaga  tgaatggcat    1625
gtcccttctc  tgaagtccgt  ttgagcagaa  ctacctggta  ccccgaaaga  aaaatcttag    1685
gctaccacat  tctattattg  agagcctgag  atgttagcca  tagtgacaa   ggttccattc    1745 acatgctcat  atgtttataa  actgtgtttt  gtagaagaaa  aagaatcata  acaatacaaa    1805
cacacattca  ttctctcttt  ttctctctac  cattctcaac  ctgtattgga  cagcactgcc    1865
tcttttgctt  acttgctgcc  tgttcaaact  gaggtggaat  gcagtggttc  ccatgcttaa    1925
cagatcatta  aaacacccta  gaacactcct  aggatagatt  aatgt                     1970
```

<210> SEQ ID NO 6
<211> LENGTH: 391
<212> TYPE: PRT
<213> ORGANISM: Homo sapiens

<400> SEQUENCE: 6

```
Met Leu Arg Pro Gly Gly Ala Glu Glu Ala Ala Gln Leu Pro Leu Arg
  1               5                  10                  15

Arg Ala Ser Ala Pro Val Pro Val Pro Ser Pro Ala Ala Pro Asp Gly
                 20                  25                  30

Ser Arg Ala Ser Ala Arg Leu Gly Leu Ala Cys Leu Leu Leu Leu Leu
             35                  40                  45

Leu Leu Thr Leu Pro Ala Arg Val Asp Thr Ser Trp Trp Tyr Ile Gly
         50                  55                  60

Ala Leu Gly Ala Arg Val Ile Cys Asp Asn Ile Pro Gly Leu Val Ser
 65                  70                  75                  80

Arg Gln Arg Gln Leu Cys Gln Arg Tyr Pro Asp Ile Met Arg Ser Val
                 85                  90                  95

Gly Glu Gly Ala Arg Glu Trp Ile Arg Glu Cys Gln His Gln Phe Arg
            100                 105                 110

His His Arg Trp Asn Cys Thr Thr Leu Asp Arg Asp His Thr Val Phe
        115                 120                 125

Gly Arg Val Met Leu Arg Ser Ser Arg Glu Ala Ala Phe Val Tyr Ala
    130                 135                 140

Ile Ser Ser Ala Gly Val Val His Ala Ile Thr Arg Ala Cys Ser Gln
145                 150                 155                 160

Gly Glu Leu Ser Val Cys Ser Cys Asp Pro Tyr Thr Arg Gly Arg His
                165                 170                 175

His Asp Gln Arg Gly Asp Phe Asp Trp Gly Gly Cys Ser Asp Asn Ile
            180                 185                 190

His Tyr Gly Val Arg Phe Ala Lys Ala Phe Val Asp Ala Lys Glu Lys
        195                 200                 205

Arg Leu Lys Asp Ala Arg Ala Leu Met Asn Leu His Asn Asn Arg Cys
    210                 215                 220

Gly Arg Thr Ala Val Arg Arg Phe Leu Lys Leu Glu Cys Lys Cys His
225                 230                 235                 240

Gly Val Ser Gly Ser Cys Thr Leu Arg Thr Cys Trp Arg Ala Leu Ser
                245                 250                 255

Asp Phe Arg Arg Thr Gly Asp Tyr Leu Arg Arg Tyr Asp Gly Ala
            260                 265                 270

Val Gln Val Met Ala Thr Gln Asp Gly Ala Asn Phe Thr Ala Ala Arg
        275                 280                 285

Gln Gly Tyr Arg Arg Ala Thr Arg Thr Asp Leu Val Tyr Phe Asp Asn
```

-continued

```
                290                 295                 300
Ser Pro Asp Tyr Cys Val Leu Asp Lys Ala Ala Gly Ser Leu Gly Thr
305                 310                 315                 320

Ala Gly Arg Val Cys Ser Lys Thr Ser Lys Gly Thr Asp Gly Cys Glu
                325                 330                 335

Ile Met Cys Cys Gly Arg Gly Tyr Asp Thr Thr Arg Val Thr Arg Val
                340                 345                 350

Thr Gln Cys Glu Cys Lys Phe His Trp Cys Cys Ala Val Arg Cys Lys
                355                 360                 365

Glu Cys Arg Asn Thr Val Asp Val His Thr Cys Lys Ala Pro Lys Lys
                370                 375                 380

Ala Glu Trp Leu Asp Gln Thr
385                 390

<210> SEQ ID NO 7
<211> LENGTH: 1506
<212> TYPE: DNA
<213> ORGANISM: Homo sapiens
<220> FEATURE:
<221> NAME/KEY: CDS
<222> LOCATION: (120)..(1187)

<400> SEQUENCE: 7
gcgcttctga caagcccgaa agtcatttcc aatctcaagt ggactttgtt ccaactattg      60
ggggcgtcgc tccccctctt catggtcgcg ggcaaactta ctcctcggcg cctcttcta    119 atg gag ccc cac ctg ctc ggg ctg ctc ctc ggc ctc ctg ctc ggt ggc      167
Met Glu Pro His Leu Leu Gly Leu Leu Leu Gly Leu Leu Leu Gly Gly
1               5                   10                  15 acc agg gtc ctc gct ggc tac cca att tgg tgg tcc ctg gcc ctg ggc      215
Thr Arg Val Leu Ala Gly Tyr Pro Ile Trp Trp Ser Leu Ala Leu Gly
                20                  25                  30 cag cag tac aca tct ctg ggc tca cag ccc ctg ctc tgc ggc tcc atc      263
Gln Gln Tyr Thr Ser Leu Gly Ser Gln Pro Leu Leu Cys Gly Ser Ile
            35                  40                  45 cca ggc ctg gtc ccc aag caa ctg cgc ttc tgc cgc aat tac atc gag      311
Pro Gly Leu Val Pro Lys Gln Leu Arg Phe Cys Arg Asn Tyr Ile Glu
        50                  55                  60 atc atg ccc agc gtg gcc gag ggc gtg aag ctg ggc atc cag gag tgc      359
Ile Met Pro Ser Val Ala Glu Gly Val Lys Leu Gly Ile Gln Glu Cys
65                  70                  75                  80 cag cac cag ttc cgg ggc cgc cgc tgg aac tgc acc acc ata gat gac      407
Gln His Gln Phe Arg Gly Arg Arg Trp Asn Cys Thr Thr Ile Asp Asp
                85                  90                  95 agc ctg gcc atc ttt ggg ccc gtc ctc gac aaa gcc acc cgc gag tcg      455
Ser Leu Ala Ile Phe Gly Pro Val Leu Asp Lys Ala Thr Arg Glu Ser
            100                 105                 110 gcc ttc gtt cac gcc atc gcc tcg gcc ggc gtg gcc ttc gcc gtc acc      503
Ala Phe Val His Ala Ile Ala Ser Ala Gly Val Ala Phe Ala Val Thr
        115                 120                 125 cgc tcc tgc gcc gag ggc acc tcc acc att tgc ggc tgt gac tcg cat      551
Arg Ser Cys Ala Glu Gly Thr Ser Thr Ile Cys Gly Cys Asp Ser His
    130                 135                 140 cat aag ggg ccg cct ggc gaa ggc tgg aag tgg ggc ggc tgc agc gag      599
His Lys Gly Pro Pro Gly Glu Gly Trp Lys Trp Gly Gly Cys Ser Glu
145                 150                 155                 160 gac gct gac ttc ggc gtg tta gtg tcc agg gag ttc gcg gat gcg cgc      647
Asp Ala Asp Phe Gly Val Leu Val Ser Arg Glu Phe Ala Asp Ala Arg
                165                 170                 175
```

| | | | | | | | | | | | | | | | |
|---|---|---|---|---|---|---|---|---|---|---|---|---|---|---|---|
| gag | aac | agg | ccg | gac | gcg | cgc | tcg | gcc | atg | aac | aag | cac | aac | aac | gag |
| Glu | Asn | Arg | Pro | Asp | Ala | Arg | Ser | Ala | Met | Asn | Lys | His | Asn | Asn | Glu |
| | | 180 | | | | | 185 | | | | | 190 | | | |

695

| | | | | | | | | | | | | | | | |
|---|---|---|---|---|---|---|---|---|---|---|---|---|---|---|---|
| gcg | ggc | cgc | acg | act | atc | ctg | gac | cac | atg | cac | ctc | aaa | tgc | aag | tgc |
| Ala | Gly | Arg | Thr | Thr | Ile | Leu | Asp | His | Met | His | Leu | Lys | Cys | Lys | Cys |
| | | | 195 | | | | | 200 | | | | | 205 | | |

743

| | | | | | | | | | | | | | | | |
|---|---|---|---|---|---|---|---|---|---|---|---|---|---|---|---|
| cac | ggg | ctg | tcg | ggc | agc | tgt | gag | gtg | aag | acc | tgc | tgg | tgg | gcg | cag |
| His | Gly | Leu | Ser | Gly | Ser | Cys | Glu | Val | Lys | Thr | Cys | Trp | Trp | Ala | Gln |
| | 210 | | | | | 215 | | | | | 220 | | | | |

791

| | | | | | | | | | | | | | | | |
|---|---|---|---|---|---|---|---|---|---|---|---|---|---|---|---|
| cct | gac | ttc | cgt | gcc | atc | ggt | gac | ttc | ctc | aag | gac | aag | tat | gac | agc |
| Pro | Asp | Phe | Arg | Ala | Ile | Gly | Asp | Phe | Leu | Lys | Asp | Lys | Tyr | Asp | Ser |
| 225 | | | | | 230 | | | | | 235 | | | | | 240 |

839

| | | | | | | | | | | | | | | | |
|---|---|---|---|---|---|---|---|---|---|---|---|---|---|---|---|
| gcc | tcg | gag | atg | gta | gta | gag | aag | cac | cgt | gag | tcc | cga | ggc | tgg | gtg |
| Ala | Ser | Glu | Met | Val | Val | Glu | Lys | His | Arg | Glu | Ser | Arg | Gly | Trp | Val |
| | | | | 245 | | | | | 250 | | | | | 255 | |

887

| | | | | | | | | | | | | | | | |
|---|---|---|---|---|---|---|---|---|---|---|---|---|---|---|---|
| gag | acc | ctc | cgg | gcc | aag | tac | tcg | ctc | ttc | aag | cca | ccc | acg | gag | agg |
| Glu | Thr | Leu | Arg | Ala | Lys | Tyr | Ser | Leu | Phe | Lys | Pro | Pro | Thr | Glu | Arg |
| | | 260 | | | | | 265 | | | | | 270 | | | |

935

| | | | | | | | | | | | | | | | |
|---|---|---|---|---|---|---|---|---|---|---|---|---|---|---|---|
| gac | ctg | gtc | tac | tac | gag | aac | tcc | ccc | aac | ttt | tgt | gag | ccc | aac | cca |
| Asp | Leu | Val | Tyr | Tyr | Glu | Asn | Ser | Pro | Asn | Phe | Cys | Glu | Pro | Asn | Pro |
| | | | 275 | | | | | 280 | | | | | 285 | | |

983

| | | | | | | | | | | | | | | | |
|---|---|---|---|---|---|---|---|---|---|---|---|---|---|---|---|
| gag | acg | ggt | tcc | ttt | ggc | aca | agg | gac | cgg | act | tgc | aat | gtc | acc | tcc |
| Glu | Thr | Gly | Ser | Phe | Gly | Thr | Arg | Asp | Arg | Thr | Cys | Asn | Val | Thr | Ser |
| | 290 | | | | | 295 | | | | | 300 | | | | |

1031

| | | | | | | | | | | | | | | | |
|---|---|---|---|---|---|---|---|---|---|---|---|---|---|---|---|
| cac | ggc | atc | gat | ggc | tgc | gat | ctg | ctc | tgc | tgt | ggc | cgg | ggc | cac | aac |
| His | Gly | Ile | Asp | Gly | Cys | Asp | Leu | Leu | Cys | Cys | Gly | Arg | Gly | His | Asn |
| 305 | | | | | 310 | | | | | 315 | | | | | 320 |

1079

| | | | | | | | | | | | | | | | |
|---|---|---|---|---|---|---|---|---|---|---|---|---|---|---|---|
| acg | agg | acg | gag | aag | cgg | aag | gaa | aaa | tgc | cac | tgc | atc | ttc | cac | tgg |
| Thr | Arg | Thr | Glu | Lys | Arg | Lys | Glu | Lys | Cys | His | Cys | Ile | Phe | His | Trp |
| | | | | 325 | | | | | 330 | | | | | 335 | |

1127

| | | | | | | | | | | | | | | | |
|---|---|---|---|---|---|---|---|---|---|---|---|---|---|---|---|
| tgc | tgc | tac | gtc | agc | tgc | cag | gag | tgt | att | cgc | atc | tac | gac | gtg | cac |
| Cys | Cys | Tyr | Val | Ser | Cys | Gln | Glu | Cys | Ile | Arg | Ile | Tyr | Asp | Val | His |
| | | | 340 | | | | | 345 | | | | | 350 | | |

1175

| | | | |
|---|---|---|---|
| acc | tgc | aag | tag ggcaccaggg cgctgggaag gggtgaagtg tgtggctggg |
| Thr | Cys | Lys | |
| | | 355 | |

1227 cggattcagc gaagtctcat gggaagcagg acctagagcc gggcacagcc ctcagcgtca   1287 gacagcaagg aactgtcacc agccgcacgc gtggtaaatg acccagaccc aactcgcctg   1347 tggacgggga ggctctccct ctctctcatc ttacatttct caccctactc tggatggtgt   1407 gtggttttta agaaggggg ctttcttttt agttctctag gtctgatag gaacagacct    1467 gaggcttatc tttgcacatg ttaaagaaaa aaaaaaaa                           1506

<210> SEQ ID NO 8
<211> LENGTH: 355
<212> TYPE: PRT
<213> ORGANISM: Homo sapiens

<400> SEQUENCE: 8

| Met | Glu | Pro | His | Leu | Leu | Gly | Leu | Leu | Leu | Gly | Leu | Leu | Leu | Gly | Gly |
|---|---|---|---|---|---|---|---|---|---|---|---|---|---|---|---|
| 1 | | | | 5 | | | | | 10 | | | | | 15 | |

| Thr | Arg | Val | Leu | Ala | Gly | Tyr | Pro | Ile | Trp | Trp | Ser | Leu | Ala | Leu | Gly |
|---|---|---|---|---|---|---|---|---|---|---|---|---|---|---|---|
| | | | 20 | | | | | 25 | | | | | 30 | | |

| Gln | Gln | Tyr | Thr | Ser | Leu | Gly | Ser | Gln | Pro | Leu | Leu | Cys | Gly | Ser | Ile |
|---|---|---|---|---|---|---|---|---|---|---|---|---|---|---|---|
| | | 35 | | | | | 40 | | | | | 45 | | | |

| Pro | Gly | Leu | Val | Pro | Lys | Gln | Leu | Arg | Phe | Cys | Arg | Asn | Tyr | Ile | Glu |
|---|---|---|---|---|---|---|---|---|---|---|---|---|---|---|---|
| | 50 | | | | | 55 | | | | | 60 | | | | |

| Ile | Met | Pro | Ser | Val | Ala | Glu | Gly | Val | Lys | Leu | Gly | Ile | Gln | Glu | Cys |
|---|---|---|---|---|---|---|---|---|---|---|---|---|---|---|---|

-continued

```
                65                  70                  75                  80
Gln His Gln Phe Arg Gly Arg Arg Trp Asn Cys Thr Thr Ile Asp Asp
                85                  90                  95

Ser Leu Ala Ile Phe Gly Pro Val Leu Asp Lys Ala Thr Arg Glu Ser
           100                 105                 110

Ala Phe Val His Ala Ile Ala Ser Ala Gly Val Ala Phe Ala Val Thr
           115                 120                 125

Arg Ser Cys Ala Glu Gly Thr Ser Thr Ile Cys Gly Cys Asp Ser His
       130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
            180                 185                 190

Ala Gly Arg Thr Thr Ile Leu Asp His Met His Leu Lys Cys Lys Cys
        195                 200                 205

His Gly Leu Ser Gly Ser Cys Glu Val Lys Thr Cys Trp Trp Ala Gln
    210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ser Leu Phe Lys Pro Pro Thr Glu Arg
            260                 265                 270

Asp Leu Val Tyr Tyr Glu Asn Ser Pro Asn Phe Cys Glu Pro Asn Pro
        275                 280                 285

Glu Thr Gly Ser Phe Gly Thr Arg Asp Arg Thr Cys Asn Val Thr Ser
    290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Ile Phe His Trp
                325                 330                 335

Cys Cys Tyr Val Ser Cys Gln Glu Cys Ile Arg Ile Tyr Asp Val His
            340                 345                 350

Thr Cys Lys
       355
```

<210> SEQ ID NO 9
<211> LENGTH: 2932
<212> TYPE: DNA
<213> ORGANISM: Homo sapiens
<220> FEATURE:
<221> NAME/KEY: CDS
<222> LOCATION: (79)..(1137)

<400> SEQUENCE: 9

```
agctcccagg gcccggcccc ccccggcgct cacgctctcg gggcggactc ccggccctcc      60
gcgccctctc gcgcggcg atg gcc cca ctc gga tac ttc tta ctc ctc tgc     111
                    Met Ala Pro Leu Gly Tyr Phe Leu Leu Leu Cys
                     1               5                      10 agc ctg aag cag gct ctg ggc agc tac ccg atc tgg tgg tcg ctg gct     159
Ser Leu Lys Gln Ala Leu Gly Ser Tyr Pro Ile Trp Trp Ser Leu Ala
            15                  20                  25 gtt ggg cca cag tat tcc tcc ctg ggc tcg cag ccc atc ctg tgt gcc     207
Val Gly Pro Gln Tyr Ser Ser Leu Gly Ser Gln Pro Ile Leu Cys Ala
```

-continued

```
                  30                  35                  40
agc atc ccg ggc ctg gtc ccc aag cag ctc cgc ttc tgc agg aac tac    255
Ser Ile Pro Gly Leu Val Pro Lys Gln Leu Arg Phe Cys Arg Asn Tyr
    45                  50                  55 gtg gag atc atg ccc agc gtg gcc gag ggc atc aag att ggc atc cag    303
Val Glu Ile Met Pro Ser Val Ala Glu Gly Ile Lys Ile Gly Ile Gln
60                  65                  70                  75 gag tgc cag cac cag ttc cgc ggc cgc cgg tgg aac tgc acc acc gtc    351
Glu Cys Gln His Gln Phe Arg Gly Arg Arg Trp Asn Cys Thr Thr Val
                80                  85                  90 cac gac agc ctg gcc atc ttc ggg ccc gtg ctg gac aaa gct acc agg    399
His Asp Ser Leu Ala Ile Phe Gly Pro Val Leu Asp Lys Ala Thr Arg
            95                  100                 105 gag tcg gcc ttt gtc cac gcc att gcc tca gcc ggt gtg gcc ttt gca    447
Glu Ser Ala Phe Val His Ala Ile Ala Ser Ala Gly Val Ala Phe Ala
        110                 115                 120 gtg aca cgc tca tgt gca gaa ggc acg gcc gcc atc tgt ggc tgc agc    495
Val Thr Arg Ser Cys Ala Glu Gly Thr Ala Ala Ile Cys Gly Cys Ser
    125                 130                 135 agc cgc cac cag ggc tca cca ggc aag ggc tgg aag tgg ggt ggc tgt    543
Ser Arg His Gln Gly Ser Pro Gly Lys Gly Trp Lys Trp Gly Gly Cys
140                 145                 150                 155 agc gag gac atc gag ttt ggt ggg atg gtg tct cgg gag ttc gcc gac    591
Ser Glu Asp Ile Glu Phe Gly Gly Met Val Ser Arg Glu Phe Ala Asp
                160                 165                 170 gcc cgg gag aac cgg cca gat gcc cgc tca gcc atg aac cgc cac aac    639
Ala Arg Glu Asn Arg Pro Asp Ala Arg Ser Ala Met Asn Arg His Asn
            175                 180                 185 aac gag gct ggg cgc cag gcc atc gcc agc cac atg cac ctc aag tgc    687
Asn Glu Ala Gly Arg Gln Ala Ile Ala Ser His Met His Leu Lys Cys
        190                 195                 200 aag tgc cac ggg ctg tcg ggc agc tgc gag gtg aag aca tgc tgg tgg    735
Lys Cys His Gly Leu Ser Gly Ser Cys Glu Val Lys Thr Cys Trp Trp
    205                 210                 215 tcg caa ccc gac ttc cgc gcc atc ggt gac ttc ctc aag gac aag tac    783
Ser Gln Pro Asp Phe Arg Ala Ile Gly Asp Phe Leu Lys Asp Lys Tyr
220                 225                 230                 235 gac agc gcc tcg gag atg gtg gtg gag aag cac cgg gag tcc cgc ggc    831
Asp Ser Ala Ser Glu Met Val Val Glu Lys His Arg Glu Ser Arg Gly
                240                 245                 250 tgg gtg gag acc ctg cgg ccg cgc tac acc tac ttc aag gtg ccc acg    879
Trp Val Glu Thr Leu Arg Pro Arg Tyr Thr Tyr Phe Lys Val Pro Thr
            255                 260                 265 gag cgc gac ctg gtc tac tac gag gcc tcg ccc aac ttc tgc gag ccc    927
Glu Arg Asp Leu Val Tyr Tyr Glu Ala Ser Pro Asn Phe Cys Glu Pro
        270                 275                 280 aac cct gag acg ggc tcc ttc ggc acg cgc gac cgc acc tgc aac gtc    975
Asn Pro Glu Thr Gly Ser Phe Gly Thr Arg Asp Arg Thr Cys Asn Val
    285                 290                 295 agc tcg cac ggc atc gac ggc tgc gac ctg ctg tgc tgc ggc cgc ggc    1023
Ser Ser His Gly Ile Asp Gly Cys Asp Leu Leu Cys Cys Gly Arg Gly
300                 305                 310                 315 cac aac gcg cga gcg gag cgg cgc cgg gag aag tgc cgc tgc gtg ttc    1071
His Asn Ala Arg Ala Glu Arg Arg Arg Glu Lys Cys Arg Cys Val Phe
                320                 325                 330 cac tgg tgc tgc tac gtc agc tgc cag gag tgc acg cgc gtc tac gac    1119
His Trp Cys Cys Tyr Val Ser Cys Gln Glu Cys Thr Arg Val Tyr Asp
            335                 340                 345 gtg cac acc tgc aag tag gcaccggccg cggctccccc tggacggggc           1167
```

-continued

```
Val His Thr Cys Lys
        350 gggccctgcc tgagggtggg cttttccctg ggtggagcag gactcccacc taaacggggc    1227 agtactcctc cctggggggcg ggactcctcc ctggggggtgg ggctcctacc tgggggcaga    1287 actcctacct gaaggcaggg ctcctccctg gagctagtgt ctcctctctg gtggctgggc    1347 tgctcctgaa tgaggcggag ctccaggatg ggagggggc ctgcgttggc ttctccctgg    1407 ggacggggct cccctggaca gaggcgggc tacagattgg gcggggcttc tcttgggtgg    1467 gacagggctt ctcctgcggg ggcgaggccc ctcccagtaa gggcgtggct ctgggtgggc    1527 gggcactag gtaggcttct acctgcaggc ggggctcctc ctgaaggagg cggggctcta    1587 ggatggggca cggctctggg gtaggctgct ccctgagggc ggagcgcctc cttaggagtg    1647 gggtttatg gtggatgagg cttcttcctg gatggggcag agcttctcct gaccagggca    1707 aggcccttc cacggggct gtggctctgg gtgggcgtgg cctgcatagg ctccttcctg    1767 tgggtggggc ttctctggga ccaggctcca atggggcggg gcttctctcc gcgggtggga    1827 ctcttccctg ggaaccgccc tcctgattaa ggcgtggctt ctgcaggaat cccggctcca    1887 gagcaggaaa ttcagcccac cagccacctc atccccaacc ccctgtaagg ttccatccac    1947 ccctgcgtcg agctgggaag gttccatgaa gcgagtcggg tccccaaccc gtgcccctgg    2007 gatccgaggg ccccctctcca agcgcctggc tttggaatgc tccaggcgcg ccgacgcctg    2067 tgccacccct tcctcagcct ggggtttgac cacccacctg accaggggcc ctacctgggg    2127 aaagcctgaa gggcctccca gccccaacc ccaagaccaa gcttagtcct gggagaggac    2187 agggacttcg cagaggcaag cgaccgaggc cctcccaaag aggcccgccc tgcccgggct    2247 cccacaccgt caggtactcc tgccaggaa ctggcctgct cgcccccagg cccgcccgt    2307 ctctgctctg ctcagctgcg ccccttctt tgcagctgcc cagcccctcc tccctgccct    2367 cgggtctccc cacctgcact ccatccagct acaggagaga tagaagcctc tcgtcccgtc    2427 cctccctttc ctccgcctgt ccacagcccc ttaagggaaa ggtaggaaga gaggtccagc    2487 ccccccaggct gcccagagct gctggtctca tttgggggcg ttcgggaggt ttgggggca    2547 tcaacccccc gactgtgctg ctcgcgaagg tcccacagcc ctgagatggg ccggcccct    2607 tcctggcccc tcatggcggg actggagaaa tggtccgctt tcctggagcc aatgcccgg    2667 ccctcctga ctcatccgcc tggcccggga atgaatgggg aggccgctga acccacccgg    2727 cccatatccc tggttgcctc atggccagcc cccctcagcc tctgccactg tgaaccggct    2787 cccaccctca aggtgcgggg agaagaagcg gccaggcggg gcgccccaag agcccaaaag    2847 agggcacacc gccatcctct gcctcaaatt ctgcgttttt ggttttaatg ttatatctga    2907 tgctgctata tccactgtcc aacgg                                           2932
```

<210> SEQ ID NO 10
<211> LENGTH: 352
<212> TYPE: PRT
<213> ORGANISM: Homo sapiens

<400> SEQUENCE: 10

```
Met Ala Pro Leu Gly Tyr Phe Leu Leu Leu Cys Ser Leu Lys Gln Ala
 1               5                  10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45
```

-continued

```
Val Pro Lys Gln Leu Arg Phe Cys Arg Asn Tyr Val Glu Ile Met Pro
     50                  55                  60
Ser Val Ala Glu Gly Ile Lys Ile Gly Ile Gln Glu Cys Gln His Gln
 65                  70                  75                  80
Phe Arg Gly Arg Arg Trp Asn Cys Thr Thr Val His Asp Ser Leu Ala
                 85                  90                  95
Ile Phe Gly Pro Val Leu Asp Lys Ala Thr Arg Glu Ser Ala Phe Val
            100                 105                 110
His Ala Ile Ala Ser Ala Gly Val Ala Phe Ala Val Thr Arg Ser Cys
        115                 120                 125
Ala Glu Gly Thr Ala Ala Ile Cys Gly Cys Ser Ser Arg His Gln Gly
    130                 135                 140
Ser Pro Gly Lys Gly Trp Lys Trp Gly Gly Cys Ser Glu Asp Ile Glu
145                 150                 155                 160
Phe Gly Gly Met Val Ser Arg Glu Phe Ala Asp Ala Arg Glu Asn Arg
                165                 170                 175
Pro Asp Ala Arg Ser Ala Met Asn Arg His Asn Asn Glu Ala Gly Arg
            180                 185                 190
Gln Ala Ile Ala Ser His Met His Leu Lys Cys Lys Cys His Gly Leu
        195                 200                 205
Ser Gly Ser Cys Glu Val Lys Thr Cys Trp Trp Ser Gln Pro Asp Phe
    210                 215                 220
Arg Ala Ile Gly Asp Phe Leu Lys Asp Lys Tyr Asp Ser Ala Ser Glu
225                 230                 235                 240
Met Val Val Glu Lys His Arg Glu Ser Arg Gly Trp Val Glu Thr Leu
                245                 250                 255
Arg Pro Arg Tyr Thr Tyr Phe Lys Val Pro Thr Glu Arg Asp Leu Val
            260                 265                 270
Tyr Tyr Glu Ala Ser Pro Asn Phe Cys Glu Pro Asn Pro Glu Thr Gly
        275                 280                 285
Ser Phe Gly Thr Arg Asp Arg Thr Cys Asn Val Ser Ser His Gly Ile
    290                 295                 300
Asp Gly Cys Asp Leu Leu Cys Cys Gly Arg Gly His Asn Ala Arg Ala
305                 310                 315                 320
Glu Arg Arg Arg Glu Lys Cys Arg Cys Val Phe His Trp Cys Cys Tyr
                325                 330                 335
Val Ser Cys Gln Glu Cys Thr Arg Val Tyr Asp Val His Thr Cys Lys
            340                 345                 350
```

<210> SEQ ID NO 11
<211> LENGTH: 1595
<212> TYPE: DNA
<213> ORGANISM: Homo sapiens
<220> FEATURE:
<221> NAME/KEY: CDS
<222> LOCATION: (196)..(1251)

<400> SEQUENCE: 11

```
ggctctgggg cggcgctgac agtctggtcc gcgccgggca gcgggcgcag cagcgggcag      60
gctgccggca ggcacacgga ggcagagccc cgccgcgcgc gccccggccc gcccgcgggc     120
gcccacctgc agccccgacg ggaggccccc cgcggccgca gccgctgccc cgggccgggc     180
gcccgcggcg gcacc atg agt ccc cgc tcg tgc ctg cgt tcg ctg cgc ctc      231
                 Met Ser Pro Arg Ser Cys Leu Arg Ser Leu Arg Leu
                  1               5                   10
```

```
ctc gtc ttc gcc gtc ttc tca gcc gcc gcg agc aac tgg ctg tac ctg      279
Leu Val Phe Ala Val Phe Ser Ala Ala Ala Ser Asn Trp Leu Tyr Leu
         15                  20                  25 gcc aag ctg tcg tcg gtg ggg agc atc tca gag gag gag acg tgc gag      327
Ala Lys Leu Ser Ser Val Gly Ser Ile Ser Glu Glu Glu Thr Cys Glu
     30                  35                  40 aaa ctc aag ggc ctg atc cag agg cag gtg cag atg tgc aag cgg aac      375
Lys Leu Lys Gly Leu Ile Gln Arg Gln Val Gln Met Cys Lys Arg Asn
 45                  50                  55                  60 ctg gaa gtc atg gac tcg gtg cgc cgc ggt gcc cag ctg gcc att gag      423
Leu Glu Val Met Asp Ser Val Arg Arg Gly Ala Gln Leu Ala Ile Glu
                 65                  70                  75 gag tgc cag tac cag ttc cgg aac cgg cgc tgg aac tgc tcc aca ctc      471
Glu Cys Gln Tyr Gln Phe Arg Asn Arg Arg Trp Asn Cys Ser Thr Leu
             80                  85                  90 gac tcc ttg ccc gtc ttc ggc aag gtg gtg acg caa ggg act cgg gag      519
Asp Ser Leu Pro Val Phe Gly Lys Val Val Thr Gln Gly Thr Arg Glu
         95                 100                 105 gcg gcc ttc gtg tac gcc atc tct tcg gca ggt gtg gcc ttt gca gtg      567
Ala Ala Phe Val Tyr Ala Ile Ser Ser Ala Gly Val Ala Phe Ala Val
    110                 115                 120 acg cgg gcg tgc agc agt ggg gag ctg gag aag tgc ggc tgt gac agg      615
Thr Arg Ala Cys Ser Ser Gly Glu Leu Glu Lys Cys Gly Cys Asp Arg
125                 130                 135                 140 aca gtg cat ggg gtc agc cca cag ggc ttc cag tgg tca gga tgc tct      663
Thr Val His Gly Val Ser Pro Gln Gly Phe Gln Trp Ser Gly Cys Ser
                145                 150                 155 gac aac atc gcc tac ggt gtg gcc ttc tca cag tcg ttt gtg gat gtg      711
Asp Asn Ile Ala Tyr Gly Val Ala Phe Ser Gln Ser Phe Val Asp Val
            160                 165                 170 cgg gag aga agc aag ggg gcc tcg tcc agc aga gcc ctc atg aac ctc      759
Arg Glu Arg Ser Lys Gly Ala Ser Ser Ser Arg Ala Leu Met Asn Leu
        175                 180                 185 cac aac aat gag gcc ggc agg aag gcc atc ctg aca cac atg cgg gtg      807
His Asn Asn Glu Ala Gly Arg Lys Ala Ile Leu Thr His Met Arg Val
    190                 195                 200 gaa tgc aag tgc cac ggg gtg tca ggc tcc tgt gag gta aag acg tgc      855
Glu Cys Lys Cys His Gly Val Ser Gly Ser Cys Glu Val Lys Thr Cys
205                 210                 215                 220 tgg cga gcc gtg ccg ccc ttc cgc cag gtg ggt cac gca ctg aag gag      903
Trp Arg Ala Val Pro Pro Phe Arg Gln Val Gly His Ala Leu Lys Glu
                225                 230                 235 aag ttt gat ggt gcc act gag gtg gag cca cgc cgc gtg ggc tcc tcc      951
Lys Phe Asp Gly Ala Thr Glu Val Glu Pro Arg Arg Val Gly Ser Ser
            240                 245                 250 agg gca ctg gtg cca cgc aac gca cag ttc aag ccg cac aca gat gag      999
Arg Ala Leu Val Pro Arg Asn Ala Gln Phe Lys Pro His Thr Asp Glu
        255                 260                 265 gac ctg gtg tac ttg gag cct agc ccc gac ttc tgt gag cag gac atg     1047
Asp Leu Val Tyr Leu Glu Pro Ser Pro Asp Phe Cys Glu Gln Asp Met
    270                 275                 280 cgc agc ggc gtg ctg ggc acg agg ggc cgc aca tgc aac aag acg tcc     1095
Arg Ser Gly Val Leu Gly Thr Arg Gly Arg Thr Cys Asn Lys Thr Ser
285                 290                 295                 300 aag gcc atc gac ggc tgt gag ctg ctg tgt tgt ggc cgc ggc ttc cac     1143
Lys Ala Ile Asp Gly Cys Glu Leu Leu Cys Cys Gly Arg Gly Phe His
                305                 310                 315 acg gcg cag gtg gag ctg gct gaa cgc tgc agc tgc aaa ttc cac tgg     1191
Thr Ala Gln Val Glu Leu Ala Glu Arg Cys Ser Cys Lys Phe His Trp
            320                 325                 330
```

```
tgc tgc ttc gtc aag tgc cgg cag tgc cag cgg ctc gtg gag ttg cac      1239
Cys Cys Phe Val Lys Cys Arg Gln Cys Gln Arg Leu Val Glu Leu His
        335                 340                 345 acg tgc cga tga ccgcctgcct agccctgcgc cggcaaccac ctagtgggcc          1291
Thr Cys Arg
    350 agggaaggcc gataatttaa acagtctccc accacctacc ccaagagata ctggttgtat    1351 ttttgttct ggtttggttt ttgggtcctc atgttattta ttgccgaaac caggcaggca     1411 accccaaggg caccaaccag ggcctcccca aagcctgggc ctttgtggct gccactgacc    1471 aaagggacct tgctcgtgcc gctggctgcc cgcatgtggc tgccactgac cactcagttg    1531 ttatctgtgt ccgttttct acttgcagac ctaaggtgga gtaacaagga gtattaccac    1591 caca                                                                 1595

<210> SEQ ID NO 12
<211> LENGTH: 351
<212> TYPE: PRT
<213> ORGANISM: Homo sapiens

<400> SEQUENCE: 12

Met Ser Pro Arg Ser Cys Leu Arg Ser Leu Arg Leu Leu Val Phe Ala
 1               5                  10                  15

Val Phe Ser Ala Ala Ala Ser Asn Trp Leu Tyr Leu Ala Lys Leu Ser
                20                  25                  30

Ser Val Gly Ser Ile Ser Glu Glu Thr Cys Glu Lys Leu Lys Gly
        35                  40                  45

Leu Ile Gln Arg Gln Val Gln Met Cys Lys Arg Asn Leu Glu Val Met
    50                  55                  60

Asp Ser Val Arg Arg Gly Ala Gln Leu Ala Ile Glu Glu Cys Gln Tyr
 65                  70                  75                  80

Gln Phe Arg Asn Arg Trp Asn Cys Ser Thr Leu Asp Ser Leu Pro
                 85                  90                  95

Val Phe Gly Lys Val Val Thr Gln Gly Thr Arg Glu Ala Ala Phe Val
                100                 105                 110

Tyr Ala Ile Ser Ser Ala Gly Val Ala Phe Ala Val Thr Arg Ala Cys
            115                 120                 125

Ser Ser Gly Glu Leu Glu Lys Cys Gly Cys Asp Arg Thr Val His Gly
        130                 135                 140

Val Ser Pro Gln Gly Phe Gln Trp Ser Gly Cys Ser Asp Asn Ile Ala
145                 150                 155                 160

Tyr Gly Val Ala Phe Ser Gln Ser Phe Val Asp Val Arg Glu Arg Ser
                165                 170                 175

Lys Gly Ala Ser Ser Ser Arg Ala Leu Met Asn Leu His Asn Asn Glu
            180                 185                 190

Ala Gly Arg Lys Ala Ile Leu Thr His Met Arg Val Glu Cys Lys Cys
        195                 200                 205

His Gly Val Ser Gly Ser Cys Glu Val Lys Thr Cys Trp Arg Ala Val
    210                 215                 220

Pro Pro Phe Arg Gln Val Gly His Ala Leu Lys Glu Lys Phe Asp Gly
225                 230                 235                 240

Ala Thr Glu Val Glu Pro Arg Arg Val Gly Ser Ser Arg Ala Leu Val
                245                 250                 255

Pro Arg Asn Ala Gln Phe Lys Pro His Thr Asp Glu Asp Leu Val Tyr
            260                 265                 270
```

```
Leu Glu Pro Ser Pro Asp Phe Cys Glu Gln Asp Met Arg Ser Gly Val
        275                 280                 285
Leu Gly Thr Arg Gly Arg Thr Cys Asn Lys Thr Ser Lys Ala Ile Asp
        290                 295                 300
Gly Cys Glu Leu Leu Cys Cys Gly Arg Gly Phe His Thr Ala Gln Val
305                 310                 315                 320
Glu Leu Ala Glu Arg Cys Ser Cys Lys Phe His Trp Cys Cys Phe Val
                325                 330                 335
Lys Cys Arg Gln Cys Gln Arg Leu Val Glu Leu His Thr Cys Arg
        340                 345                 350

<210> SEQ ID NO 13
<211> LENGTH: 5855
<212> TYPE: DNA
<213> ORGANISM: Homo sapiens
<220> FEATURE:
<221> NAME/KEY: CDS
<222> LOCATION: (319)..(1461)

<400> SEQUENCE: 13
agttgcctgc gcgccctcgc cggaccggcg gctccctagt tgcgccccga ccaggccctg      60
cccttgctgc cggctcgcgc gcgtccgcgc ccctccatt cctgggcgca tcccagctct     120
gccccaactc gggagtccag gcccgggcgc cagtgcccgc ttcagctccg gttcactgcg     180
cccgccggac gcgcgccgga ggactccgca gccctgctcc tgaccgtccc cccaggctta     240
acccggtcgc tccgctcgga ttcctcggct gcgctcgctc gggtggcgac ttcctccccg     300
cgccccctcc ccctcgcc atg aag aag tcc att gga ata tta agc cca gga       351
                    Met Lys Lys Ser Ile Gly Ile Leu Ser Pro Gly
                     1               5                   10 gtt gct ttg ggg atg gct gga agt gca atg tct tcc aag ttc ttc cta       399
Val Ala Leu Gly Met Ala Gly Ser Ala Met Ser Ser Lys Phe Phe Leu
             15                  20                  25 gtg gct ttg gcc ata ttt ttc tcc ttc gcc cag gtt gta att gaa gcc       447
Val Ala Leu Ala Ile Phe Phe Ser Phe Ala Gln Val Val Ile Glu Ala
         30                  35                  40 aat tct tgg tgg tcg cta ggt atg aat aac cct gtt cag atg tca gaa       495
Asn Ser Trp Trp Ser Leu Gly Met Asn Asn Pro Val Gln Met Ser Glu
     45                  50                  55 gta tat att ata gga gca cag cct ctc tgc agc caa ctg gca gga ctt       543
Val Tyr Ile Ile Gly Ala Gln Pro Leu Cys Ser Gln Leu Ala Gly Leu
 60                  65                  70                  75 tct caa gga cag aag aaa ctg tgc cac ttg tat cag gac cac atg cag       591
Ser Gln Gly Gln Lys Lys Leu Cys His Leu Tyr Gln Asp His Met Gln
                 80                  85                  90 tac atc gga gaa ggc gcg aag aca ggc atc aaa gaa tgc cag tat caa       639
Tyr Ile Gly Glu Gly Ala Lys Thr Gly Ile Lys Glu Cys Gln Tyr Gln
             95                 100                 105 ttc cga cat cga agg tgg aac tgc agc act gtg gat aac acc tct gtt       687
Phe Arg His Arg Arg Trp Asn Cys Ser Thr Val Asp Asn Thr Ser Val
        110                 115                 120 ttt ggc agg gtg atg cag ata ggc agc cgc gag acg gcc ttc aca tac       735
Phe Gly Arg Val Met Gln Ile Gly Ser Arg Glu Thr Ala Phe Thr Tyr
    125                 130                 135 gcg gtg agc gca gca ggg gtg gtg aac gcc atg agc cgg gcg tgc cgc       783
Ala Val Ser Ala Ala Gly Val Val Asn Ala Met Ser Arg Ala Cys Arg
140                 145                 150                 155 gag ggc gag ctg tcc acc tgc ggc tgc agc cgc gcc gcg cgc ccc aag       831
Glu Gly Glu Leu Ser Thr Cys Gly Cys Ser Arg Ala Ala Arg Pro Lys
```

```
                    160              165              170
gac ctg ccg cgg gac tgg ctc tgg ggc ggc tgc ggc gac aac atc gac      879
Asp Leu Pro Arg Asp Trp Leu Trp Gly Gly Cys Gly Asp Asn Ile Asp
            175              180              185 tat ggc tac cgc ttt gcc aag gag ttc gtg gac gcc cgc gag cgg gag      927
Tyr Gly Tyr Arg Phe Ala Lys Glu Phe Val Asp Ala Arg Glu Arg Glu
        190              195              200 cgc atc cac gcc aag ggc tcc tac gag agt gct cgc atc ctc atg aac      975
Arg Ile His Ala Lys Gly Ser Tyr Glu Ser Ala Arg Ile Leu Met Asn
        205              210              215 ctg cac aac aac gag gcc ggc cgc agg acg gtg tac aac ctg gct gat     1023
Leu His Asn Asn Glu Ala Gly Arg Arg Thr Val Tyr Asn Leu Ala Asp
220              225              230              235 gtg gcc tgc aag tgc cat ggg gtg tcc ggc tca tgt agc ctg aag aca     1071
Val Ala Cys Lys Cys His Gly Val Ser Gly Ser Cys Ser Leu Lys Thr
                240              245              250 tgc tgg ctg cag ctg gca gac ttc cgc aag gtg ggt gat gcc ctg aag     1119
Cys Trp Leu Gln Leu Ala Asp Phe Arg Lys Val Gly Asp Ala Leu Lys
            255              260              265 gag aag tac gac agc gcg gcg gcc atg cgg ctc aac agc cgg ggc aag     1167
Glu Lys Tyr Asp Ser Ala Ala Ala Met Arg Leu Asn Ser Arg Gly Lys
        270              275              280 ttg gta cag gtc aac agc cgc ttc aac tcg ccc acc aca caa gac ctg     1215
Leu Val Gln Val Asn Ser Arg Phe Asn Ser Pro Thr Thr Gln Asp Leu
285              290              295 gtc tac atc gac ccc agc cct gac tac tgc gtg cgc aat gag agc acc     1263
Val Tyr Ile Asp Pro Ser Pro Asp Tyr Cys Val Arg Asn Glu Ser Thr
300              305              310              315 ggc tcg ctg ggc acg cag ggc cgc ctg tgc aac aag acg tcg gag ggc     1311
Gly Ser Leu Gly Thr Gln Gly Arg Leu Cys Asn Lys Thr Ser Glu Gly
            320              325              330 atg gat ggc tgc gag ctc atg tgc tgc ggc cgt ggc tac gac cag ttc     1359
Met Asp Gly Cys Glu Leu Met Cys Cys Gly Arg Gly Tyr Asp Gln Phe
        335              340              345 aag acc gtg cag acg gag cgc tgc cac tgc aag ttc cac tgg tgc tgc     1407
Lys Thr Val Gln Thr Glu Arg Cys His Cys Lys Phe His Trp Cys Cys
        350              355              360 tac gtc aag tgc aag aag tgc acg gag atc gtg gac cag ttt gtg tgc     1455
Tyr Val Lys Cys Lys Lys Cys Thr Glu Ile Val Asp Gln Phe Val Cys
        365              370              375 aag tag tgggtgccac ccagcactca gccccgctcc caggacccgc ttatttatag      1511
Lys
380 aaagtacagt gattctggtt tttggttttt agaaatattt tttattttc cccaagaatt     1571 gcaaccggaa ccatttttt tcctgttacc atcaagaac tctgtggttt attattaata     1631 ttataattat tatttggcaa taatgggggt gggaaccaag aaaaatattt attttgtgga    1691 tctttgaaaa ggtaatacaa gacttctttt gatagtatag aatgaagggg aaataacaca   1751 taccctaact tagctgtgtg gacatggtac acatccagaa ggtaaagaaa tacatttct    1811 ttttctcaaa tatgccatca tatgggatgg gtaggttcca gttgaaagag ggtggtagaa   1871 atctattcac aattcagctt ctatgaccaa aatgagttgt aaattctctg gtgcaagata   1931 aaaggtcttg ggaaaacaaa acaaaacaaa acaaacctcc cttccccagc agggctgcta   1991 gcttgctttc tgcattttca aaatgataat ttacaatgga aggacaagaa tgtcatattc   2051 tcaaggaaaa aagtatatc acatgtctca ttctcctcaa atattccatt tgcagacaga   2111 ccgtcatatt ctaatagctc atgaaatttg ggcagcaggg aggaaagtcc ccagaaatta   2171
```

```
aaaaatttaa aactcttatg tcaagatgtt gatttgaagc tgttataaga attaggattc      2231
cagattgtaa aaagatcccc aaatgattct ggacactaga ttttttttgtt tggggaggtt     2291 ggcttgaaca taaatgaaaa tatcctgtta ttttcttagg gatacttggt tagtaaatta      2351
taatagtaaa aataatacat gaatcccatt cacaggttct cagcccaagc aacaaggtaa      2411
ttgcgtgcca ttcagcactg caccagagca gacaacctat ttgaggaaaa acagtgaaat      2471
ccaccttcct cttcacactg agccctctct gattcctccg tgttgtgatg tgatgctggc      2531
cacgtttcca aacggcagct ccactgggtc ccctttggtt gtaggacagg aaatgaaaca      2591
ttaggagctc tgcttggaaa acagttcact acttagggat ttttgtttcc taaaacttt       2651 attttgagga gcagtagttt tctatgtttt aatgacagaa cttggctaat ggaattcaca      2711
gaggtgttgc agcgtatcac tgttatgatc ctgtgtttag attatccact catgcttctc      2771
ctattgtact gcaggtgtac cttaaaactg ttcccagtgt acttgaacag ttgcatttat      2831 aagggggaa atgtggttta atggtgcctg atatctcaaa gtcttttgta cataacatat       2891
atatatatat acatatatat aaatataaat ataaatatat ctcattgcag ccagtgattt      2951
agatttacag tttactctgg ggttatttct ctgtctagag cattgttgtc cttcactgca      3011
gtccagttgg gattattcca aaagtttttt gagtcttgag cttgggctgt ggccctgctg      3071
tgatcatacc ttgagcacga cgaagcaacc ttgtttctga ggaagcttga gttctgactc      3131
actgaaatgc gtgttgggtt gaagatatct ttttcttttt ctgcctcacc cctttgtctc      3191
caacctccat ttctgttcac tttgtggaga gggcattact tgttcgttat agacatggac      3251
gttaagagat attcaaaact cagaagcatc agcaatgttt ctcttttctt agttcattct      3311
gcagaatgga aacccatgcc tattagaaat gacagtactt attaattgag tccctaagga     3371
atattcagcc cactacatag atagcttttt tttttttttt tttaataagg cacctctttt      3431
ccaaacagtg ccatcaaata tgttcttatc tcagacttac gttgttttaa agtttggaa       3491 agatacacat ctttcatacc ccccttaggc aggttggctt tcatatcacc tcagccaact      3551
gtggctctta atttattgca taatgatatt cacatcccct cagttgcagt gaattgtgag      3611
caaaagatct tgaaagcaaa aagcactaat tagtttaaaa tgtcactttt ttggttttta     3671
ttatacaaaa accatgaagt actttttta tttgctaaat cagattgttc ctttttagtg       3731
actcatgttt atgaagagag ttgagtttaa caatcctagc ttttaaaaga aactatttaa      3791
tgtaaaatat tctacatgtc attcagatat tatgtatatc ttctagcctt tattctgtac      3851
ttttaatgta catatttctg tcttgcgtga tttgtatatt tcactggttt aaaaaacaaa     3911
catcgaaagg cttatgccaa atggaagata gaatataaaa taaaacgtta cttgtatatt      3971
ggtaagtggt ttcaattgtc cttcagataa ttcatgtgga gattttttgga gaaaccatga    4031 cggatagttt aggatgacta catgtcaaag taataaaaga gtggtgaatt ttaccaaaac      4091
caagctattt ggaagcttca aaaggtttct atatgtaatg gaacaaaagg ggaattctct     4151
tttcctatat atgttcctta caaaaaaaaa aaaaaaagaa atcaagcaga tggcttaaag      4211
ctggttatag gattgctcac attctttag cattatgcat gtaacttaat tgttttagag       4271
cgtgttgctg ttgtaacatc ccagagaaga atgaaaaggc acatgctttt atccgtgacc     4331 agattttag tccaaaaaaa tgtattttttt tgtgtgttta ccactgcaac tattgcacct      4391
ctctatttga atttactgtg gaccatgtgt ggtgtctcta tgccctttga aagcagtttt      4451
tataaaaaga aagcccgggt ctgcagagaa tgaaaactgg ttggaaacta aaggttcatt     4511
```

-continued

```
gtgttaagtg caattaatac aagttattgt gcttttcaaa aatgtacacg gaaatctgga    4571
cagtgctgca cagattgata cattagcctt tgcttttttct ctttccggat aaccttgtaa   4631
catattgaaa cctttaagg atgccaagaa tgcattattc cacaaaaaaa cagcagacca    4691
acatatagag tgtttaaaat agcatttctg ggcaaattca aactcttgtg gttctaggac    4751
tcacatctgt ttcagttttt cctcagttgt atattgacca gtgttcttta ttgcaaaaac    4811
atatacccga tttagcagtg tcagcgtatt tttcttctc atcctggagc gtattcaaga    4871
tcttcccaat acaagaaaat taataaaaaa tttatatata ggcagcagca aaagagccat    4931
gttcaaaata gtcattatgg gctcaaatag aaagaagact tttaagtttt aatccagttt    4991
atctgttgag ttctgtgagc tactgacctc ctgagactgg cactgtgtaa gttttagttg    5051
cctaccctag ctcttttctc gtacaatttt gccaatacca agtttcaatt tgttttaca    5111
aaacattatt caagccacta gaattatcaa atatgacgct atagcagagt aaatactctg    5171
aataagagac cggtactagc taactccaag agatcgttag cagcatcagt ccacaaacac    5231
ttagtggccc acaatatata gagagataga aaaggtagtt ataacttgaa gcatgtattt    5291
aatgcaaata ggcacgaagg cacaggtcta aaatactaca ttgtcactgt aagctatact    5351
tttaaaatat ttatttttt taaagtattt tctagtcttt tctctctctg tggaatggtg    5411
aaagagagat gccgtgtttt gaaagtaaga tgatgaaatg aattttaat tcaagaaaca    5471
ttcagaaaca taggaattaa aacttagaga aatgatctaa tttccctgtt cacacaaact    5531
ttacacttta atctgatgat tggatatttt attttagtga aacatcatct tgttagctaa    5591
ctttaaaaaa tggatgtaga atgattaaag gttggtatga ttttttttta atgtatcagt    5651
ttgaacctag aatattgaat taaaatgctg tctcagtatt ttaaaagcaa aaaaggaatg    5711
gaggaaaatt gcatcttaga ccatttttat atgcagtgta caatttgctg ggctagaaat    5771
gagataaaga ttatttattt ttgttcatat cttgtacttt tctattaaaa tcattttatg    5831
aaatccaaaa aaaaaaaaaa aaaa                                            5855
```

<210> SEQ ID NO 14
<211> LENGTH: 380
<212> TYPE: PRT
<213> ORGANISM: Homo sapiens

<400> SEQUENCE: 14

```
Met Lys Lys Ser Ile Gly Ile Leu Ser Pro Gly Val Ala Leu Gly Met
 1               5                  10                  15
Ala Gly Ser Ala Met Ser Ser Lys Phe Phe Leu Val Ala Leu Ala Ile
             20                  25                  30
Phe Phe Ser Phe Ala Gln Val Val Ile Glu Ala Asn Ser Trp Trp Ser
         35                  40                  45
Leu Gly Met Asn Asn Pro Val Gln Met Ser Glu Val Tyr Ile Ile Gly
     50                  55                  60
Ala Gln Pro Leu Cys Ser Gln Leu Ala Gly Leu Ser Gln Gly Gln Lys
 65                  70                  75                  80
Lys Leu Cys His Leu Tyr Gln Asp His Met Gln Tyr Ile Gly Glu Gly
                 85                  90                  95
Ala Lys Thr Gly Ile Lys Glu Cys Gln Tyr Gln Phe Arg His Arg Arg
            100                 105                 110
Trp Asn Cys Ser Thr Val Asp Asn Thr Ser Val Phe Gly Arg Val Met
        115                 120                 125
Gln Ile Gly Ser Arg Glu Thr Ala Phe Thr Tyr Ala Val Ser Ala Ala
```

-continued

```
            130                 135                 140
Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380

<210> SEQ ID NO 15
<211> LENGTH: 2252
<212> TYPE: DNA
<213> ORGANISM: Homo sapiens
<220> FEATURE:
<221> NAME/KEY: CDS
<222> LOCATION: (184)..(1263)

<400> SEQUENCE: 15
gaccattagc aggcacccag gcctgtcttt ggctcggaaa cggtggcccc caatgtagcc      60
tagtttgaac ctaggaactg caggaccaga gagattccac tggagcctga tggacgggtg     120
acagagggaa ccctactctg gaaactgtca gtcccagggc actggggagg gctgaggccg     180 acc atg ccc agc ctg ctg ctg ctg ttc acg gct gct ctg ctg tcc agc       228
    Met Pro Ser Leu Leu Leu Leu Phe Thr Ala Ala Leu Leu Ser Ser
      1               5                  10                  15 tgg gct cag ctt ctg aca gac gcc aac tcc tgg tgg tca tta gct ttg       276
Trp Ala Gln Leu Leu Thr Asp Ala Asn Ser Trp Trp Ser Leu Ala Leu
                20                  25                  30 aac ccg gtg cag aga ccc gag atg ttt atc atc ggt gcc cag ccc gtg       324
Asn Pro Val Gln Arg Pro Glu Met Phe Ile Ile Gly Ala Gln Pro Val
            35                  40                  45 tgc agt cag ctt ccc ggg ctc tcc cct ggc cag agg aag ctg tgc caa       372
Cys Ser Gln Leu Pro Gly Leu Ser Pro Gly Gln Arg Lys Leu Cys Gln
        50                  55                  60
```

```
ttg tac cag gag cac atg gcc tac ata ggg gag gga gcc aag act ggc      420
Leu Tyr Gln Glu His Met Ala Tyr Ile Gly Glu Gly Ala Lys Thr Gly
     65                  70                  75 atc aag gaa tgc cag cac cag ttc cgg cag cgg cgg tgg aat tgc agc      468
Ile Lys Glu Cys Gln His Gln Phe Arg Gln Arg Arg Trp Asn Cys Ser
 80                  85                  90                  95 aca gcg gac aac gca tct gtc ttt ggg aga gtc atg cag ata ggc agc      516
Thr Ala Asp Asn Ala Ser Val Phe Gly Arg Val Met Gln Ile Gly Ser
                100                 105                 110 cga gag acc gcc ttc acc cac gcg gtg agc gcc gcg ggc gtg gtc aac      564
Arg Glu Thr Ala Phe Thr His Ala Val Ser Ala Ala Gly Val Val Asn
            115                 120                 125 gcc atc agc cgg gcc tgc cgc gag ggc gag ctc tcc acc tgc ggc tgc      612
Ala Ile Ser Arg Ala Cys Arg Glu Gly Glu Leu Ser Thr Cys Gly Cys
        130                 135                 140 agc cgg acg gcg cgg ccc aag gac ctg ccc cgg gac tgg ctg tgg ggc      660
Ser Arg Thr Ala Arg Pro Lys Asp Leu Pro Arg Asp Trp Leu Trp Gly
    145                 150                 155 ggc tgt ggg gac aac gtg gag tac ggc tac cgc ttc gcc aag gag ttt      708
Gly Cys Gly Asp Asn Val Glu Tyr Gly Tyr Arg Phe Ala Lys Glu Phe
160                 165                 170                 175 gtg gat gcc cgg gag cga gag aag aac ttt gcc aaa gga tca gag gag      756
Val Asp Ala Arg Glu Arg Glu Lys Asn Phe Ala Lys Gly Ser Glu Glu
                180                 185                 190 cag ggc cgg gtg ctc atg aac ctg caa aac aac gag gcc ggt cgc agg      804
Gln Gly Arg Val Leu Met Asn Leu Gln Asn Asn Glu Ala Gly Arg Arg
            195                 200                 205 gct gtg tat aag atg gca gac gta gcc tgc aaa tgc cac ggc gtc tcg      852
Ala Val Tyr Lys Met Ala Asp Val Ala Cys Lys Cys His Gly Val Ser
        210                 215                 220 ggg tcc tgc agc ctc aag acc tgc tgg ctg cag ctg gcc gag ttc cgc      900
Gly Ser Cys Ser Leu Lys Thr Cys Trp Leu Gln Leu Ala Glu Phe Arg
    225                 230                 235 aag gtc ggg gac cgg ctg aag gag aag tac gac agc gcg gcc gcc atg      948
Lys Val Gly Asp Arg Leu Lys Glu Lys Tyr Asp Ser Ala Ala Ala Met
240                 245                 250                 255 cgc gtc acc cgc aag ggc cgg ctg gag ctg gtc aac agc cgc ttc acc      996
Arg Val Thr Arg Lys Gly Arg Leu Glu Leu Val Asn Ser Arg Phe Thr
                260                 265                 270 cag ccc acc ccg gag gac ctg gtc tat gtg gac ccc agc ccc gac tac     1044
Gln Pro Thr Pro Glu Asp Leu Val Tyr Val Asp Pro Ser Pro Asp Tyr
            275                 280                 285 tgc ctg cgc aac gag agc acg ggc tcc ctg ggc acg cag ggc cgc ctc     1092
Cys Leu Arg Asn Glu Ser Thr Gly Ser Leu Gly Thr Gln Gly Arg Leu
        290                 295                 300 tgc aac aag acc tcg gag ggc atg gat ggc tgt gag ctc atg tgc tgc     1140
Cys Asn Lys Thr Ser Glu Gly Met Asp Gly Cys Glu Leu Met Cys Cys
    305                 310                 315 ggg cgt ggc tac aac cag ttc aag agc gtg cag gtg gag cgc tgc cac     1188
Gly Arg Gly Tyr Asn Gln Phe Lys Ser Val Gln Val Glu Arg Cys His
320                 325                 330                 335 tgc aag ttc cac tgg tgc tgc ttc gtc agg tgt aag aag tgc acg gag     1236
Cys Lys Phe His Trp Cys Cys Phe Val Arg Cys Lys Lys Cys Thr Glu
                340                 345                 350 atc gtg gac cag tac atc tgt aaa tag cccggagggc tgctcccgg            1283
Ile Val Asp Gln Tyr Ile Cys Lys
            355                 360 cccccctgc actctgcctc acaaaggtct atattatata aatctatata aatctatttt    1343
```

```
atatttgtat aagtaaatgg gtgggtgcta tacaatggaa agatgaaaat ggaaaggaag    1403
agcttattta agagacgctg gagatctctg aggagtggac tttgctggtt ctctcctctt    1463
ggtgggtggg agacagggct ttttctctcc ctctggcgag gactctcagg atgtagggac    1523
ttggaaatat ttactgtctg tccaccacgg cctggaggag ggaggttgtg gttggatgga    1583
ggagatgatc ttgtctggaa gtctagagtc tttgttggtt agaggactgc ctgtgatcct    1643
ggccactagg ccaagaggcc ctatgaaggt ggcgggaact cagcttcaac ctcgatgtct    1703
tcagggtctt gtccagaatg tagatgggtt ccgtaagagg cctggtgctc tcttactctt    1763
tcatccacgt gcacttgtgc ggcatctgca gtttacagga acggctcctt ccctaaaatg    1823
agaagtccaa ggtcatctct ggcccagtga ccacagagag atctgcacct cccggacttc    1883
aggcctgcct ttccagcgag aattcttcat cctccacggt tcactagctc ctacctgaag    1943
aggaaagggg gccatttgac ctgacatgtc aggaaagccc taaactgaat gtttgcgcct    2003
gggctgcaga agccagggtg catgaccagg ctgcgtggac gttatactgt cttcccccac    2063
ccccggggag gggaagcttg agctgctgct gtcactcctc caccgaggga ggcctcacaa    2123
accacaggac gctgcaacgg gtcaggctgg cgggcccggc gtgctcatca tctctgcccc    2183
aggtgtacgg tttctctctg acattaaatg cccttcatgg aaaaaaaaaa aagaaaaaaa    2243
aaaaaaaaa                                                            2252
```

<210> SEQ ID NO 16  
<211> LENGTH: 359  
<212> TYPE: PRT  
<213> ORGANISM: Homo sapiens

<400> SEQUENCE: 16

```
Met Pro Ser Leu Leu Leu Leu Phe Thr Ala Ala Leu Leu Ser Ser Trp
  1               5                  10                  15

Ala Gln Leu Leu Thr Asp Ala Asn Ser Trp Trp Ser Leu Ala Leu Asn
             20                  25                  30

Pro Val Gln Arg Pro Glu Met Phe Ile Ile Gly Ala Gln Pro Val Cys
         35                  40                  45

Ser Gln Leu Pro Gly Leu Ser Pro Gly Gln Arg Lys Leu Cys Gln Leu
     50                  55                  60

Tyr Gln Glu His Met Ala Tyr Ile Gly Glu Gly Ala Lys Thr Gly Ile
 65                  70                  75                  80

Lys Glu Cys Gln His Gln Phe Arg Gln Arg Trp Asn Cys Ser Thr
                 85                  90                  95

Ala Asp Asn Ala Ser Val Phe Gly Arg Val Met Gln Ile Gly Ser Arg
                100                 105                 110

Glu Thr Ala Phe Thr His Ala Val Ser Ala Ala Gly Val Val Asn Ala
            115                 120                 125

Ile Ser Arg Ala Cys Arg Glu Gly Glu Leu Ser Thr Cys Gly Cys Ser
        130                 135                 140

Arg Thr Ala Arg Pro Lys Asp Leu Pro Arg Asp Trp Leu Trp Gly Gly
145                 150                 155                 160

Cys Gly Asp Asn Val Glu Tyr Gly Tyr Arg Phe Ala Lys Glu Phe Val
                165                 170                 175

Asp Ala Arg Glu Arg Glu Lys Asn Phe Ala Lys Gly Ser Glu Glu Gln
            180                 185                 190

Gly Arg Val Leu Met Asn Leu Gln Asn Asn Glu Ala Gly Arg Arg Ala
        195                 200                 205
```

```
Val Tyr Lys Met Ala Asp Val Ala Cys Lys Cys His Gly Val Ser Gly
    210                 215                 220
Ser Cys Ser Leu Lys Thr Cys Trp Leu Gln Leu Ala Glu Phe Arg Lys
225                 230                 235                 240
Val Gly Asp Arg Leu Lys Glu Lys Tyr Asp Ser Ala Ala Ala Met Arg
                245                 250                 255
Val Thr Arg Lys Gly Arg Leu Glu Leu Val Asn Ser Arg Phe Thr Gln
            260                 265                 270
Pro Thr Pro Glu Asp Leu Val Tyr Val Asp Pro Ser Pro Asp Tyr Cys
        275                 280                 285
Leu Arg Asn Glu Ser Thr Gly Ser Leu Gly Thr Gln Gly Arg Leu Cys
    290                 295                 300
Asn Lys Thr Ser Glu Gly Met Asp Gly Cys Glu Leu Met Cys Cys Gly
305                 310                 315                 320
Arg Gly Tyr Asn Gln Phe Lys Ser Val Gln Val Glu Arg Cys His Cys
                325                 330                 335
Lys Phe His Trp Cys Cys Phe Val Arg Cys Lys Lys Cys Thr Glu Ile
            340                 345                 350
Val Asp Gln Tyr Ile Cys Lys
        355

<210> SEQ ID NO 17
<211> LENGTH: 1726
<212> TYPE: DNA
<213> ORGANISM: Homo sapiens
<220> FEATURE:
<221> NAME/KEY: CDS
<222> LOCATION: (224)..(1321)

<400> SEQUENCE: 17
ggcacgagcg caggagacac aggcgctggc tgccccgtcc gctctccgcc tccgccgcgc      60
cctcctcgcc cgggatgggc cccccgccg ccgccggatc cctcgcctcc cggccgccgc     120
cgttgcgctc gccgcgctcg cactgaagcc cgggccctcg cgcgccgcgg ttcgccccgc     180
agcctcgccc cctgcccacc cgggcggccg tagggcggtc acg atg ctg ccg ccc      235
                                            Met Leu Pro Pro
                                              1 tta ccc tcc cgc ctc ggg ctg ctg ctg ctg ctc ctg tgc ccg gcg           283
Leu Pro Ser Arg Leu Gly Leu Leu Leu Leu Leu Leu Cys Pro Ala
  5                  10                  15                  20 cac gtc ggc gga ctg tgg tgg gct gtg ggc agc ccc ttg gtt atg gac      331
His Val Gly Gly Leu Trp Trp Ala Val Gly Ser Pro Leu Val Met Asp
                 25                  30                  35 cct acc agc atc tgc agg aag gca cgg cgg ctg gcc ggg cgg cag gcc      379
Pro Thr Ser Ile Cys Arg Lys Ala Arg Arg Leu Ala Gly Arg Gln Ala
             40                  45                  50 gag ttg tgc cag gct gag ccg gaa gtg gtg gca gag cta gct cgg ggc      427
Glu Leu Cys Gln Ala Glu Pro Glu Val Val Ala Glu Leu Ala Arg Gly
         55                  60                  65 gcc cgg ctc ggg gtg cga gag tgc cag ttc cag ttc cgc ttc cgc cgc      475
Ala Arg Leu Gly Val Arg Glu Cys Gln Phe Gln Phe Arg Phe Arg Arg
     70                  75                  80 tgg aat tgc tcc agc cac agc aag gcc ttt gga cgc atc ctg caa cag      523
Trp Asn Cys Ser Ser His Ser Lys Ala Phe Gly Arg Ile Leu Gln Gln
 85                  90                  95                 100 gac att cgg gag acg gcc ttc gtg ttc gcc atc act gcg gcc ggc gcc      571
Asp Ile Arg Glu Thr Ala Phe Val Phe Ala Ile Thr Ala Ala Gly Ala
                105                 110                 115
```

```
                                                                          -continued
agc cac gcc gtc acg cag gcc tgt tct atg ggc gag ctg ctg cag tgc            619
Ser His Ala Val Thr Gln Ala Cys Ser Met Gly Glu Leu Leu Gln Cys
        120                 125                 130 ggc tgc cag gcg ccc cgc ggg cgg gcc cct ccc cgg ccc tcc ggc ctg            667
Gly Cys Gln Ala Pro Arg Gly Arg Ala Pro Pro Arg Pro Ser Gly Leu
        135                 140                 145 ccc ggc acc ccc gga ccc cct ggc ccc gcg ggc tcc ccg gaa ggc agc            715
Pro Gly Thr Pro Gly Pro Pro Gly Pro Ala Gly Ser Pro Glu Gly Ser
150                 155                 160 gcc gcc tgg gag tgg gga ggc tgc ggc gac gac gtg gac ttc ggg gac            763
Ala Ala Trp Glu Trp Gly Gly Cys Gly Asp Asp Val Asp Phe Gly Asp
165                 170                 175                 180 gag aag tcg agg ctc ttt atg gac gcg cgg cac aag cgg gga cgc gga            811
Glu Lys Ser Arg Leu Phe Met Asp Ala Arg His Lys Arg Gly Arg Gly
                185                 190                 195 gac atc cgc gcg ttg gtg caa ctg cac aac aac gag gcg ggc agg ctg            859
Asp Ile Arg Ala Leu Val Gln Leu His Asn Asn Glu Ala Gly Arg Leu
            200                 205                 210 gcc gtg cgg agc cac acg cgc acc gag tgc aaa tgc cac ggg ctg tcg            907
Ala Val Arg Ser His Thr Arg Thr Glu Cys Lys Cys His Gly Leu Ser
        215                 220                 225 gga tca tgc gcg ctg cgc acc tgc tgg cag aag ctg cct cca ttt cgc            955
Gly Ser Cys Ala Leu Arg Thr Cys Trp Gln Lys Leu Pro Pro Phe Arg
230                 235                 240 gag gtg ggc gcg cgg ctg ctg gag cgc ttc cac ggc gcc tca cgc gtc           1003
Glu Val Gly Ala Arg Leu Leu Glu Arg Phe His Gly Ala Ser Arg Val
245                 250                 255                 260 atg ggc acc aac gac ggc aag gcc ctg ctg ccc gcc gtc cgc acg ctc           1051
Met Gly Thr Asn Asp Gly Lys Ala Leu Leu Pro Ala Val Arg Thr Leu
                265                 270                 275 aag ccg ccg ggc cga gcg gac ctc ctc tac gcc gcc gat tcg ccc gac           1099
Lys Pro Pro Gly Arg Ala Asp Leu Leu Tyr Ala Ala Asp Ser Pro Asp
            280                 285                 290 ttt tgc gcc ccc aac cga cgc acc ggc tcc ccc ggc acg cgc ggt cgc           1147
Phe Cys Ala Pro Asn Arg Arg Thr Gly Ser Pro Gly Thr Arg Gly Arg
        295                 300                 305 gcc tgc aat agc agc gcc ccg gac ctc agc ggc tgc gac ctg ctg tgc           1195
Ala Cys Asn Ser Ser Ala Pro Asp Leu Ser Gly Cys Asp Leu Leu Cys
310                 315                 320 tgc ggc cgc ggg cac cgc cag gag agc gtg cag ctc gaa gag aac tgc           1243
Cys Gly Arg Gly His Arg Gln Glu Ser Val Gln Leu Glu Glu Asn Cys
325                 330                 335                 340 ctg tgc cgc ttc cac tgg tgc tgc gta gta cag tgc cac cgt tgc cgt           1291
Leu Cys Arg Phe His Trp Cys Cys Val Val Gln Cys His Arg Cys Arg
                345                 350                 355 gtg cgc aag gag ctc agc ctc tgc ctg tga cccgccgccc ggccgctaga            1341
Val Arg Lys Glu Leu Ser Leu Cys Leu
            360                 365 ctgacttcgc gcagcggtgg ctcgcacctg tgggacctca gggcaccggc accgggcgcc        1401
tctcgccgct cgagcccagc ctctccctgc caaagcccaa ctcccagggc tctggaaatg        1461
gtgaggcgag gggcttgaga ggaacgccca cccacgaagg cccagggcgc cagacggccc        1521
cgaaaaggcg ctcggggagc gtttaaagga cactgtacag gccctccctc ccttggcct        1581 ctaggaggaa acagtttttt agactggaaa aagccagtc  taaaggcctc tggatactgg       1641
gctccccaga actgctggcc acaggatggt gggtgaggtt agtatcaata aagatattta       1701
aaccaaaaaa aaaaaaaaaa aaaaa                                             1726
```

<210> SEQ ID NO 18
<211> LENGTH: 365
<212> TYPE: PRT
<213> ORGANISM: Homo sapiens

<400> SEQUENCE: 18

Met Leu Pro Pro Leu Pro Ser Arg Leu Gly Leu Leu Leu Leu Leu Leu
1               5                   10                  15

Leu Cys Pro Ala His Val Gly Gly Leu Trp Trp Ala Val Gly Ser Pro
            20                  25                  30

Leu Val Met Asp Pro Thr Ser Ile Cys Arg Lys Ala Arg Arg Leu Ala
        35                  40                  45

Gly Arg Gln Ala Glu Leu Cys Gln Ala Glu Pro Glu Val Val Ala Glu
    50                  55                  60

Leu Ala Arg Gly Ala Arg Leu Gly Val Arg Glu Cys Gln Phe Gln Phe
65                  70                  75                  80

Arg Phe Arg Arg Trp Asn Cys Ser Ser His Ser Lys Ala Phe Gly Arg
                85                  90                  95

Ile Leu Gln Gln Asp Ile Arg Glu Thr Ala Phe Val Phe Ala Ile Thr
            100                 105                 110

Ala Ala Gly Ala Ser His Ala Val Thr Gln Ala Cys Ser Met Gly Glu
        115                 120                 125

Leu Leu Gln Cys Gly Cys Gln Ala Pro Arg Gly Arg Ala Pro Pro Arg
    130                 135                 140

Pro Ser Gly Leu Pro Gly Thr Pro Gly Pro Pro Gly Pro Ala Gly Ser
145                 150                 155                 160

Pro Glu Gly Ser Ala Ala Trp Glu Trp Gly Gly Cys Gly Asp Asp Val
                165                 170                 175

Asp Phe Gly Asp Glu Lys Ser Arg Leu Phe Met Asp Ala Arg His Lys
            180                 185                 190

Arg Gly Arg Gly Asp Ile Arg Ala Leu Val Gln Leu His Asn Asn Glu
        195                 200                 205

Ala Gly Arg Leu Ala Val Arg Ser His Thr Arg Thr Glu Cys Lys Cys
    210                 215                 220

His Gly Leu Ser Gly Ser Cys Ala Leu Arg Thr Cys Trp Gln Lys Leu
225                 230                 235                 240

Pro Pro Phe Arg Glu Val Gly Ala Arg Leu Leu Glu Arg Phe His Gly
                245                 250                 255

Ala Ser Arg Val Met Gly Thr Asn Asp Gly Lys Ala Leu Leu Pro Ala
            260                 265                 270

Val Arg Thr Leu Lys Pro Pro Gly Arg Ala Asp Leu Leu Tyr Ala Ala
        275                 280                 285

Asp Ser Pro Asp Phe Cys Ala Pro Asn Arg Arg Thr Gly Ser Pro Gly
    290                 295                 300

Thr Arg Gly Arg Ala Cys Asn Ser Ser Ala Pro Asp Leu Ser Gly Cys
305                 310                 315                 320

Asp Leu Leu Cys Cys Gly Arg Gly His Arg Gln Glu Ser Val Gln Leu
                325                 330                 335

Glu Glu Asn Cys Leu Cys Arg Phe His Trp Cys Cys Val Val Gln Cys
            340                 345                 350

His Arg Cys Arg Val Arg Lys Glu Leu Ser Leu Cys Leu
        355                 360                 365

<210> SEQ ID NO 19
<211> LENGTH: 1732

```
<212> TYPE: DNA
<213> ORGANISM: Homo sapiens
<220> FEATURE:
<221> NAME/KEY: CDS
<222> LOCATION: (306)..(1355)

<400> SEQUENCE: 19
gaggggcggg ggctggaggc agcagcgccc ccgcactccc cgcgtctcgc acacttgcac      60
cggtcgctcg cgcgcagccc ggcgtcgccc acgccgcgc tcgctcctcc ctccctcctc     120
ccgctccgtg ctcccgtgc tcctggcgag gctcaggcgc ggagcgcgcg acgggcgca      180 ccgacagacg gccccgggga cgcctcggct cgcgcctccc gggcgggcta tgttgattgc    240
cccgccgggg ccggcccgcg ggatcagcac agcccggccc gcggcccggg cggccaatcg   300 ggact atg aac cgg aaa gcg cgg cgc tgc ctg ggc cac ctc ttt ctc agc    350
      Met Asn Arg Lys Ala Arg Arg Cys Leu Gly His Leu Phe Leu Ser
       1               5                  10                  15 ctg ggc atg gtc tac ctc cgg atc ggt ggc ttc tcc tca gtg gta gct     398
Leu Gly Met Val Tyr Leu Arg Ile Gly Gly Phe Ser Ser Val Val Ala
             20                  25                  30 ctg ggc gca agc atc atc tgt aac aag atc cca ggc ctg gct ccc aga     446
Leu Gly Ala Ser Ile Ile Cys Asn Lys Ile Pro Gly Leu Ala Pro Arg
         35                  40                  45 cag cgg gcg atc tgc cag agc cgg ccc gac gcc atc atc gtc ata gga     494
Gln Arg Ala Ile Cys Gln Ser Arg Pro Asp Ala Ile Ile Val Ile Gly
     50                  55                  60 gaa ggc tca caa atg ggc ctg gac gag tgt cag ttt cag ttc cgc aat     542
Glu Gly Ser Gln Met Gly Leu Asp Glu Cys Gln Phe Gln Phe Arg Asn
 65                  70                  75 ggc cgc tgg aac tgc tct gca ctg gga gag cgc acc gtc ttc ggg aag     590
Gly Arg Trp Asn Cys Ser Ala Leu Gly Glu Arg Thr Val Phe Gly Lys
 80                  85                  90                  95 gag ctc aaa gtg ggg agc cgg gag gct gcg ttc acc tac gcc atc att     638
Glu Leu Lys Val Gly Ser Arg Glu Ala Ala Phe Thr Tyr Ala Ile Ile
                100                 105                 110 gcc gcc ggc gtg gcc cac gcc atc aca gct gcc tgt acc cag ggc aac     686
Ala Ala Gly Val Ala His Ala Ile Thr Ala Ala Cys Thr Gln Gly Asn
            115                 120                 125 ctg agc gac tgt ggc tgc gac aaa gag aag caa ggc cag tac cac cgg     734
Leu Ser Asp Cys Gly Cys Asp Lys Glu Lys Gln Gly Gln Tyr His Arg
        130                 135                 140 gac gag ggc tgg aag tgg ggt ggc tgc tct gcc gac atc cgc tac ggc     782
Asp Glu Gly Trp Lys Trp Gly Gly Cys Ser Ala Asp Ile Arg Tyr Gly
145                 150                 155 atc ggc ttc gcc aag gtc ttt gtg gat gcc cgg gag atc aag cag aat     830
Ile Gly Phe Ala Lys Val Phe Val Asp Ala Arg Glu Ile Lys Gln Asn
160                 165                 170                 175 gcc cgg act ctc atg aac ttg cac aac aac gag gca ggc cga aag atc     878
Ala Arg Thr Leu Met Asn Leu His Asn Asn Glu Ala Gly Arg Lys Ile
                180                 185                 190 ctg gag gag aac atg aag ctg gaa tgt aag tgc cac ggc gtg tca ggc     926
Leu Glu Glu Asn Met Lys Leu Glu Cys Lys Cys His Gly Val Ser Gly
            195                 200                 205 tcg tgc acc acc aag acg tgc tgg acc aca ctg cca cag ttt cgg gag     974
Ser Cys Thr Thr Lys Thr Cys Trp Thr Thr Leu Pro Gln Phe Arg Glu
        210                 215                 220 ctg ggc tac gtg ctc aag gac aag tac aac gag gcc gtt cac gtg gag    1022
Leu Gly Tyr Val Leu Lys Asp Lys Tyr Asn Glu Ala Val His Val Glu
    225                 230                 235 cct gtg cgt gcc agc cgc aac aag cgg ccc acc ttc ctg aag atc aag    1070
```

-continued

```
Pro Val Arg Ala Ser Arg Asn Lys Arg Pro Thr Phe Leu Lys Ile Lys
240                 245                 250                 255 aag cca ctg tcg tac cgc aag ccc atg gac acg gac ctg gtg tac atc         1118
Lys Pro Leu Ser Tyr Arg Lys Pro Met Asp Thr Asp Leu Val Tyr Ile
                    260                 265                 270 gag aag tcg ccc aac tac tgc gag gag gac ccg gtg acc ggc agt gtg         1166
Glu Lys Ser Pro Asn Tyr Cys Glu Glu Asp Pro Val Thr Gly Ser Val
                275                 280                 285 ggc acc cag ggc cgc gcc tgc aac aag acg gct ccc cag gcc agc ggc         1214
Gly Thr Gln Gly Arg Ala Cys Asn Lys Thr Ala Pro Gln Ala Ser Gly
            290                 295                 300 tgt gac ctc atg tgc tgt ggg cgt ggc tac aac acc cac cag tac gcc         1262
Cys Asp Leu Met Cys Cys Gly Arg Gly Tyr Asn Thr His Gln Tyr Ala
305                 310                 315 cgc gtg tgg cag tgc aac tgt aag ttc cac tgg tgc tgc tat gtc aag         1310
Arg Val Trp Gln Cys Asn Cys Lys Phe His Trp Cys Cys Tyr Val Lys
320                 325                 330                 335 tgc aac acg tgc agc gag cgc acg gag atg tac acg tgc aag tga             1355
Cys Asn Thr Cys Ser Glu Arg Thr Glu Met Tyr Thr Cys Lys
                340                 345                 350 gccccgtgtg cacaccaccc tcccgctgca agtcagattg ctgggaggac tggaccgttt       1415
ccaagctgcg ggctccctgg caggatgctg agcttgtctt ttctgctgag gagggtactt       1475
ttcctgggtt tcctgcaggc atccgtgggg gaaaaaaaat ctctcagagc cctcaactat       1535
tctgttccac acccaatgct gctccaccct cccccagaca cagcccaggt ccctccgcgg       1595
ctggagcgaa gccttctgca gcaggaactc tggacccctg ggcctcatca cagcaatatt       1655
taacaattta ttctgataaa aataatatta atttatttaa ttaaaaagaa ttcttccaca       1715
aaaaaaaaaa aaaaaaa                                                      1732
```

<210> SEQ ID NO 20
<211> LENGTH: 349
<212> TYPE: PRT
<213> ORGANISM: Homo sapiens

<400> SEQUENCE: 20

```
Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
                20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
        50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
                100                 105                 110

Ala Gly Val Ala His Ala Ile Thr Ala Ala Cys Thr Gln Gly Asn Leu
            115                 120                 125

Ser Asp Cys Gly Cys Asp Lys Glu Lys Gln Gly Gln Tyr His Arg Asp
        130                 135                 140

Glu Gly Trp Lys Trp Gly Gly Cys Ser Ala Asp Ile Arg Tyr Gly Ile
145                 150                 155                 160
```

-continued

```
Gly Phe Ala Lys Val Phe Val Asp Ala Arg Glu Ile Lys Gln Asn Ala
                165                 170                 175
Arg Thr Leu Met Asn Leu His Asn Asn Glu Ala Gly Arg Lys Ile Leu
            180                 185                 190
Glu Glu Asn Met Lys Leu Glu Cys Lys Cys His Gly Val Ser Gly Ser
        195                 200                 205
Cys Thr Thr Lys Thr Cys Trp Thr Thr Leu Pro Gln Phe Arg Glu Leu
    210                 215                 220
Gly Tyr Val Leu Lys Asp Lys Tyr Asn Glu Ala Val His Val Glu Pro
225                 230                 235                 240
Val Arg Ala Ser Arg Asn Lys Arg Pro Thr Phe Leu Lys Ile Lys Lys
                245                 250                 255
Pro Leu Ser Tyr Arg Lys Pro Met Asp Thr Asp Leu Val Tyr Ile Glu
            260                 265                 270
Lys Ser Pro Asn Tyr Cys Glu Glu Asp Pro Val Thr Gly Ser Val Gly
        275                 280                 285
Thr Gln Gly Arg Ala Cys Asn Lys Thr Ala Pro Gln Ala Ser Gly Cys
    290                 295                 300
Asp Leu Met Cys Cys Gly Arg Gly Tyr Asn Thr His Gln Tyr Ala Arg
305                 310                 315                 320
Val Trp Gln Cys Asn Cys Lys Phe His Trp Cys Cys Tyr Val Lys Cys
                325                 330                 335
Asn Thr Cys Ser Glu Arg Thr Glu Met Tyr Thr Cys Lys
            340                 345
```

<210> SEQ ID NO 21
<211> LENGTH: 2250
<212> TYPE: DNA
<213> ORGANISM: Homo sapiens
<220> FEATURE:
<221> NAME/KEY: CDS
<222> LOCATION: (96)..(1145)

<400> SEQUENCE: 21

```
gagtctgccc gcagccccct ggccctgcc cggccctgcg tgcccgcgcg tccctccggc      60
cgcgctgtct atggcgcagc cccctcct ggatc atg cac aga aac ttt cgc        113
                                    Met His Arg Asn Phe Arg
                                      1               5 aag tgg att ttc tac gtg ttt ctc tgc ttt ggc gtc ctg tac gtg aag    161
Lys Trp Ile Phe Tyr Val Phe Leu Cys Phe Gly Val Leu Tyr Val Lys
             10                  15                  20 ctc gga gca ctg tca tcc gtg gtg gcc ctg gga gcc aac atc atc tgc    209
Leu Gly Ala Leu Ser Ser Val Val Ala Leu Gly Ala Asn Ile Ile Cys
         25                  30                  35 aac aag att cct ggc cta gcc ccg cgg cag cgt gcc atc tgc cag agt    257
Asn Lys Ile Pro Gly Leu Ala Pro Arg Gln Arg Ala Ile Cys Gln Ser
     40                  45                  50 cgg ccc gat gcc atc att gtg att ggg gag ggg gcg cag atg ggc atc    305
Arg Pro Asp Ala Ile Ile Val Ile Gly Glu Gly Ala Gln Met Gly Ile
 55                  60                  65                  70 aac gag tgc cag tac cag ttc cgc ttc gga cgc tgg aac tgc tct gcc    353
Asn Glu Cys Gln Tyr Gln Phe Arg Phe Gly Arg Trp Asn Cys Ser Ala
                 75                  80                  85 ctc ggc gag aag acc gtc ttc ggg caa gag ctc cga gta ggg agc cgt    401
Leu Gly Glu Lys Thr Val Phe Gly Gln Glu Leu Arg Val Gly Ser Arg
             90                  95                 100 gag gct gcc ttc acg tac gcc atc acc gcg gct ggc gtg gcg cac gcc    449
Glu Ala Ala Phe Thr Tyr Ala Ile Thr Ala Ala Gly Val Ala His Ala
```

-continued

```
                105                 110                 115
gtc acc gct gcc tgc agc caa ggg aac ctg agc aac tgc ggc tgc gac       497
Val Thr Ala Ala Cys Ser Gln Gly Asn Leu Ser Asn Cys Gly Cys Asp
    120                 125                 130 cgc gag aag cag ggc tac tac aac caa gcc gag ggc tgg aag tgg ggc       545
Arg Glu Lys Gln Gly Tyr Tyr Asn Gln Ala Glu Gly Trp Lys Trp Gly
135                 140                 145                 150 ggc tgc tcg gcc gac gtg cgt tac ggc atc gac ttc tcc cgg cgc ttc       593
Gly Cys Ser Ala Asp Val Arg Tyr Gly Ile Asp Phe Ser Arg Arg Phe
                155                 160                 165 gtg gac gct cgg gag atc aag aag aac gcg cgg cgc ctc atg aac ctg       641
Val Asp Ala Arg Glu Ile Lys Lys Asn Ala Arg Arg Leu Met Asn Leu
            170                 175                 180 cat aac aat gag gcc ggc agg aag gtt cta gag gac cgg atg cag ctg       689
His Asn Asn Glu Ala Gly Arg Lys Val Leu Glu Asp Arg Met Gln Leu
        185                 190                 195 gag tgc aag tgc cac ggc gtg tct ggc tcc tgc acc acc aaa acc tgc       737
Glu Cys Lys Cys His Gly Val Ser Gly Ser Cys Thr Thr Lys Thr Cys
    200                 205                 210 tgg acc acg ctg ccc aag ttc cga gag gtg ggc cac ctg ctg aag gag       785
Trp Thr Thr Leu Pro Lys Phe Arg Glu Val Gly His Leu Leu Lys Glu
215                 220                 225                 230 aag tac aac gcg gcc gtg cag gtg gag gtg gtg cgg gcc agc cgt ctg       833
Lys Tyr Asn Ala Ala Val Gln Val Glu Val Val Arg Ala Ser Arg Leu
                235                 240                 245 cgg cag ccc acc ttc ctg cgc atc aaa cag ctg cgc agc tat cag aag       881
Arg Gln Pro Thr Phe Leu Arg Ile Lys Gln Leu Arg Ser Tyr Gln Lys
            250                 255                 260 ccc atg gag aca gac ctg gtg tac att gag aag tcg ccc aac tac tgc       929
Pro Met Glu Thr Asp Leu Val Tyr Ile Glu Lys Ser Pro Asn Tyr Cys
        265                 270                 275 gag gag gac gcg gcc acg ggc agc gtg ggc acg cag ggc cgt ctc tgc       977
Glu Glu Asp Ala Ala Thr Gly Ser Val Gly Thr Gln Gly Arg Leu Cys
    280                 285                 290 aac cgc acg tcg ccc ggc gcg gac ggc tgt gac acc atg tgc tgc ggc      1025
Asn Arg Thr Ser Pro Gly Ala Asp Gly Cys Asp Thr Met Cys Cys Gly
295                 300                 305                 310 cga ggc tac aac acc cac cag tac acc aag gtg tgg cag tgc aac tgc      1073
Arg Gly Tyr Asn Thr His Gln Tyr Thr Lys Val Trp Gln Cys Asn Cys
                315                 320                 325 aaa ttc cac tgg tgc tgc ttc gtc aag tgc aac acc tgc agc gag cgc      1121
Lys Phe His Trp Cys Cys Phe Val Lys Cys Asn Thr Cys Ser Glu Arg
            330                 335                 340 acc gag gtc ttc acc tgc aag tga ggccaggccc ggaggcggcc gcgggcaccc     1175
Thr Glu Val Phe Thr Cys Lys
        345                 350 tggaacccgg cggcattttg cacatccact cctcaccttc cctgccttgg tgctgccagc    1235
agcagacata gacgggtgca gaagcgggga gctccaggtg caggagggca ccggccgggg    1295
cccacgccct ctgcccgcct ccctggggct ccttcctgcc acctcctccc atcacctcct    1355
gcggcagaac agcacccgtg acccacccag agagcaaggc caggggtctt ggtgctcccc    1415
gacggggccc ggcaagttct ctttcttctc tctgggaaaa tgaacgtcca ggacacacct    1475
gtatcccaga gagcaaagtg atgaggagac tgagcgtccc cagccccacc tggcggcatg    1535
gacacagaaa agctacgccg gctggcctct ccagaccagt tcccaggctg gtctgccgc     1595 tgggccctgg ggcggtgggg acagatgttg acacaaatta tttatgtttt cttagtatca    1655
gaagaggatt ctcggcacta acacatagcc agtcctaact ccgtactctg tgtcagccca    1715
```

-continued

```
tccccuagac acccuctgtt tcctttcccg gccccacctg gccggccctc tgccccugca    1775
gagctgaggc agcctggggt tgatggggac cacgcggtgc ctgcaggtcc tagaagtgag    1835
ctgggcaggg gctcttcaga ccacacagcc ctgaccgggc cttggaggag agccatggac    1895
aggctcctcc atgccgtctt tccttctttt gaaaatccta tcaatggctg ggcgcggtgg    1955
ctcacacctg taatcccagc actttgggag accgaggcag gtggatcacc tgaggtcagg    2015
agttcgagac cagcctggcc aacgtggtga aaccctgtct ctactaaaaa tacaaaaatt    2075
agctgggcgt ggtggcgtgc acctgtaatc ccagctactc aggaggctga gacaggacac    2135
ttgcttgaac ccgggaggtg gaggttgcaa tgagccaaga ttgtgccact gtattccaac    2195
ttgggtgaca gagcacgact ctgtctcaaa aaaaaaaaaa aaaaaaaaaa aaaaa         2250
```

<210> SEQ ID NO 22
<211> LENGTH: 349
<212> TYPE: PRT
<213> ORGANISM: Homo sapiens

<400> SEQUENCE: 22

```
Met His Arg Asn Phe Arg Lys Trp Ile Phe Tyr Val Phe Leu Cys Phe
  1               5                  10                  15

Gly Val Leu Tyr Val Lys Leu Gly Ala Leu Ser Ser Val Val Ala Leu
                 20                  25                  30

Gly Ala Asn Ile Ile Cys Asn Lys Ile Pro Gly Leu Ala Pro Arg Gln
             35                  40                  45

Arg Ala Ile Cys Gln Ser Arg Pro Asp Ala Ile Ile Val Ile Gly Glu
         50                  55                  60

Gly Ala Gln Met Gly Ile Asn Glu Cys Gln Tyr Gln Phe Arg Phe Gly
 65                  70                  75                  80

Arg Trp Asn Cys Ser Ala Leu Gly Glu Lys Thr Val Phe Gly Gln Glu
                 85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Gln Leu Glu Cys Lys Cys His Gly Val Ser Gly Ser
        195                 200                 205

Cys Thr Thr Lys Thr Cys Trp Thr Thr Leu Pro Lys Phe Arg Glu Val
    210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
```

```
                275                 280                 285
Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
                340                 345

<210> SEQ ID NO 23
<211> LENGTH: 1899
<212> TYPE: DNA
<213> ORGANISM: Homo sapiens
<220> FEATURE:
<221> NAME/KEY: CDS
<222> LOCATION: (101)..(1156)

<400> SEQUENCE: 23
cagaattttc tcacataaat actgaggaag accctgccct ctcctcactc ctctggactt      60
ggccctgagc tggacctggt ccactggggt aggcagggcg atg ggg aac ctg ttt      115
                                              Met Gly Asn Leu Phe
                                                1               5 atg ctc tgg gca gct ctg ggc ata tgc tgt gct gca ttc agt gcc tct      163
Met Leu Trp Ala Ala Leu Gly Ile Cys Cys Ala Ala Phe Ser Ala Ser
             10                  15                  20 gcc tgg tca gtg aac aat ttc ctg ata aca ggt ccc aag gcc tat ctg      211
Ala Trp Ser Val Asn Asn Phe Leu Ile Thr Gly Pro Lys Ala Tyr Leu
         25                  30                  35 acc tac acg act agt gtg gcc ttg ggt gcc cag agt ggc atc gag gag      259
Thr Tyr Thr Thr Ser Val Ala Leu Gly Ala Gln Ser Gly Ile Glu Glu
     40                  45                  50 tgc aag ttc cag ttt gct tgg gaa cgc tgg aac tgc cct gaa aat gct      307
Cys Lys Phe Gln Phe Ala Trp Glu Arg Trp Asn Cys Pro Glu Asn Ala
 55                  60                  65 ctt cag ctc tcc acc cac aac agg ctg aga agt gct acc aga gag act      355
Leu Gln Leu Ser Thr His Asn Arg Leu Arg Ser Ala Thr Arg Glu Thr
 70                  75                  80                  85 tcc ttc ata cat gct atc agc tct gct gga gtc atg tac atc atc acc      403
Ser Phe Ile His Ala Ile Ser Ser Ala Gly Val Met Tyr Ile Ile Thr
                 90                  95                 100 aag aac tgt agc atg ggt gac ttc gaa aac tgt ggc tgt gat ggg tca      451
Lys Asn Cys Ser Met Gly Asp Phe Glu Asn Cys Gly Cys Asp Gly Ser
            105                 110                 115 aac aat gga aaa aca gga ggc cat ggc tgg atc tgg gga ggc tgc agc      499
Asn Asn Gly Lys Thr Gly Gly His Gly Trp Ile Trp Gly Gly Cys Ser
        120                 125                 130 gac aat gtg gaa ttt ggg gaa agg atc tcc aaa ctc ttt gtg gac agt      547
Asp Asn Val Glu Phe Gly Glu Arg Ile Ser Lys Leu Phe Val Asp Ser
    135                 140                 145 ttg gag aag ggg aag gat gcc aga gcc ctg atg aat ctt cac aac aac      595
Leu Glu Lys Gly Lys Asp Ala Arg Ala Leu Met Asn Leu His Asn Asn
150                 155                 160                 165 agg gcc ggc aga ctg gca gtg aga gcc acc atg aaa agg aca tgc aaa      643
Arg Ala Gly Arg Leu Ala Val Arg Ala Thr Met Lys Arg Thr Cys Lys
                170                 175                 180 tgt cat ggc atc tct ggg agc tgc agc ata cag aca tgc tgg ctg cag      691
Cys His Gly Ile Ser Gly Ser Cys Ser Ile Gln Thr Cys Trp Leu Gln
            185                 190                 195
```

| | | | | | | | | | | | | | | | | |
|---|---|---|---|---|---|---|---|---|---|---|---|---|---|---|---|---|
| ctg | gct | gaa | ttc | cgg | gag | atg | gga | gac | tac | cta | aag | gcc | aag | tat | gac | 739 |
| Leu | Ala | Glu | Phe | Arg | Glu | Met | Gly | Asp | Tyr | Leu | Lys | Ala | Lys | Tyr | Asp | |
| | 200 | | | | | 205 | | | | | 210 | | | | | |

| | | | | | | | | | | | | | | | | |
|---|---|---|---|---|---|---|---|---|---|---|---|---|---|---|---|---|
| cag | gcg | ctg | aaa | att | gaa | atg | gat | aag | cgg | cag | ctg | aga | gct | ggg | aac | 787 |
| Gln | Ala | Leu | Lys | Ile | Glu | Met | Asp | Lys | Arg | Gln | Leu | Arg | Ala | Gly | Asn | |
| | | 215 | | | | | 220 | | | | | 225 | | | | |

| | | | | | | | | | | | | | | | | |
|---|---|---|---|---|---|---|---|---|---|---|---|---|---|---|---|---|
| agc | gcc | gag | ggc | cac | tgg | gtg | ccc | gct | gag | gcc | ttc | ctt | cct | agc | gca | 835 |
| Ser | Ala | Glu | Gly | His | Trp | Val | Pro | Ala | Glu | Ala | Phe | Leu | Pro | Ser | Ala | |
| 230 | | | | | 235 | | | | | 240 | | | | | 245 | |

| | | | | | | | | | | | | | | | | |
|---|---|---|---|---|---|---|---|---|---|---|---|---|---|---|---|---|
| gag | gcg | gaa | ctg | atc | ttt | tta | gag | gaa | tca | cca | gat | tac | tgt | acc | tgc | 883 |
| Glu | Ala | Glu | Leu | Ile | Phe | Leu | Glu | Glu | Ser | Pro | Asp | Tyr | Cys | Thr | Cys | |
| | | | | 250 | | | | | 255 | | | | | 260 | | |

| | | | | | | | | | | | | | | | | |
|---|---|---|---|---|---|---|---|---|---|---|---|---|---|---|---|---|
| aat | tcc | agc | ctg | ggc | atc | tat | ggc | aca | gag | ggt | cgt | gag | tgc | cta | cag | 931 |
| Asn | Ser | Ser | Leu | Gly | Ile | Tyr | Gly | Thr | Glu | Gly | Arg | Glu | Cys | Leu | Gln | |
| | | 265 | | | | | 270 | | | | | 275 | | | | |

| | | | | | | | | | | | | | | | | |
|---|---|---|---|---|---|---|---|---|---|---|---|---|---|---|---|---|
| aac | agc | cac | aac | aca | tcc | agg | tgg | gag | cga | cgt | agc | tgt | ggg | cgc | ctg | 979 |
| Asn | Ser | His | Asn | Thr | Ser | Arg | Trp | Glu | Arg | Arg | Ser | Cys | Gly | Arg | Leu | |
| | | | 280 | | | | | 285 | | | | | 290 | | | |

| | | | | | | | | | | | | | | | | |
|---|---|---|---|---|---|---|---|---|---|---|---|---|---|---|---|---|
| tgc | act | gag | tgt | ggg | ctg | cag | gtg | gaa | gag | agg | aaa | act | gag | gtc | ata | 1027 |
| Cys | Thr | Glu | Cys | Gly | Leu | Gln | Val | Glu | Glu | Arg | Lys | Thr | Glu | Val | Ile | |
| | 295 | | | | | 300 | | | | | 305 | | | | | |

| | | | | | | | | | | | | | | | | |
|---|---|---|---|---|---|---|---|---|---|---|---|---|---|---|---|---|
| agc | agc | tgt | aac | tgc | aaa | ttc | cag | tgg | tgc | tgt | acg | gtc | aag | tgt | gac | 1075 |
| Ser | Ser | Cys | Asn | Cys | Lys | Phe | Gln | Trp | Cys | Cys | Thr | Val | Lys | Cys | Asp | |
| 310 | | | | | 315 | | | | | 320 | | | | | 325 | |

| | | | | | | | | | | | | | | | | |
|---|---|---|---|---|---|---|---|---|---|---|---|---|---|---|---|---|
| cag | tgt | agg | cat | gtg | gtg | agc | aag | tat | tac | tgc | gca | cgc | tcc | cca | ggc | 1123 |
| Gln | Cys | Arg | His | Val | Val | Ser | Lys | Tyr | Tyr | Cys | Ala | Arg | Ser | Pro | Gly | |
| | | | | 330 | | | | | 335 | | | | | 340 | | |

| | | | | | | | | | | | |
|---|---|---|---|---|---|---|---|---|---|---|---|
| agt | gcc | cag | tcc | ctg | ggt | aag | ggc | agt | gcc | tga taatacccca cacaagttca | 1176 |
| Ser | Ala | Gln | Ser | Leu | Gly | Lys | Gly | Ser | Ala | | |
| | | | 345 | | | | | 350 | | | |

| | |
|---|---|
| cttgattaat tgcatcagtg aaggggaca tagcttctct cttagagaga acagattgga | 1236 |
| aagcaatcgg aaaattgcag ttttggtctg tagtcctcat gatatctgct atcagtgggg | 1296 |
| aaaatggagg cccaagattc tacagcatat tcctggcggg gctgaaattg gaacctgggc | 1356 |
| ctcctgactt tggcagaccc ccatttcatc tttcctgcaa actactttcc catctttgtg | 1416 |
| cctgtactta tgcagctttc tacagggaga gtttggtttg ggtctatat ctagagggac | 1476 |
| cttcaaagta tttgttcctt taaatttcag accatgtcca acccagctgt gctgctggga | 1536 |
| atcaggagaa tagaagcaaa aaacgaaaga gttctgttca gacttctgaa gagcagcctg | 1596 |
| tggctacaaa tctatgctga taaatgagat tgagaactca actgtatttt gccataaatg | 1656 |
| cttctaagat atatccagct gggacttcta ttactcccctt tggaaacctt aagatcaaaa | 1716 |
| agggaataag aaaccttct tctgtatccc aataatccac caggataaag gagaaactag | 1776 |
| aaatatgcaa ctcccttgat ttcagtgttt ggcaggtaac aaaaaattga gacccagaca | 1836 |
| ctggtcaaca ggaaaacaat acagactccc agaattagaa agtgttattt taatgcaacc | 1896 |
| tag | 1899 |

<210> SEQ ID NO 24
<211> LENGTH: 351
<212> TYPE: PRT
<213> ORGANISM: Homo sapiens

<400> SEQUENCE: 24

| | | | | | | | | | | | | | | |
|---|---|---|---|---|---|---|---|---|---|---|---|---|---|---|
| Met | Gly | Asn | Leu | Phe | Met | Leu | Trp | Ala | Ala | Leu | Gly | Ile | Cys | Cys Ala |
| 1 | | | | 5 | | | | | 10 | | | | | 15 |

| | | | | | | | | | | | | |
|---|---|---|---|---|---|---|---|---|---|---|---|---|
| Ala | Phe | Ser | Ala | Ser | Ala | Trp | Ser | Val | Asn | Asn | Phe | Leu Ile Thr Gly |
| | | | 20 | | | | | 25 | | | | 30 |

```
Pro Lys Ala Tyr Leu Thr Tyr Thr Thr Ser Val Ala Leu Gly Ala Gln
        35                  40                  45

Ser Gly Ile Glu Glu Cys Lys Phe Gln Phe Ala Trp Glu Arg Trp Asn
    50                  55                  60

Cys Pro Glu Asn Ala Leu Gln Leu Ser Thr His Asn Arg Leu Arg Ser
65                  70                  75                  80

Ala Thr Arg Glu Thr Ser Phe Ile His Ala Ile Ser Ser Ala Gly Val
                85                  90                  95

Met Tyr Ile Ile Thr Lys Asn Cys Ser Met Gly Asp Phe Glu Asn Cys
            100                 105                 110

Gly Cys Asp Gly Ser Asn Asn Gly Lys Thr Gly Gly His Gly Trp Ile
        115                 120                 125

Trp Gly Gly Cys Ser Asp Asn Val Glu Phe Gly Glu Arg Ile Ser Lys
    130                 135                 140

Leu Phe Val Asp Ser Leu Glu Lys Gly Lys Asp Ala Arg Ala Leu Met
145                 150                 155                 160

Asn Leu His Asn Asn Arg Ala Gly Arg Leu Ala Val Arg Ala Thr Met
                165                 170                 175

Lys Arg Thr Cys Lys Cys His Gly Ile Ser Gly Ser Cys Ser Ile Gln
            180                 185                 190

Thr Cys Trp Leu Gln Leu Ala Glu Phe Arg Glu Met Gly Asp Tyr Leu
        195                 200                 205

Lys Ala Lys Tyr Asp Gln Ala Leu Lys Ile Glu Met Asp Lys Arg Gln
    210                 215                 220

Leu Arg Ala Gly Asn Ser Ala Glu Gly His Trp Val Pro Glu Ala
225                 230                 235                 240

Phe Leu Pro Ser Ala Glu Ala Glu Leu Ile Phe Leu Glu Glu Ser Pro
                245                 250                 255

Asp Tyr Cys Thr Cys Asn Ser Ser Leu Gly Ile Tyr Gly Thr Glu Gly
            260                 265                 270

Arg Glu Cys Leu Gln Asn Ser His Asn Thr Ser Arg Trp Glu Arg Arg
        275                 280                 285

Ser Cys Gly Arg Leu Cys Thr Glu Cys Gly Leu Gln Val Glu Glu Arg
    290                 295                 300

Lys Thr Glu Val Ile Ser Ser Cys Asn Cys Lys Phe Gln Trp Cys Cys
305                 310                 315                 320

Thr Val Lys Cys Asp Gln Cys Arg His Val Val Ser Lys Tyr Tyr Cys
                325                 330                 335

Ala Arg Ser Pro Gly Ser Ala Gln Ser Leu Gly Lys Gly Ser Ala
            340                 345                 350

<210> SEQ ID NO 25
<211> LENGTH: 2117
<212> TYPE: DNA
<213> ORGANISM: Homo sapiens
<220> FEATURE:
<221> NAME/KEY: CDS
<222> LOCATION: (136)..(1191)

<400> SEQUENCE: 25
tccgcttaca caccaaggaa agttgggctt tgaagaattc catccccatg gccactggag    60
gaagaatatt tctccgtctt gcttacccat ctcccagttt tttggaattt tctctagctg   120
ttactccaga ggatt atg ttt ctt tca aag cct tct gtg tac atc tgt ctt   171
              Met Phe Leu Ser Lys Pro Ser Val Tyr Ile Cys Leu
                1               5                   10
```

-continued

| | |
|---|---|
| ttc acc tgt gtc ctc caa ctc agc cac agc tgg tcg gtg aac aat ttc<br>Phe Thr Cys Val Leu Gln Leu Ser His Ser Trp Ser Val Asn Asn Phe<br>15                    20                   25 | 219 |
| ctg atg act ggt cca aag gct tac ctg att tac tcc agc agt gtg gca<br>Leu Met Thr Gly Pro Lys Ala Tyr Leu Ile Tyr Ser Ser Ser Val Ala<br>     30                   35                   40 | 267 |
| gct ggt gcc cag agt ggt att gaa gaa tgc aag tat cag ttt gcc tgg<br>Ala Gly Ala Gln Ser Gly Ile Glu Glu Cys Lys Tyr Gln Phe Ala Trp<br>45                    50                   55                  60 | 315 |
| gac cgc tgg aac tgc cct gag aga gcc ctg cag ctg tcc agc cat ggt<br>Asp Arg Trp Asn Cys Pro Glu Arg Ala Leu Gln Leu Ser Ser His Gly<br>                 65                   70                   75 | 363 |
| ggg ctt cgc agt gcc aat cgg gag aca gca ttt gtg cat gcc atc agt<br>Gly Leu Arg Ser Ala Asn Arg Glu Thr Ala Phe Val His Ala Ile Ser<br>                     80                   85                   90 | 411 |
| tct gct gga gtc atg tac acc ctg act aga aac tgc agc ctt gga gat<br>Ser Ala Gly Val Met Tyr Thr Leu Thr Arg Asn Cys Ser Leu Gly Asp<br>               95                   100                  105 | 459 |
| ttt gat aac tgt ggc tgt gat gac tcc cgc aac ggg caa ctg ggg gga<br>Phe Asp Asn Cys Gly Cys Asp Asp Ser Arg Asn Gly Gln Leu Gly Gly<br>110                   115                   120 | 507 |
| caa ggc tgg ctg tgg gga ggc tgc agt gac aat gtg ggc ttc gga gag<br>Gln Gly Trp Leu Trp Gly Gly Cys Ser Asp Asn Val Gly Phe Gly Glu<br>125                   130                   135               140 | 555 |
| gcg att tcc aag cag ttt gtc gat gcc ctg gaa aca gga cag gat gca<br>Ala Ile Ser Lys Gln Phe Val Asp Ala Leu Glu Thr Gly Gln Asp Ala<br>                     145                   150                  155 | 603 |
| cgg gca gcc atg aac ctg cac aac aac gag gct ggc cgc aag gcg gtg<br>Arg Ala Ala Met Asn Leu His Asn Asn Glu Ala Gly Arg Lys Ala Val<br>               160                   165                  170 | 651 |
| aag ggc acc atg aaa cgc acg tgt aag tgc cat ggc gtg tct ggc agc<br>Lys Gly Thr Met Lys Arg Thr Cys Lys Cys His Gly Val Ser Gly Ser<br>             175                   180                  185 | 699 |
| tgc acc acg cag acc tgt tgg ctg cag ctg ccc gag ttc cgc gag gtg<br>Cys Thr Thr Gln Thr Cys Trp Leu Gln Leu Pro Glu Phe Arg Glu Val<br>190                   195                   200 | 747 |
| ggc gcg cac ctg aag gag aag tac cac gca gca ctc aag gtg gac ctg<br>Gly Ala His Leu Lys Glu Lys Tyr His Ala Ala Leu Lys Val Asp Leu<br>205                   210                   215               220 | 795 |
| ctg cag ggt gct ggc aac agc gcg gcc gcc cgc ggc gcc atc gcc gac<br>Leu Gln Gly Ala Gly Asn Ser Ala Ala Ala Arg Gly Ala Ile Ala Asp<br>                     225                   230                  235 | 843 |
| acc ttt cgc tcc atc tct acc cgg gag ctg gtg cac ctg gag gac tcc<br>Thr Phe Arg Ser Ile Ser Thr Arg Glu Leu Val His Leu Glu Asp Ser<br>               240                   245                  250 | 891 |
| ccg gac tac tgc ctg gag aac aaa acg cta ggg ctg ctg ggc acc gaa<br>Pro Asp Tyr Cys Leu Glu Asn Lys Thr Leu Gly Leu Leu Gly Thr Glu<br>            255                   260                  265 | 939 |
| ggc cga gag tgc cta agg cgc ggg cgg gcc ctg gtt cgc tgg gaa ctc<br>Gly Arg Glu Cys Leu Arg Arg Gly Arg Ala Leu Gly Arg Trp Glu Leu<br>270                   275                   280 | 987 |
| cgc agc tgc cgc cgg ctc tgc ggg gac tgc ggg ctg gcg gtg gag gag<br>Arg Ser Cys Arg Arg Leu Cys Gly Asp Cys Gly Leu Ala Val Glu Glu<br>285                   290                   295               300 | 1035 |
| cgc cgg gcc gag acc gtg tcc agc tgc aac tgc aag ttc cac tgg tgc<br>Arg Arg Ala Glu Thr Val Ser Ser Cys Asn Cys Lys Phe His Trp Cys<br>                     305                   310                  315 | 1083 |
| tgt gca gtc cgc tgc gag cag tgc cgc cgg agg gtc acc aag tac ttc<br>Cys Ala Val Arg Cys Glu Gln Cys Arg Arg Arg Val Thr Lys Tyr Phe | 1131 |

```
                 320                 325                 330
tgt agc cgc gca gag cgg ccg cgg ggg ggc gct gcg cac aaa ccc ggg    1179
Cys Ser Arg Ala Glu Arg Pro Arg Gly Gly Ala Ala His Lys Pro Gly
        335                 340                 345 aga aaa ccc taa gggtttcctc tgcccctcc ttttcccact ggttcttggc        1231
Arg Lys Pro
    350 ttcctttaga gaccccggta attgtggaac ctagggaatg gggaacccgc tctcccagac 1291 ctagggatcc tgaaagggaa aaactgcaat ttctccaaag cttgccactt tccagcctgt 1351 ttccccaatt cctctgtgct ctcctaaagc tctgtctgaa tcctcgcagc cacacctagg 1411 tctgaaaact caggctttga gttactgatc ttccttggat taggaaaaca ggtgttcctc 1471 ctcccctctc ctatcagccc taatctctga cctagcctat caacccttag cgctggaaa  1531 aaccttctca tacacgcagg acccaggtta actcaaagct ttgccctttt gcccactgtc 1591 tgctaccagg ggctcaccct ctgctgcacc tctcttctgc acagctcctc ccctgctact 1651 gctgaccaaa ttcccaggaa tcttgaatgc tttctctcct cttctcccttt ccttttccca 1711 aaaaaaactg aggaaactgg ccccggaaaa gcatgtcttt ggggttggtt cctagaggca 1771 gaggttgaag atggaagagg gagctctgga gtgctaactt gaacaccaag ggtgctactc 1831 atccctatgg tatcatatca tgaatggact ttactagtgg ggcaatgact ttcctagaca 1891 ataacccgag ggactccaga tacataccc gaaggtctag gaaatacgtt aagggcagat 1951 tacagtcatt tcctaccctt taaaggtaac ttctcccttc tcctgaccta cttcctccta 2011 gcaaccaact ttacctcttc ttctccaaag gatctttgtt cctctgagcc aagactgagg 2071 taaataaagc cactttcctc ttcagatcct ggtctgcacc tctaga                2117

<210> SEQ ID NO 26
<211> LENGTH: 351
<212> TYPE: PRT
<213> ORGANISM: Homo sapiens

<400> SEQUENCE: 26

Met Phe Leu Ser Lys Pro Ser Val Tyr Ile Cys Leu Phe Thr Cys Val
  1               5                  10                  15

Leu Gln Leu Ser His Ser Trp Ser Val Asn Asn Phe Leu Met Thr Gly
             20                  25                  30

Pro Lys Ala Tyr Leu Ile Tyr Ser Ser Val Ala Ala Gly Ala Gln
         35                  40                  45

Ser Gly Ile Glu Glu Cys Lys Tyr Gln Phe Ala Trp Asp Arg Trp Asn
     50                  55                  60

Cys Pro Glu Arg Ala Leu Gln Leu Ser Ser His Gly Gly Leu Arg Ser
 65                  70                  75                  80

Ala Asn Arg Glu Thr Ala Phe Val His Ala Ile Ser Ser Ala Gly Val
                 85                  90                  95

Met Tyr Thr Leu Thr Arg Asn Cys Ser Leu Gly Asp Phe Asp Asn Cys
            100                 105                 110

Gly Cys Asp Asp Ser Arg Asn Gly Gln Leu Gly Gly Gln Gly Trp Leu
        115                 120                 125

Trp Gly Gly Cys Ser Asp Asn Val Gly Phe Gly Glu Ala Ile Ser Lys
    130                 135                 140

Gln Phe Val Asp Ala Leu Glu Thr Gly Gln Asp Ala Arg Ala Ala Met
145                 150                 155                 160

Asn Leu His Asn Asn Glu Ala Gly Arg Lys Ala Val Lys Gly Thr Met
```

-continued

```
                    165                 170                 175
Lys Arg Thr Cys Lys Cys His Gly Val Ser Gly Ser Cys Thr Thr Gln
                180                 185                 190
Thr Cys Trp Leu Gln Leu Pro Glu Phe Arg Glu Val Gly Ala His Leu
            195                 200                 205
Lys Glu Lys Tyr His Ala Ala Leu Lys Val Asp Leu Leu Gln Gly Ala
        210                 215                 220
Gly Asn Ser Ala Ala Arg Gly Ala Ile Ala Asp Thr Phe Arg Ser
225                 230                 235                 240
Ile Ser Thr Arg Glu Leu Val His Leu Glu Asp Ser Pro Asp Tyr Cys
                245                 250                 255
Leu Glu Asn Lys Thr Leu Gly Leu Leu Gly Thr Glu Gly Arg Glu Cys
            260                 265                 270
Leu Arg Arg Gly Arg Ala Leu Gly Arg Trp Glu Leu Arg Ser Cys Arg
        275                 280                 285
Arg Leu Cys Gly Asp Cys Gly Leu Ala Val Glu Glu Arg Ala Glu
290                 295                 300
Thr Val Ser Ser Cys Asn Cys Lys Phe His Trp Cys Cys Ala Val Arg
305                 310                 315                 320
Cys Glu Gln Cys Arg Arg Val Thr Lys Tyr Phe Cys Ser Arg Ala
                325                 330                 335
Glu Arg Pro Arg Gly Gly Ala Ala His Lys Pro Gly Arg Lys Pro
            340                 345                 350

<210> SEQ ID NO 27
<211> LENGTH: 1631
<212> TYPE: DNA
<213> ORGANISM: Homo sapiens
<220> FEATURE:
<221> NAME/KEY: CDS
<222> LOCATION: (12)..(1109)

<400> SEQUENCE: 27
ggcgcggcaa g atg ctg gat ggg tcc ccg ctg gcg cgc tgg ctg gcc gcg         50
            Met Leu Asp Gly Ser Pro Leu Ala Arg Trp Leu Ala Ala
              1               5                  10 gcc ttc ggg ctg acg ctg ctc gcc gcg ctg cgc cct tcg gcc gcc              98
Ala Phe Gly Leu Thr Leu Leu Ala Ala Leu Arg Pro Ser Ala Ala
 15                  20                  25 tac ttc ggg ctg acg ggc agc gag ccc ctg acc atc ctc ccg ctg acc        146
Tyr Phe Gly Leu Thr Gly Ser Glu Pro Leu Thr Ile Leu Pro Leu Thr
 30                  35                  40                  45 ctg gag cca gag gcg gcc gcc cag gcg cac tac aag gcc tgc gac cgg        194
Leu Glu Pro Glu Ala Ala Ala Gln Ala His Tyr Lys Ala Cys Asp Arg
                 50                  55                  60 ctg aag ctg gag cgg aag cag cgg cgc atg tgc cgc cgg gac ccg ggc        242
Leu Lys Leu Glu Arg Lys Gln Arg Arg Met Cys Arg Arg Asp Pro Gly
             65                  70                  75 gtg gca gag acg ctg gtg gag gcc gtg agc atg agt gcg ctc gag tgc        290
Val Ala Glu Thr Leu Val Glu Ala Val Ser Met Ser Ala Leu Glu Cys
         80                  85                  90 cag ttc cag ttc cgc ttt gag cgc tgg aac tgc acg ctg gag ggc cgc        338
Gln Phe Gln Phe Arg Phe Glu Arg Trp Asn Cys Thr Leu Glu Gly Arg
     95                 100                 105 tac cgg gcc agc ctg ctc aag cga ggc ttc aag gag act gcc ttc ctc        386
Tyr Arg Ala Ser Leu Leu Lys Arg Gly Phe Lys Glu Thr Ala Phe Leu
110                 115                 120                 125 tat gcc atc tcc tcg gct ggc ctg acg cac gca ctg gcc aag gcg tgc        434
```

-continued

```
        Tyr Ala Ile Ser Ser Ala Gly Leu Thr His Ala Leu Ala Lys Ala Cys
                        130                 135                 140 agc gcg ggc cgc atg gag cgc tgt acc tgc gat gag gca ccc gac ctg        482
Ser Ala Gly Arg Met Glu Arg Cys Thr Cys Asp Glu Ala Pro Asp Leu
                145                 150                 155 gag aac cgt gag gcc tgg cag tgg ggg ggc tgc gga gac aac ctt aag        530
Glu Asn Arg Glu Ala Trp Gln Trp Gly Gly Cys Gly Asp Asn Leu Lys
            160                 165                 170 tac agc agc aag ttc gtc aag gaa ttc ctg ggc aga cgg tca agc aag        578
Tyr Ser Ser Lys Phe Val Lys Glu Phe Leu Gly Arg Arg Ser Ser Lys
        175                 180                 185 gat ctg cga gcc cgt gtg gac ttc cac aac aac ctc gtg ggt gtg aag        626
Asp Leu Arg Ala Arg Val Asp Phe His Asn Asn Leu Val Gly Val Lys
190                 195                 200                 205 gtg atc aag gct ggg gtg gag acc acc tgc aag tgc cac ggc gtg tca        674
Val Ile Lys Ala Gly Val Glu Thr Thr Cys Lys Cys His Gly Val Ser
                210                 215                 220 ggc tca tgc acg gtg cgg acc tgc tgg cgg cag ttg gcg cct ttc cat        722
Gly Ser Cys Thr Val Arg Thr Cys Trp Arg Gln Leu Ala Pro Phe His
                225                 230                 235 gag gtg ggc aag cat ctg aag cac aag tat gag acg gca ctc aag gtg        770
Glu Val Gly Lys His Leu Lys His Lys Tyr Glu Thr Ala Leu Lys Val
            240                 245                 250 ggc agc acc acc aat gaa gct gcc ggc gag gca ggt gcc atc tcc cca        818
Gly Ser Thr Thr Asn Glu Ala Ala Gly Glu Ala Gly Ala Ile Ser Pro
        255                 260                 265 cca cgg ggc cgt gcc tcg ggg gca ggt ggc agc gac ccg ctg ccc cgc        866
Pro Arg Gly Arg Ala Ser Gly Ala Gly Gly Ser Asp Pro Leu Pro Arg
270                 275                 280                 285 act cca gag ctg gtg cac ctg gat gac tcg cct agc ttc tgc ctg gct        914
Thr Pro Glu Leu Val His Leu Asp Asp Ser Pro Ser Phe Cys Leu Ala
                290                 295                 300 ggc cgc ttc tcc ccg ggc acc gct ggc cgt agg tgc cac cgt gag aag        962
Gly Arg Phe Ser Pro Gly Thr Ala Gly Arg Arg Cys His Arg Glu Lys
                305                 310                 315 aac tgc gag agc atc tgt tgt ggc cgc ggc cat aac aca cag agc cgg       1010
Asn Cys Glu Ser Ile Cys Cys Gly Arg Gly His Asn Thr Gln Ser Arg
            320                 325                 330 gtg gtg aca agg ccc tgc cag tgc cag gtg cgt tgg tgc tgc tat gtg       1058
Val Val Thr Arg Pro Cys Gln Cys Gln Val Arg Trp Cys Cys Tyr Val
        335                 340                 345 gag tgc agg cag tgc acg cag cgt gag gag gtc tac acc tgc aag ggc       1106
Glu Cys Arg Gln Cys Thr Gln Arg Glu Glu Val Tyr Thr Cys Lys Gly
350                 355                 360                 365 tga gttcccaggc cctgccagcc ctgctgcaca gggtgcaggc attgcacacg             1159
gtgtgaaggg tctacacctg cacaggctga gttcctgggc tcgaccagcc cagctgcgtg     1219
gggtacaggc attgcacaca gtgtgaatgg gtctacacct gcatgggctg agtccctggg     1279
ctcagaccta gcagcgtggg gtagtccctg ggctcagtcc tagctgcatg gggtgcaggc     1339
attgcacaga gcatgaatgg gcctacacct gccaaggctg aatccctggg cccagccagc     1399
cctgctgcac atggcacagg cattgcacac ggtgtgagga gtgtacacct gcaagggctg     1459
aggccctggg cccagtcagc cctgctgctc agagtgcagg cattgcacat ggtgtgagaa     1519
ggtctacacc tgcaagggac gagtccccgg gcctggccaa ccctgctgtg cagggtgagg     1579
gccatgcatg ctagtatgag gggtctacac ctgcaaggac tgagaggctt tt             1631
```

<210> SEQ ID NO 28

```
<211> LENGTH: 365
<212> TYPE: PRT
<213> ORGANISM: Homo sapiens

<400> SEQUENCE: 28
```

| | | | | | | | | | | | | | | |
|---|---|---|---|---|---|---|---|---|---|---|---|---|---|---|
|Met|Leu|Asp|Gly|Ser|Pro|Leu|Ala|Arg|Trp|Leu|Ala|Ala|Phe|Gly|
|1| | | |5| | | | |10| | | | |15|
|Leu|Thr|Leu|Leu|Leu|Ala|Ala|Leu|Arg|Pro|Ser|Ala|Ala|Tyr|Phe|Gly|
| | | |20| | | | |25| | | | |30| | |
|Leu|Thr|Gly|Ser|Glu|Pro|Leu|Thr|Ile|Leu|Pro|Leu|Thr|Leu|Glu|Pro|
| | |35| | | | |40| | | | |45| | | |
|Glu|Ala|Ala|Gln|Ala|His|Tyr|Lys|Ala|Cys|Asp|Arg|Leu|Lys|Leu|
| |50| | | | |55| | | | |60| | | |
|Glu|Arg|Lys|Gln|Arg|Arg|Met|Cys|Arg|Arg|Asp|Pro|Gly|Val|Ala|Glu|
|65| | | | |70| | | | |75| | | | |80|
|Thr|Leu|Val|Glu|Ala|Val|Ser|Met|Ser|Ala|Leu|Glu|Cys|Gln|Phe|Gln|
| | | | |85| | | | |90| | | | |95| |
|Phe|Arg|Phe|Glu|Arg|Trp|Asn|Cys|Thr|Leu|Glu|Gly|Arg|Tyr|Arg|Ala|
| | | |100| | | | |105| | | | |110| | |
|Ser|Leu|Leu|Lys|Arg|Gly|Phe|Lys|Glu|Thr|Ala|Phe|Leu|Tyr|Ala|Ile|
| | |115| | | | |120| | | | |125| | | |
|Ser|Ser|Ala|Gly|Leu|Thr|His|Ala|Leu|Ala|Lys|Ala|Cys|Ser|Ala|Gly|
| |130| | | | |135| | | | |140| | | | |
|Arg|Met|Glu|Arg|Cys|Thr|Cys|Asp|Glu|Ala|Pro|Asp|Leu|Glu|Asn|Arg|
|145| | | | |150| | | | |155| | | | |160|
|Glu|Ala|Trp|Gln|Trp|Gly|Gly|Cys|Gly|Asp|Asn|Leu|Lys|Tyr|Ser|Ser|
| | | | |165| | | | |170| | | | |175| |
|Lys|Phe|Val|Lys|Glu|Phe|Leu|Gly|Arg|Arg|Ser|Ser|Lys|Asp|Leu|Arg|
| | | |180| | | | |185| | | | |190| | |
|Ala|Arg|Val|Asp|Phe|His|Asn|Asn|Leu|Val|Gly|Val|Lys|Val|Ile|Lys|
| | |195| | | | |200| | | | |205| | | |
|Ala|Gly|Val|Glu|Thr|Thr|Cys|Lys|Cys|His|Gly|Val|Ser|Gly|Ser|Cys|
| |210| | | | |215| | | | |220| | | | |
|Thr|Val|Arg|Thr|Cys|Trp|Arg|Gln|Leu|Ala|Pro|Phe|His|Glu|Val|Gly|
|225| | | | |230| | | | |235| | | | |240|
|Lys|His|Leu|Lys|His|Lys|Tyr|Glu|Thr|Ala|Leu|Lys|Val|Gly|Ser|Thr|
| | | | |245| | | | |250| | | | |255| |
|Thr|Asn|Glu|Ala|Ala|Gly|Glu|Ala|Gly|Ala|Ile|Ser|Pro|Pro|Arg|Gly|
| | | |260| | | | |265| | | | |270| | |
|Arg|Ala|Ser|Gly|Ala|Gly|Ser|Asp|Pro|Leu|Pro|Arg|Thr|Pro|Glu|
| | |275| | | | |280| | | | |285| | | |
|Leu|Val|His|Leu|Asp|Asp|Ser|Pro|Ser|Phe|Cys|Leu|Ala|Gly|Arg|Phe|
| |290| | | | |295| | | | |300| | | | |
|Ser|Pro|Gly|Thr|Ala|Gly|Arg|Arg|Cys|His|Arg|Glu|Lys|Asn|Cys|Glu|
|305| | | | |310| | | | |315| | | | |320|
|Ser|Ile|Cys|Cys|Gly|Arg|Gly|His|Asn|Thr|Gln|Ser|Arg|Val|Val|Thr|
| | | | |325| | | | |330| | | | |335| |
|Arg|Pro|Cys|Gln|Cys|Gln|Val|Arg|Trp|Cys|Cys|Tyr|Val|Glu|Cys|Arg|
| | | |340| | | | |345| | | | |350| | |
|Gln|Cys|Thr|Gln|Arg|Glu|Glu|Val|Tyr|Thr|Cys|Lys|Gly|
| | |355| | | | |360| | | | |365| | | |

```
<210> SEQ ID NO 29
<211> LENGTH: 1464
<212> TYPE: DNA
```

```
<213> ORGANISM: Homo sapiens
<220> FEATURE:
<221> NAME/KEY: CDS
<222> LOCATION: (38)..(1111)

<400> SEQUENCE: 29
gcgaggagat gctagagggc gcagcgccgc cagcacc atg cgc ccc ccg ccc gcg      55
                                         Met Arg Pro Pro Pro Ala
                                          1               5 ctg gcc ctg gcc ggg ctc tgc ctg ctg gcg ctg ccc gcc gcc gcc gcc     103
Leu Ala Leu Ala Gly Leu Cys Leu Leu Ala Leu Pro Ala Ala Ala Ala
             10                  15                  20 tcc tac ttc ggc ctg acc ggg cgg gaa gtc ctg acg ccc ttc cca gga     151
Ser Tyr Phe Gly Leu Thr Gly Arg Glu Val Leu Thr Pro Phe Pro Gly
         25                  30                  35 ttg ggc act gcg gca gcc ccg gca cag ggc ggg gcc cac ctg aag cag     199
Leu Gly Thr Ala Ala Ala Pro Ala Gln Gly Gly Ala His Leu Lys Gln
     40                  45                  50 tgt gac ctg ctg aag ctg tcc cgg cgg cag aag cag ctc tgc cgg agg     247
Cys Asp Leu Leu Lys Leu Ser Arg Arg Gln Lys Gln Leu Cys Arg Arg
 55                  60                  65                  70 gag ccc ggc ctg gct gag acc ctg agg gat gct gcg cac ctc ggc ctg     295
Glu Pro Gly Leu Ala Glu Thr Leu Arg Asp Ala Ala His Leu Gly Leu
                 75                  80                  85 ctt gag tgc cag ttt cag ttc cgg cat gag cgc tgg aac tgt agc ctg     343
Leu Glu Cys Gln Phe Gln Phe Arg His Glu Arg Trp Asn Cys Ser Leu
             90                  95                 100 gag ggc agg atg ggc ctg ctc aag aga ggc ttc aaa gag aca gct ttc     391
Glu Gly Arg Met Gly Leu Leu Lys Arg Gly Phe Lys Glu Thr Ala Phe
        105                 110                 115 ctg tac gcg gtg tcc tct gcc gcc ctc acc cac acc ctg gcc cgg gcc     439
Leu Tyr Ala Val Ser Ser Ala Ala Leu Thr His Thr Leu Ala Arg Ala
    120                 125                 130 tgc agc gct ggg cgc atg gag cgc tgc acc tgt gat gac tct ccg ggg     487
Cys Ser Ala Gly Arg Met Glu Arg Cys Thr Cys Asp Asp Ser Pro Gly
135                 140                 145                 150 ctg gag agc cgg cag gcc tgg cag tgg ggc gtg tgc ggt gac aac ctc     535
Leu Glu Ser Arg Gln Ala Trp Gln Trp Gly Val Cys Gly Asp Asn Leu
                155                 160                 165 aag tac agc acc aag ttt ctg agc aac ttc ctg ggg tcc aag aga gga     583
Lys Tyr Ser Thr Lys Phe Leu Ser Asn Phe Leu Gly Ser Lys Arg Gly
            170                 175                 180 aac aag gac ctg cgg gca cgg gca gac gcc cac aat acc cac gtg ggc     631
Asn Lys Asp Leu Arg Ala Arg Ala Asp Ala His Asn Thr His Val Gly
        185                 190                 195 atc aag gct gtg aag agt ggc ctc agg acc acg tgt aag tgc cat ggc     679
Ile Lys Ala Val Lys Ser Gly Leu Arg Thr Thr Cys Lys Cys His Gly
    200                 205                 210 gta tca ggc tcc tgt gcc gtg cgc acc tgc tgg aag cag ctc tcc ccg     727
Val Ser Gly Ser Cys Ala Val Arg Thr Cys Trp Lys Gln Leu Ser Pro
215                 220                 225                 230 ttc cgt gag acg ggc cag gtg ctg aaa ctg cgc tat gac tcg gct gtc     775
Phe Arg Glu Thr Gly Gln Val Leu Lys Leu Arg Tyr Asp Ser Ala Val
                235                 240                 245 aag gtg tcc agt gcc acc aat gag gcc ttg ggc cgc cta gag ctg tgg     823
Lys Val Ser Ser Ala Thr Asn Glu Ala Leu Gly Arg Leu Glu Leu Trp
            250                 255                 260 gcc cct gcc agg cag ggc agc ctc acc aaa ggc ctg gcc cca agg tct     871
Ala Pro Ala Arg Gln Gly Ser Leu Thr Lys Gly Leu Ala Pro Arg Ser
        265                 270                 275
```

-continued

```
ggg gac ctg gtg tac atg gag gac tca ccc agc ttc tgc cgg ccc agc      919
Gly Asp Leu Val Tyr Met Glu Asp Ser Pro Ser Phe Cys Arg Pro Ser
280                 285                 290 aag tac tca cct ggc aca gca ggt agg gtg tgc tcc cgg gag gcc agc      967
Lys Tyr Ser Pro Gly Thr Ala Gly Arg Val Cys Ser Arg Glu Ala Ser
295                 300                 305                 310 tgc agc agc ctg tgc tgc ggg cgg ggc tat gac acc cag agc cgc ctg     1015
Cys Ser Ser Leu Cys Cys Gly Arg Gly Tyr Asp Thr Gln Ser Arg Leu
                315                 320                 325 gtg gcc ttc tcc tgc cac tgc cag gtg cag tgg tgc tgc tac gtg gag     1063
Val Ala Phe Ser Cys His Cys Gln Val Gln Trp Cys Cys Tyr Val Glu
            330                 335                 340 tgc cag caa tgt gtg cag gag gag ctt gtg tac acc tgc aag cac tag     1111
Cys Gln Gln Cys Val Gln Glu Glu Leu Val Tyr Thr Cys Lys His
        345                 350                 355 gcctactgcc cagcaagcca gtctggcact gccaggacct cctgtggcac ccttcaagct   1171
gcccagccgg ccctctgggc agactgtcat cacatgcatg cataaaccgg catgtgtgcc   1231
aatgcacacg agtgtgccac tcaccaccat tccttggcca gccttttgcc tccctcgata   1291
ctcaacaaag agaagcaaag cctcctccct taacccaagc atccccaacc ttgttgagga   1351
cttggagagg agggcagagt gagaaagaca tggagggaaa taagggagac caagagcaca   1411
gcaggactga aattttggac gggagagagg ggctattcca tcttgcttcc tgg          1464
```

<210> SEQ ID NO 30
<211> LENGTH: 357
<212> TYPE: PRT
<213> ORGANISM: Homo sapiens

<400> SEQUENCE: 30

```
Met Arg Pro Pro Pro Ala Leu Ala Leu Ala Gly Leu Cys Leu Leu Ala
1               5                   10                  15

Leu Pro Ala Ala Ala Ser Tyr Phe Gly Leu Thr Gly Arg Glu Val
            20                  25                  30

Leu Thr Pro Phe Pro Gly Leu Gly Thr Ala Ala Pro Ala Gln Gly
        35                  40                  45

Gly Ala His Leu Lys Gln Cys Asp Leu Leu Lys Leu Ser Arg Arg Gln
    50                  55                  60

Lys Gln Leu Cys Arg Arg Glu Pro Gly Leu Ala Glu Thr Leu Arg Asp
65                  70                  75                  80

Ala Ala His Leu Gly Leu Leu Glu Cys Gln Phe Gln Phe Arg His Glu
                85                  90                  95

Arg Trp Asn Cys Ser Leu Glu Gly Arg Met Gly Leu Leu Lys Arg Gly
            100                 105                 110

Phe Lys Glu Thr Ala Phe Leu Tyr Ala Val Ser Ser Ala Ala Leu Thr
        115                 120                 125

His Thr Leu Ala Arg Ala Cys Ser Ala Gly Arg Met Glu Arg Cys Thr
    130                 135                 140

Cys Asp Asp Ser Pro Gly Leu Glu Ser Arg Gln Ala Trp Gln Trp Gly
145                 150                 155                 160

Val Cys Gly Asp Asn Leu Lys Tyr Ser Thr Lys Phe Leu Ser Asn Phe
                165                 170                 175

Leu Gly Ser Lys Arg Gly Asn Lys Asp Leu Arg Ala Arg Ala Asp Ala
            180                 185                 190

His Asn Thr His Val Gly Ile Lys Ala Val Lys Ser Gly Leu Arg Thr
        195                 200                 205
```

```
Thr Cys Lys Cys His Gly Val Ser Gly Ser Cys Ala Val Arg Thr Cys
            210                 215                 220

Trp Lys Gln Leu Ser Pro Phe Arg Glu Thr Gly Gln Val Leu Lys Leu
225                 230                 235                 240

Arg Tyr Asp Ser Ala Val Lys Val Ser Ser Ala Thr Asn Glu Ala Leu
                245                 250                 255

Gly Arg Leu Glu Leu Trp Ala Pro Ala Arg Gln Gly Ser Leu Thr Lys
                260                 265                 270

Gly Leu Ala Pro Arg Ser Gly Asp Leu Val Tyr Met Glu Asp Ser Pro
                275                 280                 285

Ser Phe Cys Arg Pro Ser Lys Tyr Ser Pro Gly Thr Ala Gly Arg Val
            290                 295                 300

Cys Ser Arg Glu Ala Ser Cys Ser Ser Leu Cys Cys Gly Arg Gly Tyr
305                 310                 315                 320

Asp Thr Gln Ser Arg Leu Val Ala Phe Ser Cys His Cys Gln Val Gln
                325                 330                 335

Trp Cys Cys Tyr Val Glu Cys Gln Gln Cys Val Gln Glu Glu Leu Val
            340                 345                 350

Tyr Thr Cys Lys His
            355

<210> SEQ ID NO 31
<211> LENGTH: 2405
<212> TYPE: DNA
<213> ORGANISM: Homo sapiens
<220> FEATURE:
<221> NAME/KEY: CDS
<222> LOCATION: (475)..(1728)

<400> SEQUENCE: 31
cccgagccgg  acagtcact  tactctacag  gcagtggggc  ccgacacaga  cagcgccgcc    60
cccgccagcc  agcctcgcac  gccctcggaa  gcgcaggctc  ccggcgctgc  gctggagggt   120
tccccggcac  cccagcctcc  cgtccccagc  ccgctgcacc  tccgggcccc  ccttacccct   180
gagaggcacc  gggagttgtc  gcgggggggc  ctcgggaaat  tccccggacc  cctgtgccag   240
gaggtgcccg  gttcgcccgc  tcttcacccc  ccgcccccc   cgagggcggt  gcccggggt    300 gctgccccat  ggagcgggga  ggcgggcgcc  gtctgctccg  ggagccctga  cccgagtcgg   360
agctgtgtgt  cgcagccgcc  ccgaccccc   gccgatcatg  cgccggcgcc  cctggctctc   420
cagtcccact  gggctgtgag  cccccactc   ccagcccgtc  agggcctgcg  cgcc atg     477
                                                              Met
                                                               1 ggc agc gcc cac cct cgc ccc tgg ctg cgg ctc cga ccc cag ccc cag         525
Gly Ser Ala His Pro Arg Pro Trp Leu Arg Leu Arg Pro Gln Pro Gln
             5                  10                  15 ccg cgg cca gcg ctc tgg gtg ctc ctg ttc ttc cta ctg ctg ctg gct         573
Pro Arg Pro Ala Leu Trp Val Leu Leu Phe Phe Leu Leu Leu Leu Ala
            20                  25                  30 gct gcc atg ccc agg tca gca ccc aat gac att ctg gac ctc cgc ctc         621
Ala Ala Met Pro Arg Ser Ala Pro Asn Asp Ile Leu Asp Leu Arg Leu
        35                  40                  45 ccc ccg gag ccc gtg ctc aat gcc aac aca gtg tgc cta aca ttg cca         669
Pro Pro Glu Pro Val Leu Asn Ala Asn Thr Val Cys Leu Thr Leu Pro
 50                  55                  60                  65 ggc ctg agc cgg cgg cag atg gag gtg tgt gtg cgt cac cct gat gtg         717
Gly Leu Ser Arg Arg Gln Met Glu Val Cys Val Arg His Pro Asp Val
                70                  75                  80
```

-continued

```
gct gcc tca gcc ata cag ggc atc cag atc gcc atc cac gaa tgc caa     765
Ala Ala Ser Ala Ile Gln Gly Ile Gln Ile Ala Ile His Glu Cys Gln
            85                  90                  95 cac caa ttc agg gac cag cgc tgg aac tgc tca agc ctg gag act cgc     813
His Gln Phe Arg Asp Gln Arg Trp Asn Cys Ser Ser Leu Glu Thr Arg
        100                 105                 110 aac aag atc ccc tat gag agt ccc atc ttc agc aga ggt ttc cga gag     861
Asn Lys Ile Pro Tyr Glu Ser Pro Ile Phe Ser Arg Gly Phe Arg Glu
    115                 120                 125 agc gct ttt gcc tac gcc atc gca gca gct ggc gtg gtg cac gcc gtg     909
Ser Ala Phe Ala Tyr Ala Ile Ala Ala Ala Gly Val Val His Ala Val
130                 135                 140                 145 tcc aat gcg tgt gcc ctg ggc aaa ctg aag gcc tgt ggc tgt gat gcg     957
Ser Asn Ala Cys Ala Leu Gly Lys Leu Lys Ala Cys Gly Cys Asp Ala
            150                 155                 160 tcc cgg cga ggg gac gag gag gcc ttc gtt agg aag ctg cac cgc tta    1005
Ser Arg Arg Gly Asp Glu Glu Ala Phe Arg Arg Lys Leu His Arg Leu
        165                 170                 175 caa ctg gat gca ctg cag cgt ggt aag ggc ctg agc cat ggg gtc ccg    1053
Gln Leu Asp Ala Leu Gln Arg Gly Lys Gly Leu Ser His Gly Val Pro
    180                 185                 190 gaa cac cca gcc ctg ccc aca gcc agc cca ggc ctg cag gac tcc tgg    1101
Glu His Pro Ala Leu Pro Thr Ala Ser Pro Gly Leu Gln Asp Ser Trp
195                 200                 205 gag tgg ggc ggc tgc agc ccc gac atg ggc ttc ggg gag cgc ttt tct    1149
Glu Trp Gly Gly Cys Ser Pro Asp Met Gly Phe Gly Glu Arg Phe Ser
210                 215                 220                 225 aag gac ttt ctg gac tcc cgg gag cct cac aga gac atc cac gcg aga    1197
Lys Asp Phe Leu Asp Ser Arg Glu Pro His Arg Asp Ile His Ala Arg
            230                 235                 240 atg agg ctt cac aac aac cga gtt ggg agg cag gca gtg atg gag aac    1245
Met Arg Leu His Asn Asn Arg Val Gly Arg Gln Ala Val Met Glu Asn
        245                 250                 255 atg cgg cgg aag tgc aag tgc cac ggc acg tca ggc agc tgc cag ctc    1293
Met Arg Arg Lys Cys Lys Cys His Gly Thr Ser Gly Ser Cys Gln Leu
    260                 265                 270 aag acg tgc tgg cag gtg acg ccc gag ttc cgc acc gtg ggg gcg ctg    1341
Lys Thr Cys Trp Gln Val Thr Pro Glu Phe Arg Thr Val Gly Ala Leu
275                 280                 285 ctg cgc agc cgc ttc cac cgc gcc acg ctc atc cgg ccg cac aac cgc    1389
Leu Arg Ser Arg Phe His Arg Ala Thr Leu Ile Arg Pro His Asn Arg
290                 295                 300                 305 aac ggc ggc cag ctg gag ccg ggc cca gcg ggg gca ccc tcg ccg gct    1437
Asn Gly Gly Gln Leu Glu Pro Gly Pro Ala Gly Ala Pro Ser Pro Ala
            310                 315                 320 ccg ggc gct ccc ggg ccg cgc cga cgg gcc agc ccc gcc gac ctg gtc    1485
Pro Gly Ala Pro Gly Pro Arg Arg Arg Ala Ser Pro Ala Asp Leu Val
        325                 330                 335 tac ttc gaa aag tct ccc gac ttc tgc gag cgc gag ccg cgc ctg gac    1533
Tyr Phe Glu Lys Ser Pro Asp Phe Cys Glu Arg Glu Pro Arg Leu Asp
    340                 345                 350 tcg gcg ggc acc gtg ggc cgc ctg tgc aac aag agc agc gcc ggc tcg    1581
Ser Ala Gly Thr Val Gly Arg Leu Cys Asn Lys Ser Ser Ala Gly Ser
355                 360                 365 gat ggc tgc ggc agc atg tgc tgc ggc cgc ggc cac aac atc ctg cgc    1629
Asp Gly Cys Gly Ser Met Cys Cys Gly Arg Gly His Asn Ile Leu Arg
370                 375                 380                 385 cag acg cgc agc gag cgc tgc cac tgc cgc ttc cac tgg tgc tgt ttc    1677
Gln Thr Arg Ser Glu Arg Cys His Cys Arg Phe His Trp Cys Cys Phe
            390                 395                 400
```

```
gtg gtc tgc gaa gag tgc cgc atc acc gag tgg gtc agc gtc tgc aag      1725
Val Val Cys Glu Glu Cys Arg Ile Thr Glu Trp Val Ser Val Cys Lys
        405                 410                 415 tga gcggcccggg gtcccctggg ccctgatcga ggtccccctcc tggagcctgg          1778 ccctctgagg cttacggtct tggcaaggca gcatcgcctt ggctcttggg aagaggagat    1838
tggaccacat gatcttatag gaacccctca gctctgaggt ctgtgatcgc cggacagtcc    1898
aggcctgtct gaaccccacc actcacttct gtgggctcta ggactgactg ggttcttcct    1958
ccctccccga agcccagaca gttcagttgg gctgggggtt gctccacacc ctaaaacaag    2018
cctcagccag gcaacccgtc agtctgtctc catcctttca cccttccct ggagatggga     2078 ggtggggaat gaatggaagc tgacgggcag agagaggagg attaaaaaaa agaaatagac    2138
ataactgagc tgaagtaatt ccataaaggg cccagacagc ctcctccacc attcccttca    2198
tcattcattt aacaaatatt tattttgcac tctctttgcg gcactctggg ggcggtgggg    2258
tgcgtggggg tggcaatgca aggcactgag gccacagatg tgagtaagcg agacacaaca    2318
cttgtcctct tggaggttac attcttgctg gggggaggca tgggcaataa acaagtaaat    2378
atacaaacaa aaaaaaaaaa aaaaaaa                                        2405

<210> SEQ ID NO 32
<211> LENGTH: 417
<212> TYPE: PRT
<213> ORGANISM: Homo sapiens

<400> SEQUENCE: 32

Met Gly Ser Ala His Pro Arg Pro Trp Leu Arg Leu Arg Pro Gln Pro
 1               5                  10                  15

Gln Pro Arg Pro Ala Leu Trp Val Leu Leu Phe Leu Leu Leu Leu
            20                  25                  30

Ala Ala Ala Met Pro Arg Ser Ala Pro Asn Asp Ile Leu Asp Leu Arg
        35                  40                  45

Leu Pro Pro Glu Pro Val Leu Asn Ala Asn Thr Val Cys Leu Thr Leu
    50                  55                  60

Pro Gly Leu Ser Arg Arg Gln Met Glu Val Cys Val Arg His Pro Asp
65                  70                  75                  80

Val Ala Ala Ser Ala Ile Gln Gly Ile Gln Ile Ala Ile His Glu Cys
                85                  90                  95

Gln His Gln Phe Arg Asp Gln Arg Trp Asn Cys Ser Ser Leu Glu Thr
            100                 105                 110

Arg Asn Lys Ile Pro Tyr Glu Ser Pro Ile Phe Ser Arg Gly Phe Arg
        115                 120                 125

Glu Ser Ala Phe Ala Tyr Ala Ile Ala Ala Ala Gly Val Val His Ala
    130                 135                 140

Val Ser Asn Ala Cys Ala Leu Gly Lys Leu Lys Ala Cys Gly Cys Asp
145                 150                 155                 160

Ala Ser Arg Arg Gly Asp Glu Glu Ala Phe Arg Arg Lys Leu His Arg
                165                 170                 175

Leu Gln Leu Asp Ala Leu Gln Arg Gly Lys Gly Leu Ser His Gly Val
            180                 185                 190

Pro Glu His Pro Ala Leu Pro Thr Ala Ser Pro Gly Leu Gln Asp Ser
        195                 200                 205

Trp Glu Trp Gly Gly Cys Ser Pro Asp Met Gly Phe Gly Glu Arg Phe
    210                 215                 220
```

-continued

```
Ser Lys Asp Phe Leu Asp Ser Arg Glu Pro His Arg Asp Ile His Ala
225                 230                 235                 240

Arg Met Arg Leu His Asn Asn Arg Val Gly Arg Gln Ala Val Met Glu
            245                 250                 255

Asn Met Arg Lys Cys Lys Cys His Gly Thr Ser Gly Ser Cys Gln
        260                 265                 270

Leu Lys Thr Cys Trp Gln Val Thr Pro Glu Phe Arg Thr Val Gly Ala
    275                 280                 285

Leu Leu Arg Ser Arg Phe His Arg Ala Thr Leu Ile Arg Pro His Asn
290                 295                 300

Arg Asn Gly Gly Gln Leu Glu Pro Gly Pro Ala Gly Ala Pro Ser Pro
305                 310                 315                 320

Ala Pro Gly Ala Pro Gly Pro Arg Arg Ala Ser Pro Ala Asp Leu
            325                 330                 335

Val Tyr Phe Glu Lys Ser Pro Asp Phe Cys Glu Arg Glu Pro Arg Leu
            340                 345                 350

Asp Ser Ala Gly Thr Val Gly Arg Leu Cys Asn Lys Ser Ser Ala Gly
        355                 360                 365

Ser Asp Gly Cys Gly Ser Met Cys Cys Gly Arg Gly His Asn Ile Leu
    370                 375                 380

Arg Gln Thr Arg Ser Glu Arg Cys His Cys Arg Phe His Trp Cys Cys
385                 390                 395                 400

Phe Val Val Cys Glu Glu Cys Arg Ile Thr Glu Trp Val Ser Val Cys
            405                 410                 415

Lys

<210> SEQ ID NO 33
<211> LENGTH: 2288
<212> TYPE: DNA
<213> ORGANISM: Homo sapiens
<220> FEATURE:
<221> NAME/KEY: CDS
<222> LOCATION: (347)..(1516)

<400> SEQUENCE: 33
ggggctgcag ctccgtcagc ccggcagagc caccctgagc tcggtgagag caaagccaga      60
gcccccagtc ctttgctcgc cggcttgcta tctctctcga tcactccctc ccttcctccc    120
tcccttcctc ccggcggccg cggcggcgct ggggaagcgg tgaagaggag tggcccggcc    180
ctggaagaat gcggctctga caaggggaca gaacccagcg cagtctcccc acggtttaag    240
cagcactagt gaagcccagg caacccaacc gtgcctgtct cggacccccgc acccaaacca   300 ctggaggtcc tgatcgatct gcccaccgga gcctccgggc ttcgac atg ctg gag       355
                                                Met Leu Glu
                                                  1 gag ccc cgg ccg cgg cct ccg ccc tcg ggc ctc gcg ggt ctc ctg ttc      403
Glu Pro Arg Pro Arg Pro Pro Ser Gly Leu Ala Gly Leu Leu Phe
  5                  10                  15 ctg gcg ttg tgc agt cgg gct cta agc aat gag att ctg ggc ctg aag     451
Leu Ala Leu Cys Ser Arg Ala Leu Ser Asn Glu Ile Leu Gly Leu Lys
 20                  25                  30                  35 ttg cct ggc gag ccg ccg ctg acg gcc aac acc gtg tgc ttg acg ctg     499
Leu Pro Gly Glu Pro Pro Leu Thr Ala Asn Thr Val Cys Leu Thr Leu
                 40                  45                  50 tcc ggc ctg agc aag cgg cag cta ggc ctg tgc ctg cgc aac ccc gac     547
Ser Gly Leu Ser Lys Arg Gln Leu Gly Leu Cys Leu Arg Asn Pro Asp
         55                  60                  65
```

```
gtg acg gcg tcc gcg ctt cag ggt ctg cac atc gcg gtc cac gag tgt        595
Val Thr Ala Ser Ala Leu Gln Gly Leu His Ile Ala Val His Glu Cys
         70                  75                  80 cag cac cag ctg cgc gac cag cgc tgg aac tgc tcc gcg ctt gag ggc        643
Gln His Gln Leu Arg Asp Gln Arg Trp Asn Cys Ser Ala Leu Glu Gly
     85                  90                  95 ggc ggc cgc ctg ccg cac cac agc gcc atc ctc aag cgc ggt ttc cga        691
Gly Gly Arg Leu Pro His His Ser Ala Ile Leu Lys Arg Gly Phe Arg
100                 105                 110                 115 gaa agt gct ttt tcc ttc tcc atg ctg gct gct ggg gtc atg cac gca        739
Glu Ser Ala Phe Ser Phe Ser Met Leu Ala Ala Gly Val Met His Ala
                    120                 125                 130 gta gcc acg gcc tgc agc ctg ggc aag ctg gtg agc tgt ggc tgt ggc        787
Val Ala Thr Ala Cys Ser Leu Gly Lys Leu Val Ser Cys Gly Cys Gly
            135                 140                 145 tgg aag ggc agt ggt gag cag gat cgg ctg agg gcc aaa ctg ctg cag        835
Trp Lys Gly Ser Gly Glu Gln Asp Arg Leu Arg Ala Lys Leu Leu Gln
        150                 155                 160 ctg cag gca ctg tcc cga ggc aag agt ttc ccc cac tct ctg ccc agc        883
Leu Gln Ala Leu Ser Arg Gly Lys Ser Phe Pro His Ser Leu Pro Ser
    165                 170                 175 cct ggc cct ggc tca agc ccc agc cct ggc ccc cag gac aca tgg gaa        931
Pro Gly Pro Gly Ser Ser Pro Ser Pro Gly Pro Gln Asp Thr Trp Glu
180                 185                 190                 195 tgg ggt ggc tgt aac cat gac atg gac ttt gga gag aag ttc tct cgg        979
Trp Gly Gly Cys Asn His Asp Met Asp Phe Gly Glu Lys Phe Ser Arg
                    200                 205                 210 gat ttc ttg gat tcc agg gaa gct ccc cgg gac atc cag gca cga atg       1027
Asp Phe Leu Asp Ser Arg Glu Ala Pro Arg Asp Ile Gln Ala Arg Met
            215                 220                 225 cga atc cac aac aac agg gtg ggg cgc cag gtg gta act gaa aac ctg       1075
Arg Ile His Asn Asn Arg Val Gly Arg Gln Val Val Thr Glu Asn Leu
        230                 235                 240 aag cgg aaa tgc aag tgt cat ggc aca tca ggc agc tgc cag ttc aag       1123
Lys Arg Lys Cys Lys Cys His Gly Thr Ser Gly Ser Cys Gln Phe Lys
    245                 250                 255 aca tgc tgg agg gcg gcc cca gag ttc cgg gca gtg ggg gcg gcg ttg       1171
Thr Cys Trp Arg Ala Ala Pro Glu Phe Arg Ala Val Gly Ala Ala Leu
260                 265                 270                 275 agg gag cgg ctg ggc cgg gcc atc ttc att gat acc cac aac cgc aat       1219
Arg Glu Arg Leu Gly Arg Ala Ile Phe Ile Asp Thr His Asn Arg Asn
                    280                 285                 290 tct gga gcc ttc cag ccc cgt ctg cgt ccc cgt cgc ctc tca gga gag       1267
Ser Gly Ala Phe Gln Pro Arg Leu Arg Pro Arg Arg Leu Ser Gly Glu
            295                 300                 305 ctg gtc tac ttt gag aag tct cct gac ttc tgt gag cga gac ccc act       1315
Leu Val Tyr Phe Glu Lys Ser Pro Asp Phe Cys Glu Arg Asp Pro Thr
        310                 315                 320 atg ggc tcc cca ggg aca agg ggc cgg gcc tgc aac aag acc agc cgc       1363
Met Gly Ser Pro Gly Thr Arg Gly Arg Ala Cys Asn Lys Thr Ser Arg
    325                 330                 335 ctg ttg gat ggc tgt ggc agc ctg tgt tgg cgt ggg cac aac gtg            1411
Leu Leu Asp Gly Cys Gly Ser Leu Cys Cys Gly Arg Gly His Asn Val
340                 345                 350                 355 ctc cgg cag aca cga gtt gag cgc tgc cat tgc cgc ttc cac tgg tgc       1459
Leu Arg Gln Thr Arg Val Glu Arg Cys His Cys Arg Phe His Trp Cys
                    360                 365                 370 tgc tat gtg ctg tgt gat gag tgc aag gtt aca gag tgg gtg aat gtg       1507
Cys Tyr Val Leu Cys Asp Glu Cys Lys Val Thr Glu Trp Val Asn Val
            375                 380                 385
```

-continued

```
tgt aag tga gggtcagcct taccttgggg ctggggaaga ggactgtgtg       1556
Cys Lys
    390 agagggcgc cttttcagcc ctttgctctg atttccttcc aaggtcactc ttggtccctg   1616
gaagcttaaa gtatctacct ggaaacagct ttaggggtgg tggggtcag gtggactctg   1676 ggatgtgtag cctctccccc aacaattgga gggtcttgag gggaagctgc caccctctt    1736 ctgctcctta gacacctgaa tggactaaga tgaaatgcac tgtattgctc ctcccacttc   1796
tcaactccag agccccttta accctgattc atactccttt tggctgggga gtccctatag   1856
tttcaccact cctctccctt gagggataac cccaggcact gtttggagcc ataagatctg   1916
tatctagaaa gagatcaccc actcctatgt actatcccca aactcctta ctgcagcctg    1976 ggctccctct tgtgggataa tgggagacag tggtagagag gtttttcttg ggaaagagac   2036
agagtgctga ggggcactct cccctgaatc ctcagagagt tgtctgtcca ggcccttagg   2096
gaagttgtct ccttccattc agatgttaat ggggaccctc caaggaagg ggttttccca    2156 tgactcttgg agcctctttt tccttcttca gcaggaaggg tgggaaggga taatttatca   2216
tactgagact tgttcttggt tcctgtttga aactaaaata aattaagtta ctggaaaaaa   2276
aaaaaaaaaa aa                                                       2288
```

<210> SEQ ID NO 34
<211> LENGTH: 389
<212> TYPE: PRT
<213> ORGANISM: Homo sapiens

<400> SEQUENCE: 34

```
Met Leu Glu Glu Pro Arg Pro Arg Pro Pro Ser Gly Leu Ala Gly
  1               5                  10                  15

Leu Leu Phe Leu Ala Leu Cys Ser Arg Ala Leu Ser Asn Glu Ile Leu
                 20                  25                  30

Gly Leu Lys Leu Pro Gly Glu Pro Leu Thr Ala Asn Thr Val Cys
         35                  40                  45

Leu Thr Leu Ser Gly Leu Ser Lys Arg Gln Leu Gly Leu Cys Leu Arg
 50                  55                  60

Asn Pro Asp Val Thr Ala Ser Ala Leu Gln Gly Leu His Ile Ala Val
 65                  70                  75                  80

His Glu Cys Gln His Gln Leu Arg Asp Gln Arg Trp Asn Cys Ser Ala
                 85                  90                  95

Leu Glu Gly Gly Gly Arg Leu Pro His His Ser Ala Ile Leu Lys Arg
            100                 105                 110

Gly Phe Arg Glu Ser Ala Phe Ser Phe Ser Met Leu Ala Ala Gly Val
        115                 120                 125

Met His Ala Val Ala Thr Ala Cys Ser Leu Gly Lys Leu Val Ser Cys
130                 135                 140

Gly Cys Gly Trp Lys Gly Ser Gly Glu Gln Asp Arg Leu Arg Ala Lys
145                 150                 155                 160

Leu Leu Gln Leu Gln Ala Leu Ser Arg Gly Lys Ser Phe Pro His Ser
                165                 170                 175

Leu Pro Ser Pro Gly Pro Gly Ser Ser Pro Ser Pro Gly Pro Gln Asp
            180                 185                 190

Thr Trp Glu Trp Gly Gly Cys Asn His Asp Met Asp Phe Gly Glu Lys
        195                 200                 205

Phe Ser Arg Asp Phe Leu Asp Ser Arg Glu Ala Pro Arg Asp Ile Gln
```

-continued

```
            210                 215                 220
Ala Arg Met Arg Ile His Asn Asn Arg Val Gly Arg Gln Val Val Thr
225                 230                 235                 240

Glu Asn Leu Lys Arg Lys Cys Lys Cys His Gly Thr Ser Gly Ser Cys
                245                 250                 255

Gln Phe Lys Thr Cys Trp Arg Ala Ala Pro Glu Phe Arg Ala Val Gly
            260                 265                 270

Ala Ala Leu Arg Glu Arg Leu Gly Arg Ala Ile Phe Ile Asp Thr His
            275                 280                 285

Asn Arg Asn Ser Gly Ala Phe Gln Pro Arg Leu Arg Pro Arg Arg Leu
290                 295                 300

Ser Gly Glu Leu Val Tyr Phe Glu Lys Ser Pro Asp Phe Cys Glu Arg
305                 310                 315                 320

Asp Pro Thr Met Gly Ser Pro Gly Thr Arg Gly Arg Ala Cys Asn Lys
                325                 330                 335

Thr Ser Arg Leu Leu Asp Gly Cys Gly Ser Leu Cys Cys Gly Arg Gly
                340                 345                 350

His Asn Val Leu Arg Gln Thr Arg Val Glu Arg Cys His Cys Arg Phe
                355                 360                 365

His Trp Cys Cys Tyr Val Leu Cys Asp Glu Cys Lys Val Thr Glu Trp
            370                 375                 380

Val Asn Val Cys Lys
385

<210> SEQ ID NO 35
<211> LENGTH: 1927
<212> TYPE: DNA
<213> ORGANISM: Homo sapiens
<220> FEATURE:
<221> NAME/KEY: CDS
<222> LOCATION: (124)..(1188)

<400> SEQUENCE: 35
taacccgccg cctccgctct ccccggctgc aggcggcgtg caggaccagc ggcggccgtg      60
caggcggagg acttcggcgc ggctcctcct gggtgtgacc ccgggcgcgc ccgccgcgcg     120 acg atg agg gcg cgg ccg cag gtc tgc gag gcg ctg ctc ttc gcc ctg      168
    Met Arg Ala Arg Pro Gln Val Cys Glu Ala Leu Leu Phe Ala Leu
    1               5                   10                  15 gcg ctc cag acc ggc gtg tgc tat ggc atc aag tgg ctg gcg ctg tcc      216
Ala Leu Gln Thr Gly Val Cys Tyr Gly Ile Lys Trp Leu Ala Leu Ser
                20                  25                  30 aag aca cca tcg gcc ctg gca ctg aac cag acg caa cac tgc aag cag      264
Lys Thr Pro Ser Ala Leu Ala Leu Asn Gln Thr Gln His Cys Lys Gln
            35                  40                  45 ctg gag ggt ctg gtg tct gca cag gtg cag ctg tgc cgc agc aac ctg      312
Leu Glu Gly Leu Val Ser Ala Gln Val Gln Leu Cys Arg Ser Asn Leu
        50                  55                  60 gag ctc atg cac acg gtg gtg cac gcc gcc cgc gag gtc atg aag gcc      360
Glu Leu Met His Thr Val Val His Ala Ala Arg Glu Val Met Lys Ala
    65                  70                  75 tgt cgc cgg gcc ttt gcc gac atg cgc tgg aac tgt tcc tcc att gag      408
Cys Arg Arg Ala Phe Ala Asp Met Arg Trp Asn Cys Ser Ser Ile Glu
80                  85                  90                  95 ctc gcc ccc aac tat ttg ctt gac ctg gag aga ggg acc cgg gag tcg      456
Leu Ala Pro Asn Tyr Leu Leu Asp Leu Glu Arg Gly Thr Arg Glu Ser
                100                 105                 110 gcc ttc gtg tat gcg ctg tcg gcc gcc gcc atc agc cac gcc atc gcc      504
```

```
Ala Phe Val Tyr Ala Leu Ser Ala Ala Ala Ile Ser His Ala Ile Ala
            115                 120                 125 cgg gcc tgc acc tcc ggc gac ctg ccc ggc tgc tcc tgc ggc ccc gtc    552
Arg Ala Cys Thr Ser Gly Asp Leu Pro Gly Cys Ser Cys Gly Pro Val
        130                 135                 140 cca ggt gag cca ccc ggg ccc ggg aac cgc tgg gga gga tgt gcg gac    600
Pro Gly Glu Pro Pro Gly Pro Gly Asn Arg Trp Gly Gly Cys Ala Asp
    145                 150                 155 aac ctc agc tac ggg ctc ctc atg ggg gcc aag ttt tcc gat gct cct    648
Asn Leu Ser Tyr Gly Leu Leu Met Gly Ala Lys Phe Ser Asp Ala Pro
160                 165                 170                 175 atg aag gtg aaa aaa aca gga tcc caa gcc aat aaa ctg atg cgt cta    696
Met Lys Val Lys Lys Thr Gly Ser Gln Ala Asn Lys Leu Met Arg Leu
            180                 185                 190 cac aac agt gaa gtg ggg aga cag gct ctg cgc gcc tct ctg gaa atg    744
His Asn Ser Glu Val Gly Arg Gln Ala Leu Arg Ala Ser Leu Glu Met
                195                 200                 205 aag tgt aag tgc cat ggg gtg tct ggc tcc tgc tcc atc cgc acc tgc    792
Lys Cys Lys Cys His Gly Val Ser Gly Ser Cys Ser Ile Arg Thr Cys
        210                 215                 220 tgg aag ggg ctg cag gag ctg cag gat gtg gct gct gac ctc aag acc    840
Trp Lys Gly Leu Gln Glu Leu Gln Asp Val Ala Ala Asp Leu Lys Thr
    225                 230                 235 cga tac ctg tcg gcc acc aag gta gtg cac cga ccc atg ggc acc cgc    888
Arg Tyr Leu Ser Ala Thr Lys Val Val His Arg Pro Met Gly Thr Arg
240                 245                 250                 255 aag cac ctg gtg ccc aag gac ctg gat atc cgg cct gtg aag gac tcg    936
Lys His Leu Val Pro Lys Asp Leu Asp Ile Arg Pro Val Lys Asp Ser
            260                 265                 270 gaa ctc gtc tat ctg cag agc tca cct gac ttc tgc atg aag aat gag    984
Glu Leu Val Tyr Leu Gln Ser Ser Pro Asp Phe Cys Met Lys Asn Glu
                275                 280                 285 aag gtg ggc tcc cac ggg aca caa gac agg cag tgc aac aag aca tcc   1032
Lys Val Gly Ser His Gly Thr Gln Asp Arg Gln Cys Asn Lys Thr Ser
        290                 295                 300 aac gga agc gac agc tgc gac ctt atg tgc tgc ggg cgt ggc tac aac   1080
Asn Gly Ser Asp Ser Cys Asp Leu Met Cys Cys Gly Arg Gly Tyr Asn
    305                 310                 315 ccc tac aca gac cgc gtc gtc gag cgg tgc cac tgt aag tac cac tgg   1128
Pro Tyr Thr Asp Arg Val Val Glu Arg Cys His Cys Lys Tyr His Trp
320                 325                 330                 335 tgc tgc tac gtc acc tgc cgc agg tgt gag cgt acc gtg gag cgc tat   1176
Cys Cys Tyr Val Thr Cys Arg Arg Cys Glu Arg Thr Val Glu Arg Tyr
            340                 345                 350 gtc tgc aag tga ggccctgccc tccgccccac gcaggagcga ggactctgct       1228
Val Cys Lys
        355 caaggaccct cagcaactgg ggccaggggc ctggagacac tccatggagc tctgcttgtg 1288 aattccagat gccaggcatg ggaggcggct tgtgctttgc cttcacttgg aagccaccag 1348 gaacagaagg tctggccacc ctggaaggag ggcaggacat caaaggaaac cgacaagatt 1408 aaaaataact tggcagcctg aggctctgga gtgcccacag gctggtgtaa ggagcggggc 1468 ttgggatcgg tgagactgat acagacttga cctttcaggg ccacagagac cagcctccgg 1528 gaaggggtct gcccgccttc ttcagaatgt tctgcgggac cccctggccc accctggggt 1588 ctgagcctgc tgggcccacc acatggaatc actagcttgg gttgtaaatg ttttcttttg 1648 tttttttgctt tttcttcctt tgggatgtgg aagctacaga aatatttata aaacatagct 1708
```

```
ttttctttgg ggtggcactt ctcaattcct ctttatatat tttatatata taaatatata    1768
tgtatatata taatgatctc tattttaaaa ctagcttttt aagcagctgt atgaaataaa    1828
tgctgagtga gccccagccc gcccctgcag ttcccggcct cgtcaagtga actcggcaga    1888
ccctggggct ggcagaggga gctctccagt ttccaggca                          1927

<210> SEQ ID NO 36
<211> LENGTH: 354
<212> TYPE: PRT
<213> ORGANISM: Homo sapiens

<400> SEQUENCE: 36

Met Arg Ala Arg Pro Gln Val Cys Glu Ala Leu Leu Phe Ala Leu Ala
  1               5                  10                  15

Leu Gln Thr Gly Val Cys Tyr Gly Ile Lys Trp Leu Ala Leu Ser Lys
             20                  25                  30

Thr Pro Ser Ala Leu Ala Leu Asn Gln Thr Gln His Cys Lys Gln Leu
         35                  40                  45

Glu Gly Leu Val Ser Ala Gln Val Gln Leu Cys Arg Ser Asn Leu Glu
     50                  55                  60

Leu Met His Thr Val Val His Ala Ala Arg Glu Val Met Lys Ala Cys
 65                  70                  75                  80

Arg Arg Ala Phe Ala Asp Met Arg Trp Asn Cys Ser Ser Ile Glu Leu
                 85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Ile Ser His Ala Ile Ala Arg
        115                 120                 125

Ala Cys Thr Ser Gly Asp Leu Pro Gly Cys Ser Cys Gly Pro Val Pro
    130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Met Lys
        195                 200                 205

Cys Lys Cys His Gly Val Ser Gly Ser Cys Ser Ile Arg Thr Cys Trp
    210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
        275                 280                 285

Val Gly Ser His Gly Thr Gln Asp Arg Gln Cys Asn Lys Thr Ser Asn
    290                 295                 300

Gly Ser Asp Ser Cys Asp Leu Met Cys Cys Gly Arg Gly Tyr Asn Pro
305                 310                 315                 320

Tyr Thr Asp Arg Val Val Glu Arg Cys His Cys Lys Tyr His Trp Cys
                325                 330                 335
```

-continued

```
Cys Tyr Val Thr Cys Arg Arg Cys Glu Arg Thr Val Glu Arg Tyr Val
            340                 345                 350

Cys Lys

<210> SEQ ID NO 37
<211> LENGTH: 3132
<212> TYPE: DNA
<213> ORGANISM: Homo sapiens
<220> FEATURE:
<221> NAME/KEY: CDS
<222> LOCATION: (258)..(1355)

<400> SEQUENCE: 37
cccgcatctc ctgcacatct ccaccCctgc gcaggaggag atccccaggc tgctctctcc        60
atctctccta cagctccctg caaacgaggg ggaagctgct gagagtccct atcactgctg       120
gccttttaat gttgtatgca aggaggaaga gggcgaggga taacttggtg ctggacaact       180
gacctgcggc ccgaagggcc tctggggagg gggtgcaaaa gaggagcggc tgggctgggg       240
gactccatgc gggggcg atg gac agg gcg gcg ctc ctg gga ctg gcc cgc          290
                    Met Asp Arg Ala Ala Leu Leu Gly Leu Ala Arg
                     1               5                  10 ttg tgc gcg ctg tgg gca gcc ctg ctc gtg ctg ttc ccc tac gga gcc         338
Leu Cys Ala Leu Trp Ala Ala Leu Leu Val Leu Phe Pro Tyr Gly Ala
         15                  20                  25 caa gga aac tgg atg tgg ttg gcc att gcc tcc ttc ggg gtt cca gag         386
Gln Gly Asn Trp Met Trp Leu Gly Ile Ala Ser Phe Gly Val Pro Glu
     30                  35                  40 aag ctg ggc tgc gcc aat ttg ccg ctg aac agc cgc cag aag gag ctg         434
Lys Leu Gly Cys Ala Asn Leu Pro Leu Asn Ser Arg Gln Lys Glu Leu
 45                  50                  55 tgc aag agg aaa ccg tac ctg ctg ccg agc atc cga gag ggc gcc cgg         482
Cys Lys Arg Lys Pro Tyr Leu Leu Pro Ser Ile Arg Glu Gly Ala Arg
 60                  65                  70                  75 ctg ggc att cag gag tgc ggg agc cag ttc aga cac gag aga tgg aac         530
Leu Gly Ile Gln Glu Cys Gly Ser Gln Phe Arg His Glu Arg Trp Asn
             80                  85                  90 tgc atg atc acc gcc gcc gcc act acc gcc ccg atg ggc gcc agc ccc         578
Cys Met Ile Thr Ala Ala Ala Thr Thr Ala Pro Met Gly Ala Ser Pro
         95                 100                 105 ctc ttt ggc tac gag ctg agc agc ggc acc aaa gag aca gca ttt att         626
Leu Phe Gly Tyr Glu Leu Ser Ser Gly Thr Lys Glu Thr Ala Phe Ile
    110                 115                 120 tat gct gtg atg gct gca ggc ctg gtg cat tct gtg acc agg tca tgc         674
Tyr Ala Val Met Ala Ala Gly Leu Val His Ser Val Thr Arg Ser Cys
125                 130                 135 agt gca ggc aac atg aca gag tgt tcc tgt gac acc acc ttg cag aac         722
Ser Ala Gly Asn Met Thr Glu Cys Ser Cys Asp Thr Thr Leu Gln Asn
140                 145                 150                 155 ggc ggc tca gca agt gaa ggc tgg cac tgg ggg gct gc tcc gat gat          770
Gly Gly Ser Ala Ser Glu Gly Trp His Trp Gly Gly Cys Ser Asp Asp
                160                 165                 170 gtc cag tat ggc atg tgg ttc agc aga aag ttc cta gat ttc ccc atc         818
Val Gln Tyr Gly Met Trp Phe Ser Arg Lys Phe Leu Asp Phe Pro Ile
            175                 180                 185 gga aac acc acg ggc aaa gaa aac aaa gta cta tta gca atg aac cta         866
Gly Asn Thr Thr Gly Lys Glu Asn Lys Val Leu Leu Ala Met Asn Leu
        190                 195                 200 cat aac aat gaa gct gga agg cag gct gtc gcc aag ttg atg tca gta         914
His Asn Asn Glu Ala Gly Arg Gln Ala Val Ala Lys Leu Met Ser Val
    205                 210                 215
```

```
gac tgc cgc tgc cac gga gtt tcc ggc tcc tgt gct gtg aaa aca tgc      962
Asp Cys Arg Cys His Gly Val Ser Gly Ser Cys Ala Val Lys Thr Cys
220             225                 230                 235 tgg aaa acc atg tct tct ttt gaa aag att ggc cat ttg ttg aag gat     1010
Trp Lys Thr Met Ser Ser Phe Glu Lys Ile Gly His Leu Leu Lys Asp
                240                 245                 250 aaa tat gaa aac agt atc cag ata tca gac aaa aca aag agg aaa atg    1058
Lys Tyr Glu Asn Ser Ile Gln Ile Ser Asp Lys Thr Lys Arg Lys Met
            255                 260                 265 cgc agg aga gaa aaa gat cag agg aaa ata cca atc cat aag gat gat    1106
Arg Arg Arg Glu Lys Asp Gln Arg Lys Ile Pro Ile His Lys Asp Asp
        270                 275                 280 ctg ctc tat gtt aat aag tct ccc aac tac tgt gta gaa gat aag aaa    1154
Leu Leu Tyr Val Asn Lys Ser Pro Asn Tyr Cys Val Glu Asp Lys Lys
    285                 290                 295 ctg gga atc cca ggg aca caa ggc aga gaa tgc aac cgt aca tca gag    1202
Leu Gly Ile Pro Gly Thr Gln Gly Arg Glu Cys Asn Arg Thr Ser Glu
300                 305                 310                 315 ggt gca gat ggc tgc aac ctc ctc tgc tgt ggc cga ggt tac aac acc    1250
Gly Ala Asp Gly Cys Asn Leu Leu Cys Cys Gly Arg Gly Tyr Asn Thr
                320                 325                 330 cat gtg gtc agg cac gtg gag agg tgt gag tgt aag ttc atc tgg tgc    1298
His Val Val Arg His Val Glu Arg Cys Glu Cys Lys Phe Ile Trp Cys
            335                 340                 345 tgc tat gtc cgt tgc agg agg tgt gaa agc atg act gat gtc cac act    1346
Cys Tyr Val Arg Cys Arg Arg Cys Glu Ser Met Thr Asp Val His Thr
        350                 355                 360 tgc aag taa ccactccatc cagccttggg caagatgcct cagcaatata            1395
Cys Lys
    365 caatggcatt gcaaccagag aggtgcccat ccctgtgcag cgctagtaaa gttgactctt  1455 gcagtggaat ccctagaacc ttggacctga gagtttccct tacctgatcg acatattttc  1515 ctttatctga tcaacccatc aatcatgtgg atttcttggg attctaatgt tgaaaaggtt  1575 tatattcacc ttttgatgat tggggaata tatattgaca tacaaggaag ataatctgtt   1635 tcctaagcaa gaaataacag gaaagatccc ttatgccagg aggcctgcca tactcaggat  1695 aagatccttg aatatggaac ttagttacag gactcaataa tggtgggtga acattagtca  1755 tttttaaaag acacctctta tagcaataag gagacattaa catgaatctc atttattctc  1815 tcagtatttt aactgaagaa attatactgt ttgtgtgtgg atagaagatg ttgaaaagtt  1875 aacataagca ttgggtgctg acttacccct tcatgtactt ccaaagaaag gtaatcaaaa  1935 agaatcttct taagtgatat aatatcccta aaaaaatgat cattacagat gtttagtgac  1995 aaagaatcaa tatgtaaaaa gtataatgaa tgatttagat tttaagtgcc ttttcactgg  2055 gagaatctgg aaaaacctcc ataaggtata tagcaatctt tgatctttag attcatactt  2115 ttatcacaga tcagtttcaa ctgttaaaaa cccacctctg agatactggg gggaggatcc  2175 tgaaacatgc gggaaaagga gaggtaaaca gtggaggtaa aaatataatt tcatacattg  2235 taaagaaaag caccctttaa atgtgtaaag acagtgtttt gtaaagaatt ttgtttaaaa  2295 agtttctatt ttgtaaatac agtacttaag ttatatgatt tatattaaaa catttattga  2355 caaagcctaa gagctaaggc agtaaaatta tctcataaat aatattagct tatttttttt  2415 catactatta atgctatttt tttggacatc gaagagaatt taacttagca gttagttata  2475 tggatgtgta tttcttgcta aaatgacagt tttatatgtt atagattaaa atatgttgca  2535
```

```
aaatatcaaa aatttgtgtt atttcagcag taagattaat tgaattctct tttcacatta    2595
gttatgctta actcataagg ttattataat aaattatatt agtaaaagtc ttaactggaa    2655
aaaagaatct aaatcagaat agtgatcaat ttgtggattt gatatcctgg atatttatta   2715
tattttatgt aatgctgcat ttctatttga atgttaagtg gtctttcttg ttttaatat    2775 tcatgcatgt atattcatca tattttacaa ggttcctggt aaaaattaca gggctctatt   2835
taaggatgta ttttaatgta aatgcttatg ttttttatga attgttaaat atttcagtat   2895
tatatagaaa aaaatagatt tttaaaattc agaatggaca aagagaatat tcattttctt   2955
attaataaga taaagaaatg tttccctgcc ccacagtctt cattctattt ctctttaatt   3015
ttattcactg aggcagagaa acaattttg aaaaagagca aacccatgga aaatgtctca    3075 gatctaaatat taaaatcaag actaagcatt taactgtgaa aaaaaaaaaa aaaaaaa     3132
```

<210> SEQ ID NO 38
<211> LENGTH: 365
<212> TYPE: PRT
<213> ORGANISM: Homo sapiens

<400> SEQUENCE: 38

```
Met Asp Arg Ala Ala Leu Leu Gly Leu Ala Arg Leu Cys Ala Leu Trp
 1               5                  10                  15

Ala Ala Leu Leu Val Leu Phe Pro Tyr Gly Ala Gln Gly Asn Trp Met
            20                  25                  30

Trp Leu Gly Ile Ala Ser Phe Gly Val Pro Glu Lys Leu Gly Cys Ala
        35                  40                  45

Asn Leu Pro Leu Asn Ser Arg Gln Lys Glu Leu Cys Lys Arg Lys Pro
    50                  55                  60

Tyr Leu Leu Pro Ser Ile Arg Glu Gly Ala Arg Leu Gly Ile Gln Glu
65                  70                  75                  80

Cys Gly Ser Gln Phe Arg His Glu Arg Trp Asn Cys Met Ile Thr Ala
                85                  90                  95

Ala Ala Thr Thr Ala Pro Met Gly Ala Ser Pro Leu Phe Gly Tyr Glu
            100                 105                 110

Leu Ser Ser Gly Thr Lys Glu Thr Ala Phe Ile Tyr Ala Val Met Ala
        115                 120                 125

Ala Gly Leu Val His Ser Val Thr Arg Ser Cys Ser Ala Gly Asn Met
    130                 135                 140

Thr Glu Cys Ser Cys Asp Thr Thr Leu Gln Asn Gly Gly Ser Ala Ser
145                 150                 155                 160

Glu Gly Trp His Trp Gly Gly Cys Ser Asp Asp Val Gln Tyr Gly Met
                165                 170                 175

Trp Phe Ser Arg Lys Phe Leu Asp Phe Pro Ile Gly Asn Thr Thr Gly
            180                 185                 190

Lys Glu Asn Lys Val Leu Leu Ala Met Asn Leu His Asn Asn Glu Ala
        195                 200                 205

Gly Arg Gln Ala Val Ala Lys Leu Met Ser Val Asp Cys Arg Cys His
    210                 215                 220

Gly Val Ser Gly Ser Cys Ala Val Lys Thr Cys Trp Lys Thr Met Ser
225                 230                 235                 240

Ser Phe Glu Lys Ile Gly His Leu Leu Lys Asp Lys Tyr Glu Asn Ser
                245                 250                 255

Ile Gln Ile Ser Asp Lys Thr Lys Arg Lys Met Arg Arg Arg Glu Lys
            260                 265                 270
```

```
Asp Gln Arg Lys Ile Pro Ile His Lys Asp Asp Leu Leu Tyr Val Asn
            275                 280                 285

Lys Ser Pro Asn Tyr Cys Val Glu Asp Lys Lys Leu Gly Ile Pro Gly
        290                 295                 300

Thr Gln Gly Arg Glu Cys Asn Arg Thr Ser Glu Gly Ala Asp Gly Cys
305                 310                 315                 320

Asn Leu Leu Cys Cys Gly Arg Gly Tyr Asn Thr His Val Val Arg His
                325                 330                 335

Val Glu Arg Cys Glu Cys Lys Phe Ile Trp Cys Cys Tyr Val Arg Cys
            340                 345                 350

Arg Arg Cys Glu Ser Met Thr Asp Val His Thr Cys Lys
            355                 360                 365

<210> SEQ ID NO 39
<211> LENGTH: 3364
<212> TYPE: DNA
<213> ORGANISM: Mus musculus
<220> FEATURE:
<221> NAME/KEY: CDS
<222> LOCATION: (18)..(803)

<400> SEQUENCE: 39
gcggccgccg ccccgcg atg gcc ccg cag caa ggc cgg ccg gcg ctg ccc          50
                   Met Ala Pro Gln Gln Gly Arg Pro Ala Leu Pro
                     1               5                  10 gcc cgc tgc gag ccg ccg gcg gcg ccg ccg gta ccg cct cgc cga gag         98
Ala Arg Cys Glu Pro Pro Ala Ala Pro Pro Val Pro Pro Arg Arg Glu
             15                  20                  25 cgc ggg ggg cgc ggg gcg cgc ggg ccc ggg gtg tcc ggg ggt cgg ggg        146
Arg Gly Gly Arg Gly Ala Arg Gly Pro Gly Val Ser Gly Gly Arg Gly
         30                  35                  40 cgc gcg ggc ggc gcc gag gga cgc ggc gtc aag tgc gtg ctg gtc ggc        194
Arg Ala Gly Gly Ala Glu Gly Arg Gly Val Lys Cys Val Leu Val Gly
     45                  50                  55 gac ggc gcg gtg ggc aag acc agc ctg gtg gtc agc tac acc act aac        242
Asp Gly Ala Val Gly Lys Thr Ser Leu Val Val Ser Tyr Thr Thr Asn
 60                  65                  70                  75 ggc tac ccc acc gag tac atc cct acg gcc ttc gac aac ttc tcg gcc        290
Gly Tyr Pro Thr Glu Tyr Ile Pro Thr Ala Phe Asp Asn Phe Ser Ala
                 80                  85                  90 gtg gtg tct gta gat ggg cgg cct gtg aga ctc cag ctc tgt gac act        338
Val Val Ser Val Asp Gly Arg Pro Val Arg Leu Gln Leu Cys Asp Thr
             95                 100                 105 gca gga cag gat gag ttt gac aag ctg agg ccc ctc tgc tac acc aac        386
Ala Gly Gln Asp Glu Phe Asp Lys Leu Arg Pro Leu Cys Tyr Thr Asn
        110                 115                 120 aca gac atc ttc ctg ctg tgc ttc agc gtg gtg agc ccc aca tcc ttc        434
Thr Asp Ile Phe Leu Leu Cys Phe Ser Val Val Ser Pro Thr Ser Phe
    125                 130                 135 cag aac gtg ggc gag aag tgg gtt cca gag att cga cgt cac tgc cca        482
Gln Asn Val Gly Glu Lys Trp Val Pro Glu Ile Arg Arg His Cys Pro
140                 145                 150                 155 aag gcc ccc atc atc ctg gtc ggg aca cag tcg gac ctc agg gag gac        530
Lys Ala Pro Ile Ile Leu Val Gly Thr Gln Ser Asp Leu Arg Glu Asp
                160                 165                 170 gtc aaa gtg ctc ata gaa ctg gac aag tgc aaa gag aag ccg gtg cct        578
Val Lys Val Leu Ile Glu Leu Asp Lys Cys Lys Glu Lys Pro Val Pro
            175                 180                 185 gaa gag gcg gcg aag ctg tgc gcg gag gaa gtc aaa gct gtc tcc tac        626
Glu Glu Ala Ala Lys Leu Cys Ala Glu Glu Val Lys Ala Val Ser Tyr
```

```
                190                 195                 200
atc gag tgc tca gcg ttg act cag aaa aac ctc aaa gag gtt ttc gac    674
Ile Glu Cys Ser Ala Leu Thr Gln Lys Asn Leu Lys Glu Val Phe Asp
    205                 210                 215 gcc gcc att gtt gct ggt atc cag cac tca gac tcc cag cta cag cca    722
Ala Ala Ile Val Ala Gly Ile Gln His Ser Asp Ser Gln Leu Gln Pro
220                 225                 230                 235 aag aag tct aaa agc agg acc ccg gat aag gtg cgg gac ctg tcc aag    770
Lys Lys Ser Lys Ser Arg Thr Pro Asp Lys Val Arg Asp Leu Ser Lys
                240                 245                 250 tct tgg tgg agg aag tat tgc tgc ctg gcc tga ctctcgcaaa tagcaggtgt  823
Ser Trp Trp Arg Lys Tyr Cys Cys Leu Ala
                255                 260 ttaagctgca acagctcttt atggacgagg ctgtcatagg atgagcccca aagcaccctc   883
ttctgccctt aacttcctgt gtgcgggagc ttagggctga gattcatatg caaaatacgt   943
ttttttaaaa attgaaagtt acatttttt tctgttaagt ctggaagctt tgagctgtag   1003
acctccggat taatttatat tccatatgaa aagggctctt caaagcgggg tgtcagcatg   1063
aagttctgct gtgttgtaca ggacaaagga gaatgaatgg gaccttctcc tgattaaggg   1123
ctactgaggg ctcagtgcag ggcactgtgc accaggcttg gtgagagtga gcaagcgtga   1183
gctttgaaac cacacgagcc accccccggtt ttgtaagggc aaagatctga aaccagcaag   1243
ggccttctgc ttacgaaacc tcgagcccat cccttctgtt tactcagatt ctcttaggat   1303
tttaaaacaa ccaaacatcc cacagcctac tggcatagtg ttggcgaaca gtgcacttgc   1363
ttgttacggt tttgttttgt ttttttaaat cacgtgacca gttatattgc tatgaaaatg   1423
gtggagatgc ctcgtagaag gcgagtgctg ggtgcacatg tgacattttc ttcagggagc   1483
gactcatggt gagaccagag agggctctta gcttgcagga ctggcttctg cagggcatct   1543
gtgtcctgct gttaaaagca ggaggaggtg cttgtctggg agctttaagt gtgctgggct   1603
catatcgtcc cgtttgcaag gaattgggcc accttgagag gccatagttg atggctatgg   1663
gacacacaca cacttttttcc ttaagtccac caaaatgcct gcctgtacac acacacacac   1723
acacacacac acacacacac acactggctg gtttgctgat ggaacccctta gaccaccctc   1783
ccacccccac ccctcccaa gcatggctgc aagtgtcagg gcaccacacc ttcctcttct   1843
tgacatttct ttgaacagac atcattttgt aggatcttaa tttatacatt tttttcaggt   1903
cataaaatgt gggatgaaca tactttgaac cccagtgcct tcagggtcca ttgactaggg   1963
aggcactgtc ttaggggaca ggtatgtgca aggccttacc caccagtggc ttctcgctgc   2023
aggtcatgtt tgtggcactt gttctttaag gtgagggtct tatgaccgac tgttctgaga   2083
cagccctgtg tcaggcaagc tctttcacag ggttgtaggt atttccaaga cgccatagga   2143
accagacagt gaatcatagc tatcagtttg ctgtgggcaa ggaacctctt tttggccacc   2203
tggtaacaaa attttatgtc tgtaaatttt ttcttgctat ttaaaaaaaa aaatcaatct   2263
tacgttttc tgtaggaaaa aaaaaaacaa gtaaagaaac aggccatatt tcaggtcaaa   2323
ggcttcttcc tgctggtaaa tgggactgaa gactttctta catcattatt aaaaggctaa   2383
ttgctgaacc actagagtat atgaactgtt tgtgaatgat attagccata gtctcctgag   2443
gtgtttcctt gtggcctgag tggtaacatt gttttgctta tggagatgct gtaactgacc   2503
tagtgactca gcttatccta ttgtgcatgg ctgtctggaa agccagcgta caagtgggc   2563
tttgcatgcc ctgtgtacag agggtggggt ggaaagagtg aattatttaa ttttaaatgt   2623
tataataaag ccaatgtagt tgagaccaag gaaatgagca ttgagaacac aaacttgaag   2683
```

-continued

```
tctggtgcca gggttgttgg acctcacacc ctgtctctga gccacccgga agtgacataa    2743
aggacgctgt gtgatcaagt tctggacact tttctgggat gcgtaccact ggactattta    2803
tgtcacaaat ctagtgggtt gacgctgccc tgcaagtttt caatgtccct gcatcctatg    2863
aagtcataat gatctgactg tactggaggt tttcctgcat tttttacttt tcgaaaatag    2923
aggtttaggc tgagaattct aaacgcatgt gcctgggtgg acgtcaagt cagggttctc    2983 atcaaagctg agaagtggct ggaatgttca gcttggtgtc tggggaggat cctgtgagct    3043
atgtagagag gtggctcttc agcctgactc agtgtgggct gaacgaagta cctgcagaac    3103
acacggtagc aggctccaaa atcgtcacct caagcatgcg tgcaagcaaa cttccgagaa    3163
ctccgttttc tgctcggcag acgtgtgagc agctacccag aagtctcaag ccaaaagggg    3223
agcctcgctc gctggctcct ctgcaggtgc cttatcgacc tgtgctcttc tcttttcccg    3283
tgtcaaagat gttggacagg atcttgtact tgaaacatac tgcaaatgag ttactatgaa    3343
ataaattctg acctgtggcc g                                               3364
```

<210> SEQ ID NO 40
<211> LENGTH: 261
<212> TYPE: PRT
<213> ORGANISM: Mus musculus

<400> SEQUENCE: 40

```
Met Ala Pro Gln Gln Gly Arg Pro Ala Leu Pro Ala Arg Cys Glu Pro
  1               5                  10                  15

Pro Ala Ala Pro Pro Val Pro Pro Arg Arg Glu Arg Gly Gly Arg Gly
                 20                  25                  30

Ala Arg Gly Pro Gly Val Ser Gly Gly Arg Gly Arg Ala Gly Gly Ala
             35                  40                  45

Glu Gly Arg Gly Val Lys Cys Val Leu Val Gly Asp Gly Ala Val Gly
         50                  55                  60

Lys Thr Ser Leu Val Val Ser Tyr Thr Thr Asn Gly Tyr Pro Thr Glu
 65                  70                  75                  80

Tyr Ile Pro Thr Ala Phe Asp Asn Phe Ser Ala Val Val Ser Val Asp
                 85                  90                  95

Gly Arg Pro Val Arg Leu Gln Leu Cys Asp Thr Ala Gly Gln Asp Glu
                100                 105                 110

Phe Asp Lys Leu Arg Pro Leu Cys Tyr Thr Asn Thr Asp Ile Phe Leu
            115                 120                 125

Leu Cys Phe Ser Val Val Ser Pro Thr Ser Phe Gln Asn Val Gly Glu
        130                 135                 140

Lys Trp Val Pro Glu Ile Arg Arg His Cys Pro Lys Ala Pro Ile Ile
145                 150                 155                 160

Leu Val Gly Thr Gln Ser Asp Leu Arg Glu Asp Val Lys Val Leu Ile
                165                 170                 175

Glu Leu Asp Lys Cys Lys Glu Lys Pro Val Pro Glu Glu Ala Ala Lys
            180                 185                 190

Leu Cys Ala Glu Glu Val Lys Ala Val Ser Tyr Ile Glu Cys Ser Ala
        195                 200                 205

Leu Thr Gln Lys Asn Leu Lys Glu Val Phe Asp Ala Ala Ile Val Ala
    210                 215                 220

Gly Ile Gln His Ser Asp Ser Gln Leu Gln Pro Lys Lys Ser Lys Ser
225                 230                 235                 240

Arg Thr Pro Asp Lys Val Arg Asp Leu Ser Lys Ser Trp Trp Arg Lys
```

```
                245                 250                 255
Tyr Cys Cys Leu Ala
            260

<210> SEQ ID NO 41
<211> LENGTH: 1719
<212> TYPE: DNA
<213> ORGANISM: Mus musculus
<220> FEATURE:
<221> NAME/KEY: CDS
<222> LOCATION: (54)..(1136)

<400> SEQUENCE: 41
cgcatggcgc ccgcacacgg agtctgacct gatgtagacg caagggggtt aat atg       56
                                                              Met
                                                               1 aac gtc cct ctc ggt gga atc tgg ctc tgg ctc cct ctg ctc ttg acc     104
Asn Val Pro Leu Gly Gly Ile Trp Leu Trp Leu Pro Leu Leu Leu Thr
          5                  10                  15 tgg ctc acc cct gag gtc agc tct tca tgg tgg tac atg aga gct aca     152
Trp Leu Thr Pro Glu Val Ser Ser Ser Trp Trp Tyr Met Arg Ala Thr
         20                  25                  30 ggt ggc tcc tcc agg gtg atg tgt gac aat gtg cca ggc ctg gtg agc     200
Gly Gly Ser Ser Arg Val Met Cys Asp Asn Val Pro Gly Leu Val Ser
     35                  40                  45 cgg cag cgt cag ctg tgc cac cga cac cca gat gtg atg cgt gcc att     248
Arg Gln Arg Gln Leu Cys His Arg His Pro Asp Val Met Arg Ala Ile
 50                  55                  60                  65 ggc ctg ggt gtg gct gag tgg act gca gag tgc caa cac cag ttc cgc     296
Gly Leu Gly Val Ala Glu Trp Thr Ala Glu Cys Gln His Gln Phe Arg
                 70                  75                  80 cag cat cgc tgg aac tgc aac acc ctg gac aga gat cac agc ctc ttt     344
Gln His Arg Trp Asn Cys Asn Thr Leu Asp Arg Asp His Ser Leu Phe
             85                  90                  95 ggc cgg gtc ctc ctc cga agt agt cga gaa tcg gcc ttt gtt tac gcc     392
Gly Arg Val Leu Leu Arg Ser Ser Arg Glu Ser Ala Phe Val Tyr Ala
        100                 105                 110 atc tct tca gct ggc gtt gta ttt gcc atc acc agg gcc tgt agc caa     440
Ile Ser Ser Ala Gly Val Val Phe Ala Ile Thr Arg Ala Cys Ser Gln
    115                 120                 125 gga gaa tta aag tcc tgc tcc tgt gat cca aag aag aaa gga agt gcc     488
Gly Glu Leu Lys Ser Cys Ser Cys Asp Pro Lys Lys Lys Gly Ser Ala
130                 135                 140                 145 aag gac agc aaa ggc acc ttc gac tgg ggt ggc tgc agt gac aat att     536
Lys Asp Ser Lys Gly Thr Phe Asp Trp Gly Gly Cys Ser Asp Asn Ile
                150                 155                 160 gac tac ggg atc aag ttt gcc cgt gcc ttt gta gat gcc aag gag agg     584
Asp Tyr Gly Ile Lys Phe Ala Arg Ala Phe Val Asp Ala Lys Glu Arg
            165                 170                 175 aaa ggc aag gat gcc aga gcc ctg atg aac ctt cac aac aac aga gct     632
Lys Gly Lys Asp Ala Arg Ala Leu Met Asn Leu His Asn Asn Arg Ala
        180                 185                 190 gga agg aag gct gta aag cgc ttc ttg aaa caa gaa tgc aag tgt cat     680
Gly Arg Lys Ala Val Lys Arg Phe Leu Lys Gln Glu Cys Lys Cys His
    195                 200                 205 ggt gtg agt ggc tcc tgt act ctg agg aca tgc tgg ctg gcc atg gct     728
Gly Val Ser Gly Ser Cys Thr Leu Arg Thr Cys Trp Leu Ala Met Ala
210                 215                 220                 225 gac ttc agg aaa aca ggc gac tat ctc tgg agg aag tac aat ggg gcc     776
Asp Phe Arg Lys Thr Gly Asp Tyr Leu Trp Arg Lys Tyr Asn Gly Ala
                230                 235                 240
```

```
atc cag gta gtc atg aac cag gat ggc act ggc ttc act gta gcc aat      824
Ile Gln Val Val Met Asn Gln Asp Gly Thr Gly Phe Thr Val Ala Asn
            245                 250                 255 aag agg ttt aag aag cca acg aaa aat gac ctc gtg tat ttt gag aat      872
Lys Arg Phe Lys Lys Pro Thr Lys Asn Asp Leu Val Tyr Phe Glu Asn
        260                 265                 270 tct cca gac tac tgt atc agg gac cga gag gca ggc tcc ctg ggt aca      920
Ser Pro Asp Tyr Cys Ile Arg Asp Arg Glu Ala Gly Ser Leu Gly Thr
    275                 280                 285 gcg ggc cgt gtg tgc aac ttg act tcc cga ggc atg gac agc tgc gaa      968
Ala Gly Arg Val Cys Asn Leu Thr Ser Arg Gly Met Asp Ser Cys Glu
290                 295                 300                 305 gtt atg tgt tgt ggg aga ggc tat gac aca tcc cac gtc acc cgg atg     1016
Val Met Cys Cys Gly Arg Gly Tyr Asp Thr Ser His Val Thr Arg Met
                310                 315                 320 acc aag tgt gag tgt aaa ttc cac tgg tgc tgt gcc gtg cgc tgt cag     1064
Thr Lys Cys Glu Cys Lys Phe His Trp Cys Cys Ala Val Arg Cys Gln
            325                 330                 335 gac tgc ctg gag gcc ctg gac gtg cac aca tgc aag gcc ccc aag agt     1112
Asp Cys Leu Glu Ala Leu Asp Val His Thr Cys Lys Ala Pro Lys Ser
        340                 345                 350 gcc gac tgg gcg acg cct aca tga cctcagcaga ggtcatattc gccttttctt    1166
Ala Asp Trp Ala Thr Pro Thr
    355                 360 ccctcaagga ctccaattac atcttcaagg acactggacc tctgggttgt tttcagggc    1226 tctttcttaa ggcatgaagc cttcatctca agagaaaccc cctttcccct ctctgggggc   1286
cccaggactg gaaccacct gctgcacata agtacaccct attctgtcta tcttgggcat    1346
tctgatgtca cctctcttcc tgctgatttc tttttggaaa tggcatgaca ggctgttaga   1406
ggaggagggt catagccccc caccactgtc acctagacat ttcctctttg gctgcgggga   1466
gaaacatcac atagcgaagg aacttcctct gtgttttccc agattccaac aacccagaaa   1526
gtctgtgttt ccctggggcg cggggtaggg atggaaagca gaatgagctg acaccaaaat   1586
ttcctcggat ttttttaaaa aaagagtaag caagggcttt aactaagtga tagctgttga   1646
tagcatcctt ggtgactttc tagagaaaga tggcttccaa taaacatcag gttaaaacaa   1706
aaaaaaaaaa aaa                                                     1719

<210> SEQ ID NO 42
<211> LENGTH: 360
<212> TYPE: PRT
<213> ORGANISM: Mus musculus

<400> SEQUENCE: 42

Met Asn Val Pro Leu Gly Gly Ile Trp Leu Trp Leu Pro Leu Leu Leu
1               5                   10                  15

Thr Trp Leu Thr Pro Glu Val Ser Ser Ser Trp Trp Tyr Met Arg Ala
            20                  25                  30

Thr Gly Gly Ser Ser Arg Val Met Cys Asp Asn Val Pro Gly Leu Val
        35                  40                  45

Ser Arg Gln Arg Gln Leu Cys His Arg His Pro Asp Val Met Arg Ala
    50                  55                  60

Ile Gly Leu Gly Val Ala Glu Trp Thr Ala Glu Cys Gln His Gln Phe
65                  70                  75                  80

Arg Gln His Arg Trp Asn Cys Asn Thr Leu Asp Arg Asp His Ser Leu
                85                  90                  95
```

-continued

```
Phe Gly Arg Val Leu Arg Ser Ser Arg Glu Ser Ala Phe Val Tyr
            100                 105                 110
Ala Ile Ser Ser Ala Gly Val Val Phe Ala Ile Thr Arg Ala Cys Ser
        115                 120                 125
Gln Gly Glu Leu Lys Ser Cys Ser Cys Asp Pro Lys Lys Gly Ser
    130                 135                 140
Ala Lys Asp Ser Lys Gly Thr Phe Asp Trp Gly Gly Cys Ser Asp Asn
145                 150                 155                 160
Ile Asp Tyr Gly Ile Lys Phe Ala Arg Ala Phe Val Asp Ala Lys Glu
                165                 170                 175
Arg Lys Gly Lys Asp Ala Arg Ala Leu Met Asn Leu His Asn Asn Arg
            180                 185                 190
Ala Gly Arg Lys Ala Val Lys Arg Phe Leu Lys Gln Glu Cys Lys Cys
        195                 200                 205
His Gly Val Ser Gly Ser Cys Thr Leu Arg Thr Cys Trp Leu Ala Met
    210                 215                 220
Ala Asp Phe Arg Lys Thr Gly Asp Tyr Leu Trp Arg Lys Tyr Asn Gly
225                 230                 235                 240
Ala Ile Gln Val Val Met Asn Gln Asp Gly Thr Gly Phe Thr Val Ala
                245                 250                 255
Asn Lys Arg Phe Lys Lys Pro Thr Lys Asn Asp Leu Val Tyr Phe Glu
            260                 265                 270
Asn Ser Pro Asp Tyr Cys Ile Arg Asp Arg Glu Ala Gly Ser Leu Gly
        275                 280                 285
Thr Ala Gly Arg Val Cys Asn Leu Thr Ser Arg Gly Met Asp Ser Cys
    290                 295                 300
Glu Val Met Cys Cys Gly Arg Gly Tyr Asp Thr Ser His Val Thr Arg
305                 310                 315                 320
Met Thr Lys Cys Glu Cys Lys Phe His Trp Cys Cys Ala Val Arg Cys
                325                 330                 335
Gln Asp Cys Leu Glu Ala Leu Asp Val His Thr Cys Lys Ala Pro Lys
            340                 345                 350
Ser Ala Asp Trp Ala Thr Pro Thr
        355                 360

<210> SEQ ID NO 43
<211> LENGTH: 3576
<212> TYPE: DNA
<213> ORGANISM: Mus musculus
<220> FEATURE:
<221> NAME/KEY: CDS
<222> LOCATION: (239)..(1408)

<400> SEQUENCE: 43
ggagccactg acaccgcacc cgaccgccca caccggctc agcgctcgtc ggtctcctgg      60
ccctgcacgc tcttgggaac cctgcgtctg gctcccgggc tccacgtgcc ttgaggtcct    120
cggtcgccca tggtccccat ggccactctg tggggcgatc taggagacgc ctgagcgaag    180
cccagacagt gcccgtccac ggccctgcgg gcttcgggc gggagtctgc ggggagct      238 atg ctg aag ctg cag ggt gag gat gaa gcc gcg cag ctc gcc cct cgg     286
Met Leu Lys Leu Gln Gly Glu Asp Glu Ala Ala Gln Leu Ala Pro Arg
  1               5                  10                  15 cgt gcc cgc gtc ccc gtg ccc aga ccc acg gcc ccc gac gtg tcc cca    334
Arg Ala Arg Val Pro Val Pro Arg Pro Thr Ala Pro Asp Val Ser Pro
                20                  25                  30 tct tcc gcc cgc ctg ggt ctt gcc tgc ctg ctg ctg cta ctc ctg        382
```

```
                Ser Ser Ala Arg Leu Gly Leu Ala Cys Leu Leu Leu Leu Leu Leu
                        35                  40                  45 act ctg ccg gcc cgt gta gac acg tcc tgg tgg tac ata ggg gct ctg       430
Thr Leu Pro Ala Arg Val Asp Thr Ser Trp Trp Tyr Ile Gly Ala Leu
        50                  55                  60 gga gcc cga gtg atc tgt gac aac atc ccc ggt ctg gtg agc cgg cag       478
Gly Ala Arg Val Ile Cys Asp Asn Ile Pro Gly Leu Val Ser Arg Gln
65                  70                  75                  80 cgg cag ttg tgt caa cgc tac cca gac atc atg cgc tca gta ggt gag       526
Arg Gln Leu Cys Gln Arg Tyr Pro Asp Ile Met Arg Ser Val Gly Glu
                85                  90                  95 ggt gcc cgg gaa tgg atc cga gag tgc cag cac cag ttc cgt cac cac       574
Gly Ala Arg Glu Trp Ile Arg Glu Cys Gln His Gln Phe Arg His His
            100                 105                 110 cgc tgg aat tgc acc aca ctg gac cgg gac cac act gtc ttt ggc cgc       622
Arg Trp Asn Cys Thr Thr Leu Asp Arg Asp His Thr Val Phe Gly Arg
        115                 120                 125 gcc atg ctc aga agc agc cgg gag gca gcg ttc gtc tat gct atc tcg       670
Ala Met Leu Arg Ser Ser Arg Glu Ala Ala Phe Val Tyr Ala Ile Ser
    130                 135                 140 tca gca gga gtg gtc cac gct atc act cgg gcc tgc agc cag ggt gag       718
Ser Ala Gly Val Val His Ala Ile Thr Arg Ala Cys Ser Gln Gly Glu
145                 150                 155                 160 ctg agc gtg tgc agc tgt gac cca tat acc cgc ggt cgg cac cat gat       766
Leu Ser Val Cys Ser Cys Asp Pro Tyr Thr Arg Gly Arg His His Asp
                165                 170                 175 caa cga ggg gac ttt gac tgg ggt ggc tgt agt gac aac atc cat tac       814
Gln Arg Gly Asp Phe Asp Trp Gly Gly Cys Ser Asp Asn Ile His Tyr
            180                 185                 190 ggt gtt cgc ttt gcc aag gct ttt gtg gat gcc aaa gag aag agg ctt       862
Gly Val Arg Phe Ala Lys Ala Phe Val Asp Ala Lys Glu Lys Arg Leu
        195                 200                 205 aag gat gcc cgg gcc ctc atg aac tta cac aac aac cgc tgt ggt cgc       910
Lys Asp Ala Arg Ala Leu Met Asn Leu His Asn Asn Arg Cys Gly Arg
    210                 215                 220 acg gct gtt cgg aga ttc ctg aag ctg gag tgc aag tgt cac ggt gtg       958
Thr Ala Val Arg Arg Phe Leu Lys Leu Glu Cys Lys Cys His Gly Val
225                 230                 235                 240 agt ggc tcc tgt act ctg cgc acc tgc tgg aga gca ctc tca gac ttc      1006
Ser Gly Ser Cys Thr Leu Arg Thr Cys Trp Arg Ala Leu Ser Asp Phe
                245                 250                 255 cga cgc aca ggt gac tac ctg agg agg cga tat gat ggg gct gtg cag      1054
Arg Arg Thr Gly Asp Tyr Leu Arg Arg Arg Tyr Asp Gly Ala Val Gln
            260                 265                 270 gtg acg gcc aca cag gat ggg gcc aat ttc aca gca gcg cgc cag ggc      1102
Val Thr Ala Thr Gln Asp Gly Ala Asn Phe Thr Ala Ala Arg Gln Gly
        275                 280                 285 tat cgc cac gcc acc cgg act gat ctt gtc tac ttt gac aac tcc cct      1150
Tyr Arg His Ala Thr Arg Thr Asp Leu Val Tyr Phe Asp Asn Ser Pro
    290                 295                 300 gac tac tgt gtc ttg gac aag gct gca ggt tcc cta ggt acc gca ggc      1198
Asp Tyr Cys Val Leu Asp Lys Ala Ala Gly Ser Leu Gly Thr Ala Gly
305                 310                 315                 320 cgc gtc tgc agc aag act tct aaa gga aca gat ggg tgt gaa atc atg      1246
Arg Val Cys Ser Lys Thr Ser Lys Gly Thr Asp Gly Cys Glu Ile Met
                325                 330                 335 tgt tgt ggc cga ggg tat gac aca act cgg gtc acc cgc gtc acc cag      1294
Cys Cys Gly Arg Gly Tyr Asp Thr Thr Arg Val Thr Arg Val Thr Gln
            340                 345                 350
```

-continued

| | |
|---|---|
| tgt gag tgc aaa ttc cac tgg tgc tgt gct gtg cgg tgc aag gag tgc<br>Cys Glu Cys Lys Phe His Trp Cys Cys Ala Val Arg Cys Lys Glu Cys<br>355                      360                  365 | 1342 |
| aga aac act gtg gat gtc cac aca tgc aag gcc cct aag aag gca gag<br>Arg Asn Thr Val Asp Val His Thr Cys Lys Ala Pro Lys Lys Ala Glu<br>    370                      375                  380 | 1390 |
| tgg ctg gac cag acc tga acacacagaa acctcattct tccctccact<br>Trp Leu Asp Gln Thr<br>385                      390 | 1438 |
| tcaagcctct gactcaaaag cacaagaccc ttgcatgcgc accttcctct accctcaatc | 1498 |
| ctgggctgct atggcttctg tcacggacct ggagagtgat ccggagggac ccaatgtcc | 1558 |
| cggccgcctg gttccttagc cctagggacg tgttgatagg ggatggattt aggaggctga | 1618 |
| gtgactccct gatggtccat ctggaggttt aagggagag taggagaggt ctgtcttcag | 1678 |
| agtgatttga gttgcactaa gtcaaggctc atcctcccct ttgcttgcac tgacttctga | 1738 |
| tcctctttgg gtatgcaaca ggaagggaac ctggaggtag cttccgtgtt tgatgctact | 1798 |
| ctgcctgagg ataggacaga gataaaactg cctgtccctt tgctggagac agtacgggca | 1858 |
| gactatctta ggccatagta ttctgctgag accctgagat agctagatgg gttagccaca | 1918 |
| ttgaacaagg ctccacatca tgcttctacg cagcttataa agtagtggtt tggtgaggag | 1978 |
| gaaaatcaca atgctctaca gatacacatt ctctgtgcct cccttccac ctacatcaca | 2038 |
| cagcagcagc ctgctcactg gctgcctgtt cagagtgagg cagcttgcag tgggtcaaat | 2098 |
| tcttaccagg ccattagagg cccggaacag gattgtgaga gaatgacata gaaagcctgg | 2158 |
| ctaggccttg ggacttcccc cacatccact attccggaga ttcggtagga agggaggtaa | 2218 |
| ctcatgggaa gggtgagcgc acctgatctc aggggttcca tgaggatcag tgtatactag | 2278 |
| gaaggcagag atctcgcatt tgctagttc ttgaggatct tcagctttga agtaggaaca | 2338 |
| aaaggcagca gctatagaga gagagctggt gctggagccg aggtggcaaa catcctataa | 2398 |
| ggcctttctc atttacccag caaatctta ttttgtgatt caccaggtcc aactgttaac | 2458 |
| tactgcacgt tccacgatcg acttaaacag ggaaggttct ctctgtgcta ctgaccgttg | 2518 |
| cctaacgagg gtacacagga gtggagcctt caaagagagc aggcacagtg acatgggggt | 2578 |
| tccaaacctt gatggtctag ttttatgtga cctcgacaat ggtcatcttc ttccctattg | 2638 |
| ataaacagaa atagtataga aatccacagt tagacttagg tctaatccca gctatttact | 2698 |
| ctctattttt tattttcagc agggtcttta aattctcctc tcccattttc ttatctgtaa | 2758 |
| agtgagggtg aaactgagat ctaactgtgc cccaaactgt agccgactga tagacgtcat | 2818 |
| caacactctc actggtcaag tacttcctgc ttctctggga ccttctgatt tagggctgtc | 2878 |
| tgggcagaca acagagtaga ttcaaagggc tttcacaatg aattctggat atagctcctc | 2938 |
| tctctcttct cagggttcct cttcatccaa tcgtactctc agatgtttgt ggagcaacct | 2998 |
| ctttctgccc aggcagcagg aggctggggt ggggtgggt gggggggcac agctctggcc | 3058 |
| acagaggcag atttatttgg atgataggac taatatttgt gtaacctgct gagacctgtg | 3118 |
| tgggagagtt tagtatggtt tttcttttgg tgagggatt tgctccggtt tcacatccat | 3178 |
| taacacaaaa catgagctag tcagggccct tgtggtctgt ggtgagggga tgactggaga | 3238 |
| aacgggactg agtgagtcag gcggagggaa tgtcttcctc gcagagtaga gtcaacggga | 3298 |
| taactgatga gccagtggtg gggtcacgga gggggcggag gggaagaggg acttctcttg | 3358 |
| gaagagagga gttttggggg cagggcgag aacatccaag ttacggtatc agtgatggca | 3418 |
| ttggccttca ctggggagcc agcctgaggt aaatctactt gtgctgtatt ctctttgagt | 3478 |

```
ttgggttctt agctgtggca gacatctgtg acatctcata ttactccatg cctttgcctg    3538
ggctccaaat tctagctgat aaagatatac aaccactt                            3576
```

<210> SEQ ID NO 44
<211> LENGTH: 389
<212> TYPE: PRT
<213> ORGANISM: Mus musculus

<400> SEQUENCE: 44

```
Met Leu Lys Leu Gln Gly Glu Asp Glu Ala Ala Gln Leu Ala Pro Arg
 1               5                  10                  15

Arg Ala Arg Val Pro Val Pro Arg Pro Thr Ala Pro Asp Val Ser Pro
                20                  25                  30

Ser Ser Ala Arg Leu Gly Leu Ala Cys Leu Leu Leu Leu Leu Leu Leu
            35                  40                  45

Thr Leu Pro Ala Arg Val Asp Thr Ser Trp Trp Tyr Ile Gly Ala Leu
    50                  55                  60

Gly Ala Arg Val Ile Cys Asp Asn Ile Pro Gly Leu Val Ser Arg Gln
 65                  70                  75                  80

Arg Gln Leu Cys Gln Arg Tyr Pro Asp Ile Met Arg Ser Val Gly Glu
                85                  90                  95

Gly Ala Arg Glu Trp Ile Arg Glu Cys Gln His Gln Phe Arg His His
            100                 105                 110

Arg Trp Asn Cys Thr Thr Leu Asp Arg Asp His Thr Val Phe Gly Arg
    115                 120                 125

Ala Met Leu Arg Ser Ser Arg Glu Ala Ala Phe Val Tyr Ala Ile Ser
130                 135                 140

Ser Ala Gly Val Val His Ala Ile Thr Arg Ala Cys Ser Gln Gly Glu
145                 150                 155                 160

Leu Ser Val Cys Ser Cys Asp Pro Tyr Thr Arg Gly Arg His His Asp
                165                 170                 175

Gln Arg Gly Asp Phe Asp Trp Gly Gly Cys Ser Asp Asn Ile His Tyr
            180                 185                 190

Gly Val Arg Phe Ala Lys Ala Phe Val Asp Ala Lys Glu Lys Arg Leu
    195                 200                 205

Lys Asp Ala Arg Ala Leu Met Asn Leu His Asn Asn Arg Cys Gly Arg
210                 215                 220

Thr Ala Val Arg Arg Phe Leu Lys Leu Glu Cys Lys Cys His Gly Val
225                 230                 235                 240

Ser Gly Ser Cys Thr Leu Arg Thr Cys Trp Arg Ala Leu Ser Asp Phe
                245                 250                 255

Arg Arg Thr Gly Asp Tyr Leu Arg Arg Tyr Asp Gly Ala Val Gln
            260                 265                 270

Val Thr Ala Thr Gln Asp Gly Ala Asn Phe Thr Ala Ala Arg Gln Gly
    275                 280                 285

Tyr Arg His Ala Thr Arg Thr Asp Leu Val Tyr Phe Asp Asn Ser Pro
    290                 295                 300

Asp Tyr Cys Val Leu Asp Lys Ala Ala Gly Ser Leu Gly Thr Ala Gly
305                 310                 315                 320

Arg Val Cys Ser Lys Thr Ser Lys Gly Thr Asp Gly Cys Glu Ile Met
                325                 330                 335

Cys Cys Gly Arg Gly Tyr Asp Thr Thr Arg Val Thr Arg Val Thr Gln
            340                 345                 350
```

```
                Cys Glu Cys Lys Phe His Trp Cys Cys Ala Val Arg Cys Lys Glu Cys
                        355                 360                 365

Arg Asn Thr Val Asp Val His Thr Cys Lys Ala Pro Lys Lys Ala Glu
                370                 375                 380

Trp Leu Asp Gln Thr
                385

<210> SEQ ID NO 45
<211> LENGTH: 3000
<212> TYPE: DNA
<213> ORGANISM: Mus musculus
<220> FEATURE:
<221> NAME/KEY: CDS
<222> LOCATION: (46)..(1113)

<400> SEQUENCE: 45
cctcttcatg atcgccggca aacttcctcc tcggcgctgc ttcta atg gag ccc cac        57
                                                 Met Glu Pro His
                                                  1 ctg ctc ggg ctg cta ctc ggc ctc ctg ctc agt ggc acc agg gtc ctc        105
Leu Leu Gly Leu Leu Leu Gly Leu Leu Leu Ser Gly Thr Arg Val Leu
 5              10                  15                  20 gct ggc tac cca att tgg tgg tcc ctg gcc ctg ggc cag cag tac aca        153
Ala Gly Tyr Pro Ile Trp Trp Ser Leu Ala Leu Gly Gln Gln Tyr Thr
            25                  30                  35 tct ctg gcc tcc cag cct ctg ctc tgc ggc tcc atc cca ggc ctg gtc        201
Ser Leu Ala Ser Gln Pro Leu Leu Cys Gly Ser Ile Pro Gly Leu Val
        40                  45                  50 ccc aag caa ctg cgc ttc tgc cgc aat tac atc gag atc atg ccc agc        249
Pro Lys Gln Leu Arg Phe Cys Arg Asn Tyr Ile Glu Ile Met Pro Ser
    55                  60                  65 gta gca gaa ggt gtg aag ctg ggc atc cag gag tgc cag cat cag ttc        297
Val Ala Glu Gly Val Lys Leu Gly Ile Gln Glu Cys Gln His Gln Phe
70                  75                  80 cgg ggc cgc cgg tgg aac tgt acc acc ata gat gac agc ctg gcc atc        345
Arg Gly Arg Arg Trp Asn Cys Thr Thr Ile Asp Asp Ser Leu Ala Ile
85                  90                  95                 100 ttt ggg cct gtc ttg gac aaa gcc acc cgt gaa tcg gcc ttc gtg cat        393
Phe Gly Pro Val Leu Asp Lys Ala Thr Arg Glu Ser Ala Phe Val His
                105                 110                 115 gcc atc gcc tcg gct ggt gtc gcc ttc gca gtc aca cgc tcc tgc gct        441
Ala Ile Ala Ser Ala Gly Val Ala Phe Ala Val Thr Arg Ser Cys Ala
            120                 125                 130 gag gga acc tcc acc atc tgc ggc tgt gac tca cat cat aag ggg cca        489
Glu Gly Thr Ser Thr Ile Cys Gly Cys Asp Ser His His Lys Gly Pro
        135                 140                 145 cct gga gaa ggc tgg aag tgg ggc ggc tgc agc gag gac gcc gac ttc        537
Pro Gly Glu Gly Trp Lys Trp Gly Gly Cys Ser Glu Asp Ala Asp Phe
    150                 155                 160 ggg gtg ctg gtg tcc cgg gaa ttt gcg gat gcg cgg gag aac agg cca        585
Gly Val Leu Val Ser Arg Glu Phe Ala Asp Ala Arg Glu Asn Arg Pro
165                 170                 175                 180 gat gcc cgc tca gct atg aac aag cac aac aat gaa gca ggc cga acg        633
Asp Ala Arg Ser Ala Met Asn Lys His Asn Asn Glu Ala Gly Arg Thr
                185                 190                 195 acc atc ctg gac cac atg cac cta aag tgt aaa tgc cac ggg ttg tcc        681
Thr Ile Leu Asp His Met His Leu Lys Cys Lys Cys His Gly Leu Ser
            200                 205                 210 ggc agc tgc gag gtg aag acc tgc tgg tgg gcc cag ccc gac ttc cgt        729
Gly Ser Cys Glu Val Lys Thr Cys Trp Trp Ala Gln Pro Asp Phe Arg
        215                 220                 225
```

-continued

| | | |
|---|---|---|
| gcc att ggc gac ttc ctc aag gac aag tac gac agt gcc tcc gag atg<br>Ala Ile Gly Asp Phe Leu Lys Asp Lys Tyr Asp Ser Ala Ser Glu Met<br>230                            235                        240 | | 777 |
| gtg gtg gag aaa cac cgt gag tcc cga ggc tgg gtg gag acc ctg cgg<br>Val Val Glu Lys His Arg Glu Ser Arg Gly Trp Val Glu Thr Leu Arg<br>245                        250                          255                      260 | | 825 |
| gct aag tac gcg ctc ttc aag cca ccc acc gag agg gac ctg gtc tac<br>Ala Lys Tyr Ala Leu Phe Lys Pro Pro Thr Glu Arg Asp Leu Val Tyr<br>                    265                          270                        275 | | 873 |
| tac gag aac tcc ccc aac ttt tgt gag ccc aac cca gag acg ggc tcc<br>Tyr Glu Asn Ser Pro Asn Phe Cys Glu Pro Asn Pro Glu Thr Gly Ser<br>                280                          285                        290 | | 921 |
| ttt ggt acc agg gac cgg act tgc aat gtc acc tcc cac ggc atc gat<br>Phe Gly Thr Arg Asp Arg Thr Cys Asn Val Thr Ser His Gly Ile Asp<br>                    295                          300                        305 | | 969 |
| ggc tgc gat ctg ctg tgt tgt ggc cgg ggc cac aac acg agg acg gag<br>Gly Cys Asp Leu Leu Cys Cys Gly Arg Gly His Asn Thr Arg Thr Glu<br>310                            315                        320 | | 1017 |
| aaa cgg aag gag aaa tgc cat tgc gtc ttc cac tgg tgc tgc tat gtc<br>Lys Arg Lys Glu Lys Cys His Cys Val Phe His Trp Cys Cys Tyr Val<br>325                            330                        335                      340 | | 1065 |
| agc tgc caa gag tgt att cgc atc tac gat gtg cac acc tgc aag tag<br>Ser Cys Gln Glu Cys Ile Arg Ile Tyr Asp Val His Thr Cys Lys<br>                    345                          350                        355 | | 1113 |
| tgagccaggg cactgggaag gggtagattg tgcggctgga tccattcatc gaagtcccat | | 1173 |
| gagaagcagg atctagatcc aggccagcct tcggcactgg ccagcaagga gcatggactg | | 1233 |
| ttgccagctg catgtgataa acgacctgga cccagccggc tcggacgga cgggcggctt | | 1293 |
| ctttctcaac taacgtctct cccctgctc tggatggtgt acggctttac agaggggctt | | 1353 |
| tctttatggt tttaccaggg tctgctgggg acagactcga ggcttacctt tgcacatgtt | | 1413 |
| aaagaaaata aaaatgaaaa aaaaaaatct accgcaacag aacaggctgg gctagtgtga | | 1473 |
| gctcttggcc tggtgggaag acaagaccca tggcgagatt ctgtgtccaa gctgcctcta | | 1533 |
| ctcgtgacat tccaagatgc ctctgaggtg ggaactgtga agtaggacag agccccgcag | | 1593 |
| tccctcttg tccgtcgact cccatttaaa ttggacatac cttgtcgttc tgagaaaagc | | 1653 |
| catagatagg tgtagctggg atgtagtgat ggggaggccc ctggccaaca gtgggagcaa | | 1713 |
| gatcttgagt tttgaagacc tcagagttct gggcggcctg gaagccatc tgcagaacag | | 1773 |
| agttccttgt gggctcctgt tttcgctagc cctgttctgc cctggagcga cagtcagatc | | 1833 |
| tccacgcccc tttctgttgt tctacagtgt ccaccttac tacgcgtttt tttttttttt | | 1893 |
| ttcatgatga cctttgtaaat aggtcagatg tggaggcagg tctcttctgg ctccatccac | | 1953 |
| cacacccaga agaatgggc tgctctgccc ttctcagcct tgctaaccag cagacaccga | | 2013 |
| ggagagcagc gggcacctt agagagcaat ctaaacatgg ttggcaggtg gggagggtaa | | 2073 |
| agagtcccac ttcctttgtg ttagaaggca gactaccctg cgtcctttc tcccattggc | | 2133 |
| tgaagtaacc agaaagacaa gagatcctta acaagccctt cttcccactt gtaaagggga | | 2193 |
| tagcctatct cagttcccaa ggatctggat tagatagata ttcaaaagag gcaagcagcg | | 2253 |
| aatggaggca gctcccagct ctgttcccga cgcatgatgg tactggctgg gtttagtaag | | 2313 |
| gtgggtgggg ctgcacggat caatccatca actccgtctt aaggagaatc agaaagagga | | 2373 |
| gataaaatgg gggaatgggg cagaacaaag aatttgtcct ttcccgcttc tgtctagggt | | 2433 |
| ctgctaatgc tggcttgacg aggggtcagc cacttctttc ctgttgtgca gttggcttgc | | 2493 |

-continued

```
caagcaggct ccagtaggcc cttgcctgca ctctctacca tgtgaccatg agcactgctc   2553
tagggacacc tcccatccct tcctagcacc ccaaatgccc cttcccatct ctccttccag   2613
aagttggaaa tcaagtcaac tggataacgc ttgtgtgaga cacttgagca gaacggatac   2673
aacaatttac aagtctcttc atatctatgt attctatatt aaaagtgata aagtcatgtt   2733
tccggggcgt attcaagtag ctgacaagta attatttaat aatagtacat gagcgcattg   2793
taattatcct cgccatagtc aggtaatagc atccaatggg aggtccctac caacctgctg   2853
tatccaaagt tttgtaaaaa gttgtagaag ttgttgatct ttttgatttt atattcaaaa   2913
agtctctttt tataaatatt atttattata caatgtatat acctttgagt taactaagat   2973
tatatattat ataaatatat atatatt                                       3000
```

<210> SEQ ID NO 46
<211> LENGTH: 355
<212> TYPE: PRT
<213> ORGANISM: Mus musculus

<400> SEQUENCE: 46

```
Met Glu Pro His Leu Leu Gly Leu Leu Leu Gly Leu Leu Leu Ser Gly
  1               5                  10                  15

Thr Arg Val Leu Ala Gly Tyr Pro Ile Trp Trp Ser Leu Ala Leu Gly
             20                  25                  30

Gln Gln Tyr Thr Ser Leu Ala Ser Gln Pro Leu Leu Cys Gly Ser Ile
         35                  40                  45

Pro Gly Leu Val Pro Lys Gln Leu Arg Phe Cys Arg Asn Tyr Ile Glu
     50                  55                  60

Ile Met Pro Ser Val Ala Glu Gly Val Lys Leu Gly Ile Gln Glu Cys
 65                  70                  75                  80

Gln His Gln Phe Arg Gly Arg Arg Trp Asn Cys Thr Thr Ile Asp Asp
                 85                  90                  95

Ser Leu Ala Ile Phe Gly Pro Val Leu Asp Lys Ala Thr Arg Glu Ser
            100                 105                 110

Ala Phe Val His Ala Ile Ala Ser Ala Gly Val Ala Phe Ala Val Thr
        115                 120                 125

Arg Ser Cys Ala Glu Gly Thr Ser Thr Ile Cys Gly Cys Asp Ser His
    130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
            180                 185                 190

Ala Gly Arg Thr Thr Ile Leu Asp His Met His Leu Lys Cys Lys Cys
        195                 200                 205

His Gly Leu Ser Gly Ser Cys Glu Val Lys Thr Cys Trp Trp Ala Gln
    210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ala Leu Phe Lys Pro Pro Thr Glu Arg
            260                 265                 270

Asp Leu Val Tyr Tyr Glu Asn Ser Pro Asn Phe Cys Glu Pro Asn Pro
        275                 280                 285
```

-continued

```
Glu Thr Gly Ser Phe Gly Thr Arg Asp Arg Thr Cys Asn Val Thr Ser
    290                 295                 300
His Gly Ile Asp Gly Cys Asp Leu Leu Cys Cys Gly Arg Gly His Asn
305                 310                 315                 320
Thr Arg Thr Glu Lys Arg Lys Glu Lys Cys His Cys Val Phe His Trp
                325                 330                 335
Cys Cys Tyr Val Ser Cys Gln Glu Cys Ile Arg Ile Tyr Asp Val His
            340                 345                 350
Thr Cys Lys
        355
```

<210> SEQ ID NO 47
<211> LENGTH: 2814
<212> TYPE: DNA
<213> ORGANISM: Mus musculus
<220> FEATURE:
<221> NAME/KEY: CDS
<222> LOCATION: (129)..(1187)

<400> SEQUENCE: 47

```
gaattcatgt cttacggtca aggcagaggg cccagcgcca ctgcagccgc gccacctccc      60
agggccgggc cagcccaggc gtccgcgctc tcggggtgga ctcccccgc tgcgcgctca     120 agccggcg atg gct cct ctc gga tac ctc tta gtg ctc tgc agc ctg aag    170
         Met Ala Pro Leu Gly Tyr Leu Leu Val Leu Cys Ser Leu Lys
           1               5                   10 cag gct ctg ggc agc tac ccg atc tgg tgg tcc ttg gct gtg gga ccc     218
Gln Ala Leu Gly Ser Tyr Pro Ile Trp Trp Ser Leu Ala Val Gly Pro
 15                  20                  25                  30 cag tac tcc tct ctg agc act cag ccc att ctc tgt gcc agc atc cca     266
Gln Tyr Ser Ser Leu Ser Thr Gln Pro Ile Leu Cys Ala Ser Ile Pro
                 35                  40                  45 ggc ctg gta ccg aag cag ctg cgc ttc tgc agg aac tac gtg gag atc     314
Gly Leu Val Pro Lys Gln Leu Arg Phe Cys Arg Asn Tyr Val Glu Ile
             50                  55                  60 atg ccc agc gtg gct gag ggt gtc aaa gcg ggc atc cag gag tgc cag     362
Met Pro Ser Val Ala Glu Gly Val Lys Ala Gly Ile Gln Glu Cys Gln
         65                  70                  75 cac cag ttc cga ggc cgg cgt tgg aac tgc acc acc gtc agc aac agc     410
His Gln Phe Arg Gly Arg Arg Trp Asn Cys Thr Thr Val Ser Asn Ser
     80                  85                  90 ctg gcc atc ttt ggc cct gtt ctg gac aaa gcc acc cgg gag tca gcc     458
Leu Ala Ile Phe Gly Pro Val Leu Asp Lys Ala Thr Arg Glu Ser Ala
 95                 100                 105                 110 ttt gtc cat gcc atc gcc tcc gct gga gta gct ttc gca gtg aca cgc     506
Phe Val His Ala Ile Ala Ser Ala Gly Val Ala Phe Ala Val Thr Arg
                115                 120                 125 tcc tgt gca gag gga tca gct gct atc tgt ggg tgc agc agc cgc ctc     554
Ser Cys Ala Glu Gly Ser Ala Ala Ile Cys Gly Cys Ser Ser Arg Leu
            130                 135                 140 cag ggc tcc cca ggc gag ggc tgg aag tgg ggc ggc tgt agt gag gac     602
Gln Gly Ser Pro Gly Glu Gly Trp Lys Trp Gly Gly Cys Ser Glu Asp
        145                 150                 155 att gaa ttt gga gga atg gtc tct cgg gag ttt gcc gat gcc agg gag     650
Ile Glu Phe Gly Gly Met Val Ser Arg Glu Phe Ala Asp Ala Arg Glu
    160                 165                 170 aac cgg ccg gat gcc cgc tct gcc atg aac cgt cac aac aat gag gct     698
Asn Arg Pro Asp Ala Arg Ser Ala Met Asn Arg His Asn Asn Glu Ala
175                 180                 185                 190
```

| | | |
|---|---|---|
| ggg cgc cag gcc atc gcc agt cac atg cac ctc aag tgc aaa tgc cac<br>Gly Arg Gln Ala Ile Ala Ser His Met His Leu Lys Cys Lys Cys His<br>195 200 205 | | 746 |
| ggg cta tct ggc agc tgt gaa gtg aag acc tgc tgg tgg tcg cag ccg<br>Gly Leu Ser Gly Ser Cys Glu Val Lys Thr Cys Trp Trp Ser Gln Pro<br>210 215 220 | | 794 |
| gac ttc cgc acc atc ggg gat ttc ctc aag gac aag tat gac agt gcc<br>Asp Phe Arg Thr Ile Gly Asp Phe Leu Lys Asp Lys Tyr Asp Ser Ala<br>225 230 235 | | 842 |
| tcg gag atg gtg gta gag aaa cac cga gag tct cgt ggc tgg gtg gag<br>Ser Glu Met Val Val Glu Lys His Arg Glu Ser Arg Gly Trp Val Glu<br>240 245 250 | | 890 |
| acc ctg agg cca cgt tac acg tac ttc aag gtg ccg aca gaa cgc gac<br>Thr Leu Arg Pro Arg Tyr Thr Tyr Phe Lys Val Pro Thr Glu Arg Asp<br>255 260 265 270 | | 938 |
| ctg gtc tac tac gag gcc tca ccc aac ttc tgc gaa cct aac ccc gaa<br>Leu Val Tyr Tyr Glu Ala Ser Pro Asn Phe Cys Glu Pro Asn Pro Glu<br>275 280 285 | | 986 |
| acc ggc tcc ttc ggg acg cgt gac cgc acc tgc aat gtg agc tcg cat<br>Thr Gly Ser Phe Gly Thr Arg Asp Arg Thr Cys Asn Val Ser Ser His<br>290 295 300 | | 1034 |
| ggc ata gat ggg tgc gac ctg ttg tgc tgc ggg cgc ggg cat aac gcg<br>Gly Ile Asp Gly Cys Asp Leu Leu Cys Cys Gly Arg Gly His Asn Ala<br>305 310 315 | | 1082 |
| cgc act gag cga cgg agg gag aaa tgc cac tgt gtt ttc cat tgg tgc<br>Arg Thr Glu Arg Arg Arg Glu Lys Cys His Cys Val Phe His Trp Cys<br>320 325 330 | | 1130 |
| tgc tac gtc agc tgc cag gag tgc aca cgt gtc tat gac gtg cac acc<br>Cys Tyr Val Ser Cys Gln Glu Cys Thr Arg Val Tyr Asp Val His Thr<br>335 340 345 350 | | 1178 |
| tgc aag tag gagagctcct aacacgggag cagggttcat tccgaggggc<br>Cys Lys | | 1227 |
| aaggttccta cctgggggcg gggttcctac ttggaggggt ctcttacttg gggactcggt | | 1287 |
| tcttacttga gggcggagat cctacctgtg agggtctcat acctaaggac ccggtttctg | | 1347 |
| ccttcagcct gggctcctat ttgggatctg ggttcctttt tagggagaaa gctcctgtct | | 1407 |
| gggatacggg tttctgcccg agggtggggc tccacttggg gatggaattc caatttgggc | | 1467 |
| cggaagtcct acctcaatgg cttggactcc tctcttgacc cgacagggct caaatgagaa | | 1527 |
| caggtaagct actccctcaa ctaggtgggg ttcgtgcgga tgggtgggag gggagagatt | | 1587 |
| agggtccctc ctcccagagg cactgctcta tctagataca tgagagggtg cttcagggtg | | 1647 |
| ggccctattt gggcttgagg atcccgtggg ggcggggctt caccccgact gggtggaact | | 1707 |
| tttggagacc cccttccact gggggcaaggc ttcactgaag actcatggga tggagctcca | | 1767 |
| cggaaggagg agttcctgag cgagcctggg ctctgagcag gccatccagc tcccatctgg | | 1827 |
| cccctttcca gtcctggtgt aaggttcaac ctgcaagcct catctgcgca gagcaggatc | | 1887 |
| tcctggcaga atgaggcatg gagaagaact cagggtgat accaagacct aacaaacccc | | 1947 |
| gtgcctgggt acctctttta aagctctgca cccttcttc aagggctttc ctagtctcct | | 2007 |
| tggcagagct ttcctgagga agatttgcag tcccccagag ttcaagtgaa cacccataga | | 2067 |
| acagaacaga ctctatcctg agtagagagg gttctctagg aatctctatg ggactgcta | | 2127 |
| ggaaggatcc tgggcatgac agcctcgtat gatagcctgc atccgctctg acacttaata | | 2187 |
| ctcagatctc ccgggaaacc cagctcatcc ggtccgtgat gtccatgccc caaatgcctc | | 2247 |
| agagatgttg cctcactttg agttgtatga acttcggaga catggggaca cagtcaagcc | | 2307 |

-continued

```
gcagagccag ggttgtttca ggacccatct gattccccag agcctgctgt tgaggcaatg    2367
gtcaccagat ccgttggcca ccaccctgtc ccgagcttct ctagtgtctg tctggcctgg    2427
aagtgaggtg ctacatacag cccatctgcc acaagagctt cctgattggt accactgtga    2487
accgtccctc cccctccaga caggggaggg gatgtggcca tacaggagtg tgcccggaga    2547
gcgcggaaag aggaagagag gctgcacacg cgtggtgact gactgtcttc tgcctggaac    2607
tttgcgttcg cgcttgtaac tttattttca atgctgctat atccaccac cactggattt     2667 agacaaaagt gatttctttt ttttttttt cttttctttc tatgaaagaa attattttag     2727
tttatagtat gtttgtttca aataatgggg aaagtaaaaa gagagaaaaa aaaaaaaaaa    2787
aaaaaaaaaa aaaaaaaaaa aaaaaaa                                        2814
```

<210> SEQ ID NO 48
<211> LENGTH: 352
<212> TYPE: PRT
<213> ORGANISM: Mus musculus

<400> SEQUENCE: 48

```
Met Ala Pro Leu Gly Tyr Leu Leu Val Leu Cys Ser Leu Lys Gln Ala
  1               5                  10                  15

Leu Gly Ser Tyr Pro Ile Trp Trp Ser Leu Ala Val Gly Pro Gln Tyr
                 20                  25                  30

Ser Ser Leu Ser Thr Gln Pro Ile Leu Cys Ala Ser Ile Pro Gly Leu
             35                  40                  45

Val Pro Lys Gln Leu Arg Phe Cys Arg Asn Tyr Val Glu Ile Met Pro
 50                  55                  60

Ser Val Ala Glu Gly Val Lys Ala Gly Ile Gln Glu Cys Gln His Gln
 65                  70                  75                  80

Phe Arg Gly Arg Arg Trp Asn Cys Thr Thr Val Ser Asn Ser Leu Ala
                 85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Ser Ala Ala Ile Cys Gly Cys Ser Ser Arg Leu Gln Gly
    130                 135                 140

Ser Pro Gly Glu Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Thr Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285
```

```
Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Thr
305                 310                 315                 320

Glu Arg Arg Arg Glu Lys Cys His Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 49
<211> LENGTH: 1101
<212> TYPE: DNA
<213> ORGANISM: Mus musculus
<220> FEATURE:
<221> NAME/KEY: CDS
<222> LOCATION: (46)..(1101)

<400> SEQUENCE: 49
cgggagcctt gcggccgctg ccccgggctg ggcgcgcacg gcacc atg agc ccc cgt    57
                                                 Met Ser Pro Arg
                                                  1 tcg tgc ctg cgg tcc ctg cga ctc ctc gtc ttc gcc gtg ttc tcg gcc   105
Ser Cys Leu Arg Ser Leu Arg Leu Leu Val Phe Ala Val Phe Ser Ala
  5                  10                  15                  20 gcc gcg agc aat tgg ctg tac ctg gcc aag ctg tca tcg gtg ggc agc   153
Ala Ala Ser Asn Trp Leu Tyr Leu Ala Lys Leu Ser Ser Val Gly Ser
                 25                  30                  35 atc tcc gaa gag gag acg tgc gag aaa ctc aaa ggc ctg atc cag agg   201
Ile Ser Glu Glu Glu Thr Cys Glu Lys Leu Lys Gly Leu Ile Gln Arg
             40                  45                  50 cag gtg cag atg tgc aaa cgg aac ctt gag gtg atg gac tca gtg cgc   249
Gln Val Gln Met Cys Lys Arg Asn Leu Glu Val Met Asp Ser Val Arg
         55                  60                  65 cgt ggt gcc cag ctg gcc atc gag gag tgc caa tac cag ttc cgg aac   297
Arg Gly Ala Gln Leu Ala Ile Glu Glu Cys Gln Tyr Gln Phe Arg Asn
     70                  75                  80 cgg cgc tgg aac tgt tcc aca ctg gac tcc ctc cct gtc ttt ggg aag   345
Arg Arg Trp Asn Cys Ser Thr Leu Asp Ser Leu Pro Val Phe Gly Lys
 85                  90                  95                 100 gtg gtg aca caa ggg acc cgg gag gcg gcc ttt gta tac gcc atc tct   393
Val Val Thr Gln Gly Thr Arg Glu Ala Ala Phe Val Tyr Ala Ile Ser
                105                 110                 115 tca gca ggt gtg gcc ttt gca gtg aca agg gca tgc agc agt gga gaa   441
Ser Ala Gly Val Ala Phe Ala Val Thr Arg Ala Cys Ser Ser Gly Glu
            120                 125                 130 ctg gag aag tgt ggc tgt gac cgg aca gtg cac ggg gtc agc cca cag   489
Leu Glu Lys Cys Gly Cys Asp Arg Thr Val His Gly Val Ser Pro Gln
        135                 140                 145 ggc ttc cag tgg tca gga tgc tcg gac aac atc gcc tat ggc gta gcc   537
Gly Phe Gln Trp Ser Gly Cys Ser Asp Asn Ile Ala Tyr Gly Val Ala
    150                 155                 160 ttc tca cag tcc ttt gtg gac gtc cgg gag agg agc aag ggg gcc tcc   585
Phe Ser Gln Ser Phe Val Asp Val Arg Glu Arg Ser Lys Gly Ala Ser
165                 170                 175                 180 tcc agc cgg gca ctc atg aat ctt cac aac aac gag gct ggc agg aag   633
Ser Ser Arg Ala Leu Met Asn Leu His Asn Asn Glu Ala Gly Arg Lys
                185                 190                 195 gcc atc ttg aca cac atg cgg gtg gag tgc aag tgt cac ggg gtg tcg   681
Ala Ile Leu Thr His Met Arg Val Glu Cys Lys Cys His Gly Val Ser
            200                 205                 210
```

-continued

```
ggc tcc tgc gag gta aag acg tgc tgg cgt gct gta ccg ccc ttc cgc    729
Gly Ser Cys Glu Val Lys Thr Cys Trp Arg Ala Val Pro Pro Phe Arg
        215                 220                 225 cag gtt ggc cac gcg cta aag gag aag ttt gac ggt gcc acg gag gtg    777
Gln Val Gly His Ala Leu Lys Glu Lys Phe Asp Gly Ala Thr Glu Val
    230                 235                 240 gag cca cga cgc gta ggc tcc tcc cgg gcg ctg gtg cct cgg aat gca    825
Glu Pro Arg Arg Val Gly Ser Ser Arg Ala Leu Val Pro Arg Asn Ala
245                 250                 255                 260 cag ttc aag cca cat aca gat gag gac ctg gta tac ctg gag cct agc    873
Gln Phe Lys Pro His Thr Asp Glu Asp Leu Val Tyr Leu Glu Pro Ser
            265                 270                 275 ccg gac ttc tgt gag cag gac atc cgc agt ggc gtg cta ggc acg agg    921
Pro Asp Phe Cys Glu Gln Asp Ile Arg Ser Gly Val Leu Gly Thr Arg
        280                 285                 290 ggc cgc acg tgc aac aag aca tct aaa gcc att gac ggc tgc gag cta    969
Gly Arg Thr Cys Asn Lys Thr Ser Lys Ala Ile Asp Gly Cys Glu Leu
    295                 300                 305 ctg tgc tgt ggc cgc ggc ttc cac aca gcg caa gtg gag ctg gcc gag   1017
Leu Cys Cys Gly Arg Gly Phe His Thr Ala Gln Val Glu Leu Ala Glu
310                 315                 320 cgc tgt ggc tgc agg ttc cac tgg tgc tgc ttc gtc aag tgc cgg cag   1065
Arg Cys Gly Cys Arg Phe His Trp Cys Cys Phe Val Lys Cys Arg Gln
325                 330                 335                 340 tgc cag cgg ctc gtg gag atg cac acg tgc cgg tga                   1101
Cys Gln Arg Leu Val Glu Met His Thr Cys Arg
            345                 350
```

<210> SEQ ID NO 50
<211> LENGTH: 351
<212> TYPE: PRT
<213> ORGANISM: Mus musculus

<400> SEQUENCE: 50

```
Met Ser Pro Arg Ser Cys Leu Arg Ser Leu Arg Leu Val Phe Ala
1               5                   10                  15

Val Phe Ser Ala Ala Ala Ser Asn Trp Leu Tyr Leu Ala Lys Leu Ser
            20                  25                  30

Ser Val Gly Ser Ile Ser Glu Glu Thr Cys Glu Lys Leu Lys Gly
        35                  40                  45

Leu Ile Gln Arg Gln Val Gln Met Cys Lys Arg Asn Leu Glu Val Met
    50                  55                  60

Asp Ser Val Arg Arg Gly Ala Gln Leu Ala Ile Glu Glu Cys Gln Tyr
65                  70                  75                  80

Gln Phe Arg Asn Arg Arg Trp Asn Cys Ser Thr Leu Asp Ser Leu Pro
                85                  90                  95

Val Phe Gly Lys Val Val Thr Gln Gly Thr Arg Glu Ala Ala Phe Val
            100                 105                 110

Tyr Ala Ile Ser Ser Ala Gly Val Ala Phe Ala Val Thr Arg Ala Cys
        115                 120                 125

Ser Ser Gly Glu Leu Glu Lys Cys Gly Cys Asp Arg Thr Val His Gly
    130                 135                 140

Val Ser Pro Gln Gly Phe Gln Trp Ser Gly Cys Ser Asp Asn Ile Ala
145                 150                 155                 160

Tyr Gly Val Ala Phe Ser Gln Ser Phe Val Asp Val Arg Glu Arg Ser
                165                 170                 175

Lys Gly Ala Ser Ser Ser Arg Ala Leu Met Asn Leu His Asn Asn Glu
```

-continued

```
                180                 185                 190
Ala Gly Arg Lys Ala Ile Leu Thr His Met Arg Val Glu Cys Lys Cys
        195                 200                 205
His Gly Val Ser Gly Ser Cys Glu Val Lys Thr Cys Trp Arg Ala Val
    210                 215                 220
Pro Pro Phe Arg Gln Val Gly His Ala Leu Lys Glu Lys Phe Asp Gly
225                 230                 235                 240
Ala Thr Glu Val Glu Pro Arg Val Gly Ser Ser Arg Ala Leu Val
                245                 250                 255
Pro Arg Asn Ala Gln Phe Lys Pro His Thr Asp Glu Asp Leu Val Tyr
            260                 265                 270
Leu Glu Pro Ser Pro Asp Phe Cys Glu Gln Asp Ile Arg Ser Gly Val
        275                 280                 285
Leu Gly Thr Arg Gly Arg Thr Cys Asn Lys Thr Ser Lys Ala Ile Asp
    290                 295                 300
Gly Cys Glu Leu Leu Cys Cys Gly Arg Gly Phe His Thr Ala Gln Val
305                 310                 315                 320
Glu Leu Ala Glu Arg Cys Gly Cys Arg Phe His Trp Cys Cys Phe Val
                325                 330                 335
Lys Cys Arg Gln Cys Gln Arg Leu Val Glu Met His Thr Cys Arg
            340                 345                 350

<210> SEQ ID NO 51
<211> LENGTH: 4273
<212> TYPE: DNA
<213> ORGANISM: Mus musculus
<220> FEATURE:
<221> NAME/KEY: CDS
<222> LOCATION: (637)..(1779)

<400> SEQUENCE: 51
agtccctgga agcagacgtt tcggccacag acccagagag gaggagctga caatcaggag      60
gcgtgagccg cctggagtct gcagaattcg tggtgtgaat gaactggggg catcttgggc     120
acagggattg cccccctcc ttccccgcct cgggccacag ttgagtagtg gggcattttt      180
tttcaccttc ttgtgaagaa ttttttttat tatttgttgt aaagtctttt gcacaatcac     240
gcccacattt ggggttggaa agccctaatt accgccgtcg ctgatggacg ttagagaggg     300
agcgcctcgc cgcggaacag tcgcctgcgc gccctcgtcg acccgcggc tcctgcactg      360 tgtccccgct cggccctgcg cttgctgctc gccgcgcgc gccggcgccc tctcggttcc      420
tgggcacatt tccacgctat accaactcct ctgcccgagt ccgggcgcca gtgctcgctt     480
ccgctccggg tcgctgcgcc cacccgacgc gcccaggagg actccgcagc cctgctttgg     540
attgtccccc aaggcttaac cccgacgctt cgcttgaatt cctcggccgc cttcgctcgg     600
gtggcgactt cctctccgtg cccctcccc ctcgcc atg aag aag ccc att gga      654
                                        Met Lys Lys Pro Ile Gly
                                            1               5 ata tta agc ccg gga gtg gct ttg ggg acc gct gga ggt gcc atg tct      702
Ile Leu Ser Pro Gly Val Ala Leu Gly Thr Ala Gly Gly Ala Met Ser
        10                  15                  20 tcc aag ttc ttc cta atg gct ttg gcc acg ttt ttc tcc ttc gcc cag      750
Ser Lys Phe Phe Leu Met Ala Leu Ala Thr Phe Phe Ser Phe Ala Gln
    25                  30                  35 gtt gtt ata gaa gct aat tct tgg tgg tct cta ggt atg aat aac cct      798
Val Val Ile Glu Ala Asn Ser Trp Trp Ser Leu Gly Met Asn Asn Pro
40                  45                  50
```

-continued

| | |
|---|---|
| gtt cag atg tca gaa gta tat atc ata ggt gca cag cct ctc tgc agc<br>Val Gln Met Ser Glu Val Tyr Ile Ile Gly Ala Gln Pro Leu Cys Ser<br>55                    60                    65                    70 | 846 |
| caa ctg gca gga ctt tct caa gga cag aag aaa ctc tgc cac ttg tat<br>Gln Leu Ala Gly Leu Ser Gln Gly Gln Lys Lys Leu Cys His Leu Tyr<br>                    75                    80                    85 | 894 |
| cag gac cac atg cag tac att gga gaa ggt gcg aag aca ggc atc aag<br>Gln Asp His Met Gln Tyr Ile Gly Glu Gly Ala Lys Thr Gly Ile Lys<br>              90                    95                    100 | 942 |
| gaa tgc cag tac cag ttc cgg cat cgg aga tgg aac tgc agc aca gtg<br>Glu Cys Gln Tyr Gln Phe Arg His Arg Arg Trp Asn Cys Ser Thr Val<br>              105                  110                115 | 990 |
| gac aat act tct gtc ttt ggc agg gtg atg caa ata ggc agc cga gag<br>Asp Asn Thr Ser Val Phe Gly Arg Val Met Gln Ile Gly Ser Arg Glu<br>120                    125                  130 | 1038 |
| acg gcc ttc acg tac gcg gtg agc gca gct ggg gtg gtg aac gcc atg<br>Thr Ala Phe Thr Tyr Ala Val Ser Ala Ala Gly Val Val Asn Ala Met<br>135                    140                  145                150 | 1086 |
| agc cga gca tgc cgg gag ggc gag ctg tct acc tgt ggc tgc agc cgc<br>Ser Arg Ala Cys Arg Glu Gly Glu Leu Ser Thr Cys Gly Cys Ser Arg<br>              155                  160                165 | 1134 |
| gct gcg cgc ccc aag gac ctg cct cgg gac tgg ttg tgg ggc ggc tgc<br>Ala Ala Arg Pro Lys Asp Leu Pro Arg Asp Trp Leu Trp Gly Gly Cys<br>                  170                  175                180 | 1182 |
| gga gac aac atc gac tat ggc tac cgc ttc gcc aag gag ttc gtg gac<br>Gly Asp Asn Ile Asp Tyr Gly Tyr Arg Phe Ala Lys Glu Phe Val Asp<br>              185                  190                195 | 1230 |
| gct aga gaa agg gaa cga atc cac gct aag ggt tcc tat gag agc gca<br>Ala Arg Glu Arg Glu Arg Ile His Ala Lys Gly Ser Tyr Glu Ser Ala<br>200                    205                  210 | 1278 |
| cgc atc ctc atg aac tta cac aac aat gaa gca ggc cgt agg aca gta<br>Arg Ile Leu Met Asn Leu His Asn Asn Glu Ala Gly Arg Arg Thr Val<br>215                    220                  225                230 | 1326 |
| tac aac ctg gca gat gta gcc tgt aag tgt cat gga gtg tct ggc tcc<br>Tyr Asn Leu Ala Asp Val Ala Cys Lys Cys His Gly Val Ser Gly Ser<br>              235                  240                245 | 1374 |
| tgt agc ctc aag acg tgc tgg ctg cag ctg gcg gac ttc cgg aag gtg<br>Cys Ser Leu Lys Thr Cys Trp Leu Gln Leu Ala Asp Phe Arg Lys Val<br>              250                  255                260 | 1422 |
| ggc gat gcc ctc aag gag aag tat gat agc gcg gcg gcc atg agg ctc<br>Gly Asp Ala Leu Lys Glu Lys Tyr Asp Ser Ala Ala Ala Met Arg Leu<br>              265                  270                275 | 1470 |
| aac agc cgg ggc aag ctg gtg cag gtc aac agc cgc ttc aac tcc ccg<br>Asn Ser Arg Gly Lys Leu Val Gln Val Asn Ser Arg Phe Asn Ser Pro<br>280                    285                  290 | 1518 |
| acc acg cag gac ctg gtc tac atc gac ccc agt ccg gac tac tgt gtg<br>Thr Thr Gln Asp Leu Val Tyr Ile Asp Pro Ser Pro Asp Tyr Cys Val<br>295                    300                  305                310 | 1566 |
| cgc aac gag agc act ggc tcg ctg ggc acg cag gga cgc ctg tgc aac<br>Arg Asn Glu Ser Thr Gly Ser Leu Gly Thr Gln Gly Arg Leu Cys Asn<br>              315                  320                325 | 1614 |
| aag acc tca gag ggg atg gac ggc tgc gag ctc atg tgc tgt ggg cgt<br>Lys Thr Ser Glu Gly Met Asp Gly Cys Glu Leu Met Cys Cys Gly Arg<br>              330                  335                340 | 1662 |
| ggc tat gac cag ttt aag aca gtg cag acc gaa cgc tgt cat tgc aag<br>Gly Tyr Asp Gln Phe Lys Thr Val Gln Thr Glu Arg Cys His Cys Lys<br>              345                  350                355 | 1710 |
| ttt cac tgg tgc tgc tat gtc aaa tgc aag aag tgc acg gag att gtg<br>Phe His Trp Cys Cys Tyr Val Lys Cys Lys Lys Cys Thr Glu Ile Val<br>360                    365                  370 | 1758 |

```
gat cag ttc gtg tgc aaa tag tggtgtgcct gcccttcacc cagtcccact      1809
Asp Gln Phe Val Cys Lys
375                 380 cccaggaccc acttatttat agaaagtaca gtgcttctgg ttcttttat ttctcccca    1869 agaattgcag ctggaaccat gtgttttgtt ttgttttatt ttgtttttc ttttctgtta  1929 ccatctaaga actctgtggt ttattattaa tattataatt aatatttggc aatagtgggg  1989
gaaactaaga aaatattta ttttgaggat ctttgcaaag ttagtacaaa atttctttct   2049
tctgatgcta caggataaag gggaaaaact atgtattcga acttagctgt gcagttgggg  2109
gttcacatct agaaggtgta ggagccattt tcttctcaaa cagagagtcc tttgagatgg  2169
gtggtatcca ggtgaaggag gaggtacaga cccatgaata acagttcctg tgaccaaaat 2229 gaattgcagg tgctctggta caaagatct taaatataga tatattaaat atacatatat   2289
gccaaaaata cagaatatga gacactccct aacccagagg ttaccagcct ggttttgtgg  2349
gttttttgtt ttgttttgtt ttttcttttt ttgggttttg tttgtttgtt tgtttgtttg  2409 tattttggt gtgtgtgtgt gtgtattct agaatgatct tttagaaggt acaagcaaga    2469
atctcatatc ttcagaagca ggcatatcat gtatgttact gtgtcccacc tacagatact  2529
ccattcatga atgggccttt ttctaacagt tcatgaatat tggggagccg gtgggctggg  2589
ggagggaggt ccccagaaat tagaaaactt gaagtttcct acattgaggc cataatcttg  2649
tgttagccca gctgattctt aataccgac ttttagatcc ataaaggaat ttttgactaa   2709 aaaaaaaaa tcttgttttg aaagccatct tattttctta aaaatgaaaa attacccatg   2769
aatcccattt gcaaccccctc accccacag gcaacaagaa agtcccatgt agttgagcac  2829
tgcgaacacc tctgtgagga gatgatggca gccatcttcc tgcatgatcc catgcccttt  2889
ctggactctc tgctggccat gcttccgaat ggcagccctg gtggacactc actgctggta  2949
gggcagaaaa tgtacacgag gagccatgtt cagaaccagc cacttagggg ttgttctctg  3009 aggctttct ttggaggtac ggtaacttga tgtgttttga tgatatctct tggcccaggg   3069
agtccacaga ggtgttgcag ctgtttggtt gttatcctcc tgcgtttaga cttccattt   3129 gtgcttttcc tattaccctg caggtgtacc ctaaaactgt tcctagtgta cttgaacagt  3189
tgcatttata aggggggatg tggtttaatg gtgcctgata tctcagtttt tttgtatata  3249
acatatatat aaatatacat atataaatat agatataatt atatctcagt gcagtctggg  3309
atttagacct acagttttct ctgggcttgc tctctgcctg gagtatcgtc cttcattgca  3369
gtccaattgg gatttctttt tttccaaaaa ttttgagtct taacattgac ctgtgacagg  3429
atcctaccac gaataccagg aagcaagcta agactcggag gaagctctca gggctcatgt  3489
cctgaatgta tgttggttag aaagtagcct ttctgcttcc tgcccatggc cagttctcca  3549
ccctctcttt ggtgttcttt gtggggaggg cactgtggtt gtcgcagcc ctggacttcg   3609 agaggctccc agaacccagg atcaccagcc tcctgtctgt ttgcttcact cctttcccag  3669
ggaggacttg ggactgtcct gtctgacagg acggatctga gttcccgaag caaaccagct  3729
caccacatag atagctagtt taaacaatgt tttaaaataa gggcacctct gtttcaaaag  3789
tgacatctgc tgtgttgttt tcgaggcctg atactcttac aaggtttgaa aaaaatgtg   3849 tgtatccatt catgggcttg gtagccttct ggtcacctca gtcctgtggc tcttaactta  3909
ttgcccaaca atattcattt ccctctcagct acaatgaatt gcaagcaaaa gatgttgaaa 3969 aaaagcacta atttagttta aatgtcact ttttggtttt tattctacaa aaaccatgaa   4029
```

```
gttctctctc tctctctctc tctctcttat ttgttaaatc agattatgtt cttttttgt      4089 ttttgttttt agtgattcat gtttatgagc agagtggagt ttaacaatcc tagctttaaa      4149
aaaaacctat ttaatgtaag atattctacg catccttcag atattttgta tatccctat      4209 ggcctttatt ctgtactttt aatgtacata tttctgtctt gtgtgatttg tatatttcac      4269
tggt                                                                  4273
```

<210> SEQ ID NO 52
<211> LENGTH: 380
<212> TYPE: PRT
<213> ORGANISM: Mus musculus

<400> SEQUENCE: 52

```
Met Lys Lys Pro Ile Gly Ile Leu Ser Pro Gly Val Ala Leu Gly Thr
  1               5                  10                  15

Ala Gly Gly Ala Met Ser Ser Lys Phe Phe Leu Met Ala Leu Ala Thr
             20                  25                  30

Phe Phe Ser Phe Ala Gln Val Val Ile Glu Ala Asn Ser Trp Trp Ser
         35                  40                  45

Leu Gly Met Asn Asn Pro Val Gln Met Ser Glu Val Tyr Ile Ile Gly
 50                  55                  60

Ala Gln Pro Leu Cys Ser Gln Leu Ala Gly Leu Ser Gln Gly Gln Lys
 65                  70                  75                  80

Lys Leu Cys His Leu Tyr Gln Asp His Met Gln Tyr Ile Gly Glu Gly
                 85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
```

```
                325                 330                 335
Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380

<210> SEQ ID NO 53
<211> LENGTH: 2129
<212> TYPE: DNA
<213> ORGANISM: Mus musculus
<220> FEATURE:
<221> NAME/KEY: CDS
<222> LOCATION: (132)..(1250)

<400> SEQUENCE: 53
ccttgctgct tctcattcca tgagctgggg agagacagtg tggaagtcaa accatgtgtt      60
tcttgagagc aggtgctgct ggggctccct gaatggcggc taggtgccaa gagggagctc    120
cgctttggaa g atg ttg gtc cca ggg cat tgg gat ggg ttg agg ccg gcc    170
            Met Leu Val Pro Gly His Trp Asp Gly Leu Arg Pro Ala
              1               5                  10 atg ccc agc ctg ctg ctg gtg gtc gtg gca gct ctg ctc tcc agc tgg    218
Met Pro Ser Leu Leu Leu Val Val Val Ala Ala Leu Leu Ser Ser Trp
 15                  20                  25 gca cag ctg ctg act gac gcc aac tcc tgg tgg tca cta gct ctg aac    266
Ala Gln Leu Leu Thr Asp Ala Asn Ser Trp Trp Ser Leu Ala Leu Asn
 30                  35                  40                  45 cca gtg cag aga ccg gag atg ttc atc att ggc gct cag ccc gtg tgc    314
Pro Val Gln Arg Pro Glu Met Phe Ile Ile Gly Ala Gln Pro Val Cys
                 50                  55                  60 agc caa ctt cct ggg ctt tcc cca ggc cag aga aag ctg tgt cag ttg    362
Ser Gln Leu Pro Gly Leu Ser Pro Gly Gln Arg Lys Leu Cys Gln Leu
             65                  70                  75 tat cag gag cac atg tcc tac atc ggg gag gga gcc aag acg ggc atc    410
Tyr Gln Glu His Met Ser Tyr Ile Gly Glu Gly Ala Lys Thr Gly Ile
         80                  85                  90 aga gag tgc caa cac cag ttt cga cag agg cgc tgg aac tgc agc acc    458
Arg Glu Cys Gln His Gln Phe Arg Gln Arg Arg Trp Asn Cys Ser Thr
     95                 100                 105 gtg gac aac aca tct gtc ttt ggc aga gtt atg cag ata ggt agc cga    506
Val Asp Asn Thr Ser Val Phe Gly Arg Val Met Gln Ile Gly Ser Arg
110                 115                 120                 125 gag act gcc ttc acg tat gca gtg agc gcc gct ggc gtg gtg aat gcc    554
Glu Thr Ala Phe Thr Tyr Ala Val Ser Ala Ala Gly Val Val Asn Ala
                130                 135                 140 atc agc cga gcc tgc aga gag ggt gag ctg tcc acc tgt ggc tgc agc    602
Ile Ser Arg Ala Cys Arg Glu Gly Glu Leu Ser Thr Cys Gly Cys Ser
            145                 150                 155 cgt gct gcg agg ccc aag gac ctg cct cgg gac tgg ctg tgg ggt ggc    650
Arg Ala Ala Arg Pro Lys Asp Leu Pro Arg Asp Trp Leu Trp Gly Gly
        160                 165                 170 tgt gga gac aac gtg gag tac ggc tac cgc ttt gcc aag gag ttt gtg    698
Cys Gly Asp Asn Val Glu Tyr Gly Tyr Arg Phe Ala Lys Glu Phe Val
    175                 180                 185 gat gcc cga gag cgt gag aag aac ttt gcc aag gga tcg gag gag cag    746
Asp Ala Arg Glu Arg Glu Lys Asn Phe Ala Lys Gly Ser Glu Glu Gln
190                 195                 200                 205 ggc cga gct ctc atg aac cta cag aac aac gag gct ggc cgc cgg gcc    794
```

```
                                                                               -continued Gly Arg Ala Leu Met Asn Leu Gln Asn Asn Glu Ala Gly Arg Arg Ala
                210                 215                 220 gtg tat aag atg gct gat gtc gcc tgc aaa tgt cac gga gtc tcc ggg         842
Val Tyr Lys Met Ala Asp Val Ala Cys Lys Cys His Gly Val Ser Gly
                225                 230                 235 tcc tgc agc ctc aag acc tgc tgg ctc cag ctg gcc gag ttc cgc aag         890
Ser Cys Ser Leu Lys Thr Cys Trp Leu Gln Leu Ala Glu Phe Arg Lys
                240                 245                 250 gtt ggg gac cgt ttg aag gag aag tac gac agc gcc gcg gcc atg cgc         938
Val Gly Asp Arg Leu Lys Glu Lys Tyr Asp Ser Ala Ala Ala Met Arg
                255                 260                 265 atc acc cgc cag ggc aag ctg gag ctg gcc aac agc cgc ttc aac cag         986
Ile Thr Arg Gln Gly Lys Leu Glu Leu Ala Asn Ser Arg Phe Asn Gln
270                 275                 280                 285 ccc acc cca gag gac ctg gtc tac gtg gac ccc agt cct gac tac tgc        1034
Pro Thr Pro Glu Asp Leu Val Tyr Val Asp Pro Ser Pro Asp Tyr Cys
                290                 295                 300 ttg cgt aat gag acc aca ggc tcc ctg ggc acc cag ggt cgc ctc tgc        1082
Leu Arg Asn Glu Thr Thr Gly Ser Leu Gly Thr Gln Gly Arg Leu Cys
                305                 310                 315 aac aag acc tca gag ggc atg gac ggc tgc gag ctc atg tgc tgt ggc        1130
Asn Lys Thr Ser Glu Gly Met Asp Gly Cys Glu Leu Met Cys Cys Gly
                320                 325                 330 cgc ggc tat gac cgc ttc aag agc gtt cag gtg gaa cgc tgc cac tgc        1178
Arg Gly Tyr Asp Arg Phe Lys Ser Val Gln Val Glu Arg Cys His Cys
                335                 340                 345 agg ttc cac tgg tgt tgc ttt gtc aga tgc aaa aaa tgc acc gag gtt        1226
Arg Phe His Trp Cys Cys Phe Val Arg Cys Lys Lys Cys Thr Glu Val
350                 355                 360                 365 gtg gac cag tat gtc tgt aag tga ctgcaccaca cgggccttca ggccgctcct       1280
Val Asp Gln Tyr Val Cys Lys
                370 ctccgcctta caaaagtcta tattatataa atctatctaa atatatttta tatttgtaca      1340 aatggatgga tggatggatg atagataatc aagagaagaa agtggagagg aagagcttag      1400 gagatgctgg ccctctgtga ggactggatt ttgctggaaa tccacaacca gtgggagaga      1460 aacgggcttt tccccatttt ctggccagga cttttgggac atgggcttga gagtgtctgt      1520 gtgccatagc ctccaggagt caggtgggga ttagatgaag gaactggact tattccacat      1580 ctacagtcct gtggggaaga tgagtgtctg tgaccctggc caggagaccc agaggccctg      1640 tggaaagacc tgataactgg gatggtagcc taggtcttcc tgaaaatgga gccagctttg      1700 ggaaggggct ctgtacttcc ttcttttctc atctgagtac acactgcagg aaagtcccct      1760 gccccaatat gggggagtgg tctcaagtca ctccaaccgg tgaccgtaag agatctgggc      1820 ctccctggac cctggctctg ccttctgatg agaatgtcac tagctcctgc ctcaagctct      1880 tgtgccaaga gaaagactgt tccgtcacct gctacagcca ggaagacgtg gagcaaacct      1940 gggttttgac tggggaccaa gtgcctgttg cacaggacag gaatctgctg tcactctgtc      2000 aagggaggct ttgagaatga cagggcatgc tagcaggtca ggtcaactgc ctgtgagact      2060 gtcatctctg cccacatgta cagcgtccct ctgacattaa atatcttttt actgaaaaaa      2120 aaaaaaaaa                                                              2129

<210> SEQ ID NO 54
<211> LENGTH: 372
<212> TYPE: PRT
<213> ORGANISM: Mus musculus
```

<400> SEQUENCE: 54

```
Met Leu Val Pro Gly His Trp Asp Gly Leu Arg Pro Ala Met Pro Ser
 1               5                  10                  15

Leu Leu Leu Val Val Ala Leu Leu Ser Ser Trp Ala Gln Leu
             20                  25                  30

Leu Thr Asp Ala Asn Ser Trp Trp Ser Leu Ala Leu Asn Pro Val Gln
         35                  40                  45

Arg Pro Glu Met Phe Ile Ile Gly Ala Gln Pro Val Cys Ser Gln Leu
     50                  55                  60

Pro Gly Leu Ser Pro Gly Gln Arg Lys Leu Cys Gln Leu Tyr Gln Glu
 65                  70                  75                  80

His Met Ser Tyr Ile Gly Glu Gly Ala Lys Thr Gly Ile Arg Glu Cys
                 85                  90                  95

Gln His Gln Phe Arg Gln Arg Trp Asn Cys Ser Thr Val Asp Asn
            100                 105                 110

Thr Ser Val Phe Gly Arg Val Met Gln Ile Gly Ser Arg Glu Thr Ala
            115                 120                 125

Phe Thr Tyr Ala Val Ser Ala Ala Gly Val Val Asn Ala Ile Ser Arg
        130                 135                 140

Ala Cys Arg Glu Gly Glu Leu Ser Thr Cys Gly Cys Ser Arg Ala Ala
145                 150                 155                 160

Arg Pro Lys Asp Leu Pro Arg Asp Trp Leu Trp Gly Gly Cys Gly Asp
                165                 170                 175

Asn Val Glu Tyr Gly Tyr Arg Phe Ala Lys Glu Phe Val Asp Ala Arg
            180                 185                 190

Glu Arg Glu Lys Asn Phe Ala Lys Gly Ser Glu Glu Gln Gly Arg Ala
        195                 200                 205

Leu Met Asn Leu Gln Asn Asn Glu Ala Gly Arg Arg Ala Val Tyr Lys
    210                 215                 220

Met Ala Asp Val Ala Cys Lys Cys His Gly Val Ser Gly Ser Cys Ser
225                 230                 235                 240

Leu Lys Thr Cys Trp Leu Gln Leu Ala Glu Phe Arg Lys Val Gly Asp
                245                 250                 255

Arg Leu Lys Glu Lys Tyr Asp Ser Ala Ala Ala Met Arg Ile Thr Arg
            260                 265                 270

Gln Gly Lys Leu Glu Leu Ala Asn Ser Arg Phe Asn Gln Pro Thr Pro
        275                 280                 285

Glu Asp Leu Val Tyr Val Asp Pro Ser Pro Asp Tyr Cys Leu Arg Asn
    290                 295                 300

Glu Thr Thr Gly Ser Leu Gly Thr Gln Gly Arg Leu Cys Asn Lys Thr
305                 310                 315                 320

Ser Glu Gly Met Asp Gly Cys Glu Leu Met Cys Cys Gly Arg Gly Tyr
                325                 330                 335

Asp Arg Phe Lys Ser Val Gln Val Glu Arg Cys His Cys Arg Phe His
            340                 345                 350

Trp Cys Cys Phe Val Arg Cys Lys Lys Cys Thr Glu Val Val Asp Gln
        355                 360                 365

Tyr Val Cys Lys
    370
```

<210> SEQ ID NO 55
<211> LENGTH: 1669
<212> TYPE: DNA
<213> ORGANISM: Mus musculus

```
<220> FEATURE:
<221> NAME/KEY: CDS
<222> LOCATION: (189)..(1283)

<400> SEQUENCE: 55
ccgccgcgcc ctcctcgccc gggatgggcc ccccgccgc accgccgcc ggagccctag      60 tctccgggcc gccgcctcgg tcgccgcgtt tgccctgaag cccggtgccc gcgcgccccg    120
gctcaccccg cagcttcact ccccaccccc agccgcctcc ccggcagac tgcggtagag    180 ctctcagg atg ctg ccg ccg gtg ccc tcc cgc ctc gga ctg ctg ctg ctg   230
         Met Leu Pro Pro Val Pro Ser Arg Leu Gly Leu Leu Leu
         1               5                   10 ctc ttg tgc ccc gcg cac gtc gat gga ctg tgg tgg gcc gtg ggc agc    278
Leu Leu Cys Pro Ala His Val Asp Gly Leu Trp Trp Ala Val Gly Ser
15                  20                  25                  30 ccc ttg gtc atg gat cct acc agc atc tgc agg aag gcc agg cgg ctg    326
Pro Leu Val Met Asp Pro Thr Ser Ile Cys Arg Lys Ala Arg Arg Leu
                35                  40                  45 gca gga aga cag gcc gag ctg tgc cag gcg gag ccg gaa gta gtg gca    374
Ala Gly Arg Gln Ala Glu Leu Cys Gln Ala Glu Pro Glu Val Val Ala
            50                  55                  60 gag ctt gcc cga ggc gca aga ctg ggg gtt cga gaa tgt cag ttc cag    422
Glu Leu Ala Arg Gly Ala Arg Leu Gly Val Arg Glu Cys Gln Phe Gln
        65                  70                  75 ttc cgt ttc cga cgc tgg aac tgc tcc agc cac agc aag gcc ttt ggg    470
Phe Arg Phe Arg Arg Trp Asn Cys Ser Ser His Ser Lys Ala Phe Gly
80                  85                  90 cgc gtc ctg cag cag gac atc cga gag aca gct ttc gtg ttt gca atc    518
Arg Val Leu Gln Gln Asp Ile Arg Glu Thr Ala Phe Val Phe Ala Ile
95                  100                 105                 110 acc gca gct ggt gcc agc cac gcg gtc act caa gcc tgt tcc atg gga    566
Thr Ala Ala Gly Ala Ser His Ala Val Thr Gln Ala Cys Ser Met Gly
                115                 120                 125 gag ctc cta cag tgt ggt tgt cag gca ccc cgc ggg cgg gca ccg cct    614
Glu Leu Leu Gln Cys Gly Cys Gln Ala Pro Arg Gly Arg Ala Pro Pro
            130                 135                 140 agg ccc tcc ggc ctt ctg ggc act cct gga cct cca gga cca act ggc    662
Arg Pro Ser Gly Leu Leu Gly Thr Pro Gly Pro Pro Gly Pro Thr Gly
        145                 150                 155 tct cca gat gct agc gca gcc tgg gag tgg gga ggc tgc gga gac gat    710
Ser Pro Asp Ala Ser Ala Ala Trp Glu Trp Gly Gly Cys Gly Asp Asp
160                 165                 170 gtg gac ttc ggg gat gag aag tca aga ctc ttt atg gat gcg cag cac    758
Val Asp Phe Gly Asp Glu Lys Ser Arg Leu Phe Met Asp Ala Gln His
175                 180                 185                 190 aag cgg ggc cgt gga gat atc cgt gca ttg gtg caa ctg cac aac aac    806
Lys Arg Gly Arg Gly Asp Ile Arg Ala Leu Val Gln Leu His Asn Asn
                195                 200                 205 gag gcg ggc agg ctg gcg gtg cgg agt cac acg cgc acc gag tgt aag    854
Glu Ala Gly Arg Leu Ala Val Arg Ser His Thr Arg Thr Glu Cys Lys
            210                 215                 220 tgc cat ggg ctt tcg ggt tcc tgc gct ctg cgc acc tgc tgg cag aag    902
Cys His Gly Leu Ser Gly Ser Cys Ala Leu Arg Thr Cys Trp Gln Lys
        225                 230                 235 ctg cct ccg ttc cgc gag gtg ggc gca cgg ctg ctg gag cgc ttc cac    950
Leu Pro Pro Phe Arg Glu Val Gly Ala Arg Leu Leu Glu Arg Phe His
240                 245                 250 ggc gcc tcg cgc gtc atg ggc acc aac gac ggc aaa gct ctg ctg cct    998
Gly Ala Ser Arg Val Met Gly Thr Asn Asp Gly Lys Ala Leu Leu Pro
255                 260                 265                 270
```

```
gcg gtc cgc aca ctc aag cct ccc gga cga gcg gat ctc ctc tac gca    1046
Ala Val Arg Thr Leu Lys Pro Pro Gly Arg Ala Asp Leu Leu Tyr Ala
            275                 280                 285 gcc gat tca ccc gac ttc tgc gcc ccc aac cgg cgc acg ggt tcg ccg    1094
Ala Asp Ser Pro Asp Phe Cys Ala Pro Asn Arg Arg Thr Gly Ser Pro
        290                 295                 300 ggc acg cgc gga cgc gcc tgc aac agc agt gcc ccg gac ctc agc ggc    1142
Gly Thr Arg Gly Arg Ala Cys Asn Ser Ser Ala Pro Asp Leu Ser Gly
        305                 310                 315 tgc gac ctg ttg tgc tgc ggt cgc ggg cac cgc cag gag agc gta cag    1190
Cys Asp Leu Leu Cys Cys Gly Arg Gly His Arg Gln Glu Ser Val Gln
320                 325                 330 ctc gag gag aac tgt ctg tgc cgc ttc cac tgg tgc tgc gtg gtg caa    1238
Leu Glu Glu Asn Cys Leu Cys Arg Phe His Trp Cys Cys Val Val Gln
335                 340                 345                 350 tgc cac cgc tgc cgg gtg cgc aag gaa ctc agc ctg tgc ctc tga        1283
Cys His Arg Cys Arg Val Arg Lys Glu Leu Ser Leu Cys Leu
                355                 360                 365 cccgtcgcct gcctcggaac tgctggcagc cacctctggg ccatctcag gactattaga   1343 ttccagcagg gggcgctgtc tgagtccagc agctccctag gaaaagtacc tatccaggcc  1403
ttgggaaatt acaggggcca gccaggaact tggggtttac accagcccac gaaagcccgg  1463
gggaacatac ccctccagca ttcccctgaa aggccctttg ctagttcctg caggagatca  1523
ctccccttgg ccccccagat ggaaataaga aagccagact ctgccctctg gaataatat   1583 tcctcagaat tactgggatg gatgggtgag tttagtatca ataagacat ttaaatccac   1643 aaaaaaaaaa aaaaaaaaaa aaaaaa                                       1669

<210> SEQ ID NO 56
<211> LENGTH: 364
<212> TYPE: PRT
<213> ORGANISM: Mus musculus

<400> SEQUENCE: 56

Met Leu Pro Pro Val Pro Ser Arg Leu Gly Leu Leu Leu Leu Leu Leu
1               5                   10                  15

Cys Pro Ala His Val Asp Gly Leu Trp Trp Ala Val Gly Ser Pro Leu
            20                  25                  30

Val Met Asp Pro Thr Ser Ile Cys Arg Lys Ala Arg Arg Leu Ala Gly
        35                  40                  45

Arg Gln Ala Glu Leu Cys Gln Ala Glu Pro Val Val Ala Glu Leu
    50                  55                  60

Ala Arg Gly Ala Arg Leu Gly Val Arg Glu Cys Gln Phe Gln Phe Arg
65                  70                  75                  80

Phe Arg Arg Trp Asn Cys Ser Ser His Ser Lys Ala Phe Gly Arg Val
                85                  90                  95

Leu Gln Gln Asp Ile Arg Glu Thr Ala Phe Val Phe Ala Ile Thr Ala
            100                 105                 110

Ala Gly Ala Ser His Ala Val Thr Gln Ala Cys Ser Met Gly Glu Leu
        115                 120                 125

Leu Gln Cys Gly Cys Gln Ala Pro Arg Gly Arg Ala Pro Pro Arg Pro
    130                 135                 140

Ser Gly Leu Leu Gly Thr Pro Gly Pro Pro Gly Pro Thr Gly Ser Pro
145                 150                 155                 160

Asp Ala Ser Ala Ala Trp Glu Trp Gly Gly Cys Gly Asp Asp Val Asp
                165                 170                 175
```

```
Phe Gly Asp Glu Lys Ser Arg Leu Phe Met Asp Ala Gln His Lys Arg
            180                 185                 190
Gly Arg Gly Asp Ile Arg Ala Leu Val Gln Leu His Asn Asn Glu Ala
        195                 200                 205
Gly Arg Leu Ala Val Arg Ser His Thr Arg Thr Glu Cys Lys Cys His
    210                 215                 220
Gly Leu Ser Gly Ser Cys Ala Leu Arg Thr Cys Trp Gln Lys Leu Pro
225                 230                 235                 240
Pro Phe Arg Glu Val Gly Ala Arg Leu Leu Glu Arg Phe His Gly Ala
                245                 250                 255
Ser Arg Val Met Gly Thr Asn Asp Gly Lys Ala Leu Leu Pro Ala Val
            260                 265                 270
Arg Thr Leu Lys Pro Pro Gly Arg Ala Asp Leu Leu Tyr Ala Ala Asp
        275                 280                 285
Ser Pro Asp Phe Cys Ala Pro Asn Arg Arg Thr Gly Ser Pro Gly Thr
    290                 295                 300
Arg Gly Arg Ala Cys Asn Ser Ser Ala Pro Asp Leu Ser Gly Cys Asp
305                 310                 315                 320
Leu Leu Cys Cys Gly Arg Gly His Arg Gln Glu Ser Val Gln Leu Glu
                325                 330                 335
Glu Asn Cys Leu Cys Arg Phe His Trp Cys Cys Val Val Gln Cys His
            340                 345                 350
Arg Cys Arg Val Arg Lys Glu Leu Ser Leu Cys Leu
        355                 360
```

```
<210> SEQ ID NO 57
<211> LENGTH: 3189
<212> TYPE: DNA
<213> ORGANISM: Mus musculus
<220> FEATURE:
<221> NAME/KEY: CDS
<222> LOCATION: (255)..(1304)

<400> SEQUENCE: 57
```

```
cccgcgcctc aaacacttgc cgcgatcgct ggcgcgcagc ggcgccccTT gttgcgcttg     60
ttctcccctc ctctggctcc gcggctcccg cgctctggga cagtctccag tgcctagcgc    120
ggaccgacgc accgacggac cgcccaggga gcctcggccc gcgccccctg cgcaggctat    180
gtggattgcc ccgccgggcc cggctggcgg gatcagcaca gcccggcccg tggcacccgc    240
caccagcggg gact atg acc cgg aaa gcg cgg cgc tgc ctg ggc cac ctc       290
              Met Thr Arg Lys Ala Arg Arg Cys Leu Gly His Leu
                1               5                   10 ttt ctc agc ctg ggc ata gtc tac ctc cgg atc ggt ggc ttc tct tcg      338
Phe Leu Ser Leu Gly Ile Val Tyr Leu Arg Ile Gly Gly Phe Ser Ser
            15                  20                  25 gtg gta gct ctg ggt gcg agc atc atc tgt aac aag atc cca ggc ctg      386
Val Val Ala Leu Gly Ala Ser Ile Ile Cys Asn Lys Ile Pro Gly Leu
        30                  35                  40 gct ccc aga cag cgg gca atc tgc cag agc cgg ccg gac gcc atc atc      434
Ala Pro Arg Gln Arg Ala Ile Cys Gln Ser Arg Pro Asp Ala Ile Ile
    45                  50                  55                  60 gtc ata gga gaa ggc tcc caa atg ggc ctg gac gag tgt cag ttt cag      482
Val Ile Gly Glu Gly Ser Gln Met Gly Leu Asp Glu Cys Gln Phe Gln
                65                  70                  75 ttc cga aat ggc cgt tgg aac tgc tca gcg ctg gga gag cgt act gtc      530
Phe Arg Asn Gly Arg Trp Asn Cys Ser Ala Leu Gly Glu Arg Thr Val
            80                  85                  90
```

-continued

| | | |
|---|---|---|
| ttc ggg aag gag ctc aaa gtg ggg agt cgg gag gct gcc ttc acc tat<br>Phe Gly Lys Glu Leu Lys Val Gly Ser Arg Glu Ala Ala Phe Thr Tyr<br>         95                             100                          105 | 578 |

```
ttc ggg aag gag ctc aaa gtg ggg agt cgg gag gct gcc ttc acc tat      578
Phe Gly Lys Glu Leu Lys Val Gly Ser Arg Glu Ala Ala Phe Thr Tyr
         95                  100                 105 gcg att atc gct gcg ggc gtg gcc cat gcc atc act gct gcc tgc acc      626
Ala Ile Ile Ala Ala Gly Val Ala His Ala Ile Thr Ala Ala Cys Thr
    110                 115                 120 cag ggc aac ctg agc gac tgt ggc tgc gac aag gag aag caa ggc cag      674
Gln Gly Asn Leu Ser Asp Cys Gly Cys Asp Lys Glu Lys Gln Gly Gln
125                 130                 135                 140 tac cac cgg gac gag ggc tgg aag tgg ggt ggc tgc tct gcc gac atc      722
Tyr His Arg Asp Glu Gly Trp Lys Trp Gly Gly Cys Ser Ala Asp Ile
                145                 150                 155 cgc tac ggc atc ggc ttc gcc aag gtc ttc gtg gat gcc cgg gag atc      770
Arg Tyr Gly Ile Gly Phe Ala Lys Val Phe Val Asp Ala Arg Glu Ile
            160                 165                 170 aag cag aat gcc cgg acg ctc atg aac tta cac aat aac gag gcg ggt      818
Lys Gln Asn Ala Arg Thr Leu Met Asn Leu His Asn Asn Glu Ala Gly
        175                 180                 185 cgg aag atc ctg gag gag aac atg aag ctg gag tgt aag tgc cat ggt      866
Arg Lys Ile Leu Glu Glu Asn Met Lys Leu Glu Cys Lys Cys His Gly
    190                 195                 200 gtg tca ggc tcc tgt acc act aag acg tgc tgg acc aca ctg cca cag      914
Val Ser Gly Ser Cys Thr Thr Lys Thr Cys Trp Thr Thr Leu Pro Gln
205                 210                 215                 220 ttc cga gag cta ggc tac gtg ctc aag gac aaa tac aac gag gcc gtc      962
Phe Arg Glu Leu Gly Tyr Val Leu Lys Asp Lys Tyr Asn Glu Ala Val
                225                 230                 235 cac gtg gag cct gtg cgt gcc agt cga aac aag cgg ccc acc ttt ctg     1010
His Val Glu Pro Val Arg Ala Ser Arg Asn Lys Arg Pro Thr Phe Leu
            240                 245                 250 aag atc aag aag ccc ctg tcc tac cgc aag ccc atg gac act gac ctg     1058
Lys Ile Lys Lys Pro Leu Ser Tyr Arg Lys Pro Met Asp Thr Asp Leu
        255                 260                 265 gtg tat atc gag aag tca ccc aat tac tgt gaa gag gac cca gtg aca     1106
Val Tyr Ile Glu Lys Ser Pro Asn Tyr Cys Glu Glu Asp Pro Val Thr
    270                 275                 280 ggc agc gtg ggt acc cag ggc cga gcc tgc aat aag aca gcc cct cag     1154
Gly Ser Val Gly Thr Gln Gly Arg Ala Cys Asn Lys Thr Ala Pro Gln
285                 290                 295                 300 gcc agt ggc tgt gac ctc atg tgc tgt ggc cgt ggc tac aac aca cac     1202
Ala Ser Gly Cys Asp Leu Met Cys Cys Gly Arg Gly Tyr Asn Thr His
                305                 310                 315 cag tac gcc cgg gtg tgg cag tgc aac tgc aaa ttc cac tgg tgc tgc     1250
Gln Tyr Ala Arg Val Trp Gln Cys Asn Cys Lys Phe His Trp Cys Cys
            320                 325                 330 tac gtc aag tgt aac acg tgc agc gag cgc acg gag atg tat acg tgc     1298
Tyr Val Lys Cys Asn Thr Cys Ser Glu Arg Thr Glu Met Tyr Thr Cys
        335                 340                 345 aag tga atgcggtcac aggtcagatc acaggcagga tacagtttcc ctgcaggcca     1354
Lys
    350 ctgcctggat gctcacaggg aaagaaccac agaagcactg tccttgtctt ttctgctgag   1414 gggggagggg tattctgggt ttcctgcaga ctcccgtggg aagcatctct cagaggcccg   1474 cccattcttc tccacatgga tgctgctcag ccaccctccc ccagacaccg cccgagcctc   1534 tccagggctg gaacaaagtt ttctacggca ggagctctgg agcctcgggc ctcgtcatag   1594 caatatttaa cagtttattc tgatatgaga taatattaat ttatttaatt aaagagaatt   1654
```

```
cttccacttc gtcgggatcc gtcttctgca atcaaagtgg actgcttgag gtcctggtgg      1714
gatgacttgc taggactggg agctgagaac agctgtacat aattattctt tatgcagatg      1774
tttctactag ttgatttcac aagtacccct ctgcagcgct aggtgttaag tacaaagaga      1834
agacggtctt tatacacata tagatatata tatgcataca catttgtaac tttgttttgt      1894
tttgttttg  ctgtttgctg ctacctatcc agactctaag ctggtccaga tctggaattg      1954
tttttctcca ggacgtgctc ctatccttt  gcccttttaca gttcaaacct ctccgttaga     2014
aaagttccat tgggaatggc gtgtgtgtga tggggacgag gatcacaaat tcccagcagt      2074
ttccatcctg aaacgtgaac cactggataa gaggctttct aagagactat ttttctatgg      2134
atattttatt tatatggagt ctgcctgcgg tgccccatgg cccatgcctc ttcttaacac      2194
tggtactcac tcaggggcag aaggacaagg ccaggtgtgt gggcaggtcc cccgggacc       2254
ctcacacagc tggagcctgg agttctattt gccaaggggg ccatagcagt taccagatgc      2314
ctgggttggg tatcttctgt gttaaacaag agggaaccat cccctggctt tagcctgcta      2374
agctcagggc ttggaatggg gtcactggat ggttatcttg ggagatgacc tctggatgag      2434
cctcagcggt gggtcagtca gtgtctcaca cactttgaga agcatgggac ctggcattca      2494
tcatcaggca gaggccagct cagggatgcc gctatcccat caggacagcc caggcactgc      2554
ctctaggtga ggtgtagtcc taagagaagg ggtcaaggag ggggaaggag gaagccaagg      2614
agtgttggcc atcctcagtg aaagcgatgg gagcgttctc tcagcagcag agacacagct      2674
gtacctgtat ctctccaatg ggaaaccccct ccagaaggct ggggatattt tttatgtgtt     2734
tccacatgca tttccacctg tgtgcatgta agcacatgcg cacactcctg tgccagcact      2794
ctgcggcacc tccagggtgc tcacgggtac atgtgcttac atgtatctct ctgtgcttgg      2854
gagatcagac catgtgcatg gagctgtatg cctgagcact tgtggtctca ggggttattt      2914
ccaggtatct gcatttgtgg gtggggtgca aggtagacag cagggaactg atttgattgt      2974
gttgagccac agtgagactg caactctgaa ctctgtctcc acagctgctg gtgaaactca      3034
gatgcctgtg agacaacagc cctgagcctc atggcccaca tgctgggagc ccctcagtgt      3094
ctaggtcatg tccagtcccc cacctgggtt acatcacgac caataaacat ggctgtatgg      3154
ctgatttctt cccttgaaaa aaaaaaaaaa aaaaa                                 3189
```

<210> SEQ ID NO 58
<211> LENGTH: 349
<212> TYPE: PRT
<213> ORGANISM: Mus musculus

<400> SEQUENCE: 58

```
Met Thr Arg Lys Ala Arg Arg Cys Leu Gly His Leu Phe Leu Ser Leu
  1               5                  10                  15

Gly Ile Val Tyr Leu Arg Ile Gly Gly Phe Ser Ser Val Val Ala Leu
             20                  25                  30

Gly Ala Ser Ile Ile Cys Asn Lys Ile Pro Gly Leu Ala Pro Arg Gln
         35                  40                  45

Arg Ala Ile Cys Gln Ser Arg Pro Asp Ala Ile Val Ile Gly Glu
     50                  55                  60

Gly Ser Gln Met Gly Leu Asp Glu Cys Gln Phe Gln Phe Arg Asn Gly
 65                  70                  75                  80

Arg Trp Asn Cys Ser Ala Leu Gly Glu Arg Thr Val Phe Gly Lys Glu
                 85                  90                  95

Leu Lys Val Gly Ser Arg Glu Ala Ala Phe Thr Tyr Ala Ile Ile Ala
```

```
              100                 105                 110
Ala Gly Val Ala His Ala Ile Thr Ala Ala Cys Thr Gln Gly Asn Leu
            115                 120                 125

Ser Asp Cys Gly Cys Asp Lys Glu Lys Gln Gly Gln Tyr His Arg Asp
        130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 59
<211> LENGTH: 3154
<212> TYPE: DNA
<213> ORGANISM: Mus musculus
<220> FEATURE:
<221> NAME/KEY: CDS
<222> LOCATION: (133)..(1182)

<400> SEQUENCE: 59
cgcccgcctc ccgagccgaa gcgccggctg agcgtggtcc taccgcagct ccctggctcc      60 tgccggccc ctgccaccc gcgcgtcccc tccggccgca gctgtctatg gcgcagcccc      120
cctccctgga tc atg cac aga aac ttt cga aag tgg atc ttt tac gtg ttt    171
              Met His Arg Asn Phe Arg Lys Trp Ile Phe Tyr Val Phe
                1               5                  10 ctc tgc ttt ggc gtc ctc tac gtg aag ctc gga gca ttg tca tcc gtg      219
Leu Cys Phe Gly Val Leu Tyr Val Lys Leu Gly Ala Leu Ser Ser Val
    15                  20                  25 gtg gcc ctg gta gcc aac atc atc tgc aac aag att cct ggc ctg gcc      267
Val Ala Leu Val Ala Asn Ile Ile Cys Asn Lys Ile Pro Gly Leu Ala
30                  35                  40                  45 cca cgg cag cgt gcc atc tgc cag agc cga ccc gat gcc atc att gtg      315
Pro Arg Gln Arg Ala Ile Cys Gln Ser Arg Pro Asp Ala Ile Ile Val
                50                  55                  60 atc ggg gag ggg gcg cag atg ggc atc gac gag tgc cag cac cag ttc      363
```

```
               Ile Gly Glu Gly Ala Gln Met Gly Ile Asp Glu Cys Gln His Gln Phe
                           65                  70                  75 cga ttc ggc cgc tgg aac tgc tcc gcc ctg ggc gag aag acc gtc ttc         411
Arg Phe Gly Arg Trp Asn Cys Ser Ala Leu Gly Glu Lys Thr Val Phe
             80                  85                  90 ggg caa gaa ctc cga gta ggg agt cga gag gct gcc ttc acc tat gcc         459
Gly Gln Glu Leu Arg Val Gly Ser Arg Glu Ala Ala Phe Thr Tyr Ala
         95                 100                 105 atc acg gcg gcg ggc gtg gcg cat gct gtc acc gct gcc tgc agc cag         507
Ile Thr Ala Ala Gly Val Ala His Ala Val Thr Ala Ala Cys Ser Gln
110                 115                 120                 125 ggc aat ctg agc aat tgt ggc tgt gac cgg gag aag caa ggc tac tac         555
Gly Asn Leu Ser Asn Cys Gly Cys Asp Arg Glu Lys Gln Gly Tyr Tyr
                130                 135                 140 aac cag gcg gaa ggc tgg aag tgg ggg ggc tgc tca gcg gac gtc cgc         603
Asn Gln Ala Glu Gly Trp Lys Trp Gly Gly Cys Ser Ala Asp Val Arg
            145                 150                 155 tac ggc atc gac ttt tct cgt cgc ttt gtg gat gcc cgt gag atc aaa         651
Tyr Gly Ile Asp Phe Ser Arg Arg Phe Val Asp Ala Arg Glu Ile Lys
        160                 165                 170 aag aac gcc agg cgc ctc atg aac ctt cac aac aat gag gcg ggc aga         699
Lys Asn Ala Arg Arg Leu Met Asn Leu His Asn Asn Glu Ala Gly Arg
175                 180                 185 aag gtt ctg gag gac cgc atg aag ctg gaa tgt aag tgt cac ggt gtg         747
Lys Val Leu Glu Asp Arg Met Lys Leu Glu Cys Lys Cys His Gly Val
190                 195                 200                 205 tca ggc tcc tgt acc acc aaa act tgc tgg acc acg cta cct aag ttc         795
Ser Gly Ser Cys Thr Thr Lys Thr Cys Trp Thr Thr Leu Pro Lys Phe
                210                 215                 220 cgc gag gtg ggc cac ctg ctc aag gag aag tac aac gca gcg gtg cag         843
Arg Glu Val Gly His Leu Leu Lys Glu Lys Tyr Asn Ala Ala Val Gln
            225                 230                 235 gtg gag gtg gtg cga gcc agc cgc ctg cgc cag ccc acc ttc ctg cgc         891
Val Glu Val Val Arg Ala Ser Arg Leu Arg Gln Pro Thr Phe Leu Arg
        240                 245                 250 atc aag cag cta cgc agc tac cag aag cct atg gag acg gac ctg gtg         939
Ile Lys Gln Leu Arg Ser Tyr Gln Lys Pro Met Glu Thr Asp Leu Val
255                 260                 265 tac atc gag aag tcg ccc aac tac tgc gag gag gac gcg gcc acg ggc         987
Tyr Ile Glu Lys Ser Pro Asn Tyr Cys Glu Glu Asp Ala Ala Thr Gly
270                 275                 280                 285 agc gtg ggc acg cag ggc cgt ctg tgc aac cgc acc tcg ccg ggg gcc        1035
Ser Val Gly Thr Gln Gly Arg Leu Cys Asn Arg Thr Ser Pro Gly Ala
                290                 295                 300 gac ggc tgt gac acc atg tgc tgc ggc cgc ggc tac aac acg cac cag        1083
Asp Gly Cys Asp Thr Met Cys Cys Gly Arg Gly Tyr Asn Thr His Gln
            305                 310                 315 tac acc aag gtg tgg cag tgt aac tgc aaa ttc cac tgg tgt tgc ttc        1131
Tyr Thr Lys Val Trp Gln Cys Asn Cys Lys Phe His Trp Cys Cys Phe
        320                 325                 330 gtc aag tgc aac acg tgc agc gag cgc acc gag gtc ttc acc tgc aag        1179
Val Lys Cys Asn Thr Cys Ser Glu Arg Thr Glu Val Phe Thr Cys Lys
335                 340                 345 tga ggctcccgcg caggcgcgct cggcccctgc cgaccctgcg gccctcgcca             1232
ttattttgca catccttctt tgcttctgga gctgccagct gcaggcacag gagggtgggg      1292
atagaggtgg ggagctcgag atactccagg ctccttccta ctcgtctgt ccccgcccag      1352 catccaaggt caacgcaatg gtggtctggt acccaatgga gacaaatccc tttacttctc     1412
```

```
tttgggaaag tgaaccacaa agggaccatg agactctgag ggtcacctcc ctgcctgtga    1472
ctggacacag aaaggccaca cccaccagtc acactcaaaa cggtttcctg ggctgtttcc    1532
tgccggccct gggcagtgtg gatggatgtt gacaaaatta tttatgtttt cttagcatca    1592
gatgaggact cagtactaac gactgggtag ccagacctaa ccctatttga ggacacccctt   1652 ccctcactcc tcccggcccc tccctgcagg gtcctctgct ccttgcagaa ctcgaggatg    1712
tcagaattgg cacggaagct ggctggtggg gggactcctt atcagcacct tgggaggggc    1772
ttggtggccc tacaaggcct gagatggccg cagaggacag ccaatcttcc attccatttg    1832
gagactgtca tgcaaatcaa atgtcccttg tgtcaggctc caggcatgcc tcgtcctctc    1892
cctggtcctt caccctccca gcctgctgcc aacctccacc tccagtttac aaattctctt    1952
ctcctctgga gccaacctga cacccaggac tgccccacag gttcaggaga ggtcagggac    2012
agttgcccca catgacagat ggacagaggg caatctgaag atttactgga gccccacgg    2072 ctctgtgaaa taaatatact gacacagccc catccagccc aactctggaa gttgccaggg    2132
tgatgggagg ctgcaccccc ttttcagtac ctggggtttt gtccttcttc tgtgatcctg    2192
atgccagaga actgacatcc agaatttagg gatgtattgg tcaggccccc tgcctagtgt    2252
ccactgatac ctgcttcagg gtccttatat tatgaggaca tgggaccctc aaacaggggt    2312
ccgtgggaag cttaatgtcc catttcctca ggcccttcca gatggggaca gaagaactca    2372
ggcctgggca tatcccaccc tttcctccac aacacatggc agggtaagaa actgccaggg    2432
ctgataatac aactgcccac agcctacccc acactaaggt gtttcatagc agaagtccat    2492
ggaaatgtgg ggtttggtgg ccaccaagcc aggtggcctg acattgacc tggggaaggt     2552 gacccttgtt tgcccttgcc ttgcatccag ctgtgtgtcc ctatcatgtc aggatgttcc    2612
aagcctctgg gccactggaa atgtcccacc ctgatcctgg ccccatctcc tcaccccaag    2672
tcctgggata cccacgtccg tcgcccagtg tccctgtga ggagcctggt taacttatat      2732
tgttatatag cgtcccctgt ctgtcatgtc tcttaagtta ttgtgaccta cactgggtac    2792 cggagggggat gggggatggc ttcagctgct gtccccaag ccaggctcct ccttctgctt    2852
gaaacagacc ctcgggggcc cctgatgcca ccgaggcaat tcgcactgtc cctgggctgc    2912
caggcacctg cgcctgcact cggtcagccg cagaccttgc cttgggggag agaggtggtt    2972
agtggaccca ggcagggcac tggctgtccc aatgctgtgt gctggggtgg aggtggccgg    3032
gcaccacatg tccttgaagt gccctacttc tgatgggctg tgttcctgcc tcctctggag    3092
gggagcactt agccccaata aaagctggaa tcagaaaaaa aaaaaaaaa aaaaaaaaa      3152 aa                                                                    3154
```

<210> SEQ ID NO 60
<211> LENGTH: 349
<212> TYPE: PRT
<213> ORGANISM: Mus musculus

<400> SEQUENCE: 60

```
Met His Arg Asn Phe Arg Lys Trp Ile Phe Tyr Val Phe Leu Cys Phe
 1               5                  10                  15

Gly Val Leu Tyr Val Lys Leu Gly Ala Leu Ser Ser Val Val Ala Leu
             20                  25                  30

Val Ala Asn Ile Ile Cys Asn Lys Ile Pro Gly Leu Ala Pro Arg Gln
         35                  40                  45

Arg Ala Ile Cys Gln Ser Arg Pro Asp Ala Ile Ile Val Ile Gly Glu
     50                  55                  60
```

```
Gly Ala Gln Met Gly Ile Asp Glu Cys Gln His Gln Phe Arg Phe Gly
 65                  70                  75                  80

Arg Trp Asn Cys Ser Ala Leu Gly Glu Lys Thr Val Phe Gly Gln Glu
                 85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Lys Leu Glu Cys Lys Cys His Gly Val Ser Gly Ser
        195                 200                 205

Cys Thr Thr Lys Thr Cys Trp Thr Thr Leu Pro Lys Phe Arg Glu Val
210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Asp Ala Ala Thr Gly Ser Val Gly
        275                 280                 285

Thr Gln Gly Arg Leu Cys Asn Arg Thr Ser Pro Gly Ala Asp Gly Cys
290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
            340                 345

<210> SEQ ID NO 61
<211> LENGTH: 1747
<212> TYPE: DNA
<213> ORGANISM: Mus musculus
<220> FEATURE:
<221> NAME/KEY: CDS
<222> LOCATION: (57)..(1121)

<400> SEQUENCE: 61
gctctgccga ccttacttct ctgcgcttgg tcctggttcc cggactgggc aggacc atg      59
                                                              Met
                                                               1 gga cac ttg tta atg ctg tgg gtg gct gcg ggc atg tgc tat cca gcc      107
Gly His Leu Leu Met Leu Trp Val Ala Ala Gly Met Cys Tyr Pro Ala
        5                   10                  15 ctg ggt gct tct gcc tgg tca gtg aac aac ttc ctg ata acc ggt ccc      155
Leu Gly Ala Ser Ala Trp Ser Val Asn Asn Phe Leu Ile Thr Gly Pro
    20                  25                  30 aag gcc tat ctg acc tac acc gcc agt gtg gcc ttg gga gct cag att      203
```

```
                -continued

Lys Ala Tyr Leu Thr Tyr Thr Ala Ser Val Ala Leu Gly Ala Gln Ile
 35                  40                  45 ggc atc gaa gag tgt aag ttc cag ttt gcc tgg gaa cgg tgg aat tgt      251
Gly Ile Glu Glu Cys Lys Phe Gln Phe Ala Trp Glu Arg Trp Asn Cys
 50                  55                  60                  65 cct gag cat gct ttt cag ttt tca acc cac aac agg ctg cga gct gcc      299
Pro Glu His Ala Phe Gln Phe Ser Thr His Asn Arg Leu Arg Ala Ala
                 70                  75                  80 acg aga gag aca tcc ttc att cat gcc atc cgc tct gcc gcc atc atg      347
Thr Arg Glu Thr Ser Phe Ile His Ala Ile Arg Ser Ala Ala Ile Met
             85                  90                  95 tac gca gtc acc aag aac tgc agc atg ggt gac ttg gaa aac tgc ggc      395
Tyr Ala Val Thr Lys Asn Cys Ser Met Gly Asp Leu Glu Asn Cys Gly
         100                 105                 110 tgt gac gag tca caa aat gga aaa aca ggt ggc cat ggc tgg atc tgg      443
Cys Asp Glu Ser Gln Asn Gly Lys Thr Gly Gly His Gly Trp Ile Trp
     115                 120                 125 gga ggc tgc agc gac aac gtg gag ttc ggg gaa aaa atc tcc aga ctc      491
Gly Gly Cys Ser Asp Asn Val Glu Phe Gly Glu Lys Ile Ser Arg Leu
130                 135                 140                 145 ttc gtg gac agt ttg gag aaa ggg aag gat gcc aga gcc ctg gtg aac      539
Phe Val Asp Ser Leu Glu Lys Gly Lys Asp Ala Arg Ala Leu Val Asn
                150                 155                 160 ctt cac aac aac agg gcc ggc aga ctg gca gtg agg gcc tcc acg aaa      587
Leu His Asn Asn Arg Ala Gly Arg Leu Ala Val Arg Ala Ser Thr Lys
            165                 170                 175 agg acc tgc aag tgt cat ggc atc tca gga agc tgc agc atc cag acg      635
Arg Thr Cys Lys Cys His Gly Ile Ser Gly Ser Cys Ser Ile Gln Thr
        180                 185                 190 tgt tgg ctg cag ctg gct gac ttc cgg cag atg gga aat tac cta aag      683
Cys Trp Leu Gln Leu Ala Asp Phe Arg Gln Met Gly Asn Tyr Leu Lys
    195                 200                 205 gcc aag tat gac cgc gcg ctg aaa att gag atg gac aag cgc cag cta      731
Ala Lys Tyr Asp Arg Ala Leu Lys Ile Glu Met Asp Lys Arg Gln Leu
210                 215                 220                 225 agg gct ggc aac aga gcc gag ggc cgc tgg gct ctc acg gag gcc ttc      779
Arg Ala Gly Asn Arg Ala Glu Gly Arg Trp Ala Leu Thr Glu Ala Phe
                230                 235                 240 ctt ccc agc aca gag gct gag ctg atc ttc tta gag ggg tct cct gac      827
Leu Pro Ser Thr Glu Ala Glu Leu Ile Phe Leu Glu Gly Ser Pro Asp
            245                 250                 255 tac tgc aac cgc aac gcc agc ctg agc atc cag ggc aca gag ggg agg      875
Tyr Cys Asn Arg Asn Ala Ser Leu Ser Ile Gln Gly Thr Glu Gly Arg
        260                 265                 270 gag tgc ctg cag aat gcc cgc agt gct tcc cgg cgg gag cag cgc agc      923
Glu Cys Leu Gln Asn Ala Arg Ser Ala Ser Arg Arg Glu Gln Arg Ser
    275                 280                 285 tgt ggg cgc ctg tgc acg gag tgc ggg ctg cag gtg gag gag agg aga      971
Cys Gly Arg Leu Cys Thr Glu Cys Gly Leu Gln Val Glu Glu Arg Arg
290                 295                 300                 305 gca gag gcc gtg agc agc tgt gac tgc aac ttt cag tgg tgt tgc act     1019
Ala Glu Ala Val Ser Ser Cys Asp Cys Asn Phe Gln Trp Cys Cys Thr
                310                 315                 320 gtc aag tgt ggc cag tgc agg cgt gtg gtg agc aga tac tac tgc aca     1067
Val Lys Cys Gly Gln Cys Arg Arg Val Val Ser Arg Tyr Tyr Cys Thr
            325                 330                 335 cgc cct gta ggt agt gcc agg ccc cgg gca agg ggc aag gac agt gcc     1115
Arg Pro Val Gly Ser Ala Arg Pro Arg Gly Arg Gly Lys Asp Ser Ala
        340                 345                 350
```

```
tgg taa caccaccacc aaattcacgt gctgcctagt gcaggacag tggagataga        1171
Trp
    355 gcctgaactt ctggcctagg ggacacagac tggaaaacaa ttgggacatc acagggttgg    1231 cctgtagacc ttccacgata ggtgggttag cctgtagacc ttccacgata ggcggggtag    1291 atggatgatc tttaagcatc ttcttcgcag gagtgaaatc ggaaccttgt tctcctggct    1351 tgtggaccca gcctttcctg cgcagttact cttggactta agcagcttgt taaagaggga    1411 gtttgatttg ggtgcacatc cagaggagcc tggaagaacc gtattccatt aagtttcaga    1471 taccgttcca cccagctgtg ctgctgggag tgcgagggaa gagaagttaa aggaaaggaa    1531 ttctggggc gggagagatg gctcagtggt taagggccct ggctggccct ccagaggact     1591 ggctcacttc acagcaccca cttgatggct gtgaaccatc tgtacttcta gttccagggg    1651 atccaatgtc cttgcctggt ctctgtgacc accaggcaca aatgtgcaca gacagacatt    1711 tatacatata aaataataaa gtaaaaactt acattt                              1747
```

<210> SEQ ID NO 62
<211> LENGTH: 354
<212> TYPE: PRT
<213> ORGANISM: Mus musculus

<400> SEQUENCE: 62

```
Met Gly His Leu Leu Met Leu Trp Val Ala Ala Gly Met Cys Tyr Pro
1               5                   10                  15

Ala Leu Gly Ala Ser Ala Trp Ser Val Asn Asn Phe Leu Ile Thr Gly
            20                  25                  30

Pro Lys Ala Tyr Leu Thr Tyr Thr Ala Ser Val Ala Leu Gly Ala Gln
        35                  40                  45

Ile Gly Ile Glu Glu Cys Lys Phe Gln Phe Ala Trp Glu Arg Trp Asn
    50                  55                  60

Cys Pro Glu His Ala Phe Gln Phe Ser Thr His Asn Arg Leu Arg Ala
65                  70                  75                  80

Ala Thr Arg Glu Thr Ser Phe Ile His Ala Ile Arg Ser Ala Ala Ile
                85                  90                  95

Met Tyr Ala Val Thr Lys Asn Cys Ser Met Gly Asp Leu Glu Asn Cys
            100                 105                 110

Gly Cys Asp Glu Ser Gln Asn Gly Lys Thr Gly Gly His Gly Trp Ile
        115                 120                 125

Trp Gly Gly Cys Ser Asp Asn Val Glu Phe Gly Glu Lys Ile Ser Arg
    130                 135                 140

Leu Phe Val Asp Ser Leu Glu Lys Gly Lys Asp Ala Arg Ala Leu Val
145                 150                 155                 160

Asn Leu His Asn Asn Arg Ala Gly Arg Leu Ala Val Arg Ala Ser Thr
                165                 170                 175

Lys Arg Thr Cys Lys Cys His Gly Ile Ser Gly Ser Cys Ser Ile Gln
            180                 185                 190

Thr Cys Trp Leu Gln Leu Ala Asp Phe Arg Gln Met Gly Asn Tyr Leu
        195                 200                 205

Lys Ala Lys Tyr Asp Arg Ala Leu Lys Ile Glu Met Asp Lys Arg Gln
    210                 215                 220

Leu Arg Ala Gly Asn Arg Ala Glu Gly Arg Trp Ala Leu Thr Glu Ala
225                 230                 235                 240

Phe Leu Pro Ser Thr Glu Ala Glu Leu Ile Phe Leu Glu Gly Ser Pro
                245                 250                 255
```

```
Asp Tyr Cys Asn Arg Asn Ala Ser Leu Ser Ile Gln Gly Thr Glu Gly
            260                 265                 270

Arg Glu Cys Leu Gln Asn Ala Arg Ser Ala Ser Arg Arg Glu Gln Arg
        275                 280                 285

Ser Cys Gly Arg Leu Cys Thr Glu Cys Gly Leu Gln Val Glu Glu Arg
        290                 295                 300

Arg Ala Glu Ala Val Ser Ser Cys Asp Cys Asn Phe Gln Trp Cys Cys
305                 310                 315                 320

Thr Val Lys Cys Gly Gln Cys Arg Arg Val Ser Arg Tyr Tyr Cys
                325                 330                 335

Thr Arg Pro Val Gly Ser Ala Arg Pro Arg Gly Arg Gly Lys Asp Ser
            340                 345                 350

Ala Trp

<210> SEQ ID NO 63
<211> LENGTH: 1634
<212> TYPE: DNA
<213> ORGANISM: Mus musculus
<220> FEATURE:
<221> NAME/KEY: CDS
<222> LOCATION: (135)..(1187)

<400> SEQUENCE: 63
tccgcttcat ttcaccaccc cttaacactg tttgggatcg cttacacacc aaggtagcca       60 ccctctgcc tccgaggaga atgcttccca tctctcaatg tttgagtcgc tcaccctgcc      120
tttctccgaa gacc atg ttt ctt atg aag ccc gtg tgc gtt ctt cta gtc      170
              Met Phe Leu Met Lys Pro Val Cys Val Leu Leu Val
                1               5                  10 act tgt gtc ctt cac cgc agc cac gcc tgg tca gtg aac aat ttt ctg      218
Thr Cys Val Leu His Arg Ser His Ala Trp Ser Val Asn Asn Phe Leu
            15                  20                  25 atg acc ggt cca aag gct tac ctg gtc tac tcc agc agc gtg gcc gct      266
Met Thr Gly Pro Lys Ala Tyr Leu Val Tyr Ser Ser Ser Val Ala Ala
        30                  35                  40 ggc gcc cag agt ggt att gaa gaa tgt aaa tac cag ttt gct tgg gac      314
Gly Ala Gln Ser Gly Ile Glu Glu Cys Lys Tyr Gln Phe Ala Trp Asp
 45                 50                  55                  60 cgt tgg aat tgc ccc gag aga gct tta cag ctg tcc agc cat ggt gga      362
Arg Trp Asn Cys Pro Glu Arg Ala Leu Gln Leu Ser Ser His Gly Gly
                65                  70                  75 ctt cga agc gct aac cgg gag aca gca ttt gtg cac gcc atc agc tct      410
Leu Arg Ser Ala Asn Arg Glu Thr Ala Phe Val His Ala Ile Ser Ser
            80                  85                  90 gct ggg gtt atg tac acc ctg act aga aac tgc agc ctc gga gac ttt      458
Ala Gly Val Met Tyr Thr Leu Thr Arg Asn Cys Ser Leu Gly Asp Phe
        95                  100                 105 gac aac tgt ggc tgt gat gac tcc cga aat gga caa ctg ggg ggc caa      506
Asp Asn Cys Gly Cys Asp Asp Ser Arg Asn Gly Gln Leu Gly Gly Gln
    110                 115                 120 ggt tgg ctc tgg gga ggc tgc agt gac aac gtg ggc ttc gga gag gca      554
Gly Trp Leu Trp Gly Gly Cys Ser Asp Asn Val Gly Phe Gly Glu Ala
125                 130                 135                 140 att tcc aag cag ttt gtg gat gcc ctc gag aca gga caa gat gcc cgg      602
Ile Ser Lys Gln Phe Val Asp Ala Leu Glu Thr Gly Gln Asp Ala Arg
                145                 150                 155 gca gcc atg aat ctg cac aac aat gag gct ggc cgc aag gcg gtc aag      650
Ala Ala Met Asn Leu His Asn Asn Glu Ala Gly Arg Lys Ala Val Lys
            160                 165                 170
```

-continued

| | | |
|---|---|---|
| ggc acc atg aaa cgc acg tgt aag tgc cac ggt gtg tcc ggc agc tgc<br>Gly Thr Met Lys Arg Thr Cys Lys Cys His Gly Val Ser Gly Ser Cys<br>175                      180                      185 | 698 |
| acc acg cag acc tgc tgg ttg caa ctg cca gag ttc cgg gag gta ggc<br>Thr Thr Gln Thr Cys Trp Leu Gln Leu Pro Glu Phe Arg Glu Val Gly<br>      190                    195                      200 | 746 |
| gcg cac ttg aag gag aag tat cat gcg gcg ctc aag gtg gac ctg ctg<br>Ala His Leu Lys Glu Lys Tyr His Ala Ala Leu Lys Val Asp Leu Leu<br>205                      210                      215                      220 | 794 |
| caa ggc gcg ggc aac agc gcg gcg ggc cgc gga gcc atc gcc gac acc<br>Gln Gly Ala Gly Asn Ser Ala Ala Gly Arg Gly Ala Ile Ala Asp Thr<br>                    225                    230                      235 | 842 |
| ttc cgc tcc atc tcc acc cgc gag ctg gtg cat ctg gag gac tcc cca<br>Phe Arg Ser Ile Ser Thr Arg Glu Leu Val His Leu Glu Asp Ser Pro<br>240                      245                      250 | 890 |
| gac tac tgc ctg gag aac aag acc ctg ggg ctg ctg ggc acc gag ggc<br>Asp Tyr Cys Leu Glu Asn Lys Thr Leu Gly Leu Leu Gly Thr Glu Gly<br>                255                    260                      265 | 938 |
| cga gag tgt ctg cgg cgc ggg cgc gcc ctg ggt cgc tgg gag cgc cgc<br>Arg Glu Cys Leu Arg Arg Gly Arg Ala Leu Gly Arg Trp Glu Arg Arg<br>270                      275                      280 | 986 |
| agt tgt cgc cgg ctg tgc ggg gac tgc ggg cta gcg gtg gag gag cgc<br>Ser Cys Arg Arg Leu Cys Gly Asp Cys Gly Leu Ala Val Glu Glu Arg<br>285                      290                    295                      300 | 1034 |
| cgc gcc gag aca gtg tcc agc tgc aac tgc aag ttt cac tgg tgc tgc<br>Arg Ala Glu Thr Val Ser Ser Cys Asn Cys Lys Phe His Trp Cys Cys<br>                    305                    310                      315 | 1082 |
| gcg gtc cgc tgc gag cag tgc cgc cgg cgg gtc acc aag tac ttc tgc<br>Ala Val Arg Cys Glu Gln Cys Arg Arg Arg Val Thr Lys Tyr Phe Cys<br>320                      325                      330 | 1130 |
| agc cgc gca gag cgg ccg ccc aga ggc gct gcg cac aaa ccg gga aag<br>Ser Arg Ala Glu Arg Pro Pro Arg Gly Ala Ala His Lys Pro Gly Lys<br>              335                    340                    345 | 1178 |
| aac tcc taa gggtatctat ccctcccgcc tccacccctg ttcgtcctcg<br>Asn Ser<br>    350 | 1227 |
| gcttccttta gagaccccg gaaatagagg aacccagaat gggggacctc gcactcccta | 1287 |
| gcccagagat tctgacagga ggaggctgca gtctctaccg agtgacactt tgtagctcac | 1347 |
| tcgtaggtct caaaactgtt ataaaattct gcaagttgtt cctgaaaaga ggatgagaac | 1407 |
| aggcgagtct cctcaccca ctttacctac ttcggacccc aatggtcgct caatgctgga | 1467 |
| cctagcttat caggcctagg aagggcccct ctcagatatt cagggtccag ggaaagacgt | 1527 |
| ggcccttctc ttgctcgcca tagcttcacc tccctcctgt gagccagagc ttctaggcct | 1587 |
| agactccccg ctgttgatta ttcaagaatc taaaaacctt gaccgta | 1634 |

<210> SEQ ID NO 64
<211> LENGTH: 350
<212> TYPE: PRT
<213> ORGANISM: Mus musculus

<400> SEQUENCE: 64

Met Phe Leu Met Lys Pro Val Cys Val Leu Leu Val Thr Cys Val Leu
1                  5                      10                      15

His Arg Ser His Ala Trp Ser Val Asn Asn Phe Leu Met Thr Gly Pro
                20                      25                      30

Lys Ala Tyr Leu Val Tyr Ser Ser Ser Val Ala Ala Gly Ala Gln Ser
                35                      40                      45

```
Gly Ile Glu Glu Cys Lys Tyr Gln Phe Ala Trp Asp Arg Trp Asn Cys
 50                  55                  60

Pro Glu Arg Ala Leu Gln Leu Ser Ser His Gly Gly Leu Arg Ser Ala
 65                  70                  75                  80

Asn Arg Glu Thr Ala Phe Val His Ala Ile Ser Ser Ala Gly Val Met
                 85                  90                  95

Tyr Thr Leu Thr Arg Asn Cys Ser Leu Gly Asp Phe Asp Asn Cys Gly
            100                 105                 110

Cys Asp Asp Ser Arg Asn Gly Gln Leu Gly Gly Gln Gly Trp Leu Trp
        115                 120                 125

Gly Gly Cys Ser Asp Asn Val Gly Phe Gly Glu Ala Ile Ser Lys Gln
130                 135                 140

Phe Val Asp Ala Leu Glu Thr Gly Gln Asp Ala Arg Ala Ala Met Asn
145                 150                 155                 160

Leu His Asn Asn Glu Ala Gly Arg Lys Ala Val Lys Gly Thr Met Lys
                165                 170                 175

Arg Thr Cys Lys Cys His Gly Val Ser Gly Ser Cys Thr Thr Gln Thr
            180                 185                 190

Cys Trp Leu Gln Leu Pro Glu Phe Arg Glu Val Gly Ala His Leu Lys
        195                 200                 205

Glu Lys Tyr His Ala Ala Leu Lys Val Asp Leu Leu Gln Gly Ala Gly
    210                 215                 220

Asn Ser Ala Ala Gly Arg Gly Ala Ile Ala Asp Thr Phe Arg Ser Ile
225                 230                 235                 240

Ser Thr Arg Glu Leu Val His Leu Glu Asp Ser Pro Asp Tyr Cys Leu
                245                 250                 255

Glu Asn Lys Thr Leu Gly Leu Leu Gly Thr Glu Gly Arg Glu Cys Leu
            260                 265                 270

Arg Arg Gly Arg Ala Leu Gly Arg Trp Glu Arg Arg Ser Cys Arg Arg
        275                 280                 285

Leu Cys Gly Asp Cys Gly Leu Ala Val Glu Glu Arg Arg Ala Glu Thr
290                 295                 300

Val Ser Ser Cys Asn Cys Lys Phe His Trp Cys Cys Ala Val Arg Cys
305                 310                 315                 320

Glu Gln Cys Arg Arg Arg Val Thr Lys Tyr Phe Cys Ser Arg Ala Glu
                325                 330                 335

Arg Pro Pro Arg Gly Ala Ala His Lys Pro Gly Lys Asn Ser
            340                 345                 350

<210> SEQ ID NO 65
<211> LENGTH: 1106
<212> TYPE: DNA
<213> ORGANISM: Mus musculus
<220> FEATURE:
<221> NAME/KEY: CDS
<222> LOCATION: (8)..(1105)

<400> SEQUENCE: 65 cggcaag atg ctg gat ggg tcc ctt ctg gcg cgc tgg ctg gcc gcg gcc       49
        Met Leu Asp Gly Ser Leu Leu Ala Arg Trp Leu Ala Ala Ala
          1               5                  10 ttc ggg ctg acg ctg ctc gcc gcg ctg cgc cct tcg gcc gcc tac           97
Phe Gly Leu Thr Leu Leu Ala Ala Leu Arg Pro Ser Ala Ala Tyr
 15                  20                  25                  30 ttc ggg cta aca ggc agt gaa ccc ctg act atc ctc cct ctg acc ctg      145
Phe Gly Leu Thr Gly Ser Glu Pro Leu Thr Ile Leu Pro Leu Thr Leu
```

-continued

```
             35                  40                  45
gag acc gag gct gcg gcc caa gca cac tac aag gcc tgc gac agg ctg      193
Glu Thr Glu Ala Ala Ala Gln Ala His Tyr Lys Ala Cys Asp Arg Leu
             50                  55                  60 aag ctg gag cgc aag cag cgc cgc atg tgc cgc agg gac ccg ggt gtg      241
Lys Leu Glu Arg Lys Gln Arg Arg Met Cys Arg Arg Asp Pro Gly Val
         65                  70                  75 gcc gag aca ctg gtg gag gcc gta agc atg agt gcc ctg gag tgc cag      289
Ala Glu Thr Leu Val Glu Ala Val Ser Met Ser Ala Leu Glu Cys Gln
     80                  85                  90 tac cag ttc cgc ttt gag cgc tgg aac tgc acc ctg gag ggc cgc tac      337
Tyr Gln Phe Arg Phe Glu Arg Trp Asn Cys Thr Leu Glu Gly Arg Tyr
 95                 100                 105                 110 cga gcc agc ctg ctc aag cga ggc ttc aag gag act gct ttc ctc tac      385
Arg Ala Ser Leu Leu Lys Arg Gly Phe Lys Glu Thr Ala Phe Leu Tyr
                115                 120                 125 gcc atc tct tct gcc ggc ctg acg cat gca ctg gcc aag gcc tgc agt      433
Ala Ile Ser Ser Ala Gly Leu Thr His Ala Leu Ala Lys Ala Cys Ser
            130                 135                 140 gca ggc cgc atg gag cgc tgc acg tgt gat gag gca ccc gac ctg gaa      481
Ala Gly Arg Met Glu Arg Cys Thr Cys Asp Glu Ala Pro Asp Leu Glu
        145                 150                 155 aac cgc gag gcc tgg cag tgg ggc ggc tgc ggg gac aac ctc aag tac      529
Asn Arg Glu Ala Trp Gln Trp Gly Gly Cys Gly Asp Asn Leu Lys Tyr
    160                 165                 170 agc agc aag ttt gtc aag gag ttc ctg ggc cgg cgc tct agc aag gat      577
Ser Ser Lys Phe Val Lys Glu Phe Leu Gly Arg Arg Ser Ser Lys Asp
175                 180                 185                 190 ttg cga gcc cga gtg gac ttc cac aac aac ctc gtg ggt gtg aag gtg      625
Leu Arg Ala Arg Val Asp Phe His Asn Asn Leu Val Gly Val Lys Val
                195                 200                 205 ata aag gct gga gtg gaa acc act tgc aaa tgc cat ggt gtg tct ggc      673
Ile Lys Ala Gly Val Glu Thr Thr Cys Lys Cys His Gly Val Ser Gly
            210                 215                 220 tcc tgc acc gtg cgg acc tgc tgg cgg cag cta gca ccc ttc cac gag      721
Ser Cys Thr Val Arg Thr Cys Trp Arg Gln Leu Ala Pro Phe His Glu
        225                 230                 235 gtg ggc aag cac cta aaa cac aaa tat gag acc tcg ctc aag gtg ggc      769
Val Gly Lys His Leu Lys His Lys Tyr Glu Thr Ser Leu Lys Val Gly
    240                 245                 250 agc act acc aat gaa gcc act gga gag gca ggt gcc atc tcc cca ccg      817
Ser Thr Thr Asn Glu Ala Thr Gly Glu Ala Gly Ala Ile Ser Pro Pro
255                 260                 265                 270 cgg ggc cgg gct tct ggg tca gga ggt ggc gac cca ctg ccc cga aca      865
Arg Gly Arg Ala Ser Gly Ser Gly Gly Asp Pro Leu Pro Arg Thr
                275                 280                 285 cca gag ctt gta cac ctg gac gac tct ccc agc ttc tgc ctg gct ggc      913
Pro Glu Leu Val His Leu Asp Asp Ser Pro Ser Phe Cys Leu Ala Gly
            290                 295                 300 cgc ttt tcc cct ggc acg gca ggc cgc agg tgt cac cgg gag aag aac      961
Arg Phe Ser Pro Gly Thr Ala Gly Arg Arg Cys His Arg Glu Lys Asn
        305                 310                 315 tgt gag agt att tgt tgt ggc cga ggc cac aac aca cag agt cgt gtg     1009
Cys Glu Ser Ile Cys Cys Gly Arg Gly His Asn Thr Gln Ser Arg Val
    320                 325                 330 gtg aca agg ccc tgc caa tgc cag gtc cgc tgg tgc tgc tac gtg gag     1057
Val Thr Arg Pro Cys Gln Cys Gln Val Arg Trp Cys Cys Tyr Val Glu
335                 340                 345                 350 tgc agg cag tgt aca cag aga gag gag gtc tat acc tgc aag ggc tga c  1106
Cys Arg Gln Cys Thr Gln Arg Glu Glu Val Tyr Thr Cys Lys Gly
```

Cys Arg Gln Cys Thr Gln Arg Glu Glu Val Tyr Thr Cys Lys Gly
                355                 360                 365

<210> SEQ ID NO 66
<211> LENGTH: 365
<212> TYPE: PRT
<213> ORGANISM: Mus musculus

<400> SEQUENCE: 66

Met Leu Asp Gly Ser Leu Leu Ala Arg Trp Leu Ala Ala Phe Gly
 1               5                  10                  15

Leu Thr Leu Leu Leu Ala Ala Leu Arg Pro Ser Ala Ala Tyr Phe Gly
                20                  25                  30

Leu Thr Gly Ser Glu Pro Leu Thr Ile Leu Pro Leu Thr Leu Glu Thr
                35                  40                  45

Glu Ala Ala Gln Ala His Tyr Lys Ala Cys Asp Arg Leu Lys Leu
            50                  55                  60

Glu Arg Lys Gln Arg Arg Met Cys Arg Arg Asp Pro Gly Val Ala Glu
 65                 70                  75                  80

Thr Leu Val Glu Ala Val Ser Met Ser Ala Leu Glu Cys Gln Tyr Gln
                85                  90                  95

Phe Arg Phe Glu Arg Trp Asn Cys Thr Leu Glu Gly Arg Tyr Arg Ala
            100                 105                 110

Ser Leu Leu Lys Arg Gly Phe Lys Glu Thr Ala Phe Leu Tyr Ala Ile
            115                 120                 125

Ser Ser Ala Gly Leu Thr His Ala Leu Ala Lys Ala Cys Ser Ala Gly
            130                 135                 140

Arg Met Glu Arg Cys Thr Cys Asp Glu Ala Pro Asp Leu Glu Asn Arg
145                 150                 155                 160

Glu Ala Trp Gln Trp Gly Gly Cys Gly Asp Asn Leu Lys Tyr Ser Ser
            165                 170                 175

Lys Phe Val Lys Glu Phe Leu Gly Arg Arg Ser Ser Lys Asp Leu Arg
            180                 185                 190

Ala Arg Val Asp Phe His Asn Asn Leu Val Gly Val Lys Val Ile Lys
            195                 200                 205

Ala Gly Val Glu Thr Thr Cys Lys Cys His Gly Val Ser Gly Ser Cys
210                 215                 220

Thr Val Arg Thr Cys Trp Arg Gln Leu Ala Pro Phe His Glu Val Gly
225                 230                 235                 240

Lys His Leu Lys His Lys Tyr Glu Thr Ser Leu Lys Val Gly Ser Thr
            245                 250                 255

Thr Asn Glu Ala Thr Gly Glu Ala Gly Ala Ile Ser Pro Pro Arg Gly
            260                 265                 270

Arg Ala Ser Gly Ser Gly Gly Asp Pro Leu Pro Arg Thr Pro Glu
            275                 280                 285

Leu Val His Leu Asp Asp Ser Pro Ser Phe Cys Leu Ala Gly Arg Phe
            290                 295                 300

Ser Pro Gly Thr Ala Gly Arg Arg Cys His Arg Glu Lys Asn Cys Glu
305                 310                 315                 320

Ser Ile Cys Cys Gly Arg Gly His Asn Thr Gln Ser Arg Val Val Thr
            325                 330                 335

Arg Pro Cys Gln Cys Gln Val Arg Trp Cys Cys Tyr Val Glu Cys Arg
            340                 345                 350

Gln Cys Thr Gln Arg Glu Glu Val Tyr Thr Cys Lys Gly
            355                 360                 365

```
<210> SEQ ID NO 67
<211> LENGTH: 4522
<212> TYPE: DNA
<213> ORGANISM: Mus musculus
<220> FEATURE:
<221> NAME/KEY: CDS
<222> LOCATION: (54)..(1133)

<400> SEQUENCE: 67
gacgagcgcc tagtggcgcg aggagatgcg agagtgcacc ggccgcctgc acc atg        56
                                                            Met
                                                              1 cgc ccc gcg ccc gcg ctg gcc ctg gct gcg ctc tgc ctg ctg gtg ctg       104
Arg Pro Ala Pro Ala Leu Ala Leu Ala Ala Leu Cys Leu Leu Val Leu
              5                  10                  15 cct gcc gct gcc gcc gcc gcc gcc tac ttc ggc ctg acc ggt cgt gag       152
Pro Ala Ala Ala Ala Ala Ala Ala Tyr Phe Gly Leu Thr Gly Arg Glu
         20                  25                  30 gtc ctg aca ccc ttc cca ggc ctg ggt acg gca gca ccg gca cag            200
Val Leu Thr Pro Phe Pro Gly Leu Gly Thr Ala Ala Pro Ala Gln
     35                  40                  45 gct ggt gct cac ctg aag cag tgt gac cta ctg aag ctg tcc agg cgg       248
Ala Gly Ala His Leu Lys Gln Cys Asp Leu Leu Lys Leu Ser Arg Arg
 50                  55                  60                  65 cag aag cag ctc tgc agg cgg gag ccc ggc ctg gct gag acc ctg agg       296
Gln Lys Gln Leu Cys Arg Arg Glu Pro Gly Leu Ala Glu Thr Leu Arg
                 70                  75                  80 gat gct gca cac ctg ggg ctg ctg gaa tgt cag ttc cag ttc agg cag       344
Asp Ala Ala His Leu Gly Leu Leu Glu Cys Gln Phe Gln Phe Arg Gln
             85                  90                  95 gag cgc tgg aac tgc agc ctg gag ggg agg act ggc ctg ctc cag aga       392
Glu Arg Trp Asn Cys Ser Leu Glu Gly Arg Thr Gly Leu Leu Gln Arg
        100                 105                 110 ggc ttt aag gag acg gcc ttc ctg tat gca gtg tct gca gct gcc ctc       440
Gly Phe Lys Glu Thr Ala Phe Leu Tyr Ala Val Ser Ala Ala Ala Leu
    115                 120                 125 acg cat gca ctg gcc agg gcc tgc agt gct ggg cgc atg gag cgc tgt       488
Thr His Ala Leu Ala Arg Ala Cys Ser Ala Gly Arg Met Glu Arg Cys
130                 135                 140                 145 act tgt gac gac tcc cca ggc ctg gag agc cgg cag gcc tgg cag tgg       536
Thr Cys Asp Asp Ser Pro Gly Leu Glu Ser Arg Gln Ala Trp Gln Trp
                150                 155                 160 ggt gtg tgt ggt gac aat ctg aag tac agc acc aag ttc ctc agc aac       584
Gly Val Cys Gly Asp Asn Leu Lys Tyr Ser Thr Lys Phe Leu Ser Asn
            165                 170                 175 ttc ctg ggg ccc aag aga gga agc aag gac ctg agg gcg agg gct gac       632
Phe Leu Gly Pro Lys Arg Gly Ser Lys Asp Leu Arg Ala Arg Ala Asp
        180                 185                 190 gcc cac aac acc cac gtg ggc atc aag gct gtg aag agc ggc ctg aga       680
Ala His Asn Thr His Val Gly Ile Lys Ala Val Lys Ser Gly Leu Arg
    195                 200                 205 aca acc tgc aag tgc cat ggt gtg tca ggc tcc tgt gct gtt cgt acc       728
Thr Thr Cys Lys Cys His Gly Val Ser Gly Ser Cys Ala Val Arg Thr
210                 215                 220                 225 tgt tgg aag cag ctc tcc ccg ttt cgc gag acc ggc cag gtg ctg aag       776
Cys Trp Lys Gln Leu Ser Pro Phe Arg Glu Thr Gly Gln Val Leu Lys
                230                 235                 240 cta cgc tat gac acg gct gtc aag gtg tcc agt gcc acc aac gag gcc       824
Leu Arg Tyr Asp Thr Ala Val Lys Val Ser Ser Ala Thr Asn Glu Ala
            245                 250                 255
```

-continued

| | |
|---|---|
| ttg ggt cgt ctg gag cta tgg gcc ccc gct aag cca ggt ggt acc gcc<br>Leu Gly Arg Leu Glu Leu Trp Ala Pro Ala Lys Pro Gly Gly Thr Ala<br>260     265     270 | 872 |
| aag ggc cta gcc cct cgt ccc ggg gac ctg gtc tac atg gaa gat tct<br>Lys Gly Leu Ala Pro Arg Pro Gly Asp Leu Val Tyr Met Glu Asp Ser<br>275     280     285 | 920 |
| ccc agc ttc tgc cgg ccc agc aag tac tct ccg ggc acg gca ggc agg<br>Pro Ser Phe Cys Arg Pro Ser Lys Tyr Ser Pro Gly Thr Ala Gly Arg<br>290     295     300     305 | 968 |
| gtg tgt tct cga gac tcc agt tgc agc agc cta tgc tgt ggg cga ggc<br>Val Cys Ser Arg Asp Ser Ser Cys Ser Ser Leu Cys Cys Gly Arg Gly<br>310     315     320 | 1016 |
| tac gac acc cag agc cgc atg gtg gtt ttc tcc tgc cac tgt cag gtg<br>Tyr Asp Thr Gln Ser Arg Met Val Val Phe Ser Cys His Cys Gln Val<br>325     330     335 | 1064 |
| cag tgg tgc tgc tac gtg gag tgc cag cag tgt gca cag cag gag ctc<br>Gln Trp Cys Cys Tyr Val Glu Cys Gln Gln Cys Ala Gln Gln Glu Leu<br>340     345     350 | 1112 |
| gtg tat acc tgc aag cgc tag gcctccacag cgaatcccgc ggaacagcgc<br>Val Tyr Thr Cys Lys Arg<br>355     360 | 1163 |
| gcaagcgcgc acctgtcgac gcacctgccg tgcacaagag tgtgcgactc atctctcttc | 1223 |
| cccaacagat ggttggccag cccttctgcc ttccccgaca ctcagcaaag agaaagaaag | 1283 |
| ccctgcctcc tagtcccagg atcaccaacc tgctggagga cttggggccg agaacagac | 1343 |
| tgagaagggg aatctttgag gaccagggta gggcaggaat gatgctgtgc gggaagagag | 1403 |
| aaacatcctc ctatctcaag gccaaaaact gggaggatgg ggaagaggga ggcggagcca | 1463 |
| gctggagtgt ggggtcaggg catccatctg gcgtggccg atctcttgtg gtcccactct | 1523 |
| aatagcagag cgctctgggt gctgcatgcc taccctgctc ttgtggcttc gtgcactgga | 1583 |
| gacttcgaaa tgtttattag gagcaaggga agcactttag gctgggtgg attgagtcgc | 1643 |
| agagcccatg ccctgaagtc ttacgtcctg gcactcaggg ctgccacctt gtctccttgt | 1703 |
| cttgagatcc cctgtccccc aaagccattg agctctgctc aacgagaccc ctaatatgta | 1763 |
| taagaagggt gcaggagcca gtctcctcgg tgagactcag ataaacataa ctaggttga | 1823 |
| gcggggagac agtgaccctt tctctttcct ttggtccaag gaacctttaa tcacagccca | 1883 |
| gaggtggaga gaggcagggt ccaaatgcct ggaagagata tgacaggctc tgtattgaga | 1943 |
| taccactctg gagtgtgtcc taccaattcc tgtgaccagg gaccccaag aaccgagggg | 2003 |
| ccccatcca tgttagtgat acataagaac gagtgactca tgggccacac gtctgcttcc | 2063 |
| accccctgct ctcaaagatg cttgtgcagg ctttttgcc attgctaagt ctttgccaag | 2123 |
| tctgcctcct caatggtctt actcatttac taacgacctg tcacttgggc tccaccaga | 2183 |
| ggaacaaaat gactgctggt gaatcctttg gtcatttta atgcccccat caaggccctc | 2243 |
| tgtgagagga gaggaagtag tgtacaggta caggctcaca cgtgcacaca ctcagcctag | 2303 |
| ccaggcacag acatcccaag gagcagtgcg gcgtctctcc agcccaggc aaagacctca | 2363 |
| ctggggtcac ttctggaggc tgtgagctac tccagggcag ggcccaaggc caaccaggag | 2423 |
| gaagtgacct cctttgggaa gcctttggcc atgtggctgg ctgtgctgca ccctcctgtg | 2483 |
| agcttccttc caccctgaaa tctgttgggg ttactgtctc tctaagggag caggaagctt | 2543 |
| cggaatcagc cggtactcag cactactggc cctgccagct ccaggaaaga gacactgtgg | 2603 |
| cggagaggtc cgtggggcag aaggggctac cctttcttca gtgcctccgg gcagcatgct | 2663 |

```
gggaagatct tgatggtgg aaagccccga ggcggagcca ccgtgacctg agacccttct    2723
ctgggacgac tttgccaccc acccgcagct tggcaggagg ggtaaacaga ttgggagctg    2783 cttctactt ccctgatgaa gacagatgtg ttccttggca acccaaggca tccttctcta    2843
tgaccctaat cctgctctgg ctcgagggta caaggcaaga atggagcctg gcaaaacttg    2903
gggactagaa cacctggacc tacagccaaa tcacctgtac cctgactcta tggccaggag    2963
ggccaggggt ggaggagggt taaagatgaa cttgaagttg agggctgagg ctgaccaacc    3023
attaagactg gtgccttaag gcaccctcag tcaggtcctc tccctcctt ctccattctt    3083 tctccaaggc cccgttcccc ctaaaatccc accatagcca tgctgggtcc cccttcccc    3143 cacactggga actttaagga agatattcac agggtatttc tgcctacctc atacatgtaa    3203
ttttcaaaaa aaattaattt atatagttaa gatatatggg aaagtattta tgttatttat    3263
atatcttctc tatttcctgg gcaccatatg gggggttgtg tgtttaccca gaagcctctg    3323
aggaaacatg gctgggtctg tctggggcct cgcagagctg gatgcgcata gctgagaggt    3383
cacagctcct gtgtctcact gtcttggagc tcgggaagca catgtacctc ctgagataaa    3443
ccccgtgaca ccaagcaggg ccttccttgt gaagtctgtg gattctctgc ctctggcccc    3503
agaggccttt ctgctctggc ccaagggttt tgctcataaa ggacaaaaag ggtgagcagc    3563
tctggatttg taaagcactt tccatcttca gaaacactcc tctcttctct ctccctcggt    3623 taccccggt tccctatgag gtcatgccac tgttaccacg ttccaggccc agagacggag    3683
gcaggttggt caaagccagt cactctctga acccagaggt tgaggaagag tgcatgctgc    3743
gtggaacgct ggtcttcccc catggatggc atgctagttt ctccagcaag ctgagtctca    3803
tgtccccaaa gacggggact tcctgagaag cctggagaga caagggctcc gtggatgtca    3863
ctcttaggga gggtgtcctg cagccctcat tgacctccac gactaggcta tggtctccag    3923 ccctcacag ctcgtggata atttgtgttt cttcgctttt gttttttgtc ttttcaaagt    3983
gactttttcc ccactggatt tctaagtttc tctttgaaaa tcagttcact ggcaaatggg    4043
acctgcatcc tgacctggct gcctgcatca ggagcgacac caaacagagt gcgtggggat    4103
ccccaattgg cccagtgtcc cccggccctt ccttaagtca cacaagctcc cgtgtggctt    4163
tcgtgagcat ggagaacctg tcccctggtc ttagagaaag ccagccattc tgccaccctc    4223
tgtttgtctg gcagacagat taccacaccg tggctgtctt tctagccaaa gcttcctctc    4283
tcaacaccca tgaacgtcca tgcttcctgt ctgagcactg aggagaaccc cagcggagct    4343
cattgttcag tgctggaata cccatccccc ctcccgttga ttatttaggg agtgtctgat    4403
aatgccaggg gatactctgg gtgctagggc gcagaagtac ttaagagcaa gtcccagcct    4463
caggggactt atatgccggc gaggagaaag ccaacaaacc aataaactat gcactggtt    4522
```

<210> SEQ ID NO 68
<211> LENGTH: 359
<212> TYPE: PRT
<213> ORGANISM: Mus musculus

<400> SEQUENCE: 68

Met Arg Pro Ala Pro Ala Leu Ala Leu Ala Ala Leu Cys Leu Leu Val
1               5                   10                  15

Leu Pro Ala Ala Ala Ala Ala Ala Ala Tyr Phe Gly Leu Thr Gly Arg
                20                  25                  30

Glu Val Leu Thr Pro Phe Pro Gly Leu Gly Thr Ala Ala Ala Pro Ala
        35                  40                  45

```
        Gln Ala Gly Ala His Leu Lys Gln Cys Asp Leu Leu Lys Leu Ser Arg
                50                  55                  60

Arg Gln Lys Gln Leu Cys Arg Arg Glu Pro Gly Leu Ala Glu Thr Leu
         65                  70                  75                  80

Arg Asp Ala Ala His Leu Gly Leu Leu Glu Cys Gln Phe Gln Phe Arg
                            85                  90                  95

Gln Glu Arg Trp Asn Cys Ser Leu Glu Gly Arg Thr Gly Leu Leu Gln
                        100                 105                 110

Arg Gly Phe Lys Glu Thr Ala Phe Leu Tyr Ala Val Ser Ala Ala Ala
                    115                 120                 125

Leu Thr His Ala Leu Ala Arg Ala Cys Ser Ala Gly Arg Met Glu Arg
                130                 135                 140

Cys Thr Cys Asp Asp Ser Pro Gly Leu Glu Ser Arg Gln Ala Trp Gln
        145                 150                 155                 160

Trp Gly Val Cys Gly Asp Asn Leu Lys Tyr Ser Thr Lys Phe Leu Ser
                        165                 170                 175

Asn Phe Leu Gly Pro Lys Arg Gly Ser Lys Asp Leu Arg Ala Arg Ala
                    180                 185                 190

Asp Ala His Asn Thr His Val Gly Ile Lys Ala Val Lys Ser Gly Leu
                195                 200                 205

Arg Thr Thr Cys Lys Cys His Gly Val Ser Gly Ser Cys Ala Val Arg
        210                 215                 220

Thr Cys Trp Lys Gln Leu Ser Pro Phe Arg Glu Thr Gly Gln Val Leu
        225                 230                 235                 240

Lys Leu Arg Tyr Asp Thr Ala Val Lys Val Ser Ser Ala Thr Asn Glu
                        245                 250                 255

Ala Leu Gly Arg Leu Glu Leu Trp Ala Pro Ala Lys Pro Gly Gly Thr
                    260                 265                 270

Ala Lys Gly Leu Ala Pro Arg Pro Gly Asp Leu Val Tyr Met Glu Asp
                275                 280                 285

Ser Pro Ser Phe Cys Arg Pro Ser Lys Tyr Ser Pro Gly Thr Ala Gly
                290                 295                 300

Arg Val Cys Ser Arg Asp Ser Ser Cys Ser Ser Leu Cys Cys Gly Arg
        305                 310                 315                 320

Gly Tyr Asp Thr Gln Ser Arg Met Val Val Phe Ser Cys His Cys Gln
                        325                 330                 335

Val Gln Trp Cys Cys Tyr Val Glu Cys Gln Gln Cys Ala Gln Gln Glu
                    340                 345                 350

Leu Val Tyr Thr Cys Lys Arg
                355

<210> SEQ ID NO 69
<211> LENGTH: 1974
<212> TYPE: DNA
<213> ORGANISM: Mus musculus
<220> FEATURE:
<221> NAME/KEY: CDS
<222> LOCATION: (153)..(1406)

<400> SEQUENCE: 69
ggcgggcgcc gtctgctgcg ggagctgtga cctgagtagg agctgtgtgt cgcagccgcc      60 ccaccctgc cgatcatgcg ccggcgacc tggttcgcca gtcccactgg gctgtgagcc      120
ccccactcct ggcctgtcac ggcccgcgcg cc atg ggc agc gcc cac cct cgc      173
                                   Met Gly Ser Ala His Pro Arg
                                    1               5
```

```
ccc tgg ctg cgg ctc cca caa ggg ccc cag ccg cgg cct gag ttc tgg      221
Pro Trp Leu Arg Leu Pro Gln Gly Pro Gln Pro Arg Pro Glu Phe Trp
        10                  15                  20 gcg ctc ctg ttc ttc cta ctg ctg gct gcc gct gtg ccc agg tca          269
Ala Leu Leu Phe Phe Leu Leu Leu Ala Ala Ala Val Pro Arg Ser
    25                  30                  35 gca ccc aac gac atc ctg ggc ctc cgc cta ccc cca gag ccc gtg ctc      317
Ala Pro Asn Asp Ile Leu Gly Leu Arg Leu Pro Pro Glu Pro Val Leu
40                  45                  50                  55 aac gcc aac aca gtg tgc ctg aca ttg ccc ggc ctg agc cgg cgg cag      365
Asn Ala Asn Thr Val Cys Leu Thr Leu Pro Gly Leu Ser Arg Arg Gln
                60                  65                  70 atg gag gtg tgt gtg cgt cac cct gac gtg gcc gcc tct gct atc cag      413
Met Glu Val Cys Val Arg His Pro Asp Val Ala Ala Ser Ala Ile Gln
            75                  80                  85 ggc atc cag atc gcc atc cat gag tgc cag cat cag ttc cgg gac cag      461
Gly Ile Gln Ile Ala Ile His Glu Cys Gln His Gln Phe Arg Asp Gln
        90                  95                  100 cgc tgg aac tgc tcc agc ctg gag act cgg aac aaa gtc ccc tac gag      509
Arg Trp Asn Cys Ser Ser Leu Glu Thr Arg Asn Lys Val Pro Tyr Glu
    105                 110                 115 agc ccc atc ttc agc cga ggt ttt cga gag agt gct ttc gcc tac gcc      557
Ser Pro Ile Phe Ser Arg Gly Phe Arg Glu Ser Ala Phe Ala Tyr Ala
120                 125                 130                 135 ata gca gct gcc ggg gtg gtg cac gca gtg tcc aac gcg tgc gct ctg      605
Ile Ala Ala Ala Gly Val Val His Ala Val Ser Asn Ala Cys Ala Leu
                140                 145                 150 ggt aaa ctg aag gct tgc ggt tgc gac gcc tcc aga cgt ggg gac gaa      653
Gly Lys Leu Lys Ala Cys Gly Cys Asp Ala Ser Arg Arg Gly Asp Glu
            155                 160                 165 gaa gct ttc cgt cgg aag ctg cac cgc ttg cag ctg gac gcg ctg cag      701
Glu Ala Phe Arg Arg Lys Leu His Arg Leu Gln Leu Asp Ala Leu Gln
        170                 175                 180 cgc gga aag ggc ttg agc cac ggg gtc cct gaa cac ccg gcc ata ctt      749
Arg Gly Lys Gly Leu Ser His Gly Val Pro Glu His Pro Ala Ile Leu
    185                 190                 195 cct gcc agc cca ggt ctg cag gac tcc tgg gag tgg ggt ggc tgc agt      797
Pro Ala Ser Pro Gly Leu Gln Asp Ser Trp Glu Trp Gly Gly Cys Ser
200                 205                 210                 215 ccg gat gtg ggc ttc gga gaa cgc ttc tct aag gac ttt ctg gac tcc      845
Pro Asp Val Gly Phe Gly Glu Arg Phe Ser Lys Asp Phe Leu Asp Ser
                220                 225                 230 cga gag cct cac aga gac atc cat gct cga atg aga ctc cac aac aac      893
Arg Glu Pro His Arg Asp Ile His Ala Arg Met Arg Leu His Asn Asn
            235                 240                 245 cgt gtg ggc cgg cag gcg gtg atg gag aac atg cgg cgt aag tgc aaa      941
Arg Val Gly Arg Gln Ala Val Met Glu Asn Met Arg Arg Lys Cys Lys
        250                 255                 260 tgc cac ggc acc tca ggc agc tgc cag ctc aag acc tgc tgg cag gtg      989
Cys His Gly Thr Ser Gly Ser Cys Gln Leu Lys Thr Cys Trp Gln Val
    265                 270                 275 acg cct gag ttc cgc aca gta ggg gcg ctg ctc gcc aac cgc ttc cac      1037
Thr Pro Glu Phe Arg Thr Val Gly Ala Leu Leu Arg Asn Arg Phe His
280                 285                 290                 295 cgc gcc acg ctc atc cgg ccg cac aac cgc aac ggt ggc cag ctg gag      1085
Arg Ala Thr Leu Ile Arg Pro His Asn Arg Asn Gly Gly Gln Leu Glu
                300                 305                 310 ccc ggc ccc gcg gga gca ccc tcg cca gca ccg ggc act cca ggg ctg      1133
Pro Gly Pro Ala Gly Ala Pro Ser Pro Ala Pro Gly Thr Pro Gly Leu
            315                 320                 325
```

```
cgc cgc agg gcc agc cac tcc gac ctg gtc tac ttt gag aaa tct ccc     1181
Arg Arg Arg Ala Ser His Ser Asp Leu Val Tyr Phe Glu Lys Ser Pro
        330                 335                 340 gac ttc tgt gag cgc gag ccg cgc ctg gac tcg gca ggc act gtg ggc     1229
Asp Phe Cys Glu Arg Glu Pro Arg Leu Asp Ser Ala Gly Thr Val Gly
345                 350                 355 cgc ctg tgc aat aag agc agc acg ggt ccc gat ggc tgc ggc agc atg     1277
Arg Leu Cys Asn Lys Ser Ser Thr Gly Pro Asp Gly Cys Gly Ser Met
    360                 365                 370                 375 tgc tgt ggc cgc ggc cac aac att ctg cgc cag acg cgc agc gag cgc     1325
Cys Cys Gly Arg Gly His Asn Ile Leu Arg Gln Thr Arg Ser Glu Arg
                380                 385                 390 tgc cac tgc cgg ttc cac tgg tgc tgc ttc gtg gtc tgc gaa gaa tgc     1373
Cys His Cys Arg Phe His Trp Cys Cys Phe Val Val Cys Glu Glu Cys
            395                 400                 405 cgc atc acc gag tgg gtc agc gtc tgc aag tga gcagacccaa gctcctctgg  1426
Arg Ile Thr Glu Trp Val Ser Val Cys Lys
        410                 415 gtctcaagaa tggttgtcct cttggtgcct ggcttctgcc gctagcggat ctgagccagg  1486
cagcaagcag cagccttggc tcctgagaga ggtggttggc tcttacagcc ccgagggtct  1546
acaatcacca gacagtccag atctgattga cattcctccg ctcacctctg taggttcccc  1606
tctttctgtt cctagctcag acagctgggg gtgatagtgg agactgttcc acaccctagg  1666
acaggtcacc aaagcagccc agcctggcat gcctacctcc tgtcatctct tcttcccttc  1726
cccaggagtg ataggcaatg cactgaagct gatgggcacc ggggaagaaa actaaaaggc  1786
agaaatggcc gtcatcgggc tgaagtgact ctaagggctc cagacctctg ctcctgtctt  1846
tcacttaaca gatattttat tttgcgctct ctttgagaca ctctctgggg aaaaagaagc  1906
tccggagtct acaggctgat taagggacat ggacaataaa ccagtaaaca cacaaaaaaa  1966
aaaaaaaa                                                            1974

<210> SEQ ID NO 70
<211> LENGTH: 417
<212> TYPE: PRT
<213> ORGANISM: Mus musculus

<400> SEQUENCE: 70

Met Gly Ser Ala His Pro Arg Pro Trp Leu Arg Leu Pro Gln Gly Pro
1               5                   10                  15

Gln Pro Arg Pro Glu Phe Trp Ala Leu Leu Phe Phe Leu Leu Leu Leu
            20                  25                  30

Ala Ala Ala Val Pro Arg Ser Ala Pro Asn Asp Ile Leu Gly Leu Arg
        35                  40                  45

Leu Pro Pro Glu Pro Val Leu Asn Ala Asn Thr Val Cys Leu Thr Leu
    50                  55                  60

Pro Gly Leu Ser Arg Arg Gln Met Glu Val Cys Val Arg His Pro Asp
65                  70                  75                  80

Val Ala Ala Ser Ala Ile Gln Gly Ile Gln Ile Ala Ile His Glu Cys
                85                  90                  95

Gln His Gln Phe Arg Asp Gln Arg Trp Asn Cys Ser Ser Leu Glu Thr
            100                 105                 110

Arg Asn Lys Val Pro Tyr Glu Ser Pro Ile Phe Ser Arg Gly Phe Arg
        115                 120                 125

Glu Ser Ala Phe Ala Tyr Ala Ile Ala Ala Ala Gly Val Val His Ala
    130                 135                 140
```

-continued

```
Val Ser Asn Ala Cys Ala Leu Gly Lys Leu Lys Ala Cys Gly Cys Asp
145                 150                 155                 160

Ala Ser Arg Arg Gly Asp Glu Glu Ala Phe Arg Arg Lys Leu His Arg
                165                 170                 175

Leu Gln Leu Asp Ala Leu Gln Arg Gly Lys Gly Leu Ser His Gly Val
            180                 185                 190

Pro Glu His Pro Ala Ile Leu Pro Ala Ser Pro Gly Leu Gln Asp Ser
        195                 200                 205

Trp Glu Trp Gly Gly Cys Ser Pro Asp Val Gly Phe Gly Glu Arg Phe
    210                 215                 220

Ser Lys Asp Phe Leu Asp Ser Arg Glu Pro His Arg Asp Ile His Ala
225                 230                 235                 240

Arg Met Arg Leu His Asn Asn Arg Val Gly Arg Gln Ala Val Met Glu
                245                 250                 255

Asn Met Arg Arg Lys Cys Lys Cys His Gly Thr Ser Gly Ser Cys Gln
                260                 265                 270

Leu Lys Thr Cys Trp Gln Val Thr Pro Glu Phe Arg Thr Val Gly Ala
            275                 280                 285

Leu Leu Arg Asn Arg Phe His Arg Ala Thr Leu Ile Arg Pro His Asn
        290                 295                 300

Arg Asn Gly Gly Gln Leu Glu Pro Gly Pro Ala Gly Ala Pro Ser Pro
305                 310                 315                 320

Ala Pro Gly Thr Pro Gly Leu Arg Arg Arg Ala Ser His Ser Asp Leu
                325                 330                 335

Val Tyr Phe Glu Lys Ser Pro Asp Phe Cys Glu Arg Glu Pro Arg Leu
                340                 345                 350

Asp Ser Ala Gly Thr Val Gly Arg Leu Cys Asn Lys Ser Ser Thr Gly
            355                 360                 365

Pro Asp Gly Cys Gly Ser Met Cys Cys Gly Arg Gly His Asn Ile Leu
        370                 375                 380

Arg Gln Thr Arg Ser Glu Arg Cys His Cys Arg Phe His Trp Cys Cys
385                 390                 395                 400

Phe Val Val Cys Glu Glu Cys Arg Ile Thr Glu Trp Val Ser Val Cys
                405                 410                 415

Lys
```

<210> SEQ ID NO 71
<211> LENGTH: 2215
<212> TYPE: DNA
<213> ORGANISM: Mus musculus
<220> FEATURE:
<221> NAME/KEY: CDS
<222> LOCATION: (332)..(1501)

<400> SEQUENCE: 71

```
ctcgagcaga accacccgtg agttaggtcg agcagagcca aagcccccgg tgcttcgtcg      60
cgggttcgct cgctagctat ctggatcact ccctcccttt taccctccct tcctcccggc     120
gggcggccgc ggcgacgccg gggaagcggc agagaggagt ggctgggcgc tgggagaatg     180
ctgctccgcc gagggggctg aacccgacag tttccccacg gtttaagccc caagagccgg     240
gcccgagtga ctcaaccgcg agccttgtgg atcctgcacc tgaaccgctg gaggctgact     300
gactcgccca ccggagcctc cgggcttcga c atg ctg gag gag ccc cgg tct       352
                                    Met Leu Glu Glu Pro Arg Ser
                                     1               5
```

```
cgg cct ccg ccc tta ggc ctc gcg ggt ctc ctg ttc ttg gct ttg ttc      400
Arg Pro Pro Pro Leu Gly Leu Ala Gly Leu Leu Phe Leu Ala Leu Phe
         10              15                  20 agt cgg gct cta agc aat gag att ctg ggc ctt aaa ctt ccc ggt gag      448
Ser Arg Ala Leu Ser Asn Glu Ile Leu Gly Leu Lys Leu Pro Gly Glu
     25              30                  35 ccg ccg ctg acg gcc aac acc gtg tgc ttg acc ctg tcc gga ctg agt      496
Pro Pro Leu Thr Ala Asn Thr Val Cys Leu Thr Leu Ser Gly Leu Ser
 40              45                  50                  55 aag cga cag ctg ggg ctg tgc ctg cgc agc ccc gac gtg acg gcg tcg      544
Lys Arg Gln Leu Gly Leu Cys Leu Arg Ser Pro Asp Val Thr Ala Ser
             60                  65                  70 gcg ctc cag ggg ctg cac atc gcc gtt cac gag tgt cag cac cag ctg      592
Ala Leu Gln Gly Leu His Ile Ala Val His Glu Cys Gln His Gln Leu
             75                  80                  85 cgc gac cag cgc tgg aac tgc tcg gca ctg gag ggc ggc ggc cgg ctg      640
Arg Asp Gln Arg Trp Asn Cys Ser Ala Leu Glu Gly Gly Gly Arg Leu
         90                  95                 100 ccg cac cac agc gcc atc ctc aag cgc ggt ttc cgt gag agt gct ttc      688
Pro His His Ser Ala Ile Leu Lys Arg Gly Phe Arg Glu Ser Ala Phe
        105                 110                 115 tcc ttc tcc atg ctg gct gct ggg gtc atg cat gct gtt gcc aca gcc      736
Ser Phe Ser Met Leu Ala Ala Gly Val Met His Ala Val Ala Thr Ala
120                 125                 130                 135 tgc agc ctg ggc aag ctg gtg agc tgc ggc tgc gga tgg aag ggt agt      784
Cys Ser Leu Gly Lys Leu Val Ser Cys Gly Cys Gly Trp Lys Gly Ser
                140                 145                 150 ggt gag caa gac cgg ctt aga gcc aag ctg ctg cag ctt cag gca ctg      832
Gly Glu Gln Asp Arg Leu Arg Ala Lys Leu Leu Gln Leu Gln Ala Leu
            155                 160                 165 tct cgg ggc aag act ttc ccc atc tcc cag ccc agc cct gtt cct ggc      880
Ser Arg Gly Lys Thr Phe Pro Ile Ser Gln Pro Ser Pro Val Pro Gly
        170                 175                 180 tca gtc ccc agc ccc ggc ccc cag gac acg tgg gaa tgg ggt ggc tgt      928
Ser Val Pro Ser Pro Gly Pro Gln Asp Thr Trp Glu Trp Gly Gly Cys
        185                 190                 195 aac cac gac atg gac ttc gga gag aag ttc tct cgg gat ttc ttg gat      976
Asn His Asp Met Asp Phe Gly Glu Lys Phe Ser Arg Asp Phe Leu Asp
200                 205                 210                 215 tcc agg gag gct ccc cgg gac atc cag gcg aga atg cgg atc cac aac     1024
Ser Arg Glu Ala Pro Arg Asp Ile Gln Ala Arg Met Arg Ile His Asn
                220                 225                 230 aac agg gtg gga cgc cag gtg gta acg gaa aac ctg aag cgg aag tgc     1072
Asn Arg Val Gly Arg Gln Val Val Thr Glu Asn Leu Lys Arg Lys Cys
            235                 240                 245 aaa tgc cat gga acg tca ggc agc tgc caa ttc aag acc tgt tgg agg     1120
Lys Cys His Gly Thr Ser Gly Ser Cys Gln Phe Lys Thr Cys Trp Arg
        250                 255                 260 gca gcg cca gag ttc cgg gcc atc ggg gca gca ctg agg gag cgg ctg     1168
Ala Ala Pro Glu Phe Arg Ala Ile Gly Ala Ala Leu Arg Glu Arg Leu
        265                 270                 275 agc aga gcc atc ttt atc gat acc cac aac cgc aac tct gga gcg ttc     1216
Ser Arg Ala Ile Phe Ile Asp Thr His Asn Arg Asn Ser Gly Ala Phe
280                 285                 290                 295 cag ccc cgc cta cgt ccg cgg cgc ctc tct gga gag ctg gtt tac ttt     1264
Gln Pro Arg Leu Arg Pro Arg Arg Leu Ser Gly Glu Leu Val Tyr Phe
                300                 305                 310 gag aag tct cct gac ttc tgc gag cga gac cct act ctg ggc tcc cca     1312
Glu Lys Ser Pro Asp Phe Cys Glu Arg Asp Pro Thr Leu Gly Ser Pro
                315                 320                 325
```

-continued

```
ggc acg aga ggc cgg gct tgc aac aag acc agc cgc ctc ttg gat ggc        1360
Gly Thr Arg Gly Arg Ala Cys Asn Lys Thr Ser Arg Leu Leu Asp Gly
        330                 335                 340 tgt ggc agc ctg tgc tgt ggc cgt ggg cac aac gtg ctc cgg cag acg        1408
Cys Gly Ser Leu Cys Cys Gly Arg Gly His Asn Val Leu Arg Gln Thr
345                 350                 355 cga gtg gag cgc tgc cac tgt cgt ttc cac tgg tgc tgt tat gtg ctg        1456
Arg Val Glu Arg Cys His Cys Arg Phe His Trp Cys Cys Tyr Val Leu
    360                 365                 370                 375 tgt gat gag tgt aaa gtc aca gag tgg gtc aat gtg tgt aaa tga            1501
Cys Asp Glu Cys Lys Val Thr Glu Trp Val Asn Val Cys Lys
                380                 385                 390 aggtgagcct cgcctaggca cgacgaggag gagaagcact gtgtgagggc tgctctcttt      1561 cagcccttg ctcggatttc tgtctagggt ttatcgtggc tcccggaagc tcagagcatc      1621
tgcctgagaa cagctctggg ggtgtagggt caggtgaaat ctgtaacgag cagccttttg     1681
tgggggaagt ggccccacac tctgttctta aacactcgaa tagactaaga tgaaatgcac    1741
tgtactgtta gcgtcttctc tacctacagc tccctcgggc tcaggttcct acttcctttg    1801
gatagggagt ctatcttttg gccactcctc ttcctcgaag gataatagca ggcattgtgt    1861
ggagtcaata agacccgtat atatagcaag agaccacctc ttcctatttg tggttctcaa    1921
actcctccac tacagcccag aacctcctct tatgggacct cgggtgacaa taatgagagg    1981
ttttcggttg gaaaggaca gagggcaggg aagcctcaga cagctgtctt gtcaggctct     2041
tgggaggctt ctccttccgt tcagttgttg aaagggtctc tccaaaggaa aggttttagc   2101
cataactctt ggaggcccctt ttccttcttc agcaggaagg gtgggaatgg ataatttatt    2161
ttactgagat gtgttcttgg ttcctgtttg aaactaaaat aaattaagtt actg          2215
```

<210> SEQ ID NO 72
<211> LENGTH: 389
<212> TYPE: PRT
<213> ORGANISM: Mus musculus

<400> SEQUENCE: 72

```
Met Leu Glu Glu Pro Arg Ser Arg Pro Pro Pro Leu Gly Leu Ala Gly
1               5                   10                  15

Leu Leu Phe Leu Ala Leu Phe Ser Arg Ala Leu Ser Asn Glu Ile Leu
            20                  25                  30

Gly Leu Lys Leu Pro Gly Glu Pro Pro Leu Thr Ala Asn Thr Val Cys
        35                  40                  45

Leu Thr Leu Ser Gly Leu Ser Lys Arg Gln Leu Gly Leu Cys Leu Arg
    50                  55                  60

Ser Pro Asp Val Thr Ala Ser Ala Leu Gln Gly Leu His Ile Ala Val
65                  70                  75                  80

His Glu Cys Gln His Gln Leu Arg Asp Gln Arg Trp Asn Cys Ser Ala
                85                  90                  95

Leu Glu Gly Gly Gly Arg Leu Pro His His Ser Ala Ile Leu Lys Arg
            100                 105                 110

Gly Phe Arg Glu Ser Ala Phe Ser Phe Ser Met Leu Ala Ala Gly Val
        115                 120                 125

Met His Ala Val Ala Thr Ala Cys Ser Leu Gly Lys Leu Val Ser Cys
    130                 135                 140

Gly Cys Gly Trp Lys Gly Ser Gly Glu Gln Asp Arg Leu Arg Ala Lys
145                 150                 155                 160
```

```
Leu Leu Gln Leu Gln Ala Leu Ser Arg Gly Lys Thr Phe Pro Ile Ser
            165                 170                 175

Gln Pro Ser Pro Val Pro Gly Ser Val Pro Ser Pro Gly Pro Gln Asp
        180                 185                 190

Thr Trp Glu Trp Gly Gly Cys Asn His Asp Met Asp Phe Gly Glu Lys
    195                 200                 205

Phe Ser Arg Asp Phe Leu Asp Ser Arg Glu Ala Pro Arg Asp Ile Gln
210                 215                 220

Ala Arg Met Arg Ile His Asn Asn Arg Val Gly Arg Gln Val Val Thr
225                 230                 235                 240

Glu Asn Leu Lys Arg Lys Cys Lys Cys His Gly Thr Ser Gly Ser Cys
                245                 250                 255

Gln Phe Lys Thr Cys Trp Arg Ala Ala Pro Glu Phe Arg Ala Ile Gly
            260                 265                 270

Ala Ala Leu Arg Glu Arg Leu Ser Arg Ala Ile Phe Ile Asp Thr His
        275                 280                 285

Asn Arg Asn Ser Gly Ala Phe Gln Pro Arg Leu Arg Pro Arg Arg Leu
    290                 295                 300

Ser Gly Glu Leu Val Tyr Phe Glu Lys Ser Pro Asp Phe Cys Glu Arg
305                 310                 315                 320

Asp Pro Thr Leu Gly Ser Pro Gly Thr Arg Gly Arg Ala Cys Asn Lys
                325                 330                 335

Thr Ser Arg Leu Leu Asp Gly Cys Gly Ser Leu Cys Cys Gly Arg Gly
            340                 345                 350

His Asn Val Leu Arg Gln Thr Arg Val Glu Arg Cys His Cys Arg Phe
        355                 360                 365

His Trp Cys Cys Tyr Val Leu Cys Asp Glu Cys Lys Val Thr Glu Trp
    370                 375                 380

Val Asn Val Cys Lys
385

<210> SEQ ID NO 73
<211> LENGTH: 1821
<212> TYPE: DNA
<213> ORGANISM: Mus musculus
<220> FEATURE:
<221> NAME/KEY: CDS
<222> LOCATION: (271)..(1335)

<400> SEQUENCE: 73
gaattcgggc ctaatccgag cctgacgccg gcgggtctcg ggcggttcgg ggagagagcg    60
gactccttcc tcgctcagcc tccccggccc gaccctcct ttgtaatttg aataaaacgc   120
ctcccagccc gcgcgccgcc ttaacccgcc gccctgttct ccgtgattgc aggcggcgtg   180
cgcgcaggaa cagcagcggt ggcctgcagg cggcggagtt cggtgcggct cctgcagggt   240 gcgaccccg  ggacgccggg ccgcgcgacg atg agg gcg cgg ccg cag gtc tgc   294
                                   Met Arg Ala Arg Pro Gln Val Cys
                                    1               5 gag gct ctg ctc ttt gcc ttg gcg ctc cac acc ggc gtg tgc tat ggc   342
Glu Ala Leu Leu Phe Ala Leu Ala Leu His Thr Gly Val Cys Tyr Gly
     10                  15                  20 atc aag tgg ctg gca ctg tcc aag act ccg gca gcc ttg gca ctg aat   390
Ile Lys Trp Leu Ala Leu Ser Lys Thr Pro Ala Ala Leu Ala Leu Asn
 25                  30                  35                  40 cag acg caa cac tgt aaa cag ctg gag ggc ctg gtg tct gcg cag gtg   438
Gln Thr Gln His Cys Lys Gln Leu Glu Gly Leu Val Ser Ala Gln Val
                 45                  50                  55
```

-continued

```
cag ctc tgc cgc agc aac ctg gag ctc atg cgc acc atc gtg cac gcc      486
Gln Leu Cys Arg Ser Asn Leu Glu Leu Met Arg Thr Ile Val His Ala
             60                  65                  70 gcc cgg ggg gcc atg aag gcc tgc cgt agg gcc ttc gct gac atg cgc      534
Ala Arg Gly Ala Met Lys Ala Cys Arg Arg Ala Phe Ala Asp Met Arg
     75                  80                  85 tgg aac tgc tcc tcc atc gag ctc gcc ccc aac tac ctg ctt gac ctg      582
Trp Asn Cys Ser Ser Ile Glu Leu Ala Pro Asn Tyr Leu Leu Asp Leu
 90                  95                 100 gag aga ggt aca cgg gag tca gcc ttc gtg tat gcc ctg tcg gcc gcc      630
Glu Arg Gly Thr Arg Glu Ser Ala Phe Val Tyr Ala Leu Ser Ala Ala
105                 110                 115                 120 acc atc agt cac acc atc gcc cgg gcc tgc acc tct ggc gac ctg ccc      678
Thr Ile Ser His Thr Ile Ala Arg Ala Cys Thr Ser Gly Asp Leu Pro
                125                 130                 135 ggc tgc tcc tgc ggc ccc gtc cca ggt gag cca ccc ggg ccc ggg aac      726
Gly Cys Ser Cys Gly Pro Val Pro Gly Glu Pro Pro Gly Pro Gly Asn
            140                 145                 150 cgc tgg gga gga tgt gcg gac aac ctc agc tac ggg ctc ctc atg ggg      774
Arg Trp Gly Gly Cys Ala Asp Asn Leu Ser Tyr Gly Leu Leu Met Gly
        155                 160                 165 gcc aag ttt tcc gat gct cct atg aag gtg aaa aaa aca gga tcc caa      822
Ala Lys Phe Ser Asp Ala Pro Met Lys Val Lys Lys Thr Gly Ser Gln
170                 175                 180 gcc aat aaa ctg atg cgt cta cac aac agt gaa gtg ggg aga cag gct      870
Ala Asn Lys Leu Met Arg Leu His Asn Ser Glu Val Gly Arg Gln Ala
185                 190                 195                 200 cta cgt gcc tcc ctg gaa acg aag tgt aaa tgc cat ggg gtg tct ggc      918
Leu Arg Ala Ser Leu Glu Thr Lys Cys Lys Cys His Gly Val Ser Gly
                205                 210                 215 tcc tgc tcc atc cgc acc tgt tgg aag ggg ctg caa gag ctc cag gac      966
Ser Cys Ser Ile Arg Thr Cys Trp Lys Gly Leu Gln Glu Leu Gln Asp
            220                 225                 230 gtg gct gct gac ctc aag acc cgc tac ctg tca gcc acg aag gtg gta     1014
Val Ala Ala Asp Leu Lys Thr Arg Tyr Leu Ser Ala Thr Lys Val Val
        235                 240                 245 cac cgg cct atg ggc acc cgc aaa cac ttg gtg ccc aag gac ctg gat     1062
His Arg Pro Met Gly Thr Arg Lys His Leu Val Pro Lys Asp Leu Asp
250                 255                 260 atc cgg cct gtg aag gac tca gaa ctt gtg tat cta cag agc tcc cct     1110
Ile Arg Pro Val Lys Asp Ser Glu Leu Val Tyr Leu Gln Ser Ser Pro
265                 270                 275                 280 gac ttc tgc atg aag aat gag aag gtg gga tcc cat ggg acc caa gac     1158
Asp Phe Cys Met Lys Asn Glu Lys Val Gly Ser His Gly Thr Gln Asp
                285                 290                 295 agg cag tgc aac aag act tcc aac ggc agt gac agc tgc gac ctc atg     1206
Arg Gln Cys Asn Lys Thr Ser Asn Gly Ser Asp Ser Cys Asp Leu Met
            300                 305                 310 tgc tgt ggg cgc ggc tac aac ccc tac acg gac aga gtg gtg gag cga     1254
Cys Cys Gly Arg Gly Tyr Asn Pro Tyr Thr Asp Arg Val Val Glu Arg
        315                 320                 325 tgt cac tgc aag tac cac tgg tgc tgc tac gtc acc tgc cgc agg tgt     1302
Cys His Cys Lys Tyr His Trp Cys Cys Tyr Val Thr Cys Arg Arg Cys
330                 335                 340 gag cgc acg gtg gag cgc tac gtc tgc aag tga gaccatatgc cccacccctg   1355
Glu Arg Thr Val Glu Arg Tyr Val Cys Lys
345                 350                 355 aggaggggtg ctgctcctct gaggacccac tcaagggcct agagaccttg gtggacttcc   1415
```

```
ctgcagatgc cagatgccag gcgtgggagg cggcttgtgc tgtgcctcca cttggaagac    1475
accacaccag gaggcctggt cgccctggga gagccggggc ttcaaaggaa actgatagga    1535
ttaaaaataa cctggcagcc tggggcctga gtgccacatg ttgccttcca ggctgctcca    1595
agaagtcagg gcagggatgg gtaagactgt gcatttgacc tttcaaggcc agaaagaccg    1655
gctttctgga atgttctttg ggaccctgtg cccaccacat ggaaccacta acttgggttg    1715
taaattttta ttttccttcc cctctccgtg ggatgtggga gttacagaaa tatttataaa    1775
aatacagctt tttcctttgg gggtgaaaaa aaaaaaaaa gaattc                    1821
```

<210> SEQ ID NO 74
<211> LENGTH: 354
<212> TYPE: PRT
<213> ORGANISM: Mus musculus

<400> SEQUENCE: 74

```
Met Arg Ala Arg Pro Gln Val Cys Glu Ala Leu Leu Phe Ala Leu Ala
  1               5                  10                  15

Leu His Thr Gly Val Cys Tyr Gly Ile Lys Trp Leu Ala Leu Ser Lys
             20                  25                  30

Thr Pro Ala Ala Leu Ala Leu Asn Gln Thr Gln His Cys Lys Gln Leu
         35                  40                  45

Glu Gly Leu Val Ser Ala Gln Val Gln Leu Cys Arg Ser Asn Leu Glu
     50                  55                  60

Leu Met Arg Thr Ile Val His Ala Ala Arg Gly Ala Met Lys Ala Cys
 65                  70                  75                  80

Arg Arg Ala Phe Ala Asp Met Arg Trp Asn Cys Ser Ser Ile Glu Leu
                 85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Thr Ile Ser His Thr Ile Ala Arg
        115                 120                 125

Ala Cys Thr Ser Gly Asp Leu Pro Gly Cys Ser Cys Gly Pro Val Pro
    130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Thr Lys
        195                 200                 205

Cys Lys Cys His Gly Val Ser Gly Ser Cys Ser Ile Arg Thr Cys Trp
    210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
        275                 280                 285

Val Gly Ser His Gly Thr Gln Asp Arg Gln Cys Asn Lys Thr Ser Asn
    290                 295                 300
```

```
Gly Ser Asp Ser Cys Asp Leu Met Cys Cys Gly Arg Gly Tyr Asn Pro
305                 310                 315                 320

Tyr Thr Asp Arg Val Val Glu Arg Cys His Cys Lys Tyr His Trp Cys
            325                 330                 335

Cys Tyr Val Thr Cys Arg Arg Cys Glu Arg Thr Val Gly Arg Tyr Val
            340                 345                 350

Cys Lys

<210> SEQ ID NO 75
<211> LENGTH: 1664
<212> TYPE: DNA
<213> ORGANISM: Mus musculus
<220> FEATURE:
<221> NAME/KEY: CDS
<222> LOCATION: (279)..(1373)

<400> SEQUENCE: 75
gagcagaagg ttctcacctt ggaaagtgag ggaagctccc gcatctccag ctcatcctca      60
cctctgcgcc agaggacctt aggctacttt ctccgcctta tcttgcctag gggactgctg     120
atagtctctg tccttgctgc cctgtttaat gttaccttcc aggggaaaga gagcaaggaa     180
caactgggtg ctaagaaact gaccccaggc cctgcgggcc tctggagaga ggagacagag     240
gaggagtggc tggggctggg ggtctccatg cgtgggcc atg gac aga gcg gcg ctc     296
                                          Met Asp Arg Ala Ala Leu
                                           1               5 ctg gcc ctg ccc agc ttg tgt gcg ctg tgg gca gcc gtg ctg tcg ctg       344
Leu Ala Leu Pro Ser Leu Cys Ala Leu Trp Ala Ala Val Leu Ser Leu
         10                  15                  20 ctc ccc tgc gga acc cag ggc aac tgg atg tgg ttg ggc atc gcc tct       392
Leu Pro Cys Gly Thr Gln Gly Asn Trp Met Trp Leu Gly Ile Ala Ser
     25                  30                  35 ttc ggg gta ccg gag aag ctg ggc tgc gcc gac ttg ccg ctg aac agc       440
Phe Gly Val Pro Glu Lys Leu Gly Cys Ala Asp Leu Pro Leu Asn Ser
 40                  45                  50 cgc cag aag gag ctg tgc aag agg aaa ccg tac ctg ctg cct agc atc       488
Arg Gln Lys Glu Leu Cys Lys Arg Lys Pro Tyr Leu Leu Pro Ser Ile
 55                  60                  65                  70 cgc gag ggc gcc agg ctg ggc att cag gag tgc aga agc cag ttc cga       536
Arg Glu Gly Ala Arg Leu Gly Ile Gln Glu Cys Arg Ser Gln Phe Arg
                 75                  80                  85 cac gag agg tgg aac tgt atg gtc gcc act acc act tcc acc cag ctc       584
His Glu Arg Trp Asn Cys Met Val Ala Thr Thr Thr Ser Thr Gln Leu
             90                  95                 100 gcc aca gcc ccc ctc ttt ggc tat gag ctg agt agc ggc acc aag gag       632
Ala Thr Ala Pro Leu Phe Gly Tyr Glu Leu Ser Ser Gly Thr Lys Glu
        105                 110                 115 aca gca ttc att tat gcc atc atg gca gcg ggc ctg gtg cac tct gtc       680
Thr Ala Phe Ile Tyr Ala Ile Met Ala Ala Gly Leu Val His Ser Val
    120                 125                 130 acc agg tca tgc agt gca ggc aac atg acc gaa tgt tcc tgt gaa acc       728
Thr Arg Ser Cys Ser Ala Gly Asn Met Thr Glu Cys Ser Cys Glu Thr
135                 140                 145                 150 acc ttg cag aat ggt ggc tca cca agt gaa ggc tgg cac tgg gga gga       776
Thr Leu Gln Asn Gly Gly Ser Pro Ser Glu Gly Trp His Trp Gly Gly
                155                 160                 165 tgc tcg gat gat gtc cag tac ggc atg tgg ttc agc aga aag ttt cta       824
Cys Ser Asp Asp Val Gln Tyr Gly Met Trp Phe Ser Arg Lys Phe Leu
            170                 175                 180 gat ctt ccc atc aga aac acc aca gga aaa gaa agc aga gtc ctg cta       872
```

```
Asp Leu Pro Ile Arg Asn Thr Thr Gly Lys Glu Ser Arg Val Leu Leu
        185                 190                 195 gcc atg aat cta cac aac aac gaa gcg ggg cgg cag gct gtc gcc aag    920
Ala Met Asn Leu His Asn Asn Glu Ala Gly Arg Gln Ala Val Ala Lys
        200                 205                 210 tta atg tct gtg gac tgc cgc tgc cac gga gtt tcc ggc tcc tgt gct    968
Leu Met Ser Val Asp Cys Arg Cys His Gly Val Ser Gly Ser Cys Ala
215                 220                 225                 230 gtg aaa acc tgc tgg aaa act atg tct tct ttt gaa aag att ggg cat   1016
Val Lys Thr Cys Trp Lys Thr Met Ser Ser Phe Glu Lys Ile Gly His
                235                 240                 245 ttt tta aag gat aaa tat gaa aac agc atc cag atc tca gac aaa acc   1064
Phe Leu Lys Asp Lys Tyr Glu Asn Ser Ile Gln Ile Ser Asp Lys Thr
        250                 255                 260 aag agg aaa atg cgc agg aga gaa aaa gac cag agg cag acc ccc att   1112
Lys Arg Lys Met Arg Arg Arg Glu Lys Asp Gln Arg Gln Thr Pro Ile
        265                 270                 275 ctc aag gat gac ttg ctg tac gtt cat aag tct ccc aac tac tgc gtg   1160
Leu Lys Asp Asp Leu Leu Tyr Val His Lys Ser Pro Asn Tyr Cys Val
        280                 285                 290 gag aac aag aaa ctg ggg att cct ggg acc cag ggc aga gag tgc aac   1208
Glu Asn Lys Lys Leu Gly Ile Pro Gly Thr Gln Gly Arg Glu Cys Asn
295                 300                 305                 310 cgg aca tca gga ggc gca gat ggc tgt aac ctc ctc tgc tgt ggc cga   1256
Arg Thr Ser Gly Gly Ala Asp Gly Cys Asn Leu Leu Cys Cys Gly Arg
                315                 320                 325 ggc tac aac acc cat gta gtc agg cac gtg gag agg tgt gag tgt aag   1304
Gly Tyr Asn Thr His Val Val Arg His Val Glu Arg Cys Glu Cys Lys
        330                 335                 340 ttt atc tgg tgc tgc tac gtc cgc tgc agg agg tgt gaa agt atg acc   1352
Phe Ile Trp Cys Cys Tyr Val Arg Cys Arg Arg Cys Glu Ser Met Thr
        345                 350                 355 gat gtc cac acg tgt aag taa cctctccgtc cagcctagca tgagacgcct      1403
Asp Val His Thr Cys Lys
        360                 365 ctgtagtaac caaggtgtgg tgttggcatc tggagggcgc ccctactgtg cactgatggg  1463
gaagtcgctg cctgtaagag tgttcccaga cccctgggct agtctacgat ttctttcttt  1523
ctggcaggct tcaaatcaca agctgatcca gaggattgct tgggattctg aagttgaaaa  1583
ggttggcagt cgcctttgga tgatttggga aatatacatt gatatacagg aaacatcaaa  1643
tctgtttctg aagcaatgtg g                                            1664

<210> SEQ ID NO 76
<211> LENGTH: 364
<212> TYPE: PRT
<213> ORGANISM: Mus musculus

<400> SEQUENCE: 76

Met Asp Arg Ala Ala Leu Leu Ala Leu Pro Ser Leu Cys Ala Leu Trp
1               5                   10                  15

Ala Ala Val Leu Ser Leu Leu Pro Cys Gly Thr Gln Gly Asn Trp Met
            20                  25                  30

Trp Leu Gly Ile Ala Ser Phe Gly Val Pro Glu Lys Leu Gly Cys Ala
        35                  40                  45

Asp Leu Pro Leu Asn Ser Arg Gln Lys Glu Leu Cys Lys Arg Lys Pro
    50                  55                  60

Tyr Leu Leu Pro Ser Ile Arg Glu Gly Ala Arg Leu Gly Ile Gln Glu
65                  70                  75                  80
```

```
Cys Arg Ser Gln Phe Arg His Glu Arg Trp Asn Cys Met Val Ala Thr
                85                  90                  95

Thr Thr Ser Thr Gln Leu Ala Thr Ala Pro Leu Phe Gly Tyr Glu Leu
            100                 105                 110

Ser Ser Gly Thr Lys Glu Thr Ala Phe Ile Tyr Ala Ile Met Ala Ala
            115                 120                 125

Gly Leu Val His Ser Val Thr Arg Ser Cys Ser Ala Gly Asn Met Thr
        130                 135                 140

Glu Cys Ser Cys Glu Thr Thr Leu Gln Asn Gly Gly Ser Pro Ser Glu
145                 150                 155                 160

Gly Trp His Trp Gly Gly Cys Ser Asp Asp Val Gln Tyr Gly Met Trp
                165                 170                 175

Phe Ser Arg Lys Phe Leu Asp Leu Pro Ile Arg Asn Thr Thr Gly Lys
            180                 185                 190

Glu Ser Arg Val Leu Leu Ala Met Asn Leu His Asn Asn Glu Ala Gly
        195                 200                 205

Arg Gln Ala Val Ala Lys Leu Met Ser Val Asp Cys Arg Cys His Gly
    210                 215                 220

Val Ser Gly Ser Cys Ala Val Lys Thr Cys Trp Lys Thr Met Ser Ser
225                 230                 235                 240

Phe Glu Lys Ile Gly His Phe Leu Lys Asp Lys Tyr Glu Asn Ser Ile
                245                 250                 255

Gln Ile Ser Asp Lys Thr Lys Arg Lys Met Arg Arg Arg Glu Lys Asp
            260                 265                 270

Gln Arg Gln Thr Pro Ile Leu Lys Asp Asp Leu Leu Tyr Val His Lys
        275                 280                 285

Ser Pro Asn Tyr Cys Val Glu Asn Lys Lys Leu Gly Ile Pro Gly Thr
    290                 295                 300

Gln Gly Arg Glu Cys Asn Arg Thr Ser Gly Gly Ala Asp Gly Cys Asn
305                 310                 315                 320

Leu Leu Cys Cys Gly Arg Gly Tyr Asn Thr His Val Val Arg His Val
                325                 330                 335

Glu Arg Cys Glu Cys Lys Phe Ile Trp Cys Cys Tyr Val Arg Cys Arg
            340                 345                 350

Arg Cys Glu Ser Met Thr Asp Val His Thr Cys Lys
        355                 360

<210> SEQ ID NO 77
<211> LENGTH: 313
<212> TYPE: PRT
<213> ORGANISM: Homo sapiens

<400> SEQUENCE: 77

Met Gly Ile Gly Arg Ser Glu Gly Gly Arg Arg Gly Ala Leu Gly Val
1               5                   10                  15

Leu Leu Ala Leu Gly Ala Ala Leu Leu Ala Val Gly Ser Ala Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gln Gln Ala Ser Ser Trp
```

```
                    85                  90                  95
Val Pro Leu Leu Asn Lys Asn Cys His Ala Gly Thr Gln Val Phe Leu
                100                 105                 110
Cys Ser Leu Phe Ala Pro Val Cys Leu Asp Arg Pro Ile Tyr Pro Cys
                115                 120                 125
Arg Trp Leu Cys Glu Ala Val Arg Asp Ser Cys Glu Pro Val Met Gln
            130                 135                 140
Phe Phe Gly Phe Tyr Trp Pro Glu Met Leu Lys Cys Asp Lys Phe Pro
145                 150                 155                 160
Glu Gly Asp Val Cys Ile Ala Met Thr Pro Pro Asn Ala Thr Glu Ala
                165                 170                 175
Ser Lys Pro Gln Gly Thr Thr Val Cys Pro Pro Cys Asp Asn Glu Leu
                180                 185                 190
Lys Ser Glu Ala Ile Ile Glu His Leu Cys Ala Ser Glu Phe Ala Leu
                195                 200                 205
Arg Met Lys Ile Lys Glu Val Lys Lys Glu Asn Gly Asp Lys Lys Ile
            210                 215                 220
Val Pro Lys Lys Lys Pro Leu Lys Leu Gly Pro Ile Lys Lys Lys
225                 230                 235                 240
Asp Leu Lys Lys Leu Val Leu Tyr Leu Lys Asn Gly Ala Asp Cys Pro
                245                 250                 255
Cys His Gln Leu Asp Asn Leu Ser His His Phe Leu Ile Met Gly Arg
                260                 265                 270
Lys Val Lys Ser Gln Tyr Leu Leu Thr Ala Ile His Lys Trp Asp Lys
                275                 280                 285
Lys Asn Lys Glu Phe Lys Asn Phe Met Lys Lys Met Lys Asn His Glu
                290                 295                 300
Cys Pro Thr Phe Gln Ser Val Phe Lys
305                 310

<210> SEQ ID NO 78
<211> LENGTH: 295
<212> TYPE: PRT
<213> ORGANISM: Homo sapiens

<400> SEQUENCE: 78

Met Leu Gln Gly Pro Gly Ser Leu Leu Leu Phe Leu Ala Ser His
  1               5                  10                  15

Cys Cys Leu Gly Ser Ala Arg Gly Leu Phe Leu Phe Gly Gln Pro Asp
                20                  25                  30
Phe Ser Tyr Lys Arg Ser Asn Cys Lys Pro Ile Pro Ala Asn Leu Gln
                35                  40                  45
Leu Cys His Gly Ile Glu Tyr Gln Asn Met Arg Leu Pro Asn Leu Leu
            50                  55                  60
Gly His Glu Thr Met Lys Glu Val Leu Glu Gln Ala Gly Ala Trp Ile
65                  70                  75                  80
Pro Leu Val Met Lys Gln Cys His Pro Asp Thr Lys Lys Phe Leu Cys
                85                  90                  95
Ser Leu Phe Ala Pro Val Cys Leu Asp Asp Leu Asp Glu Thr Ile Gln
                100                 105                 110
Pro Cys His Ser Leu Cys Val Gln Val Lys Asp Arg Cys Ala Pro Val
                115                 120                 125
Met Ser Ala Phe Gly Phe Pro Trp Pro Asp Met Leu Glu Cys Asp Arg
            130                 135                 140
```

```
Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
            195                 200                 205

Asp Thr Lys Ile Ile Leu Glu Thr Lys Ser Lys Thr Ile Tyr Lys Leu
        210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Glu Leu Val Ile Thr Ser
            260                 265                 270

Val Lys Arg Trp Gln Lys Gly Gln Arg Glu Phe Lys Arg Ile Ser Arg
        275                 280                 285

Ser Ile Arg Lys Leu Gln Cys
        290                 295

<210> SEQ ID NO 79
<211> LENGTH: 325
<212> TYPE: PRT
<213> ORGANISM: Homo sapiens

<400> SEQUENCE: 79

Met Val Cys Gly Ser Pro Gly Gly Met Leu Leu Leu Arg Ala Gly Leu
1               5                   10                  15

Leu Ala Leu Ala Ala Leu Cys Leu Leu Arg Val Pro Gly Ala Arg Ala
                20                  25                  30

Ala Ala Cys Glu Pro Val Arg Ile Pro Leu Cys Lys Ser Leu Pro Trp
            35                  40                  45

Asn Met Thr Lys Met Pro Asn His Leu His His Ser Thr Gln Ala Asn
    50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
            115                 120                 125

Ser Trp Pro Glu Asn Leu Ala Cys Glu Glu Leu Pro Val Tyr Asp Arg
        130                 135                 140

Gly Val Cys Ile Ser Pro Glu Ala Ile Val Thr Ala Asp Gly Ala Asp
145                 150                 155                 160

Phe Pro Met Asp Ser Ser Asn Gly Asn Cys Arg Gly Ala Ser Ser Glu
                165                 170                 175

Arg Cys Lys Cys Lys Pro Ile Arg Ala Thr Gln Lys Thr Tyr Phe Arg
            180                 185                 190

Asn Asn Tyr Asn Tyr Val Ile Arg Ala Lys Val Lys Glu Ile Lys Thr
        195                 200                 205

Lys Cys His Asp Val Thr Ala Val Val Glu Val Lys Glu Ile Leu Lys
    210                 215                 220
```

```
Ser Ser Leu Val Asn Ile Pro Arg Asp Thr Val Asn Leu Tyr Thr Ser
225                 230                 235                 240

Ser Gly Cys Leu Cys Pro Pro Leu Asn Val Asn Glu Glu Tyr Ile Ile
                245                 250                 255

Met Gly Tyr Glu Asp Glu Arg Ser Arg Leu Leu Val Glu Gly
                260                 265                 270

Ser Ile Ala Glu Lys Trp Lys Asp Arg Leu Gly Lys Lys Val Lys Arg
                275                 280                 285

Trp Asp Met Lys Leu Arg His Leu Gly Leu Ser Lys Ser Asp Ser Ser
290                 295                 300

Asn Ser Asp Ser Thr Gln Ser Gln Lys Ser Gly Arg Asn Ser Asn Pro
305                 310                 315                 320

Arg Gln Ala Arg Asn
                325

<210> SEQ ID NO 80
<211> LENGTH: 314
<212> TYPE: PRT
<213> ORGANISM: Mus musculus

<400> SEQUENCE: 80

Met Gly Val Gly Arg Ser Ala Arg Gly Arg Gly Ala Ala Ser Gly
1               5                   10                  15

Val Leu Leu Ala Leu Ala Ala Ala Leu Leu Ala Ala Gly Ser Ala Ser
                20                  25                  30

Glu Tyr Asp Tyr Val Ser Phe Gln Ser Asp Ile Gly Ser Tyr Gln Ser
                35                  40                  45

Gly Arg Phe Tyr Thr Lys Pro Pro Gln Cys Val Asp Ile Pro Val Asp
            50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gln Gln Ala Ser Ser
                85                  90                  95

Trp Val Pro Leu Leu Asn Lys Asn Cys His Met Gly Thr Gln Val Phe
                100                 105                 110

Leu Cys Ser Leu Phe Ala Pro Val Cys Leu Asp Arg Pro Ile Tyr Pro
            115                 120                 125

Cys Arg Trp Leu Cys Glu Ala Val Arg Asp Ser Cys Glu Pro Val Met
130                 135                 140

Gln Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Thr Thr Glu
                165                 170                 175

Ala Ser Lys Pro Gln Gly Thr Thr Val Cys Pro Pro Cys Asp Asn Glu
            180                 185                 190

Leu Lys Ser Glu Ala Ile Ile Glu His Leu Cys Ala Ser Glu Phe Ala
        195                 200                 205

Leu Arg Met Lys Ile Lys Glu Val Lys Lys Glu Asn Gly Asp Lys Lys
210                 215                 220

Ile Val Pro Lys Lys Lys Pro Leu Lys Leu Gly Pro Ile Lys Lys
225                 230                 235                 240

Lys Glu Leu Lys Ala Leu Val Leu Phe Leu Asn Gly Ala Asp Cys
                245                 250                 255

Pro Cys His Gln Leu Asp Asn Leu Ser His Asn Phe Leu Ile Met Gly
```

```
                    260                 265                 270
Arg Lys Val Lys Ser Gln Tyr Leu Leu Thr Ala Ile His Lys Trp Asp
            275                 280                 285

Lys Lys Asn Lys Glu Phe Lys Asn Phe Met Lys Arg Met Lys Asn His
    290                 295                 300

Glu Cys Pro Thr Phe Gln Ser Val Phe Lys
305                 310

<210> SEQ ID NO 81
<211> LENGTH: 295
<212> TYPE: PRT
<213> ORGANISM: Mus musculus

<400> SEQUENCE: 81

Met Pro Arg Gly Pro Ala Ser Leu Leu Leu Val Leu Ala Ser His
 1               5                  10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
        35                  40                  45

Leu Cys His Gly Ile Glu Tyr Gln Asn Met Arg Leu Pro Asn Leu Leu
    50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Thr Lys Asn Glu Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
            260                 265                 270

Val Lys Arg Trp Gln Lys Gly Gln Arg Glu Phe Lys Arg Ile Ser Arg
        275                 280                 285

Ser Ile Arg Lys Leu Gln Cys
    290                 295

<210> SEQ ID NO 82
<211> LENGTH: 323
```

```
<212> TYPE: PRT
<213> ORGANISM: Mus musculus

<400> SEQUENCE: 82

Met Val Cys Cys Gly Pro Gly Arg Met Leu Leu Gly Trp Ala Gly Leu
 1               5                  10                  15

Leu Val Leu Ala Ala Leu Cys Leu Leu Gln Val Pro Gly Ala Gln Ala
                20                  25                  30

Ala Ala Cys Glu Pro Val Arg Ile Pro Leu Cys Lys Ser Leu Pro Trp
            35                  40                  45

Asn Met Thr Lys Met Pro Asn His Leu His His Ser Thr Gln Ala Asn
 50                  55                  60

Ala Ile Leu Ala Met Glu Gln Phe Glu Gly Leu Leu Gly Thr His Cys
 65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
                100                 105                 110

Glu Arg Ala Arg Gln Gly Cys Glu Pro Ile Leu Ile Lys Tyr Arg His
            115                 120                 125

Ser Trp Pro Glu Ser Leu Ala Cys Asp Glu Leu Pro Val Tyr Asp Arg
130                 135                 140

Gly Val Cys Ile Ser Pro Glu Ala Ile Val Thr Ala Asp Gly Ala Asp
145                 150                 155                 160

Phe Pro Met Asp Ser Ser Thr Gly His Cys Arg Gly Ala Ser Ser Glu
                165                 170                 175

Arg Cys Lys Cys Lys Pro Val Arg Ala Thr Gln Lys Thr Tyr Phe Arg
            180                 185                 190

Asn Asn Tyr Asn Tyr Val Ile Arg Ala Lys Val Lys Glu Val Lys Met
            195                 200                 205

Lys Cys His Asp Val Thr Ala Val Val Glu Val Lys Glu Ile Leu Lys
210                 215                 220

Ala Ser Leu Val Asn Ile Pro Arg Asp Thr Val Asn Leu Tyr Thr Thr
225                 230                 235                 240

Ser Gly Cys Leu Cys Pro Pro Leu Thr Val Asn Glu Glu Tyr Val Ile
                245                 250                 255

Met Gly Tyr Glu Asp Glu Arg Ser Arg Leu Leu Leu Val Glu Gly Val
            260                 265                 270

Ser Ile Ala Glu Lys Trp Lys Asp Arg Leu Gly Lys Lys Val Lys Arg
            275                 280                 285

Trp Asp Met Lys Leu Arg His Leu Gly Leu Gly Lys Thr Asp Ala Ser
290                 295                 300

Asp Ser Thr Gln Asn Gln Lys Ser Gly Arg Asn Ser Asn Pro Arg Pro
305                 310                 315                 320

Ala Arg Ser

<210> SEQ ID NO 83
<211> LENGTH: 604
<212> TYPE: PRT
<213> ORGANISM: Homo sapiens

<400> SEQUENCE: 83

Met Arg Gly Ala Ala Arg Leu Gly Arg Pro Gly Arg Ser Cys Leu Pro
 1               5                  10                  15

Gly Pro Ala Leu Arg Ala Ala Ala Ala Pro Ala Leu Leu Leu Ala Arg
```

-continued

```
                20                  25                  30
Cys Ala Val Ala Ala Ala Gly Leu Arg Ala Ala Arg Pro Arg
         35                  40                  45
Pro Pro Glu Leu Gln Ser Ala Ser Ala Gly Pro Ser Val Ser Leu Tyr
 50                  55                  60
Leu Ser Glu Asp Glu Val Arg Arg Leu Ile Gly Leu Asp Ala Glu Leu
 65                  70                  75                  80
Tyr Tyr Val Arg Asn Asp Leu Ile Ser His Tyr Ala Leu Ser Phe Asn
                 85                  90                  95
Leu Leu Val Pro Ser Glu Thr Asn Phe Leu His Phe Thr Trp His Ala
                100                 105                 110
Lys Ser Lys Val Glu Tyr Lys Leu Gly Phe Gln Val Asp Asn Val Leu
                115                 120                 125
Ala Met Asp Met Pro Gln Val Asn Ile Ser Val Gln Gly Glu Val Pro
                130                 135                 140
Arg Thr Leu Ser Val Phe Arg Val Glu Leu Ser Cys Thr Gly Lys Val
145                 150                 155                 160
Asp Ser Glu Val Met Ile Leu Met Gln Leu Asn Leu Thr Val Asn Ser
                165                 170                 175
Ser Lys Asn Phe Thr Val Leu Asn Phe Lys Arg Arg Lys Met Cys Tyr
                180                 185                 190
Lys Lys Leu Glu Glu Val Lys Thr Ser Ala Leu Asp Lys Asn Thr Ser
                195                 200                 205
Arg Thr Ile Tyr Asp Pro Val His Ala Ala Pro Thr Thr Ser Thr Arg
                210                 215                 220
Val Phe Tyr Ile Ser Val Gly Val Cys Cys Ala Val Ile Phe Leu Val
225                 230                 235                 240
Ala Ile Ile Leu Ala Val Leu His Leu His Asn Met Lys Arg Ile Glu
                245                 250                 255
Leu Asp Asp Ser Ile Ser Ala Ser Ser Ser Gln Gly Leu Ser Gln
                260                 265                 270
Pro Ser Thr Gln Thr Thr Gln Tyr Leu Arg Ala Asp Thr Pro Asn Asn
                275                 280                 285
Ala Thr Pro Ile Thr Ser Tyr Pro Thr Leu Arg Ile Glu Lys Asn Asp
                290                 295                 300
Leu Arg Ser Val Thr Leu Leu Glu Ala Lys Gly Lys Val Lys Asp Ile
305                 310                 315                 320
Ala Ile Ser Arg Glu Arg Ile Thr Leu Lys Asp Val Leu Gln Glu Gly
                325                 330                 335
Thr Phe Gly Arg Ile Phe His Gly Ile Leu Ile Asp Glu Lys Asp Pro
                340                 345                 350
Asn Lys Glu Lys Gln Ala Phe Val Lys Thr Val Lys Asp Gln Ala Ser
                355                 360                 365
Glu Ile Gln Val Thr Met Met Leu Thr Glu Ser Cys Lys Leu Arg Gly
                370                 375                 380
Leu His His Arg Asn Leu Leu Pro Ile Thr His Val Cys Ile Glu Glu
385                 390                 395                 400
Gly Glu Lys Pro Met Val Ile Leu Pro Tyr Met Asn Trp Gly Asn Leu
                405                 410                 415
Lys Leu Phe Leu Arg Gln Cys Lys Leu Val Glu Ala Asn Asn Pro Gln
                420                 425                 430
Ala Ile Ser Gln Gln Asp Leu Val His Met Ala Ile Gln Ile Ala Cys
                435                 440                 445
```

```
Gly Met Ser Tyr Leu Ala Arg Arg Glu Val Ile His Lys Asp Leu Ala
    450                 455                 460

Ala Arg Asn Cys Val Ile Asp Asp Thr Leu Gln Val Lys Ile Thr Asp
465                 470                 475                 480

Asn Ala Leu Ser Arg Asp Leu Phe Pro Met Asp Tyr His Cys Leu Gly
                485                 490                 495

Asp Asn Glu Asn Arg Pro Val Arg Trp Met Ala Leu Glu Ser Leu Val
            500                 505                 510

Asn Asn Glu Phe Ser Ser Ala Ser Asp Val Trp Ala Phe Gly Val Thr
        515                 520                 525

Leu Trp Glu Leu Met Thr Leu Gly Gln Thr Pro Tyr Val Asp Ile Asp
    530                 535                 540

Pro Phe Glu Met Ala Ala Tyr Leu Lys Asp Gly Tyr Arg Ile Ala Gln
545                 550                 555                 560

Pro Ile Asn Cys Pro Asp Glu Leu Phe Ala Val Met Ala Cys Cys Trp
                565                 570                 575

Ala Leu Asp Pro Glu Glu Arg Pro Lys Phe Gln Gln Leu Val Gln Cys
            580                 585                 590

Leu Thr Glu Phe His Ala Ala Leu Gly Ala Tyr Val
    595                 600

<210> SEQ ID NO 84
<211> LENGTH: 405
<212> TYPE: PRT
<213> ORGANISM: Mus musculus

<400> SEQUENCE: 84

Leu Asp Lys Asn Thr Ser Arg Thr Ile Tyr Asp Pro Val His Ala Ala
  1               5                  10                  15

Pro Thr Thr Ser Thr Arg Val Phe Tyr Ile Ser Val Gly Val Cys Cys
                20                  25                  30

Ala Val Ile Phe Leu Val Ala Ile Ile Leu Ala Val Leu His Leu His
            35                  40                  45

Ser Met Lys Arg Ile Glu Leu Asp Asp Ser Ile Ser Ala Ser Ser Ser
    50                  55                  60

Ser Gln Gly Leu Ser Gln Pro Ser Thr Gln Thr Thr Gln Tyr Leu Arg
65                  70                  75                  80

Ala Asp Thr Pro Asn Asn Ala Thr Pro Ile Thr Ser Ser Ser Gly Tyr
                85                  90                  95

Pro Thr Leu Arg Ile Glu Lys Asn Asp Leu Arg Ser Val Thr Leu Leu
            100                 105                 110

Glu Ala Lys Ala Lys Val Lys Asp Ile Ala Ile Ser Arg Glu Arg Ile
        115                 120                 125

Thr Leu Lys Asp Val Leu Gln Glu Gly Thr Phe Gly Arg Ile Phe His
    130                 135                 140

Gly Ile Leu Val Asp Glu Lys Asp Pro Asn Lys Glu Lys Gln Thr Phe
145                 150                 155                 160

Val Lys Thr Val Lys Asp Gln Ala Ser Glu Val Gln Val Thr Met Met
                165                 170                 175

Leu Thr Glu Ser Cys Lys Leu Arg Gly Leu His His Arg Asn Leu Leu
            180                 185                 190

Pro Ile Thr His Val Cys Ile Glu Glu Gly Glu Lys Pro Met Val Val
        195                 200                 205

Leu Pro Tyr Met Asn Trp Gly Asn Leu Lys Leu Phe Leu Arg Gln Cys
```

-continued

```
            210                 215                 220
Lys Leu Val Glu Ala Asn Asn Pro Gln Ala Ile Ser Gln Gln Asp Leu
225                 230                 235                 240

Val His Met Ala Ile Gln Ile Ala Cys Gly Met Ser Tyr Leu Ala Arg
                245                 250                 255

Arg Glu Val Ile His Arg Asp Leu Ala Ala Arg Asn Cys Val Ile Asp
                260                 265                 270

Asp Thr Leu Gln Val Lys Ile Thr Asp Asn Ala Leu Ser Arg Asp Leu
            275                 280                 285

Phe Pro Met Asp Tyr His Cys Leu Gly Asp Asn Glu Asn Arg Pro Val
290                 295                 300

Arg Trp Met Ala Leu Glu Ser Leu Val Asn Asn Glu Phe Ser Ser Ala
305                 310                 315                 320

Ser Asp Val Trp Ala Phe Gly Val Thr Leu Trp Glu Leu Met Thr Leu
                325                 330                 335

Gly Gln Thr Pro Tyr Val Asp Ile Asp Pro Phe Glu Met Ala Ala Tyr
                340                 345                 350

Leu Lys Asp Gly Tyr Arg Ile Ala Gln Pro Ile Asn Cys Pro Asp Glu
            355                 360                 365

Leu Phe Ala Val Met Ala Cys Cys Trp Ala Leu Asp Pro Glu Glu Arg
370                 375                 380

Pro Lys Phe Gln Gln Leu Val Gln Cys Leu Thr Glu Phe His Ala Ala
385                 390                 395                 400

Leu Gly Ala Tyr Val
            405

<210> SEQ ID NO 85
<211> LENGTH: 610
<212> TYPE: PRT
<213> ORGANISM: Drosophila melanogaster

<400> SEQUENCE: 85

Met Ala Pro Asn Leu Leu Thr Ile Gly Leu Leu Thr Leu Ile Ala
1               5                   10                  15

Ser Gly Gln Ala His Leu Asn Ile Phe Leu Asn Leu His Glu Val Leu
                20                  25                  30

Arg Leu Ile Gly Val Ser Ala Glu Leu Tyr Tyr Val Arg Glu Gly Ala
            35                  40                  45

Ile Asn Asp Tyr Ala Leu Asn Phe Ala Val Pro Val Pro Ala Asn Ile
        50                  55                  60

Ser Asp Val Thr Phe Thr Trp Gln Ser Leu Val Asp His Pro Leu Pro
65                  70                  75                  80

Tyr Ser Ile Asn Ile Ala Thr Ser Asp Thr Glu Val Leu Pro Arg Pro
                85                  90                  95

Ile Leu Asn Ile Ser Arg Ile Gly Asp Val Pro Val Glu Pro Gln Thr
            100                 105                 110

Trp Gly Ile Ala Leu Lys Cys Ser Gly Thr Arg Asn Ala Glu Val Thr
        115                 120                 125

Val Thr Ile Asn Val Glu Val Ile Leu Asp Arg Ala Thr Asn Asn Asn
130                 135                 140

Thr Asn Leu Ile Phe Lys Arg Lys Lys Ile Cys Leu Arg Glu Glu Gln
145                 150                 155                 160

Asp Ser Ala His Glu Glu Tyr Asp Asp Asp Leu Asp Leu Leu Gln
                165                 170                 175
```

-continued

```
Thr Ala Arg Lys Gly His Gly Gly Asp Ile His Tyr Val Asp Arg Asn
            180                 185                 190

Asp Glu His Val Val Ala Asn Gly His Gln Ala Pro Glu Lys Gln Arg
            195                 200                 205

Pro Val Val Thr Glu Ser Pro Val Gly Arg Gly Asn Ser Gly Gly Ser
210                 215                 220

Lys Arg Asp Phe Asp Pro Met Leu Arg Glu Asn Leu Val Pro Pro Ala
225                 230                 235                 240

Ser Gly Leu Val Thr Leu Ile Val Gly Ile Leu Ala Leu Val Leu
            245                 250                 255

Val Ser Thr Leu Ile Leu Ile Ala Tyr Cys Ala Lys Gly Pro Ser Lys
            260                 265                 270

Arg His Pro Ser Asn Gly Val His Leu Ile Lys Thr Ser Ser Phe Gln
            275                 280                 285

Arg Leu Pro Thr Ile Ser Ser Thr Ala His Asn Ser Ile Tyr Val Cys
            290                 295                 300

Pro Ser Thr Ile Thr Pro Thr Tyr Ala Thr Leu Thr Arg Pro Phe Arg
305                 310                 315                 320

Glu Tyr Glu His Glu Pro Glu Glu Phe Asn Arg Arg Leu Gln Glu Leu
            325                 330                 335

Thr Val Gln Lys Cys Arg Val Arg Leu Ser Cys Leu Val Gln Glu Gly
            340                 345                 350

Asn Phe Gly Arg Ile Tyr Arg Gly Thr Tyr Asn Asp Cys Gln Glu Val
            355                 360                 365

Leu Val Lys Thr Val Ala Gln His Ala Ser Gln Leu Gln Val Asn Leu
            370                 375                 380

Leu Leu Gln Glu Ser Met Met Leu Tyr Glu Ala Ser His Pro Asn Val
385                 390                 395                 400

Leu Ser Val Leu Gly Ile Ser Ile Glu Asp Tyr Ala Thr Pro Phe Val
            405                 410                 415

Leu Tyr Ala Ala Thr Gly Ser Val Arg Asn Leu Lys Ser Phe Leu Gln
            420                 425                 430

Asp Pro Ser Tyr Ala Arg Ser Val Thr Thr Ile Gln Thr Val Leu Met
            435                 440                 445

Gly Ser Gln Leu Ala Met Ala Met Glu His Leu His Asn His Gly Val
            450                 455                 460

Ile His Lys Asp Ile Ala Ala Arg Asn Cys Val Ile Asp Asp Gln Leu
465                 470                 475                 480

Arg Val Lys Leu Thr Asp Ser Ala Leu Ser Arg Asp Leu Phe Pro Gly
            485                 490                 495

Asp Tyr Asn Ser Leu Gly Asp Gly Glu Tyr Arg Pro Ile Lys Trp Leu
            500                 505                 510

Ser Leu Glu Ala Leu Gln Lys Ser His Tyr Asn Glu Gly Ser Asp Val
            515                 520                 525

Trp Ser Phe Gly Val Leu Met Trp Glu Met Cys Thr Leu Gly Lys Leu
            530                 535                 540

Pro Tyr Ala Glu Ile Asp Pro Tyr Glu Met His Tyr Leu Lys Asp
545                 550                 555                 560

Gly Tyr Arg Leu Ala Gln Pro Phe Asn Cys Pro Asp Glu Leu Phe Thr
            565                 570                 575

Ile Met Ala Tyr Cys Trp Ala Ser Met Pro Ala Glu Arg Pro Ser Phe
            580                 585                 590

Ser Gln Leu Gln Ile Cys Leu Ser Glu Phe His Thr Gln Ile Thr Arg
```

```
                595              600              605
Tyr Val
    610
```

METHODS AND COMPOSITIONS FOR NERVE REGENERATION

CROSS-REFERENCE TO RELATED APPLICATIONS

This application claims the benefit of U.S. Provisional Application No. 60/470,913 filed May 15, 2003.

BACKGROUND OF THE INVENTION

1. Field of the Invention

The present invention relates generally to the fields of molecular biology, cell biology, pharmacology, developmental neuroscience, neurology, neurosurgery and regenerative biology. More particularly, it concerns methods and compositions for modulating regeneration of a nerve cell using a Wnt, a Wnt-like substance, and/or a chemical compound affecting a Wnt signaling pathway. It also concerns methods and compositions for inhibiting growth of a neuron using inhibitors of neuronal growth that act via the Wnt signaling pathways, such as a Secreted Frizzled-Related Protein (sFRP), sFRP-like substance, Ryk, or Ryk-like substance.

2. Description of Related Art

The central nervous system (CNS) is connected by ascending sensory pathways and descending motor or regulatory pathways. In the CNS, somatosensory pathways ascend to the brain centers, and motor pathways controlling body movement descend from the brain to the spinal cord (Fitzgerald, 1996). The molecular mechanisms of axonal connections along the longitudinal axis of the CNS have remained a long-standing mystery.

Unlike the peripheral nervous system, damage to the central nervous system axons, such as spinal cord axons cannot be repaired, causing permanent impairment of neural function, such as in paralysis. The spinal cord serves important functions in the central nervous system. One such function is to allow communication of the body and the brain. The nerve fibers within the spinal cord carry messages to and from the brain to other parts of the body. In general sensory information from the body travels along the spinal cord up to the brain and instruction from the brain, such as motor command, travels along the spinal cord down from the brain. Thus, the spinal cord can be compared to a telephone cable, which connects the central office (brain) to the individual homes.

The term spinal cord injury refers to any injury of the neurons within the spinal canal. Spinal cord injury can occur from either trauma or disease to the vertebral column or the spinal cord itself. Most spinal cord injuries are the result of trauma to the vertebral column causing a fracture of the bone, or tearing of the ligaments with displacement of the bony column producing a pinching of the spinal cord. The majority of broken necks and broken backs, or vertebral fractures, do not cause any spinal cord damage; however, in 10-14% of the cases where a vertebral trauma has occurred, the damage is of such severity it results in damage to the spinal cord.

Spinal cord injury primarily occurs in young men with the greatest number of injuries occurring in the 16-30 age group. Patients with a spinal cord injury are designated as having tetraplegia (preferred to quadriplegia) or paraplegia. Tetraplegia refers to injuries to the cervical spinal cord and paraplegia refers to injuries below the cervical spinal cord. Patients with tetraplegia are slightly more common (51.7%) than patients with paraplegia. The majority of spinal cord injuries, about 37.4%, are sustained during a motor vehicle accident. Acts of violence are the second most common cause at 25.9%, falls are third at 21.5% and sports injuries are fourth at 7.1%.

It is estimated that the annual incidence of spinal cord injury (SCI), not including those who die at the scene of the accident, is approximately 40 cases per million population in the U.S., or approximately 11,000 new cases each year. The number of people in the U.S. who are alive today and who have SCI has been estimated to be between 721 and 906 per million population. This corresponds to between 183,000 and 230,000 persons.

Treatment options for patients with spinal cord injuries are limited. Often, patients with SCI are left with severe, permanent disabilities. A major reason for the limited availability of treatment options is the fact that there is little known about factors that can control and modulate nerve growth and regeneration following spinal cord injury. For example, the precise molecular mechanisms that guide axons along the anterior-posterior (A-P) axis of the spinal cord are unknown.

Axonal connections are patterned along the A-P and dorsal-ventral (D-V) neuraxes, wiring a large number of neurons into an intricate network. Axon guidance along the D-V axis has been a major focus of study in a number of experimental systems in recent years (Tessier-Lavigne and Goodman, 1996; Dickson, 2002). Much work has concentrated on the question of how axons are guided towards and away from the ventral midline and how midline crossing is regulated. Guidance molecules, such as Netrin-1 and members of the Slit and Semaphorin families, play pivotal roles in the dorsal-ventral guidance of axons (Tessier-Lavigne and Goodman, 1996; Dickson, 2002). The nature of the anterior-posterior guidance cues remains an enigma. Four classes of axon guidance molecules have been described (Tessier-Lavigne and Goodman, 1996): long-range attractants, long-range repellents, contact-mediated attractants and contact-mediated repellents. It is currently unknown whether a general gradient of attractant(s) or repellent(s) along the anterior-posterior axis guides axons to grow along this axis, or whether this guidance is mediated by more regional or segmental cues. The question of axon guidance along the A-P axis is of particularly interest in the spinal cord, where multiple classes of axons project either anteriorly or posteriorly along the length of the spinal cord. For example, somatosensory pathways ascend from the spinal cord to the brain and motor pathways descend from the brain to the spinal cord, with both the ascending and descending pathways carrying topographic information (FitzGerald, 1996).

The dorsal spinal cord commissural neurons form several ascending somatosensory pathways, such as the spinothalamic tracts, which send pain and temperature sensations to the brain (Ramon y Cajal, 1893; Altman and Bayer, 1984). The cell bodies of commissural neurons are located in the dorsal spinal cord. During embryonic development, commissural neurons project axons to the ventral midline. Once they reach the floor plate, they cross the midline and enter the contralateral side of the spinal cord. After midline crossing, commissural axons make a remarkably sharp anterior turn towards the brain (Ramon y Cajal, 1893; Altman and Bayer 1984; Tessier-Lavigne, 1994). All dorsal spinal cord commissural axons along the entire anterior-posterior length of the spinal cord project anteriorly after midline crossing. The initial ventral growth of the commissural axons is controlled by a gradient of a diffusible chemoattractant, Netrin-1 (Serafini et al., 1994; Kennedy et al., 1994; Serafini et al., 1996). As the axons cross the midline, they lose responsiveness to Netrin-1 (Shirasaki et al., 1998). Interestingly, while losing responsiveness to Netrin-1 during midline crossing, commissural axons gain responsiveness to several chemorepellents, which are located in the midline and the ventral spinal cord (Zou et al., 2000). These repellents help to expel the axons from the midline and to turn axons from their dorsal-ventral trajectory into their longitudinal pathways along the anterior-posterior axis by preventing axons from overshooting into the contralateral ventral spinal cord and recrossing the floor plate; the axons thus become "squeezed" into their longitudinal pathway (Zou et al., 2000). The expression pattern of the Slits and Semaphorins identified in these studies have been examined, but no anterior-posterior gradient of these chemorepellents in the spinal cord has been identified, suggesting that these repellents do not control anterior-posterior pathfinding.

Wnt polypeptides are secreted cysteine-rich glycosylated polypeptides that play a role in the development of a wide range of organisms. The Wnt family of polypeptides bind to an extracellular domain of a family of cell surface proteins called Frizzled receptors, and may play a role in embryonic induction, generation of cell polarity, and specification of cell fate.

Wnts are encoded by a large gene family, whose members have been found in round worms, insects, cartilaginous fish and vertebrates (Sidow, 1994). Wnts are thought to function in a variety of developmental and physiological processes since many diverse species have multiple conserved Wnt genes (McMahon, 1992; Nusse and Varmus, 1992). The Wnt growth factor family includes at least 18 genes identified in the human by cDNA cloning (see, e.g., Vant Veer et al., 1984; Miller, 2001).

Wnts may play a role in local cell signaling and neurogenesis. Biochemical studies have shown that much of the secreted Wnt protein can be found associated with the cell surface or extracellular matrix rather than freely diffusible in the medium (Papkoff and Schryver, 1990; Bradley and Brown, 1990). Studies of mutations in Wnt genes have indicated a role for Wnts in growth control and tissue patterning. In *Drosophila*, wingless (wg) encodes a Wnt gene (Rijsenijk et al., 1987) and wg mutations alter the pattern of embryonic ectoderm, neurogenesis, and imaginal disc outgrowth (Morata and Lawrence, 1977; Baker, 1988; Klingensmith and Nusse, 1994). Knock-out mutations in mice have shown Wnts to be essential for brain development (McMahon and Bradley, 1990; Thomas and Cappechi, 1990). However, a role for Wnts in mammalian directional axonal growth regulation in the spinal cord has not previously been suggested or considered.

The identification of modulators of neuronal growth and regeneration following SCI could be applied in new forms of treatment of patients with this debilitating condition. The identification of modulators of neuronal growth and regeneration could also be applied in the treatment of patients with other disorders involving neuronal dysfunction, such as neurodegenerative diseases. Agents that can promote axonal growth along the A-P axis following injury to the spinal cord may be applied to help prevent the permanent paralysis that is often associated with SCI. Therefore, there is a need for better treatments of SCI, and a greater understanding of modulators of neuronal growth and regeneration might lead to improved methods of treatment of this devastating disorder.

SUMMARY OF THE INVENTION

The inventor has found that Wnt proteins play a general role in anterior-posterior patterns of CNS axons, which connect the brain and the spinal cord.

The invention disclosed herein is based on the discovery of a molecular regulatory system involving Wnt proteins that is involved in the normal formation of the spinal cord axon connection. A chemoattractant gradient exists inside the spinal cord, and this chemoattractant gradient guides the anterior projection of post-crossing spinal cord commissural neurons along the A-P axis towards the brain during embryogensis. In particular, it has been discovered that several Wnt proteins can stimulate the extension of post-crossing but not pre-crossing commissural axons in the spinal cord. Wnt4 was found to be expressed in a decreasing A-P gradient in the floor plate of the spinal cord. sFRPs, inhibitors of Wnts, were found to disrupt the A-P pathfinding of post-crossing spinal cord commissural neurons. However, Wnt4 protein was found to rescue the anterior turn of the misrouting axons and also reorient axons posteriorly, suggesting that Wnt4 plays an instructive role in orienting directional axonal growth. In addition, commissural axons in fz3 knockout mice were found to display A-P guidance defects after midline crossing. In view of these findings, Wnt, Wnt-like substances, and/or chemical compounds affecting a Wnt signaling pathway can be used as novel agents to modulate neuronal growth, and can be used in new forms of treatment of diseases and conditions associated with neuronal dysfunction, such as SCI (Lyuksyotova et al., 2003).

The inventor has further found that a different set of Wnt proteins pattern the connections of corticospinal tract (CST) axons projecting along the opposite direction by a repulsive mechanism. CST axons project from the motor cortex of the brain to the spinal cord motor circuits and send voluntary movement signals from the brain to the body. Several Wnt genes were found to be expressed at the dorsal funiculus in an anterior-to-posterior decreasing gradient at the cervical spinal cord, where CST axons first enter the spinal cord and a anterior-to-posterior increasing gradient at the lumbar spinal cord level, forming a "half-pipe" gradient. Wnt1 and Wnt5a can repel CST axons in collagen gel assays. A repulsive Wnt receptor, Ryk (Oshikawa et al., 2003; Halford et al., 2000), is expressed in the CST axons and can be detected at the pyramidal decussation and in the dorsal funiculus. Antibodies against the ectodomain of Ryk can block the repulsion of Wnt1. Finally, intrathecal injection of a Wnt inhibitor, secreted Frizzled related protein 2 (sFRP2), at the rostral cervical level (C1 and C2), can inhibit the posterior growth of CST axons in vivo, leading to weaker grip strength.

The inventor has also found that Wnts play important roles in patterning the synaptic connections once they reach their target. This process of target selection ensures the specific neuron to neuron connection and is essential to the development of the functional circuits throughout the nervous system. Therefore, Wnts can be used to ensure specific synaptic reconnection in repair damaged neural circuits.

Certain embodiments of the present invention are generally concerned with methods for modulating growth of a neuron comprising contacting the neuron with a Wnt, a Wnt-like substance, and/or a chemical compound affecting a Wnt signaling pathway. The definitions of Wnt, Wnt-like substance, and chemical compound affecting a Wnt signaling pathway are discussed in detail in the specification below.

In the context of the invention, the terms "contact" or "contacting" are defined to mean any manner in which a compound is brought into a position where it can mediate, modulate, or inhibit the growth of a neuron. "Contacting" can comprise injecting a diffusable or non-diffusable substance into the neuron or an area adjacent a neuron. "Contacting" can comprise placing a nucleic acid encoding a compound into or close to a neuron or non-neuronal cell in a manner such that the nucleic acid is expressed to make the compound in a manner in which it can act upon the neuron. Those of skill in the art, following the teachings of this specification, will be able to contact neurons with substances in any manner.

The methods for modulating growth of a neuron may, in certain embodiments, be methods for stimulating growth of a neuron, methods for regenerating a damaged neuron, or methods for guiding growth of a neuron along the anterior-posterior axis. In other embodiments, the methods for modulating growth of a neuron are further defined as methods for directionally orienting axon growth of a neuron between the spinal cord and the brain.

The neuron to be modulated may be any neuron. However, in certain embodiments, the neuron is a neuron in the spinal cord that has been damaged. For example, the spinal cord may have been damaged by traumatic spinal cord injury. The damage may have resulted in impaired function of the neuron.

In certain embodiments, the method for modulating growth of a neuron is a method for modulating growth of a neuron in a subject. Although any subject is contemplated by the present invention, in certain embodiments the subject may be a patient with a disorder of the spinal cord. The disorder of the spinal cord may be any disorder, such as a traumatic spinal cord injury. The traumatic spinal cord injury may or may not have resulted in paralysis of the subject. In further embodiments, the patient is a patient with a neurodegenerative disease.

The neuron to be modulated can be a sensory or a motor neuron. In certain embodiments, the neuron is contacted with a Wnt, a Wnt-like substance, and/or a chemical compound affecting a Wnt signaling pathway that further involves exposing the neuron to a gradient of the Wnt, Wnt-like substance, and/or chemical compound affecting a Wnt signaling pathway. The gradient may be in the spinal cord, such as a decreasing anterior-posterior gradient within the spinal cord. In other embodiments, exposing the neuron to the gradient involves stimulating directionally-oriented axon growth of the neuron along the anterior-posterior axis. Any direction of axon growth is contemplated by the present invention. In certain embodiments, the axon growth is directed from the spinal cord to the brain, such as in the growth of neurons in ascending somatosensory pathways. In other embodiments, the axon growth is directed from the brain to the spinal cord, such as in the growth of neurons in descending motor pathways or other regulatory pathways. In further embodiments, the axon growth is directed along the spinothalamic pathway.

Any Wnt is contemplated by the present invention. A detailed discussion of Wnts is provided in the specification below. For example, the Wnt protein may be Wnt1, Wnt2, Wnt2b, Wnt3, Wnt3a, Wnt4, Wnt5a, Wnt5b, Wnt 6, Wnt7a, Wnt7b, Wnt8a, Wnt8b, Wnt9a, Wnt9b, Wnt10a, Wnt10b, Wnt11, or Wnt16 protein. One of skill in the art would be familiar with the range of Wnts available that are contemplated by the present invention. In certain embodiments, the Wnt is a Wnt1, Wnt4, Wnt5a, Wnt6, or Wnt7b protein. In certain embodiments, the Wnt protein will be a mammalian Wnt protein, for example a human or murine Wnt protein, or a homolog thereof from another vertebrate species.

In further embodiments, the Wnt-like substance is a Wnt polypeptide. Any Wnt polypeptide is contemplated by the present invention. For example, the Wnt polypeptide may be a Wnt1, Wnt2, Wnt2b, Wnt3, Wnt3a, Wnt4, Wnt5a, Wnt5b, Wnt 6, Wnt7a, Wnt7b, Wnt8a, Wnt8b, Wnt9a, Wnt9b, Wnt10a, Wnt10b, Wnt11, or Wnt16 polypeptide. One of skill in the art would be familiar with the range of Wnt polypeptides available that are contemplated by the present invention. In certain embodiments, the Wnt polypeptide is a Wnt1, Wnt4, Wnt5a, Wnt6, or Wnt7b polypeptide. Wnt polypeptides are discussed in greater detail in the specification below. In certain embodiments, the Wnt polypeptide will be a mammalian Wnt protein, for example a human or murine Wnt polypeptide, or a homolog thereof from another vertebrate species.

In further embodiments, the Wnt-like substance is a Wnt peptide. Any Wnt peptide is contemplated by the present invention. For example, the Wnt peptide may be a Wnt1, Wnt2, Wnt2b, Wnt3, Wnt3a, Wnt4, Wnt5a, Wnt5b, Wnt 6, Wnt7a, Wnt7b, Wnt8a, Wnt8b, Wnt9a, Wnt9b, Wnt10a, Wnt10b, Wnt11, or Wnt16 peptide. One of skill in the art would be familiar with the range of Wnt peptides available that are contemplated by the present invention. In certain embodiments, the Wnt peptide is a Wnt1, Wnt4, Wnt5a, Wnt6, or Wnt7b peptide. Wnt peptides are discussed in greater detail in the specification below. In certain embodiments, the Wnt protein will be a mammalian Wnt peptide, for example a human or murine Wnt peptide, or a homolog thereof from another vertebrate species.

In other embodiments, the Wnt-like substance is a mimetic of Wnt or a mutant Wnt. The definitions of mimetic Wnt and mutant Wnt are discussed in the specification below. Any Wnt mimetic is contemplated by the present invention. For example, the Wnt mimetic may be a Wnt1, Wnt2, Wnt2b, Wnt3, Wnt3a, Wnt4, Wnt5a, Wnt5b, Wnt 6, Wnt7a, Wnt7b, Wnt8a, Wnt8b, Wnt9a, Wnt9b, Wnt10a, Wnt10b, Wnt11, or Wnt16 mimetic. One of skill in the art would be familiar with the range of Wnt mimetics available that are contemplated by the present invention. In certain embodiments, the Wnt mimetic is a Wnt1, Wnt4, Wnt5a, Wnt6, or Wnt7b mimetic. In certain embodiments, the Wnt mimetic will be a mammalian Wnt mimetic, for example a human or murine Wnt mimetic, or a homolog thereof from another vertebrate species. Any Wnt mutant is contemplated by the present invention. For example, the Wnt mutant may be a Wnt1, Wnt2, Wnt2b, Wnt3, Wnt3a, Wnt4, Wnt5a, Wnt5b, Wnt 6, Wnt7a, Wnt7b, Wnt8a, Wnt8b, Wnt9a, Wnt9b, Wnt10a, Wnt10b, Wnt11, or Wnt16 mutant. One of skill in the art would be familiar with the range of Wnt mutants available that are contemplated by the present invention. In certain embodiments, the Wnt mutant is a Wnt1, Wnt4, Wnt5a, Wnt6, or Wnt7b mutant. In certain embodiments, the Wnt mutant will be a mammalian Wnt mutant, for example a human or murine Wnt mutant, or a homolog thereof from another vertebrate species. In other embodiments, the Wnt-like substance is a small molecule.

Further embodiments of the present invention involve use of chemical compounds affecting a Wnt signaling pathway to modulate growth of a neuron. The definition of such chemical compounds is described in the specification below. One of ordinary skill in the art would be familiar with the wide range of such compounds available which can modulate the Wnt signaling pathway. For example, in certain embodiments, the chemical compound affecting a Wnt signaling pathway is lithium.

The Wnt, Wnt-like substance, and/or chemical compound affecting a Wnt signaling pathway may include a fused amino acid sequence that is designed to facilitate incorporation of the polypeptide into the intracellular compartment of a cell. For example, the Wnt-like substance may include a polypeptide encoding an amino acid TAT sequence from HIV. In another example, the Wnt-like substance may include a polypeptide encoding an Antp amino acid sequence. In another example, the Wnt-like substance may include a polypeptide encoding a VP22 amino acid sequence from HSV.

In certain embodiments, the Wnt, Wnt-like substance, and/or chemical compound affecting a Wnt signaling pathway further includes an expression cassette comprising a promoter, active in a cell, operably linked to a polynucleotide encoding the Wnt, Wnt-like substance, and/or chemical compound affecting a Wnt signaling pathway. For example, the polypeptide may be a Wnt1, Wnt2, Wnt2b, Wnt3, Wnt3a, Wnt4, Wnt5a, Wnt5b, Wnt 6, Wnt7a, Wnt7b, Wnt8a, Wnt8b, Wnt9a, Wnt9b, Wnt10a, Wnt10b, Wnt11, or Wnt16 polypeptide. In certain embodiments, the Wnt polypeptide is a Wnt1, Wnt4, Wnt5a, Wnt6, or Wnt7b polypeptide. In other embodiments, the expression cassette is carried in a viral vector. Although any viral vector is contemplated by the present invention, examples include an adenoviral vector, a retroviral vector, an adeno-associated viral vector, a vaccinia viral vector, or a pox viral vector. In other embodiments, the expression cassette is carried in a nonviral vector, such as a liposome. One of skill in the art would be familiar with a wide range of viral and nonviral vectors available to be of use in the present invention.

Any promoter is contemplated for use in the present invention, as long as it facilitates expression of the polynucleotide. One of skill in the art would be familiar with the wide range of promoters available. For example, the promoter may be a constitutive promoter, an inducible promoter, or a tissue-specific promoter.

Certain embodiments of the present invention involve obtaining the Wnt, Wnt-like substance, and/or chemical compound affecting a Wnt signaling pathway from media of cultured cells. Although any cultured cells are contemplated by the present invention, in certain embodiments the cultured cells comprise an expression cassette including a promoter, active in the cultured cells, operably linked to a polynucleotide encoding Wnt, a Wnt-like substance, and/or a chemical compound affecting a Wnt signaling pathway. The characteristics of expression cassettes that have been previously discussed above apply to these embodiments of the present invention.

Further embodiments of the present invention provide for methods of inhibiting growth of a neuron. In certain embodiments, these methods involve contacting the neuron with a mutant Wnt.

Additional embodiments of the present invention include methods for identifying a substance that modulates growth of a neuron, including: (a) obtaining a candidate substance; (b) contacting said candidate substance with said neuron; and (c) measuring modulation of growth of said neuron. In certain embodiments, an explant assay is used in the methods for identifying a substance that modulates growth of a neuron. For example, the explant assay may involve use of cultured spinal cord. Any method to measure modulation of neuronal growth is contemplated by the present invention. However, in certain embodiments anterior turning of axons of the neuron is measured.

Any candidate substance is contemplated by the present invention. For example, the candidate substance may include a protein, a polypeptide, a peptide, mimetic, mutant, or a small molecule as described above. In a certain embodiments, the candidate substance is a Wnt-like substance, such as a Wnt peptide. Any Wnt peptide is contemplated by the present invention. For example, the Wnt peptide may be a Wnt1 peptide, a Wnt3 peptide, a Wnt4 peptide, a Wnt5a peptide, a Wnt6 peptide, or a Wnt7b peptide. In certain embodiments, the Wnt peptide is a mimetic of Wnt, such as a mimetic of Wnt1, a mimetic of Wnt3, a mimetic of Wnt4, a mimetic of Wnt5a, a mimetic of Wnt6, or a mimetic of Wnt7b. In a further embodiment, the Wnt-like substance is a mimetic of Wnt4. Alternatively, the Wnt-like substance may be a mutant Wnt, such as a mutant Wnt1 polypeptide, a mutant Wnt3 polypeptide, a mutant Wnt4 polypeptide, a mutant Wnt5a polypeptide, a mutant Wnt6 polypeptide, or a mutant Wnt7b polypeptide. In still further embodiments, the Wnt-like substance is a small molecule. In other embodiments, the chemical compound affecting a Wnt signaling pathway is a chemical compound that functionally or structurally resembles lithium.

Any method of measuring growth of a neuron is contemplated by the present methods for identifying modulators of nerve growth. These methods have been discussed above. For example, measuring modulation of growth of a neuron may further involve measuring stimulation of growth of the neuron, measuring regeneration of a damaged neuron, or measuring growth of said neuron along the anterior-posterior axis. In addition, these methods also involve method for directionally orienting axon growth of the neuron between the spinal cord and the brain.

The present invention also includes methods of modulating growth of a neuron in a subject, including: (a) providing a composition that includes a Wnt, a Wnt-like substance, and/or a chemical compound affecting a Wnt signaling pathway; and a pharmaceutical preparation suitable for delivery to the subject; and (b) administering the composition to the subject. The methods for modulating neuron growth of the present invention contemplate measurement of neuronal growth by any known means, as discussed above. For example, the method of modulating neuron growth may be defined as a method of promoting growth and regeneration of a neuron in a subject, a method of promoting axon growth and regeneration in a subject, or a method of promoting directionally-oriented axon growth in a subject. Directionally-oriented axon growth may be along the anterior-posterior axis such as from the spinal cord to the brain, or from the brain to the spinal cord.

The methods for modulating neuron growth in a subject contemplated by the present invention also include methods of treating a subject with a spinal cord disorder. Any spinal cord disorder is contemplated by the present invention. For example, the spinal cord disorder may be a traumatic spinal cord disorder, a disorder of motor and/or sensory neurons, a neurodegenerative disorder, or a disorder resulting in paralysis.

The methods of the present invention also contemplate exposing the neuron to a gradient of said Wnt, said Wnt-like substance, and/or said chemical compound affecting a Wnt signaling pathway. As discussed above, the gradient may be in the spinal cord, such as a decreasing gradient along the anterior-posterior axis.

Any Wnt, Wnt-like substance, and chemical compound affecting a Wnt signaling pathway, as discussed above and in the specification below, is contemplated by the present methods of modulating neuron growth in a subject. Mimetics and mutants of Wnts and Wnt-like substances are contemplated by the present invention, as are embodiments wherein the Wnt or Wnt-like substance further comprises an expression cassette comprising a promoter, active in a cell, operably linked to a polynucleotide encoding the Wnt or the Wnt-like substance. These expression cassettes have been discussed above, and are discussed in greater detail in later sections of this specification.

In certain embodiments, administering the composition of Wnt, Wnt-like substance, and/or chemical compound affecting a Wnt signaling pathway involves contacting the composition with the spinal cord of the subject. In certain embodiments, a gradient of the Wnt, Wnt-like substance, and/or chemical compound affecting a Wnt signaling pathway is created along the anterior-posterior axis. For example, the gradient may be between the spinal cord and the brain, such as a decreasing anterior-posterior gradient. In certain embodiments, the nerve cell is contacted with a modulator of neuronal growth identified by one of the previously described methods.

Certain embodiments of the present invention pertain to pharmaceutical compositions for modulating growth of a neuron in a mammal, including: (a) a Wnt, a Wnt-like substance, and/or a chemical compound affecting a Wnt signaling pathway; and (b) a pharmaceutical preparation suitable for delivery to the mammal. Neuronal growth may be modulated by any of the methods discussed above. In certain embodiments, the mammal is a human, such as a patient with a spinal cord disorder. Any Wnt, Wnt-like substance, and/or chemical compound affecting a Wnt-signaling pathway, as discussed above, is contemplated by the present invention. In certain embodiments, the composition comprises an expression cassette comprising a promoter, active in a cell, operably linked to a polynucleotide encoding the Wnt, the Wnt-like substance, and/or the chemical compound affecting a Wnt signaling pathway. Expression cassettes have been discussed above in the context of other embodiments of the present invention.

Additional embodiments of the present invention involve methods of inhibiting or controlling the growth of a neuron in a subject, by administering an inhibitor of a Wnt to the subject. In some cases, that inhibitor may be an sFRP, a Ryk protein, or an analog thereof. In general some such methods include: (a) providing a composition that includes an sFRP, an sFRP-like substance, a Ryk or a Ryk-like substance and a pharmaceutical preparation suitable for delivery to the subject; and (b) administering said composition to the subject. sFRPs are compounds that can affect a Wnt signaling pathway by binding to Wnt proteins with high affinity and blocking the interaction of Wnts with their receptors, the Frizzleds. sFRPs and sFRP-like substances are defined and discussed in detail below.

In certain embodiments, the composition comprises an sFRP protein. sFRPs are diffusable proteins that bind and modulate Wnts. Any sFRP protein from any species is contemplated by the present invention. For example, the sFRP protein may be sFRP1 protein, sFRP2 protein, or sFRP3 protein. In other embodiments, the sFRP-like substance is an sFRP polypeptide. For example, the sFRP polypeptide may be sFRP1 polypeptide, sFRP2 polypeptide, or sFRP3 polypeptide. In other embodiments, the sFRP-like substance is a peptide, such as sFRP1 peptide, sFRP2 peptide, or sFRP3 peptide. In further embodiments, the sFRP-like substance is a mutant sFRP, such as a mutant sFRP1 polypeptide, a mutant sFRP2 polypeptide, or a mutant sFRP3 polypeptide. In still further embodiments, the sFRP-like substance includes a small molecule that is functionally similar to a sFRP.

In other embodiments, the composition comprises a Ryk protein. Ryk is a receptor on neurons that binds Wnts and mediates repulsion of neurons in response to Wnts. Any Ryk protein or homolog from any species is contemplated by the present invention, for example, *Drosphila* Derailed protein may be employed in some embodiments. For example, the Ryk or Ryk-like substance may be a Ryk protein, polypeptide, peptide, mutant, or mimetic. In still further embodiments, the Ryk-like substance includes a small molecule that is functionally similar to a Ryk.

Other embodiments of the invention involve the contacting of a neuron with a combination of a Wnt and another substance, in order to provide a combination therapy. Such embodiments of the invention are important because, as discussed herein, the regeneration of neurons into a properly functioning spinal cord will often involve a combination of directional and other clues.

In some embodiments, one will wish to contact a neuron with a substance that blocks activity of a neuronal growth inhibitor. Such neuronal growth inhibitors include the myelin inhibitors Nogo, MAG, and Omgp, which have been shown to inhibit the growth of sensory neurons. Further, as discussed herein, Wnts can, if expressed in the adult spinal cord, inhibit the proper growth of CST motor neurons. In this regard, there are some Wnts that are expressed in normal adult spinal cords, and a variety of Wnts that may be is abnormally expressed in the neuron upon neuronal injury, as discussed below. In some embodiments of the invention, the substance that blocks the activity of the neuronal growth inhibitor is an antibody directed against a receptor for the inhibitor on the neuron or against the inhibitor itself. For example, such an antibody can be directed against a Wnt, Nogo, MAG, or OMgp. In some preferred embodiments, the antibody is directed against Wnt5a, Wnt8, or a Wnt that is expressed abnormally in the neuron due to injury, or against a receptor of any such Wnt. In other cases, the substance that blocks activity of a neuronal growth inhibitor is a Ryk, Ryk-like substance, sFRP or sFRP-like substance. In some preferred embodiments, one will want to block the activity of two or more inhibitors in the course of treating a neuron, spinal cord, and/or patient. For example, in order to allow an injured spinal cord comprising both injured sensory and injured motor neurons to regenerate in an appropriate manner, those of skill will understand that there may be a need to apply a compound to block the myelin inhibitors and prevent them from inhibiting the growth of sensory neurons, while also applying a compound to block Wnt inhibition of the growth of motor neurons.

The instant invention also involves contacting neurons with combinations of at least one Wnt and at least one other substance that attracts or repels neuronal growth. In some embodiments, the at least one other substance will be a substance attracts neuronal growth, for example, but not limited to a Wnt, Netrin, Shh, Cell adhesion molecule, Ig superfamily member, Cadherin, Integrin, EphrinB, ECM molecule, or HGF. In some embodiments, the at least one other substance will be a substance that repels neuronal growth, for example but not limited to, a Semaphorins, Netrin, Slit, Wnt, BMP, Ephrin, or member of the Ig superfamily. In many embodiments, contacting said neuron with a substance that attracts or repels neuronal growth will comprise exposing said neuron to a gradient of said substance. And, in some embodiments, the neuron will be exposed to a gradient of at least two such substances. In some cases, it will be beneficial to apply inhibitors of these substances that attract or repel neuronal growth at various portions of a regenerating spinal cord, in order to control the growth of the spinal cord, such inhibitors can be small molecules, peptides, proteins, or polypeptides that bind the substance, antibodies directed against the substance or a receptor of the substance, etc.

Some embodiments will involve the exposure of the neuron to a gradient of an attractive Wnt, some will involve exposure of the neuron to a gradient of a repulsive Wnt, some will involve exposure of the neuron to gradients of both attractive and repulsive Wnts. Attractive Wnts can include, but not be limited to, Wnt1, Wnt4, Wnt5a, Wnt 6, and Wnt7. Repulsive Wnts can include, but not be limited to Wnt5a or Wnt1. Those of skill in the art will be able to determine attractive and repulsive Wnts following the teachings herein, and will understand that the same Wnt may have an attractive property in regard to some contexts or some types of neurons and a repulsive property in regard to other contexts or types of neurons.

In some cases, it will be beneficial to apply one or more Wnt to the site of a spinal cord injury, such that the Wnt(s) will provide attractive guidance to those neurons that need to be attracted to the site of injury during regeneration and repellant guidance to those neurons that need to grow away from the site of injury during regeneration. In this regard, Wnt(s) applied at the site of an injury will provide directional guidance to axonal growth and cause sensory neurons to grow up through the site of the injury and repel motor neurons to grow down through the site of the injury. Further, in this embodiment, it may be beneficial to inhibit the Ryk pathway at the site of the injury so that motor neurons growing through the site of the injury are not inhibited by any Wnts present in the injury site, whether those Wnts are applied to the injury site, or expressed there as a result of normal adult Wnt expression or injury-induced Wnt expression. One may also apply a blocker of myelin inhibitors to the injury site, to prevent such inhibitors from impacting the growth of sensory neurons through the site.

Of course, combinations of Wnts, substances that block inhibitors of neuronal growth, and/or substances that attract or repel neuronal growth can be determined by those of skill in the art following the teaching contained herein. These various components of these combinations may be administered simultaneously, or separated by time. Individual components may be administered a single time or in a series of administrations. They may be administered in a single pharmaceutical composition, or in separate compositions. Those of skill in the art will be able to follow the teachings of this specification to determine appropriate dosage regimes and schedules of the various active agents.

Other embodiments of the invention involve pharmaceutical compositions comprising at least one Wnt, Wnt-like substance, or compound affecting a Wnt signaling pathway in combination with at least one substance that blocks an inhibitor of neuronal growth, and/or substance that attracts or repels neuronal growth. Further, kits comprising combinations of these various components, in separate or single containers are also within the scope of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

The term "therapeutically effective" as used herein refers to an amount of a compound required to effect neuronal growth in the context of the manners described herein.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: Transverse section of an E13 rat spinal cord showing the dorsal-ventral trajectory (solid line) and the anterior-posterior trajectory (dashed line) of commissural axons. FIG. 1B: "Open-book" view of an E13 rat spinal cord showing midline-crossing and anterior turning of commissural axons. The subpopulation of commissural axons represented by the dashed line project anteriorly along a medial pathway, close to the floor plate (the ventral funiculus). The subpopulation of commissural axons represented by the solid line project along the floor plate initially, but gradually fan out to occupy more lateral positions (the lateral funiculus). Both populations project anteriorly immediately after midline crossing and were often observed in the DiI injections. FIG. 1C: A gradient of diffusible guidance cue(s) might be disrupted when the explants are cut shorter, causing misrouting of commissural axons along the A-P axis. FIG. 1D: A gradient of nondiffusible guidance cue(s) will not be affected when the explants are cut shorter and the axons should still project anteriorly. FIG. 1E: Quantification of date. Anterior turn indicates normal projection. Knotting/stalling and random A-P turns are abnormal behaviors observed in shorter explants. DiI injections usually label a cohort of axons. In the short explants, some of the axons in the cohort appeared stalling, while others turned posteriorly. These injection stiles were counted for both stalling and the random turn behavior. Therefore, the percent of all projection patterns summed up more than 100%. N=number of explants. All scale bars: 100 μm.

FIG. 2A: If the anterior guidance cue(s) is attractive, higher concentrations of the attractant(s) should be found at the anterior end of the explants. The explant tissues close to the anterior end will likely lose the gradient, whereas the posterior end will maintain the gradient. Therefore, axons close to the anterior injection sites will likely be misrouted and the axons close to the posterior end will likely project anteriorly (top panel). If the anterior guidance cue(s) is repulsive, higher concentration of the repellent(s) should be present at the posterior end. The explant tissues close to the posterior end might lose the gradient, whereas the explant tissues close to the anterior end might still maintain the A-P gradient. As a result, axons at the posterior injection sites should show abnormal behavior, whereas those at the anterior injection sites might be normal (bottom panel). FIG. 2B: Quantification of the "open-book" assays with anterior, middle and posterior injections. Note that in some of the injections sites, DiI labeled a cohort of axons. Some of the axons in the cohort appeared stalling, whereas others turned posteriorly at the anterior end of the explants. These injections sites were counted for both stalling and the random turn behavior. Therefore, the percent of all projection patterns summed up more than 100%. n=number of injection sites.

FIG. 3A: Diagram showing the design of "post-crossing" and "pre-crossing" assays. FIG. 3B: Quantification of post-crossing commissural axon extension stimulated by Wnts as described in Zou et al., 2000. FIG. 3C: Schematic diagram of commissural axons projecting towards their brain target, ventral-posterior-lateral region of the thalamus. Dotted square indicates the area of diencephalon dissected for the co-culture experiments. FIG. 3D: Quantification of post-crossing commissural axon growth in response to thalamic target.

FIG. 4A: Diagram showing the design of experiments. COS cells were transfected with vector only control or sFRP-expressing constructs and resuspended in collagen gel and embedded inside the bottom collagen gel pad. Long "open-book" explants were placed on top of the bottom collagen gel and embedded in the top collagen gel pad. After overnight culturing, tissues were fixed and DiI injected to reveal the projection of commissural axons. FIG. 4B: Quantification of effects of sFRP1, 2, 3 alone or combined. The method of quantification was the same as in FIG. 1 and FIG. 2. n=number of injection sites.

FIG. 5A, FIG. 5B, FIG. 5C, FIG. 5D, FIG. 5F. Wnt4 gradient rescues A-P guidance defects and can reorient post-crossing commissural axons posteriorly. FIG. 5A, FIG. 5B: Diagrams showing the design of the rescue experiments. COS cell aggregates transfected with either vector only or Wnt4 expression construct were placed to the anterior side of the short "open-book" explants. After overnight culturing, commissural axons were analyzed by DiI labeling of the fixed tissues. FIG. 5C: Quantifications of Wnt4 rescue experiments. The method of quantification was the same as in FIG. 1, FIG. 2, and FIG. 4. FIG. 5D, FIG. 5E: Diagram showing the design of the reorientation experiments. COS cell aggregates transfected with either vector only or Wnt4-expression construct were placed to the posterior side of the short "open-book" explants. After overnight culturing, commissural axons were analyzed by DiI labeling of the fixed explants. FIG. 5F: Quantification of the Wnt4 reorientation experiments. n=number of injection sites. Bars on the far right indicate the percentage of the injection sites whereby all axons turned posteriorly.

DESCRIPTION OF ILLUSTRATIVE EMBODIMENTS

Figure 1:
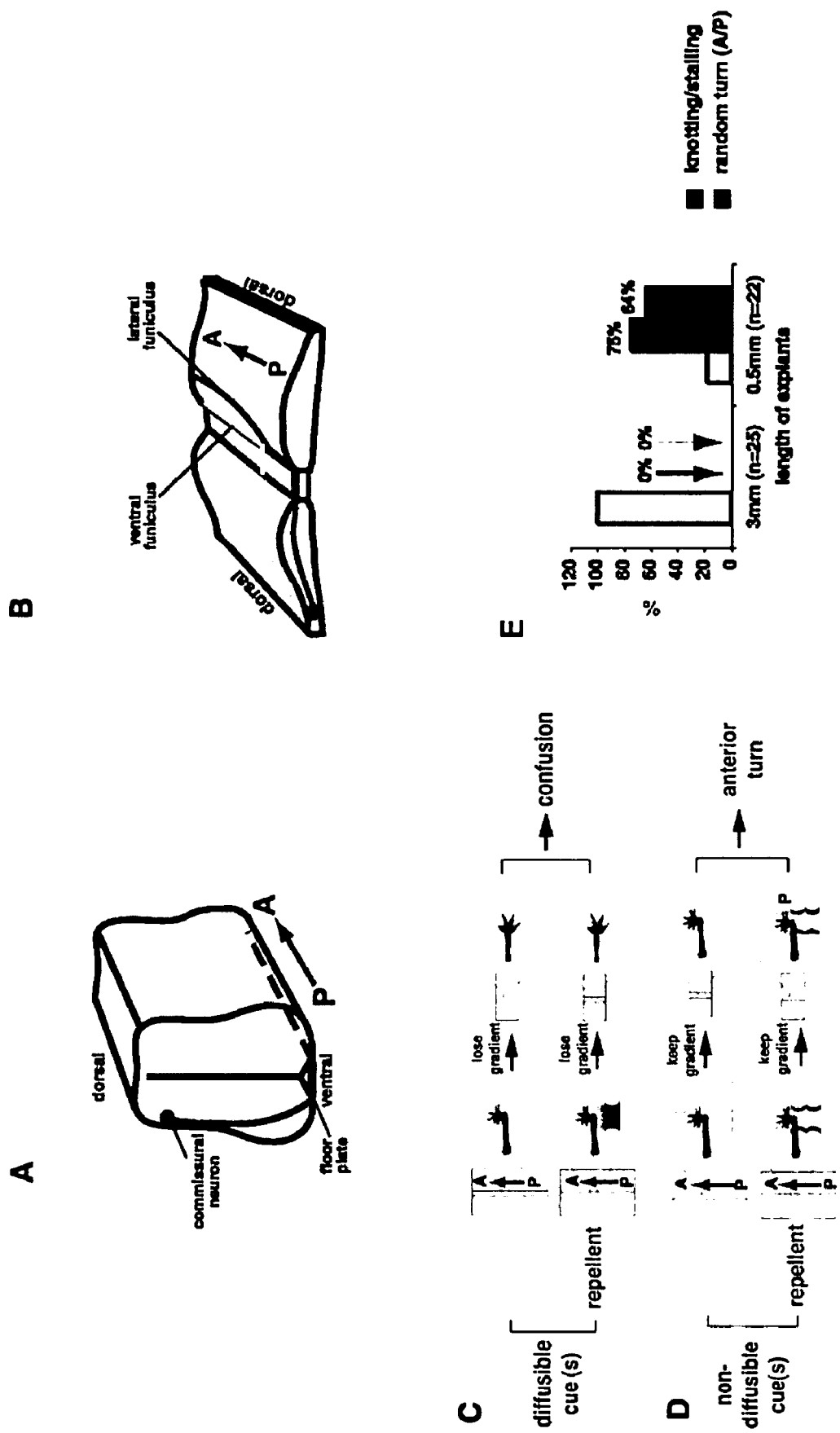
FIG. 1A, FIG. 1B, FIG. 1C, FIG. 1D, FIG. 1E. Diffusible cue(s) guides commissural axons along the anterior-posterior axis.

The present invention is based on the discovery that Wnts guide axon pathfinding in development and can play a role in correct spinal cord and neuronal regeneration.

The inventor has shown that a Wnt/Frizzled pathway mediates attractive effects in sensory axon guidance along the anterior-posterior axis. Additionally, the inventor shows here that vertebrate corticospinal cord axons are repelled by Wnts and the repulsion is mediated by the vertebrate homologue of Derailed, Ryk. Ryk is not expressed in the commissural neurons, consistent with the finding that commissural axons are attracted by Wnts. Interestingly, the repulsive effect of Wnt5 on fly axons appears to be independent of Frizzleds. Therefore, Wnts appear to attract axons via a Frizzled-dependent pathway and repel axons via a Ryk dependent pathway. CST axons do express Frizzleds, such as Frizzled 3. Therefore, it appears that Ryk is dominate over Frizzleds and mediates repulsion even in the presence of Frizzleds. Taken together, these studies provide evidence that Wnts, like other guidance cues, are bifunctional, capable of attracting some axons and repelling others, and suggest that Wnt proteins might have a widespread and phylogenetically conserved function in guiding axons during the wiring of the nervous system. These studies demonstrate that one continuous molecular gradient of diffusible guidance cue(s) along the entire anterior-posterior axis of the spinal cord controls the navigation decisions along the A-P axis.

The present invention seeks to exploit the inventor's discovery by providing for methods and compositions for modulating growth of a nerve cell using a Wnt, Wnt-like substances, and/or chemical compounds to stimulate the pathways of Wnt signaling to modulate nerve growth and guidance. These methods and compositions can be used in a wide variety of therapeutic contexts where nerve growth and regeneration would be beneficial. For example, a Wnt, a Wnt-like substance, and/or a chemical compound affecting a Wnt signaling pathway can be used to stimulate axonal growth of a damaged neuron along the A-P axis of a patient with SCI. Because it has also been observed that the Wnts are expressed in the several regions in the brain and the components of the Wnt signaling pathways are also present in axons of other central nervous system neurons, it is possible that Wnts and agents that stimulate or inhibit Wnt signaling can be used to modulate growth and directional guidance of axons in the central nervous system.

A. Wnt, Wnt-like Substances, and Compounds Affecting a Wnt Signaling Pathway

1. Wnt and Wnt-like Substances

The present invention pertains to use of Wnt and Wnt-like substances in various contexts. For example, various embodiments of the present invention pertain to methods for modulating growth of a neuron that involve contacting a neuron with a Wnt or a Wnt-like substance. Other embodiments pertain to methods for modulating growth of a neuron in a subject, that involve providing the subject with a pharmaceutical composition that includes a Wnt or a Wnt-like substance. Additional embodiments pertain to pharmaceutical compositions for modulating growth of a neuron in a mammal, that include a Wnt or a Wnt-like substance.

As discussed above, Wnts are secreted cysteine-rich glycosylated proteins that play a role in the development of a wide range of organisms. Wnts are thought to function in a variety of developmental and physiological processes since many diverse species have multiple conserved Wnt genes (McMahon, 1992; Nusse and Varmus, 1992). The Wnt growth factor family includes at least 19 genes identified in mammals, including Wnt1, Wnt2, Wnt2b, Wnt3, Wnt3a, Wnt4, Wnt5a, Wnt5b, Wnt 6, Wnt7a, Wnt7b, Wnt8Wnt8b, Wnt9a, Wnt9b, Wnt10a, Wnt10b, Wnt11, and Wnt16. Similar numbers of Wnt genes are present in other vertebrate species. Of course, further Wnts may be discovered and/or characterized in the future, and those of skill will be able to employ any such Wnts in the context of the invention. Further, those of skill will be able to use the teachings herein to obtain and use Wnts of any species in the context of the invention.

Throughout this application, the term "Wnt" is intended to refer to any consecutive amino acid sequence that includes the full-length amino acid sequence of a Wnt from any organism, such as a human or a mouse Wnt. Wnt can be a human Wnt protein, or a Wnt protein from any other species, such as mouse or chick. Thus, for example, Wnt can be used to refer to the full-length amino acid sequence encoded by any of the 19 genes identified in human. Alternatively, Wnt can refer to a murine Wnt protein, such as murine Wnt4. Wnt can also refer to an amino acid sequence that is longer than the full-length consecutive amino acid sequence of a Wnt, as long as it includes a full-length Wnt amino acid sequence.

Throughout this application, the term "Wnt protein" is intended to refer to the full-length amino acid sequence that is encoded by a Wnt gene. Thus, "Wnt" may refer to a Wnt protein or an amino acid sequence that is longer than a Wnt protein if additional non-Wnt amino acids are included in the sequence. Also included in the definition of "Wnt" is a truncated sequence of a Wnt protein, a mutated Wnt protein, or a Wnt amino acid sequence that is less than the full-length amino acid sequence of a Wnt, as long as the amino acid sequence retains an acceptable level of the equivalent biological activity of a full-length Wnt protein.

The human and murine full-length native amino acid sequences and the native nucleic acids encoding them are described by GenBank accession number in the Table 1. Further, summary of human and murine Wnts is provided in Miller, 2001. Specifically, Table I of Miller, 2001, which includes Genbank accession numbers of human and mouse Wnt genes, is herein specifically incorporated by reference.

Throughout this application, the term "Wnt-like substance" is intended to refer to a Wnt polypeptide, a Wnt peptide, a Wnt mimetic, or a small molecule that is functionally and/or structurally similar to a Wnt.

The term "Wnt polypeptide" includes any amino acid sequence that includes fewer consecutive amino acids of a Wnt than the full-length amino acid sequence of a Wnt. "Wnt polypeptide" includes not only consecutive amino acid sequences from a human Wnt, but from any other species, such as mouse. Thus, for example, a Wnt polypeptide can include, but is not limited to, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97,

TABLE 1

| | HUMAN | | | MOUSE | |
| --- | --- | --- | --- | --- | --- |
| | Nucleic Acid | Amino Acid | | Nucleic Acid | Amino Acid |
| Wnt1 | NM005430 | NP005421 | Wnt1 | NM133955 | NP598716 |
| | SEQ ID 1 | SEQ ID 2 | | SEQ ID 39 | SEQ ID 40 |
| Wnt2 | BC029854 | AAH29854 | Wnt2 | BC026373 | AAH26373 |
| | SEQ ID 3 | SEQ ID 4 | | SEQ ID 41 | SEQ ID 42 |
| Wnt2B | NM024494 | NP078613 | Wnt2B | NM009520 | NP033546 |
| | SEQ ID 5 | SEQ ID 6 | | SEQ ID 43 | SEQ ID 44 |
| Wnt3 | NM030753 | NP110380 | Wnt3 | NM009521 | P17553 |
| | SEQ ID 7 | SEQ ID 8 | | SEQ ID 45 | SEQ ID 46 |
| Wnt3A | NM033131 | NP149122 | Wnt3A | NM009522 | NP033548 |
| | SEQ ID 9 | SEQ ID 10 | | SEQ ID 47 | SEQ ID 48 |
| Wnt4 | NM030761 | NP110388 | Wnt4 | NM009523 | NP033549 |
| | SEQ ID 11 | SEQ ID 12 | | SEQ ID 49 | SEQ ID 50 |
| Wnt5A | NM003392 | NP003383 | Wnt5A | NM009524 | NP033550 |
| | SEQ ID 13 | SEQ ID 14 | | SEQ ID 51 | SEQ ID 52 |
| Wnt5B | BC001749 | AAH01749 | Wnt5B | BC010775 | AAH10775 |
| | SEQ ID 15 | SEQ ID 16 | | SEQ ID 53 | SEQ ID 54 |
| Wnt6 | NM006522 | NP006513 | Wnt6 | NM009526 | NP033552 |
| | SEQ ID 17 | SEQ ID 18 | | SEQ ID 55 | SEQ ID 56 |
| Wnt7A | BC008811 | AAH08811 | Wnt7A | BC049093 | AAH49093 |
| | SEQ ID 19 | SEQ ID 20 | | SEQ ID 57 | SEQ ID 58 |
| Wnt7B | NM058238 | NP478679 | Wnt7B | NM009528 | NP033554 |
| | SEQ ID 21 | SEQ ID 22 | | SEQ ID 59 | SEQ ID 60 |
| Wnt8A | NM058244 | NP490645 | Wnt8A | NM009290 | NP033316 |
| | SEQ ID 23 | SEQ ID 24 | | SEQ ID 61 | SEQ ID 62 |
| Wnt8B | NM003393 | NP003384 | Wnt8B | NM011720 | NP035850 |
| | SEQ ID 25 | SEQ ID 26 | | SEQ ID 63 | SEQ ID 64 |
| Wnt9A | NM003395 | NP003386 | Wnt9A | NM139298 | NP647459 |
| | SEQ ID 27 | SEQ ID 28 | | SEQ ID 65 | SEQ ID 66 |
| Wnt9B | NM003396 | NP003387 | Wnt9B | NM011719 | NP035849 |
| | SEQ ID 29 | SEQ ID 30 | | SEQ ID 67 | SEQ ID 68 |
| Wnt10A | BC052234 | AAH52234 | Wnt10A | BC014737 | AAH14737 |
| | SEQ ID 31 | SEQ ID 32 | | SEQ ID 69 | SEQ ID 70 |
| Wnt10B | NM003394 | NP003385 | Wnt10B | NM011718 | NP035848 |
| | SEQ ID 33 | SEQ ID 34 | | SEQ ID 71 | SEQ ID 72 |
| Wnt11 | NM004626 | NP004617 | Wnt11 | NM009519 | NP033545 |
| | SEQ ID 35 | SEQ ID 36 | | SEQ ID 73 | SEQ ID 74 |
| Wnt16 | NM057168 | NP476509 | Wnt16 | NM053116 | NP444346 |
| | SEQ ID 37 | SEQ ID 38 | | SEQ ID 75 | SEQ ID 76 | about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues of a Wnt, and any range derivable therein, as long as the amino acid sequence includes less than the full-length consecutive amino acid sequence of a Wnt. Included within the definition of "Wnt polypeptide" are potential amino acid sequences that include additional amino acids, other than Wnt amino acid sequences.

The term "Wnt peptide" includes any amino acid sequence that includes ten or fewer consecutive amino acid sequence of a Wnt amino acid sequence. "Wnt peptide" includes not only consecutive amino acid sequences from a human Wnt, but from any other species, such as mouse. Thus, for example, a Wnt peptide may include 1, 2, 3, 4, 5, 6, 7, 8, 9, or 10 consecutive amino acids of a Wnt. Additional amino acids can also be included, which may be other than Wnt amino acid sequences.

Included within the definition of "Wnt-like substance" is a "mimetic of Wnt." Throughout this application, "mimetic of Wnt" is intended to refer to any molecule other than the full-length sequence of a Wnt that is able to maintain an acceptable level of equivalent biological activity as a Wnt.

It is well understood by the skilled artisan that, inherent in the definition of a "mimetic of Wnt," is the concept that there is a limit to the number of changes that may be made within a defined portion of the molecule and still result in a molecule with an acceptable level of equivalent biological activity, e.g., ability of Wnt4 to modulate neuronal growth and regeneration. "Mimetic of Wnt" is thus defined herein as any Wnt polypeptide in which some, or most, of the amino acids may be substituted so long as the polypeptide retains substantially similar activity in the context of the uses set forth herein. Of course, a plurality of distinct proteins/polypeptides/peptides with different substitutions may easily be made and used in accordance with the invention. Additionally, in the context of the invention, a mimetic of Wnt can be a Wnt homologue polypeptide from any species or organism, including, but not limited to, a human polypeptide. One of ordinary skill in the art will understand that many mimetics of Wnt would likely exist and can be identified using commonly available techniques.

The present invention may utilize Wnts, Wnt polypeptides, Wnt peptides, mimetics of Wnt, or mutants of Wnt, that are purified from a natural source or from recombinantly-produced material. Those of ordinary skill in the art would know how to produce these amino acid sequences from recombinantly-produced material. This material may use the 20 common amino acids in naturally synthesized proteins, or one or more modified or unusual amino acids. Generally, "purified" will refer to an Wnt composition that has been subjected to fractionation to remove various other proteins, polypeptides, or peptides, and which composition substantially retains its activity. Purification may be substantial, in which the Wnt or Wnt-like substance is the predominant species, or to homogeneity, which purification level would permit accurate degradative sequencing.

Amino acid sequence mutants of a Wnt also are encompassed by the present invention, and are included within the definition of "Wnt-like substance." Amino acid sequence mutants of a Wnt of any species, such as human and mouse Wnt, is contemplated by the present invention. Amino acid sequence mutants of a Wnt can be substitutional mutants or insertional mutants. Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide.

Amino acid substitutions are generally based on the relative similarity of the amino acid side-chain substituents, or example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

Amino acid substitutions are generally based on the relative similarity of the amino acid side-chain substituents, or example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated by reference herein). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those which are within +1 are particularly preferred, and those within +0.5 are even more particularly preferred.

It is understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0+1); glutamate (+3.0+1); serine (+0.3); asparagine (+0.2); glutamine (+0.2); glycine (0);

threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +2 is preferred, those which are within +1 are particularly preferred, and those within +0.5 are even more particularly preferred.

Certain embodiments of the present invention utilize Wnt-like substances that are fusion proteins that are preferentially translocated through biological membranes. In particular, a Wnt or a Wnt-like substance such as a Wnt polypeptide may be fused to a particular protein, polypeptide, or peptide sequence that promotes facilitated intracellular delivery of the fusion protein into the targeted cell. Although any fusion protein with the property of facilitated intracellular delivery is contemplated by the present invention, specific examples include fusion proteins utilizing the HIV TAT sequence (Nagahara et al., 1998), the third helix of the Antennapedia homeodomain (Antp) (Derossi et al., 1994), and the HSV-1 structural protein VP22 (Elliott and O'Hare, 1997).

Small molecules are also included within the definition of "Wnt-like substance" in the context of the present invention. Throughout this application, the term "small molecule" is intended to refer to any small molecule not included within the definition of Wnt polypeptide, Wnt peptide, mimetic of Wnt, or mutant of Wnt, wherein the molecule is relatively small in size and wherein the molecule has an acceptable level of biological activity of a Wnt. For example, the small molecule may be a synthetic substance which is not an amino acid sequence, which is functionally able to promote axonal growth and regeneration in a manner analogous to a Wnt.

2. Polynucleotides Encoding a Wnt or a Wnt-like Substance

Various aspects of the present invention require polynucleotides encoding an Wnt or a Wnt-like substance. For example, various embodiments include methods for modulating neuronal growth that involve contacting the neuron with an expression cassette that includes a promoter that is a cell, operably linked to a polynucleotide encoding either an Wnt or a Wnt-like substance. In other embodiments, the invention pertains to methods for modulating growth of a neuron in a subject that include administering to the subject a composition that includes an expression cassette operably inked to a polynucleotide encoding either a Wnt or a Wnt-like substance. In still other embodiments, the invention includes pharmaceutical compositions for modulating growth of a neuron in a mammal, that include a Wnt or a Wnt-like substance.

The polynucleotide encoding the full length amino acid sequences of the known human and murine Wnts are contained in Table 1. The polynucleotides according to the present invention may encode an entire Wnt sequence (e.g., the amino acid sequence of SEQ ID NO:2), or a Wnt-like substance such as a Wnt polypeptide or a Wnt peptide. The polynucleotides may be derived from genomic DNA, i.e., cloned directly from the genome of a particular organism.

In other embodiments, however, the polynucleotides may be complementary DNA (cDNA). cDNA is DNA prepared using messenger RNA (mRNA) as a template. Thus, a cDNA does not contain any interrupted coding sequences and usually contains almost exclusively the coding region(s) for the corresponding protein. In other embodiments, the polynucleotide may be produced synthetically.

It may be advantageous to combine portions of the genomic DNA with cDNA or synthetic sequences to generate specific constructs. For example, where an intron is desired in the ultimate construct, a genomic clone will need to be used. Introns may be derived from other genes in addition to a Wnt gene. The cDNA or a synthesized polynucleotide may provide more convenient restriction sites for the remaining portion of the construct and, therefore, would be used for the rest of the sequence.

The present invention is not limited to the sequences disclosed by GenBank and SEQ ID NO in Table 1, but includes polynucleotides encoding any Wnt or Wnt-like substance (discussed above). These polynucleotides encoding a Wnt or a Wnt-like substance may be naturally-occurring homologous polynucleotide sequences from other organisms. For example, polynucleotides encoding a Wnt or a Wnt-like substance include those polynucleotides encoding the human amino acid functional equivalent sequences previously described. These sequences are provided by way of example, and are not meant to be a summary of all available polynucleotide sequences encoding a Wnt or a Wnt-like substance. A person of ordinary skill in the art would understand that commonly available experimental techniques can be used to identify or synthesize polynucleotides encoding other Wnts. The present invention also encompasses chemically synthesized mutants of these sequences.

Another kind of sequence variant results from codon variation. Because there are several codons for most of the 20 normal amino acids, many different DNAs can encode a Wnt or a Wnt-like substance. Reference to the following table will allow such variants to be identified.

TABLE 2

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have between about 50% and about 75%, or between about 76% and about 99%, of nucleotides that are identical to the nucleotides disclosed herein will be preferred. Sequences that are within the scope of "a polynucleotide encoding a Wnt or a Wnt-like substance" are those that are capable of base-pairing with a polynucleotide segment set forth above under intracellular conditions.

As stated above, the encoding sequences may be full length genomic or cDNA copies, or large fragments thereof. The present invention also may employ shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of base-pairing. Both binding affinity and sequence specificity of an oligonucleotide to its complementary target increases with increasing length. It is contemplated that oligonucleotides of 8, 9, 10, 11, 12, 13, 14, 15, 16, 17, 18, 19 or 20 base pairs will be used, for example, in the preparation of mutants of Wnt and in PCR reactions.

Any sequence of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length.

In certain embodiments, one may wish to employ constructs which include other elements, for example, those which include C-5 propyne pyrimidines. Oligonucleotides which contain C-5 propyne analogues of uridine and cytidine have been shown to bind RNA with high affinity (Wagner et al., 1993).

3. Compounds that can Affect the Wnt Signaling Pathways a. Chemical Compounds that can Affect the Wnt Signaling Pathway As an alternative approach to using the a Wnt or a Wnt-like substance to directly modulate axon growth and guidance to promote axonal regeneration to cure spinal cord injury and other central nervous system damage, chemical compounds which affect the Wnt signaling pathways and affect axonal regeneration can also be applied to promote and guidance axon regeneration. Such chemical compound can be discovered by "chemical genetics", screening libraries of chemical compounds or testing known compounds that have an effect on Wnt signaling. For example, lithium is known to stimulate Wnt signaling and can promote axon extension (Hall et al., 2000; Klein and Melton, 1996; Lucas and Salinas, 1997). Therefore, chemical substances, such as lithium, can be used to regulate the Wnt pathway and help regenerate spinal cord axons and other central nervous system axons.

b. sFRPS can Affect the Wnt Signaling Pathways

Secreted Frizzled-related proteins (sFRPs) are soluble proteins that can bind to Wnt proteins with high affinities and can block the interaction of Wnts with their receptors, the Frizzleds (Wodarz and Nusse, 1998). Any sFRP, whether from human or any other species such as mouse, is contemplated by the present invention. In addition, the definition of sFRP-like substance is defined in a similar manner as Wnt-like substance, and includes mimetics of sFRP and mutant sFRPs.

The definition of sFRP, sFRP-like substance, sFRP protein, and sFRP polypeptide are defined in a manner analogous to the definitions provided above in reference to Wnt and Wnt-like substance, discussed supra.

The full-length amino acid sequence of human sFRP1 (Genbank accession number NP_003003) is provided herein as SEQ ID NO:77. The full-length amino acid sequence of human sFRP2 (Genbank accession number XP_050625) is provided herein as SEQ ID NO:78. The full-length amino acid sequence of human sFRP3 (Genbank accession number NP_001454) is provided herein as SEQ ID NO:79. The full-length amino acid sequence of murine sFRP1 (Genbank accession number NP_038862) is provided herein as SEQ ID NO:80. The full-length amino acid sequence of murine sFRP2 (Genbank accession number NP_033170) is provided herein as SEQ ID NO:81. The full-length amino acid sequence of murine sFRP3 (Genbank accession number AAC53147) is provided herein as SEQ ID NO:82.

c. Ryk can Affect the Wnt Signaling Pathways

Ryk is a protein that can bind to Wnt proteins with high affinities and can block the activity of at least some of Wnts. Ryk is a vertebrate homolog of the *Drosphila* Derailed protein, a receptor tyrosine-like protein. Any Ryk, whether from human or any other species such as mouse, is contemplated by the present invention. In addition, the definition of Ryk-like substance is defined in a similar manner as Wnt-like substance, and includes mimetics of Ryk and mutant Ryks.

The definition of Ryk, Ryk-like substance, Ryk protein, and Ryk polypeptide are defined in a manner analogous to the definitions provided above in reference to Wnt and Wnt-like substance, discussed supra.

The full-length amino acid sequence of human Ryk (Genbank accession number NM_002958) is provided herein as SEQ ID NO:83. The full-length amino acid sequence of murine Ryk (Genbank accession number BC_006963) is provided herein as SEQ ID NO:84. The full-length amino acid sequence of Derailed (Genbank accession number L47260) is provided herein as SEQ ID NO:85.

B. Inhibitors of Axonal Growth

The adult central nervous system is a largely inhibitory environment for axonal growth and regeneration. Therefore, in the context of obtaining regeneration of the CNS, it is likely that the blocking of such inhibitors will be needed.

Additionally, multiple inhibitors present in the central nervous system myelin, such as Nogo, MAG and OMgp, prevent axonal growth after injury. Other inhibitors present in glial scar, such as CSPG, also inhibit axonal outgrowth. It is not fully understood whether CSPG are the actual active components for the inhibitors of axonal regeneration or other molecules associate with CSPG are the active components.

In order to achieve effective axonal regeneration following CNS injury, it is necessary to overcome inhibition of both type of inhibitors. Those of skill in the art will understand that there are many manners in which such inhibitors can be blocked, and will, by following the teachings contained herein, be able to develop means to block these inhibitors in the context of the invention.

C. Protein Attractants and Repellants in Axonal Guidance

There are many protein attractants and repellants that play a role in axonal guidance. Further, many such axon guidance molecules are bi-functional: attractive to one type of axons and repulsive to another, depending on the receptor composition in the responding growth cones.

A number of molecules direct axonal growth during development. These compounds are play important roles in embryonic development, and may function in the same or a similar way in the adult CNS.

Attractants and repellants can be divided into two general categories, diffusable and non-diffusable. Diffusible attractants include, but are not limited to, Netrins, Shh, Wnts, and HGF. Diffusible repellents include, but are not limited to, Secreted Semaphorins, Netrins, Slits, Wnts, and BMPs. Non-diffusible attractants include, but are not limited to: cell adhesion molecules such as members of the Ig superfamily, Cadherins, and Integrins; Ephrins; and ECM molecules. Non-diffusable repellents include, but are not limited to, Ephrins, members of the Ig superfamily, and membrane-bound Semaphorins.

Those of skill in the art will be able to use these, and any other attractants or repellants in the context of the invention. For example, those of skill in the are will be able to use these attractants or repellants to create suitable gradients for guiding neuronal growth.

In the context of the invention, native attractants or repellants may be employed. Further, proteins, polypeptides, peptides, mutants, and/or mimetics of these attractants or repellants may be employed, with the definitions of these provided above in reference to Wnt and Wnt-like substance, discussed supra.

D. Targeted Diseases and Conditions

The present invention contemplates methods of treating a subject that includes administering to the subject a composition that includes a Wnt, a Wnt-like substance, and/or a chemical compound affecting a Wnt signaling pathway in a pharmaceutical preparation suitable for delivery to the subject. Other axonal guidance molecules or substances that block neuronal inhibitors can be administered in combination. The subject can be a patient with a disease wherein neuronal dysfunction plays a prominent role in the pathophysiology. For example, the patient may have a disorder of the spinal cord. Any disorder of the spinal cord is contemplated by the present invention. In certain embodiments, the disorder of the spinal cord is traumatic spinal cord injury (discussed above). The traumatic spinal cord injury may or may not have resulted in paralysis of the subject. The neuronal dysfunction can be by any mechanism. For example, cell death can be the result of acute traumatic injury or degeneration.

In certain embodiments, the Wnt, Wnt-like substance, and/or a chemical compound affecting the Wnt signaling pathway is administered to a subject for the purpose of stimulating and promoting directed axonal growth and regeneration along the anterior-posterior axis of the spinal cord.

Any disease or condition wherein there is neuronal dysfunction is contemplated by the present invention. In addition to SCI, other examples include Parkinson's disease, where dopaminergic neurons undergo degeneration and ALS where neurons in the motor systems undergo degeneration. In these cases, stem cells are being developed so that they can be transplanted to the midbrain and the spinal cord, respectively, so that they can populate and make proper connection with their targets. The establishment of new connections require the directly growth of axons from these neural stem cells. Wnt and Wnt-like substances and other chemical compounds affecting a Wnt signaling pathway can be used in growth and guidance of regenerating axons from these stem cells.

E. Nucleic Acids

1. Overview

Certain embodiments of the invention pertain to methods utilizing compositions that include an nucleic acids. In particular, the methods for modulating growth of a neuron may involve contacting the neuron with a Wnt, a Wnt-like substance, and/or a chemical compound affecting a Wnt signaling pathway that further includes an expression cassette. The methods of treating a subject may involve administering to the subject a composition of a Wnt, a Wnt-like substance, and/or a chemical compound affecting a Wnt signaling pathway that includes an expression cassette. One of skill in the art would understand the techniques relating to use of expression cassettes to deliver polynucleotide sequences to cells or subjects. Particular aspects of these techniques of these techniques are summarized in this specification. This brief summary is in no way designed to be an exhaustive overview of all available experimental techniques related to expression cassettes since one of skill in the art would already be familiar with these techniques.

Throughout this application, the term "expression cassette" is meant to include any type of genetic construct containing a nucleic acid coding for a gene product in which part or all of the nucleic acid encoding sequence is capable of being transcribed. The transcript may be translated into a protein or polypeptide, but it need not be. Thus, in certain embodiments, expression includes both transcription of a gene and translation of a mRNA into a polypeptide.

In order for the expression cassette to effect expression of a polypeptide, the polynucleotide encoding the polynucleotide will be under the transcriptional control of a promoter. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrase "operatively linked" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. One of skill in the art would understand how to use a promoter or enhancer to promote expression of a Wnt, a Wnt-like substance, and/or a chemical compound affecting a Wnt signaling pathway.

In certain embodiments of the invention, the delivery of an expression cassette in a cell may be identified in vitro or in vivo by including a marker in the expression vector. The marker would result in an identifiable change to the transfected cell permitting easy identification of expression. The selectable marker employed is not believed to be important, so long as it is capable of being expressed along with the polynucleotide of the expression cassette. Examples of selectable markers are well known to one of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). One of skill in the art would be familiar with use of IRES in expression cassettes.

Expression cassettes can include a multiple cloning site (MCS), which is a nucleic acid region that contains multiple restriction enzyme sites, any of which can be used in conjunction with standard recombinant technology to digest the vector. See Carbonelli et al. (1999); Levenson et al. (1998); Cocea (1997). "Restriction enzyme digestion" refers to catalytic cleavage of a nucleic acid molecule with an enzyme that functions only at specific locations in a nucleic acid molecule. Techniques involving restriction enzymes and ligation reactions are well known to those of skill in the art of recombinant technology.

In expression, one will typically include a polyadenylation signal to effect proper polyadenylation of the transcript. The nature of the polyadenylation signal is not believed to be crucial to the successful practice of the invention, and/or any such sequence may be employed. One of skill in the art would understand how to use these signals to effect proper polyadenylation of the transcript.

In certain embodiments of the present invention, the expression cassette comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series. One of ordinary skill in the art would be familiar with use of viruses as tools to promote expression of the polypeptide.

In certain embodiments of the invention, a treated cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

F. Gene Transfer

1. Viral Vectors

In certain embodiments, the methods and compositions of the invention utilize expression cassette which includes a polynucleotide encoding a Wnt, a Wnt-like substance, a chemical compound affecting a Wnt signaling pathway, another axonal guidance molecule, and/or substance that blocks a neuronal inhibitor can be administered in combination, carried in a vector. One of ordinary skill in the art would understand use of vectors since these experimental methods are well-known in the art. In particular, techniques using "viral vectors" are well-known in the art. A viral vector is meant to include those constructs containing viral sequences sufficient to (a) support packaging of the expression cassette and (b) to ultimately express a recombinant gene construct that has been cloned therein.

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors.

Adenoviruses are currently the most commonly used vector for gene transfer in clinical settings. Among the advantages of these viruses is that they are efficient at gene delivery to both nondividing an dividing cells and can be produced in large quantities. The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus et al., 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. A person of ordinary skill in the art would be familiar with experimental methods using adenoviral vectors.

The adenovirus vector may be replication defective, or at least conditionally defective, and the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. A person of ordinary skill in the art would be familiar with well-known techniques that are available to construct a retroviral vector.

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. Nos. 5,139,941 and 4,797,368, each incorporated herein by reference.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). A person of ordinary skill in the art would be familiar with techniques available to generate vectors using AAV virus.

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995). A person of ordinary skill in the art would be familiar with well-known techniques for use of HSV as vectors.

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

Other viral vectors may be employed as constructs in the present invention. For example, vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells.

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Nonviral Vectors

Several non-viral methods for the transfer of expression vectors into cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and liofectamine-DNA complex, cell sonication (Fechheimer et al., 1987), gene bombardment using high velocity microprojectiles (Yang et al., 1990), polycations (Bousssif et al., 1995) and receptor-mediated transfection (Wu and Wu, 1987; Wu and Wu, 1988). Some of these techniques may be successfully adapted for in vivo or ex vivo use. A person of ordinary skill in the art would be familiar with the techniques pertaining to use of nonviral vectors, and would understand that other types of nonviral vectors than those disclosed herein are contemplated by the present invention.

In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL). One of ordinary skill in the art would be familiar with techniques utilizing liposomes and lipid formulations.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, or intracranial injection to avoid the toxicity and stability problems associated with cationic lipids in the circulation. The interaction of liposomes and plasma proteins is responsible for the disparity between the efficiency of in vitro (Felgner et al., 1987) and in vivo gene transfer (Zhu et al., 1993; Solodin et al., 1995; Thierry et al., 1995; Tsukamoto et al., 1995; Aksentijevich et al., 1996).

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

G. Screening Assays

The present invention also contemplates the screening of candidate substances for the ability to modulate growth of a neuron. Particularly preferred candidate substances will be those useful in stimulating directional axonal growth along the A-P axis of the spinal cord. In the screening assays of the present invention, the candidate substance may first be screened for basic biochemical activity and then tested for its ability to modulate activity, at the cellular, tissue or whole animal level. In certain embodiments, an explant assay such as an assay using cultured spinal cord sections may be used in the screening methods. Any method known to those of skill in the art may be used in the claimed invention to conduct the screening assays.

1. Modulators and Assay Formats a) Assay Formats

The present invention provides methods of screening for modulators of growth of a neuron. In one embodiment, the present invention is directed to a method of:

(a) obtaining a candidate substance;
(b) contacting the candidate substance with a neuron; and
(c) measuring modulation of growth of the neuron.

In an example of yet another embodiment, the assay looks at anterior turning of axons of the neuron.

b) Inhibitors and Activators

An inhibitor according to the present invention may be one which exerts an inhibitory effect on the growth of a neuron. By the same token, an activator according to the present invention may be one which exerts a stimulatory effect on the growth of a neuron.

c) Candidate Substances

As used herein, the term "candidate substance" refers to any molecule that may potentially modulate regeneration of a neuron. The candidate substance may be a protein or fragment thereof, a polypeptide, a peptide, a small molecule inhibitor, or even a nucleic acid molecule. It may prove to be the case that the most useful pharmacological compounds will be compounds that are structurally related to compounds which interact naturally with Wnts, Wnt-like substances, or chemical compounds affecting Wnt signaling pathways. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a Wnt, and then design a molecule for its ability to interact with the Wnt. Alternatively, one could design a partially functional fragment of a Wnt or a Wnt-like substance (binding, but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known modulators of neuronal growth.

Other suitable inhibitors include antisense molecules, ribozymes, and antibodies (including single chain antibodies).

It will, of course, be understood that all the screening methods of the present invention are useful in themselves notwithstanding the fact that effective candidates may not be found. The invention provides methods for screening for such candidates, not solely methods of finding them.

2. In vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to a Wnt or fragment thereof is provided The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as a Wnt). Competitive binding assays can be performed in which one of the agents (Wnt) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, with a Wnt, and washed. Bound polypeptide is detected by various methods.

Purified target, such as the Wnt, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region (e.g., the C-terminus of the Wnt) to a solid phase.

Explant culture assays, such as the collagen gel assays described above, are very convenient systems to test the function of the Wnts, Wnt-like substances, and chemical compounds affecting a Wnt signaling pathway in axonal growth and guidance before applying them to animal-based tests. They can also be used as screening methods.

3. In Cyto Assays

Various cell lines that express a Wnt, a Wnt-like substance, and/or a chemical compound affecting a Wnt signaling pathway can be utilized for screening of candidate substances. For example, cells containing a Wnt or a Wnt-like substance with an engineered indicator can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (e.g., axon growth). Alternatively, molecular analysis may be performed in which the function of a Wnt or a Wnt-like substance and related pathways may be explored. This involves assays such as those for protein expression, enzyme function, substrate utilization, mRNA expression (including differential display of whole cell or polyA RNA) and others.

4. In vivo Assays

The present invention particularly contemplates the use of various animal models. Transgenic animals may be created with constructs that permit Wnt expression and activity to be controlled and monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intrathecal, intratracheal instillation, bronchial instillation, intradermal, subcutaneous, intramuscular, intraperitoneal or intravenous injection. Specifically contemplated are systemic intravenous injection, regional administration via blood or lymph supply.

5. Production of Inhibitors

In an extension of any of the previously described screening assays, the present invention also provide for methods of producing inhibitors. The methods comprising any of the preceding screening steps followed by an additional step of "producing the candidate substance identified as a modulator of" the screened activity.

H. Pharmaceutical Preparations

Pharmaceutical preparations of a Wnt, a Wnt-like substance, and/or a chemical compound affecting a Wnt signaling pathway for modulation of growth of a neuron in a mammal are contemplated by the present invention.

1. Formulations

Any type of pharmaceutical preparation of a Wnt, a Wnt-like substance, a chemical compound affecting a Wnt signaling pathway, another axonal guidance molecule, and/or substance that blocks a neuronal inhibitor is contemplated by the current invention. One of skill in art would be familiar with the wide range of types of pharmaceutical preparations that are available, and would be familiar with skills needed to generate these pharmaceutical preparations.

In certain embodiments of the present invention, the pharmaceutical preparation will be an aqueous composition. Aqueous compositions of the present invention comprise an effective amount an of a Wnt, a Wnt-like substance, a chemical compound affecting a Wnt signaling pathway, another axonal guidance molecule, and/or substance that blocks a neuronal inhibitor, and the like, dissolved or dispersed in a pharmaceutically acceptable carrier or aqueous medium. Aqueous compositions of gene therapy vectors expressing any of the foregoing are also contemplated. The phrases "pharmaceutical composition" or "pharmaceutical preparation" or "pharmacologically effective" or "pharmaceutically acceptable" refer to molecular entities and compositions that do not produce an adverse, allergic or other untoward reaction when administered to an animal, or a human, as appropriate.

As used herein, "pharmaceutical preparation" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for administration by any known route, such as parenteral administration. The preparation of an aqueous composition containing an active agent of the invention disclosed herein as a component or active ingredient will be known to those of skill in the art in light of the present disclosure.

An agent or substance of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. A person of ordinary skill in the art would be familiar with techniques for generation of salt forms. The carrier can also be a solvent or dispersion medium containing, for example, water, ethanol, polyol (for example, glycerol, propylene glycol, and liquid polyethylene glycol, and the like), suitable mixtures thereof, and vegetable oils.

The present invention contemplates a Wnt, a Wnt-like substance, a chemical compound affecting a Wnt signaling pathway, another axonal guidance molecule, and/or substance that blocks a neuronal inhibitor that will be in pharmaceutical preparations that are sterile solutions for intravascular injection or for application by any other route. A person of ordinary skill in the art would be familiar with techniques for generating sterile solutions for injection or application by any other route. Sterile injectable solutions are prepared by incorporating the active compounds in the required amount in the appropriate solvent with various of the other ingredients familiar to a person of skill in the art.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Formulations for administration via lumbar puncture into the cerebrospinal fluid are also contemplated by the present invention.

The active agents disclosed herein may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous injection or via lumbar puncture, other pharmaceutically acceptable forms include, e.g., tablets or other solids for oral administration; liposomal formulations; and time release capsules.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. A person of ordinary skill in the art would be familiar with well-known techniques for preparation of oral formulations. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The use of liposomes and/or nanoparticles is also contemplated for the introduction of the modulator of cell death or gene therapy vectors into host cells. The formation and use of liposomes is generally known to those of skill in the art.

2. Dosage

An effective amount of the therapeutic or preventive agent is determined based on the intended goal, for example inhibition of cell death. The quantity to be administered, both according to number of treatments and dose, depends on the subject to be treated, the state of the subject and the protection desired. Precise amounts of the therapeutic composition also depend on the judgment of the practitioner and are peculiar to each individual.

In certain embodiments, it may be desirable to provide a continuous supply of the therapeutic compositions to the patient. For example, following traumatic spinal cord injury, a continuous administration of the therapeutic agent may be administered for a defined period of time, such as direct injection into the cerebrospinal fluid. For various approaches, delayed release formulations could be used that provide limited but constant amounts of the therapeutic agent over an extended period of time. Continuous perfusion of the region of interest may be preferred.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed above.

3. Tracers to Monitor Gene Expression Following Administration

Certain embodiments of the present invention employ delivery of a Wnt, a Wnt-like substance, a chemical compound affecting a Wnt signaling pathway, another axonal guidance molecule, and/or substance that blocks a neuronal inhibitor to the target area of interest using expression cassettes. It may be important to determine whether the target site has been effectively contacted with the expression cassette. This may be accomplished by identifying cells in which the expression construct is actively producing the desired polypeptide product. Tagging of the exogenous polypeptide with a tracer element would provide definitive evidence for expression of that molecule and not an endogenous version thereof. Thus, the methods and compositions of the claimed invention may involve tagging of the polypeptide encoded by the expression cassette with a tracer element. A person of ordinary skill in the art would be familiar with these methods of tagging the encoded polypeptide.

I. Combination Therapy

In order to increase the effectiveness of the compositions and methods disclosed herein, it may be desirable to combine a variety of agents into one or more pharmaceutical compositions that can be administered in a regime that is effective in the treatment of the neuronal injuries or disorders described herein. As discussed elsewhere in this specification, those of skill in the art may wish to apply a combination of neuronal attractive, repellant, inhibitory, and/or inhibition blocking substances to the neurons to facilitate appropriate neuronal growth and/or function. This may involve contacting the neuron or spinal cord with these agent(s) at the same time. This may be achieved by contacting the neuron or spinal cord with a single composition or pharmacological formulation that includes multiple agents, or by contacting the cell with two distinct compositions or formulations, at the same time.

Alternatively, the agents may be applied to the neuron or spinal cord in series or succession at intervals ranging from minutes to weeks. In embodiments where two agent are applied separately to the neuron or spinal cord, one may wish ensure that a significant period of time did not expire between the time of each delivery, such that the agents will be able to exert an advantageously combined effect on the neuron(s). In such instances, it is contemplated that one may contact the cell with both modalities within about 12-24 hours of each other and, more preferably, within about 6-12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In other embodiments, two or more agents applied separately to the neuron or spinal cord with sufficient such that the agents will be able to separately exert their beneficial therapeutic effects on the neurons. In such instances, it is contemplated that one may contact the cell with both modalities In some situations, it may be desirable to extend the time period for treatment such that several days (2, 3, 4, 5, 6 or 7) to several weeks (1, 2, 3, 4, 5, 6, 7 or 8) lapse between the respective administrations.

Various combinations, in an exemplary embodiment, may be employed. For example, any number of regimes may be employed as set forth bells where "A" is a Wnt, Wnt-like substance, or chemical compound effecting a Wnt-signaling pathway and "B" a further Wnt, Wnt-like substance, or chemical compound effecting a Wnt-signaling pathway, a compound providing attractive or repellant guidance to neuronal growth, inhibitor of neuronal growth, or blocker of an inhibitor of neuronal growth:

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the agents to a patient will follow general protocols for the administration as known to those of skill in the art and set-forth herein. It is expected that the treatment cycles may be repeated as necessary. It also is contemplated that various standard therapies, as well as surgical intervention, may be applied in combination with the application of the agents.

J. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Collagen gel assays. E13 rat spinal cord explants were cultured in collagen gel matrix as described previously (Tessier-Lavigne et al., 1988; Zou et al., 2000). These explants are either "open-book" or post-crossing or pre-crossing for the spinal cord commissural axons. COS7 cells were transfected with various expression constructs with FuGene6 reagent (Roche). The explants were typically cultured for 16-20 hours and fixed in 4% PFA for two hours. The "open-book" explants were analyzed by lipophilic DiI labelling using iontophoresis. The post-crossing explants were stained with a monoclonal antibody (E7) against β3 tubulin (Hybridoma Bank for Developmental Studies). The pre-crossing explants were stained with a monoclonal antibody (4D7) against TAG-1 (Hybridoma Bank for Developmental Studies). Both antibodies were detected using secondary antibodies conjugated with horseradish peroxidase and visualized with 3,3'-diaminobenzene (DAB) (Sigma). Quantification of the post-crossing assays was done as described previously (Zou et al., 2000). The relative total axon bundle length was obtained by normalizing the total length of axons in the presence of Wnt-expressing COS cell aggregates against that in the presence of vector-only transfected COS cell aggregates. The explant assays were performed in three to four sets of multiple explants for each Wnt and an average fold of increase and a standard error were obtained for each Wnt from these sets. Therefore, the relative total length of vector only was defined as 1. n indicates the total number of explants for each construct.

Axon labelling. To reveal the commissural axon projections inside the spinal cord tissue, the inventor used DiI labelling. DiI is a lipophilic dye that becomes highly fluorescent when incorporated in membrane to reveal the shape of the cells and membrane protrusions. In order to focus on relatively smaller numbers of axons and produce more consistent and reproducible injection results, the inventor uses iontophoresis (Fraser, 1996) and point the injection sites with a micromanipulator (Fine Science Tools). DiI was dissolved in $MeCl_2$ (Sigma) at 1 mg/ml. The Dye was delivered into spinal cord tissues with a SD9 current injector (Grass Telefactor). Glass needles were pulled with Narishige PC-10 pipette puller.

In situ hybridization. Mouse E10.9-E13.5 embryos were fixed for either whole-mount or section in situ hybridization as previously described (Keino-Masu et al., 1996; Zou et al., 1997). Specific probes for Wnt1, Wnt4, Wnt6 were obtained by PCR from Wnt1, Wnt4 and Wnt6 constructs in pcDNA1 (Fan et al., 1997) and subcloned into TOPO II vector (Invitrogen). Wnt5a and Wnt7b probes were obtained by RT-PCR from mouse E11.5 embryonic mRNA and subcloned in TOPO II vector.

Immunohistochemistry. E11.5 embryos of frizzled 3 knockout embryos, wild type and heterozygous littermates were fixed for immunohistochemistry with TAG-1 (4D7) antibody as previously described (Serafini et al., 1996).

Wnt and sFRP expression constructs. Wnt1, Wnt4 and Wnt6 full-length cDNA were subcloned into pcDNA3 with Myc epitope tag from pcDNA1 (Fan et al., 1997). Wnt5a expression construct in pCS2 was a kind gift from Dr. Xi He at Children's Hospital at Harvard Medical School and was subcloned into pcDNA3 with Myc epitope tag. Wnt7b cDNA was cloned by RT-PCR from E11.5 mouse embryonic mRNA and subcloned into pcDNA3 with Myc epitope tag. Mouse sFRP1 cDNA construct was a kind gift from Dr. Xi He (Finch et al., 1997). Mouse sFRP2 and sFRP3 cDNAs were cloned by RT-PCR from E11.5 mouse embryonic mRNA and subcloned into pcDNA3 with Myc Epitope tag.

Intrathecal injection. sFRP2 was overexpressed using the bacculovirus system (Lyuksyutova et al., 2003). The overexpressed sFRP2 is tagged with 6XHis epitope and can be purified with affinity columns. Purified sFRP2 protein was dialyzed into artificial cerebrospinal fluid and injected into postnatal day 1 mice and rats, followed by one more injection on postnatal day 3. At postnatal day 5, animals were sacrificed, fixed by cardiac perfusion, and dissected for obtaining the spinal cord tissue. Serial sections were obtained along the A-P axis, and the CST axons will be examined by immunohistochemistry.

Behavioral test of injected animals. The functional consequence of sFRP2 injection will be assessed by observing the movement behavior of the injected mice and measuring the strength of the hind paw. A pilot set of experiments with 12 rats and found that 50% of the injected animals displayed a reduction in CST fibers, and that approximately 50% of the injected animals showed splayed hind paws and slowed movement at two weeks after birth.

Example 2

The A-P Guidance Cue(s) is Diffusible

When a segment of E13 rat spinal cord is cultured in collagen gel for 16-18 hours, commissural axons were observed to project ventrally, cross the midline and turn anteriorly within the explant, mimicking their in vivo pathfinding. Commissural axon trajectories in these "open-book" explants can be revealed by lipophilic DiI injection into the dorsal side of the explants by iontophoresis (Fraser, 1996). Most of the commissural axons in E13 rat spinal cord "open-book" preparations fixed immediately after dissection (without culturing) are only just approaching the midline or in the process of midline crossing. Therefore, the midline crossing and anterior turning of the commissural axons observed with DiI labeling occurred during the "open-book" culture period.

FIG. 1A schematically demonstrates that during embryonic development, commissural neurons project axons to the ventral midline. Once they reach the floor plate, they cross the midline and enter the contralateral side of the spinal cord, as diagrammed in FIG. 1B. It was reasoned that if A-P guidance is controlled by a diffusible gradient of either an attractant(s) or a repellents(s), then cutting the "open-book" explants shorter might lead to the loss of the gradient within the explants and therefore lead to abnormal pathfinding along the anterior-posterior axis (FIG. 1C); if A-P guidance is controlled by a non-diffusible cue(s), commissural axons will still have the normal anterior turn in shorter explants, because the gradient will be maintained (FIG. 1D).

"Open-book" explants of different anterior-posterior lengths (3 mm, 2 mm, 1 mm and 0.5 mm) were systematically cultured and commissural axon growth was analyzed using focal DiI injection by iontophoresis into the dorsal spinal cord. When the length was reduced to 0.5 mm, abnormal pathfinding behavior of the post-crossing commissural axons was consistently observed, which included knotting, stalling and randomized turning along the A-P axis. This behavior contrasted sharply with that observed in 3 mm explants, in which all axons turned anteriorly. In both short and long explants, commissural axon pathfinding from the dorsal spinal cord to the floor plate was normal. These results were quantified and are shown in FIG. 1E. Because each DiI injection labels a cohort of axons, the inventor quantified the results by categorizing axonal behavior observed for each DiI injection site, as previously described (Zou et al., 2000). If all axons turned anteriorly in one injection, it was counted as an anterior (correct) turn; if many axons appeared to stall or make knots after midline crossing, it was counted as "knotting/stalling"; if a significant number of axons projected posteriorly or all axons projected posteriorly, it was counted as "random turn (A/P)". The frequency of each category is presented as percentage of all injected sites. Some of the sites display both knotting/stalling and random turn behavior so that the total percentage can be greater than 100%. All of the post-crossing commissural axons in the long explants turned correctly. In the short explants, axons formed knots or stalled after midline crossing, or turned randomly both anteriorly and posteriorly. Only 18% of the injection sites in the short explants showed normal anterior turning, presumably due to the loss of guidance information in the short explants. Therefore, the guidance cue(s) that directs the anterior turn is likely diffusible. These results do not address the source of the diffusible cue(s) in the neural tube or how the gradient is established. The diffusible cue(s) can be either expressed at differential levels along the anterior-posterior axis of the spinal cord or secreted from an anterior or a posterior tissue source.

Example 3

The A-P Guidance Cue(s) is Attractive

Figure 2:
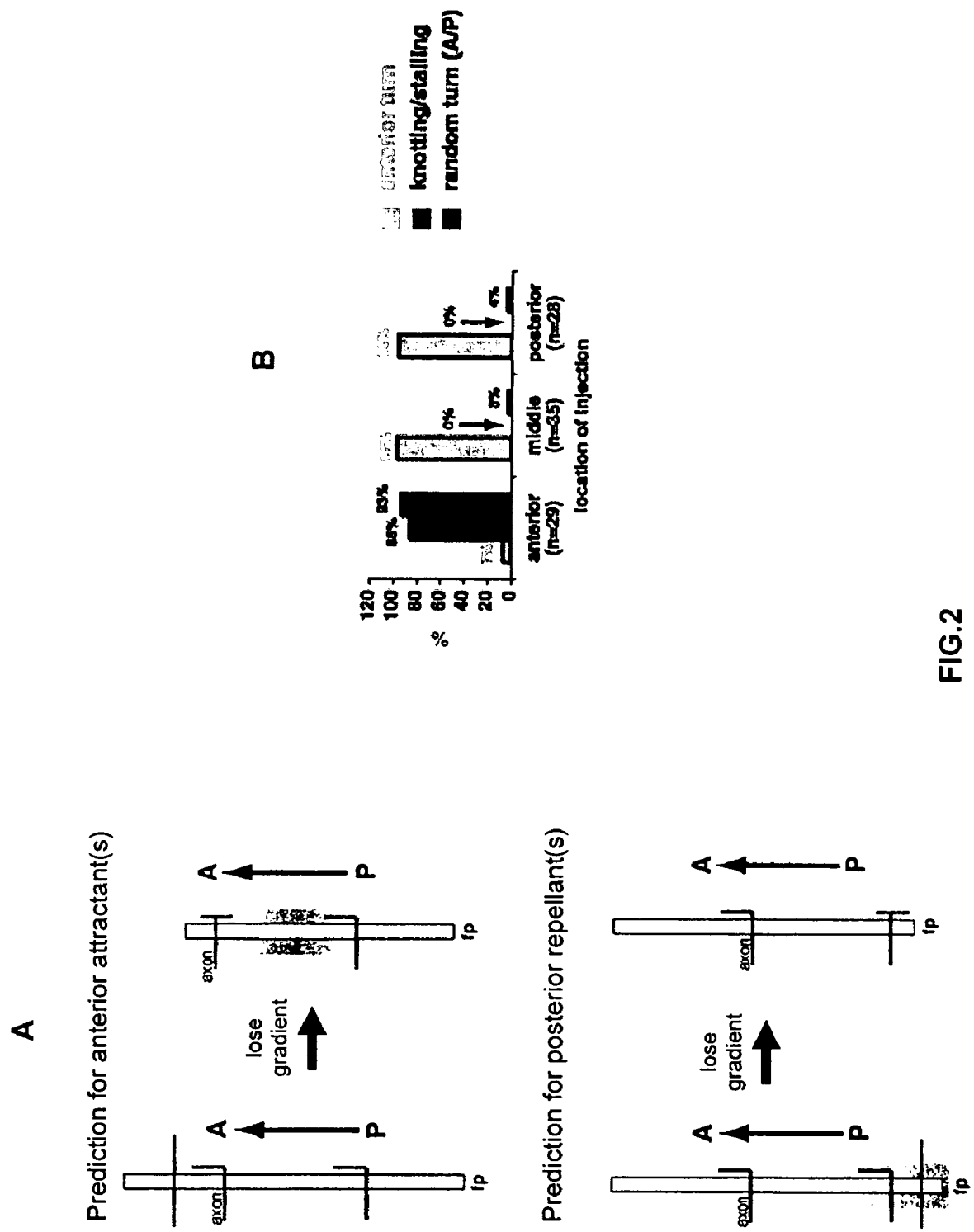
FIG. 2A, FIG. 2B. The anterior guidance cue(s).

To address whether the A-P guidance cue is attractive or repulsive, DiI was focally injected into the dorsal spinal cord close to the anterior end, in the middle and close to the posterior end of the long explants (3 mm or longer). The axons in the middle and close to the posterior end of the explants were found to always project anteriorly, whereas the axons close to the anterior end almost always make mistakes: they either stall after they cross the midline or they project both anteriorly and posteriorly after midline crossing, or sometimes only posteriorly. The results were quantified using the same criteria as shown in FIG. 1E. The quantification is shown in FIG. 2B. The axons close to the anterior end of the explants behave similarly to those in the short explants (0.5 mm), whereas the axons in the middle and posterior part of the explants behave normally. These results are consistent with the possibility that a gradient of an attractive cue(s) plays a role in the anterior turn of the post-crossing commissural axons. Interestingly, it was consistently found that the axons close to the anterior end of the explant have a much higher frequency (93%) of turning posteriorly than those in the shorter explants (64%). It is possible that the remaining attractant(s) in the middle and posterior parts of the longer explants creates a counter gradient after the attractant(s) diffuse out from the anterior end, turning the axons posteriorly. This abnormal behavior of the anterior injection sites is true for explants taken anywhere along the entire length of the spinal cord, suggesting that a general anterior-posterior gradient of diffusible attractant(s) controls the anterior turn of the post-crossing commissural axons along the length of the spinal cord.

It is possible that the axons located close to the anterior end of the long explants might be misrouted, because the gradient might be destroyed due to diffusion of the attractant(s) out of the explants, whereas the axons close to the posterior end will turn normally, as the tissue anterior to these turning points will still contain higher concentrations of the attractant(s) (FIG. 2A, upper panel). On the other hand, if the cue(s) were repulsive, the axons close to the posterior end of the explants might not be able to turn anteriorly correctly because the gradient might be disrupted due to the diffusion of the repellent(s) out of the explants, whereas the axons at the anterior end of the explants will not be affected, because the tissue posterior to the injection site will still contain higher amounts of the repellent(s) (FIG. 2A, bottom panel).

In order to rule out the possibility that cutting at the anterior end itself produces a repulsive signal, which repels post-crossing commissural axons, studies were conducted to determine whether a cut in the "open-book" explants can prevent axons from projecting rostrally. A cut was introduced within the explants on one side of the "open-book" spinal cords. The spinal cord explants were cultured overnight and the contralateral dorsal spinal cord explants were injected 200 µm-300 µm posterior to the cut site. Commissural axons still projected rostrally and could traverse the cut site, behaving as if they were in the middle of the long "open-book" explants.

Although the cut spinal cords sometimes appeared to be reconnected after overnight culture, they are not sealed back and can be easily separated again at the cut site. And yet, axons can grow through the cut site. This suggests that the A-P gradient of the guidance cue(s) is preserved in such a preparation and a cut (damage) to the spinal cord itself does not produce a cue(s) to repel post-crossing commissural axons. In fact, these axons were faced with two "copies" of cut edge compared to those in short explants. If cut edge produced a repellent, then axons posterior to the internal cut edge would display more severe defects than those in short explants alone. This also demonstrates that the distance between the anterior injection sites and the border of the explants (200 µm-300 µm) is sufficient for commissural axons to turn anteriorly and the failure of anterior turning in short "open-book" explants and at the anterior end of long "open-book" explants is not due to spatial or physical restrictions but rather due to the disruption of the gradient of a guidance cue(s). These results are all consistent with an interpretation that the abnormal axonal behavior at the anterior end of the "open-book" explants is caused by the disruption of a gradient of an attractive molecule(s).

Example 4

Wnt Family Proteins are Candidate A-P Guidance Cue(s)

Figure 3:
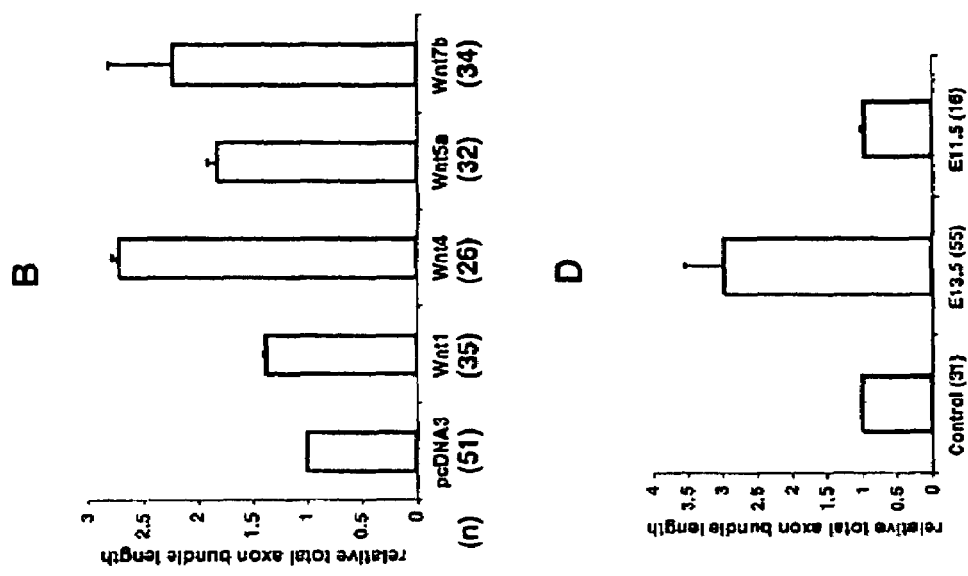
FIG. 3A, FIG. 3B, FIG. 3C, FIG. 3D. Multiple Wnt proteins stimulate the extension of post-crossing commissural axons.
Figure 3:
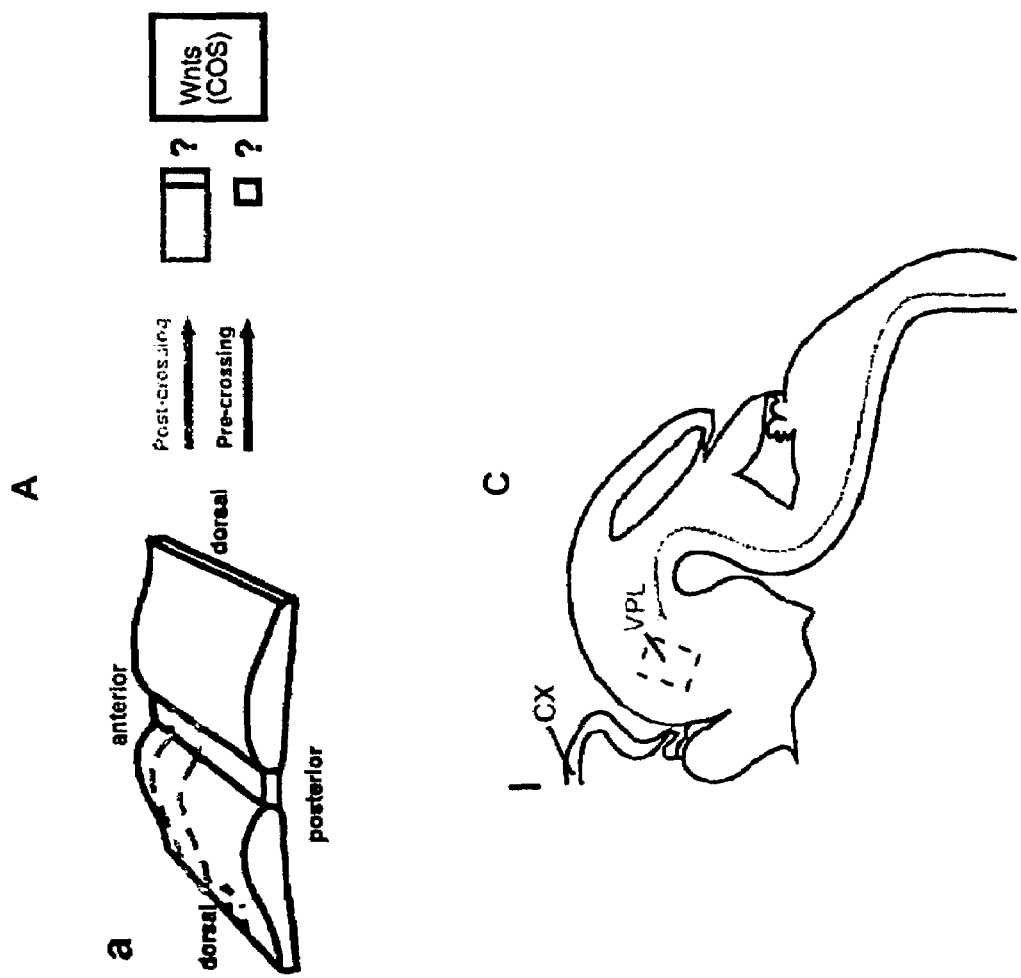

To identify the diffusible guidance cue(s) directing the anterior turn after midline crossing, a candidate gene approach was used. It had been observed that an embryonic limb bud can stimulate the extension of commissural axons only after they have crossed the midline using the "post-crossing" explant assay (Zou et al., 2000). In this assay, commissural axons grow out of the explant after crossing the floor plate, making it possible to test the effects of secreted factors on the axons (see diagram in FIG. 3A). As axon guidance molecules are often expressed in multiple tissues during development, it was hypothesized that the factor(s) in the limb bud that stimulates extension of post-crossing commissural axons might be related to the attractant(s) that affect these same axons in vivo (Serafini et al., 1996; Ebens et al., 1996). Therefore, candidates expressed in the limb bud were tested using the post-crossing commissural axon explant assay by expressing these molecules in COS cell aggregates positioned next to post-crossing explants in collagen gels (FIG. 3A). Candidate molecules found in the limb bud include HGF (Ebens et al., 1996), FGF4 (Bueno and Heath, 1996), FGF8 (Bueno and Heath, 1996), BMP4 (Francis et al., 1994), BMP7 (Hofmann et al., 1996; Augsburger et al., 1999), Shh (Bueno and Heath, 1996), and Wnt1 (Zakany and Duboule, 1993). Wnt4 was also tested, because it is expressed in the floor plate (Ungar et al., 1995; Liu et al., 2000; Saulnier et al., 2002) and Wnt 6 (Fan et al., 1997). Of these factors, only Wnt1, Wnt4 and Wnt6 were found to stimulate the extension of the post-crossing commissural axons. Additional Wnt proteins that are expressed either in the spinal cord or in the limb bud were tested, namely Wnt5a (Dealy et al., 1993) and Wnt7b (Parr et al., 2001; Shu et al., 2002), and found that these two Wnts can also stimulate the extension of the post-crossing commissural axons. Wnt1 stimulates post-crossing axon extension relatively weakly, whereas Wnt4, Wnt5a and Wnt7b can increase the extension of post-crossing axons by 2-3 fold on average (FIG. 3B). None of these Wnts affect the outgrowth of pre-crossing commissural axons, in contrast to Netrin-1, used as a positive control (Serafini et al., 1994).

If a gradient of diffusible attractant(s) guide commissural axons anteriorly, it might be expected that the tissues anterior to commissural axons can attract post-crossing commissural axons. From previous work of the inventor, both the spinal cord and the floor plate have a potent net repulsive effect to post-crossing commissural axons (Zou et al., 2000). It is possible that the attractant(s) for post-crossing axons are not as diffusible as Semaphorins and Slit proteins precluding the possibility of revealing the function of the attractant(s) in the post-crossing collagen gel assays. Alternatively, the attractant(s) might be expressed in a more restricted fashion and cannot produce a consistently strong attractive effect in assays depending on the orientations of tissues in cultures. In order to circumvent this obstacle and test the model of anterior attractant(s), the function of a major brain target for commissural axons, the ventral-posterior-lateral nucleus of the thalamus, was examined, which is the synaptic target of the spinothalamic tracts (FitzGerald, 1996). The inventor found that the E13.5 ventral-posterior-lateral nucleus can similarly stimulate the extension of the post-crossing commissural axons by three fold (FIG. 3C). In contrast, at an earlier stage (E11.5), the diencephalon region destined to be the ventral posterior thalamus does not have any growth stimulating activity, suggesting that the E13.5 thalamus activity is specific. At E11.5, the earliest populations of commissural axons just crossed the midline and turned anteriorly inside the spinal cord and have not reached the forebrain yet.

To determine whether any of these Wnts are likely to affect commissural axon growth in vivo, the expression patterns of Wnts were examined by in situ hybridization in developing mouse embryos during the stages when commissural axons are crossing the midline and turning anteriorly into their longitudinal pathway. Expression of some of these genes in the developing spinal cord has been examined before (Kispert et al., 1996; Liu et al., 2000; Saulnier et al., 2002; Shu et al., 2002; Krylova et al., 2002). At E11.5 (equivalent to E13 rat), Wnt1 is expressed at high levels in the roof plate but diffusely and weakly throughout the spinal cord. Wnt4 is specifically enriched in the floor plate and the ventricular zone and has a decreasing anterior-to-posterior gradient along the entire length of the floor plate at E10.5 as well as E13.5, whereas the expression in the ventricular zone does not show any gradient. A similar anterior-posterior gradient of Wnt4 expression was also observed in the floor plate of E11.5 and E12.5 mouse embryos (data not shown). Wnt5a is expressed widely in the spinal cord but is particularly abundant in the ventral areas of the spinal cord next to the lateral funiculus. Wnt7b is expressed in the ventricular zone of the spinal cord and specifically on the two lateral margins of the floor plate, where the anterior turning of the post-crossing commissural axons occurs. Wnt7b appears to have a decreasing anterior-to-posterior gradient in the ventricular zone but does not display an A-P gradient in the floor plate. Wnt6 and Wnt11 (Kispert et al., 1996) are not expressed in the spinal cord. Wnt3 is expressed in the motor columns but not in the ventral midline or the ventral or lateral funiculi (Krylova et al., 2002) and therefore may not be relevant to commissural axon pathfinding along the anterior-posterior axis. Therefore, several Wnts are expressed in the right place at the right developmental stages to function as regulators of the growth of the post-crossing commissural axons. In particular, the Wnt4 expression displays a clear anterior-posterior gradient along the entire length of the floor plate throughout the time when commissural axons are turning anteriorly after midline crossing (from E10.5 to E13.5). This suggests that Wnt4 might play a role in the anterior-posterior turning decision of post-crossing commissural axons along the entire length of the spinal cord. Interestingly, a similar Wnt4b gradient in the floor plate along the anterior-posterior axis has also been found in zebrafish embryos at similar developmental stages (Liu et al., 2000). Because the ventral posterior lateral nucleus of the thalamus can stimulate the extension of the post-crossing commissural axons, the inventor tested whether any of the Wnt genes are expressed in the thalamus. The inventor found that Wnt1 and Wnt4 genes are expressed at high levels in the thalamus. At E13.5, Wnt4 is expressed in a highly restricted pattern in the thalamus, including the dorsal lateral geniculate nucleus (dLGN) and the ventral-posterior-lateral nucleus (VPL). Wnt1 is also expressed in the dLGN and the VPL at the same stage. Interestingly, Wnt4 and Wnt1 have reciprocal gradients. Wnt4 is expressed at higher level in the dLGN than in the VPL, whereas Wnt1 is expressed at higher level in the VPL than in the dLGN. However, both are expressed in the VPL and the areas used in the explant assays include the VPL. At E11.5, neither Wnt1 nor Wnt4 is expressed in the dorsal diencephalon region destined to be the VPL of the thalamus, consistent with the observation that E11.5 thalamus does not stimulate the extension of the post-crossing commissural axons. Based on the expression pattern of the Wnt genes, the Wnt protein(s) gradient is more likely formed by graded expression levels along the anterior-posterior axis rather than diffusion from the brain targets.

Example 5

SFRPs Can Disrupt Anterior-Posterior Guidance of Commissural Axons

Figure 4:
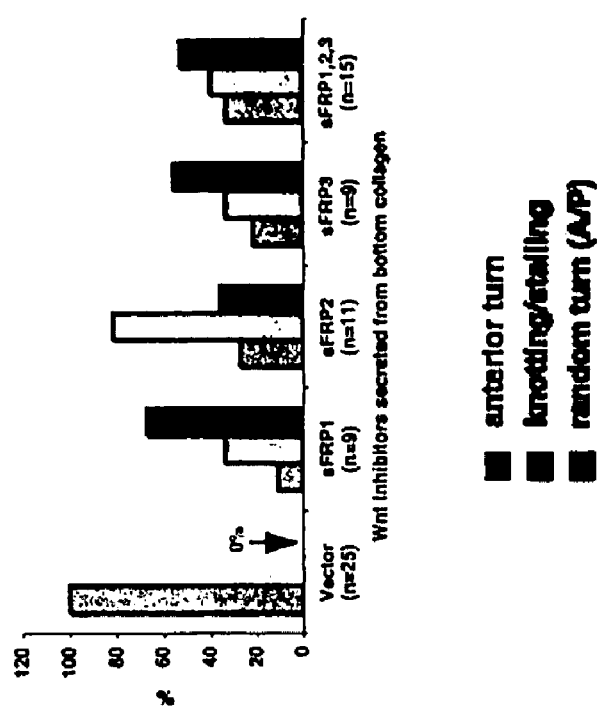
FIG. 4A, FIG. 4B: sFRPs block the anterior turning of post-crossing commissural axons in "open-book" explants.
Figure 4:
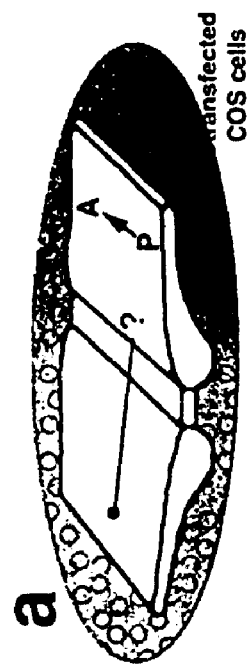

To test directly whether Wnts are required for the proper anterior turn of the post-crossing commissural axons, potent Wnt inhibitors were used to block the function of all Wnts in the "open-book" explants. Secreted Frizzled-related proteins (sFRPs), are soluble proteins that bind to Wnt proteins with high affinities and thus can block the interaction of Wnts with their receptors, the Frizzleds (Wodarz and Nusse, 1998). sFRPs were produced in the "open-book" collagen gel assays by including sFRP-expressing COS cells in the bottom layer of collagen gel (FIG. 4A). The "open-book" of long spinal cord explants were placed on top of the bottom collagen and embedded in the top collagen gel. This system was first tested with Netrin-1 expressing cells in the bottom collagen and it was found that axons can extend from the pre-crossing spinal cord explants, suggesting that the molecules expressed in the bottom collagen can diffuse effectively into the top collagen. As a control, COS cells transfected with vector only and embedded in the bottom collagen had no growth-promoting activity.

It was found that in the presence of any of the three sFRPs (sFRP1, sFRP2 and sFRP3) or a mixture of all three sFRPs, anterior turning of commissural axons after midline crossing are severely impaired. Instead, they either stall or turn randomly along the anterior-posterior axis, displaying behaviors similar to those observed in the short explant studies discussed above and the anterior injection sites discussed above. In contrast, in the presence of the vector-only-transfected COS cells in the bottom collagen, all commissural axons turned anteriorly after midline crossing. As shown in FIG. 4B, in the presence of sFRP1, only 11% of the injection sites displayed correct anterior turns; in the presence of sFRP2 or sFRP3, only about 25% of the injections sites turned correctly. Therefore, most of the injection sites showed abnormal projections along the A-P axis when the function of the Wnt proteins were blocked. A-P guidance of commissural axons at all anterior-posterior levels was disrupted in the presence of any of the sFRPs or a mixture of all sFRPs. No abnormal pathfinding behavior was observed in the pre-crossing segment of the commissural axons, suggesting that the Wnt signaling pathway is not required for the dorsal-ventral projection of the pre-crossing commissural axons. Similar anterior-posterior guidance defects of post-crossing commissural axons were observed when a purified Frizzled-8 ectodomain-Fc fusion protein was added to the "open-book" culture, whereas an Fc only control protein did not exert any effects.

Example 6

A Wnt4 Gradient Can Rescue A-P Guidance Defects and Reorient Axons Posteriorly

Figure 5:
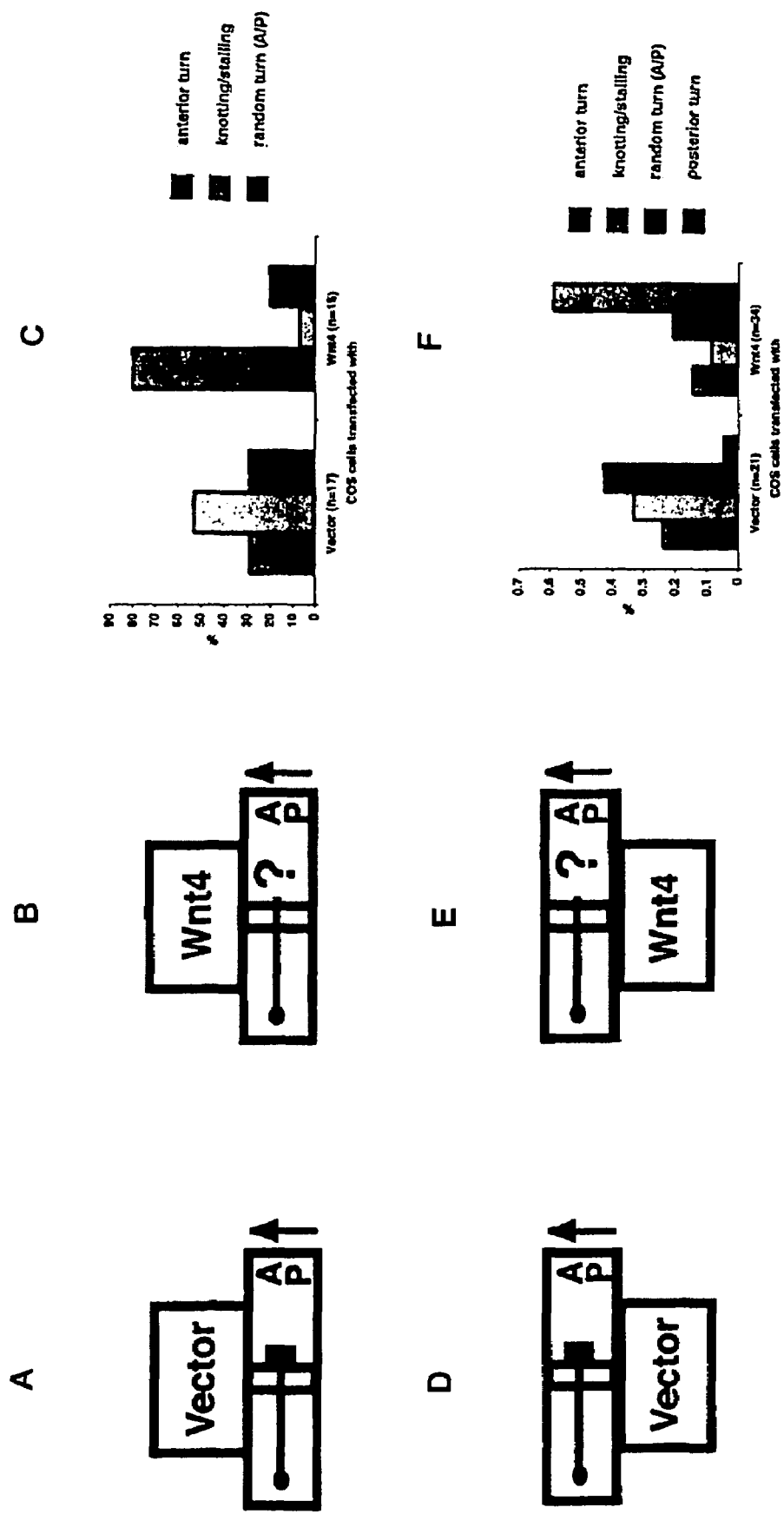
Figure 6:
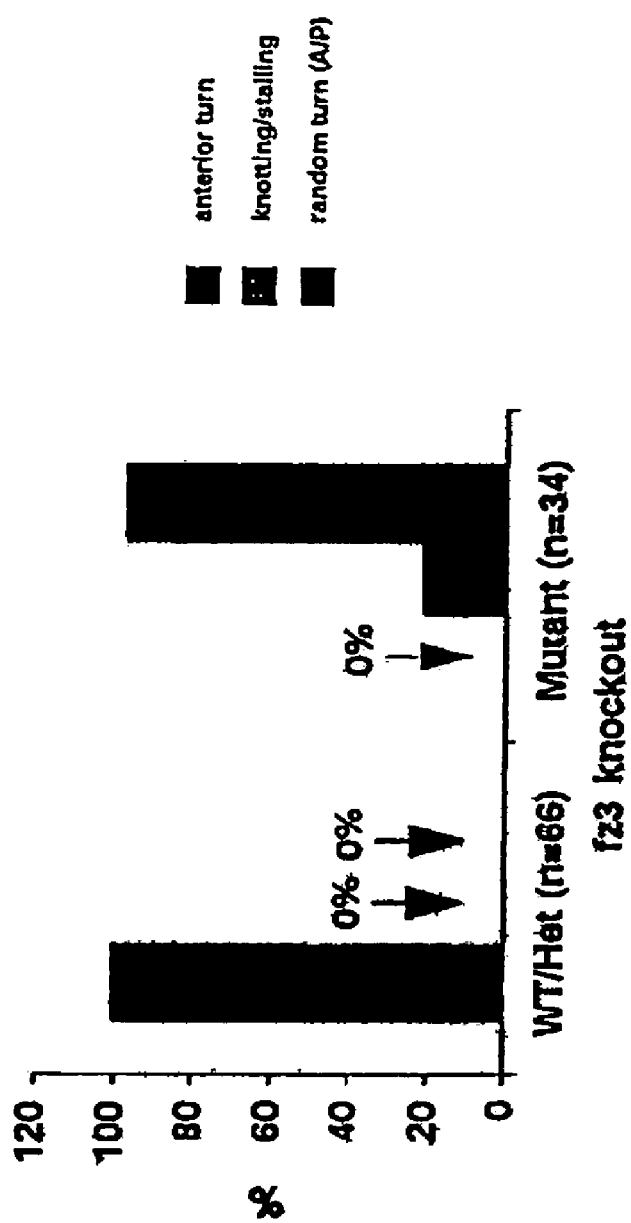
FIG. 6. Frizzled 3 is specifically required for the anterior-posterior guidance of post-crossing commissural axons. Quantification of the post-crossing A-P guidance defects in frizzled 3 knockout mice. Four litters of frizzled 3 knockout mice were analyzed (three litters were analyzed in blinded experiments). A total of 7 mutant embryos were analyzed. The A-P randomization and stalling were observed at 100% penetrance in all injections sites along the entire A-P axis of the spinal cord. n=number of injection sites.

In short "open-book" explants, post-crossing axons lose A-P directionality presumably due to the disruption of a Wnt gradient. In order to further test this hypothesis, studies were conducted to determine whether applying a localized anterior source of Wnt protein(s) can rescue the anterior turn of commissural axons after midline crossing in these short explants. The inventor placed COS cell aggregates expressing Wnt4 anterior to the short explants and tested whether the post-crossing axons can turn towards the Wnt4 cell aggregates (FIG. 5A and FIG. 5B). It was found that Wnt4 expressing COS cells can attract post-crossing commissural axons and rescue A-P guidance defects found in short explants, whereas COS cells transfected with vector only had no effects (FIG. 5C). Only 25% of the explants displayed correct anterior turns in the vector only control, whereas 75% of the explants displayed clear turning towards the Wnt4-expressing COS cell aggregates. Thus, A-P pathfinding errors caused by loss of an A-P gradient of guidance cue(s) can be rescued when a Wnt4 gradient is applied.

To further test whether Wnt4 can function as an instructive cue to direct axon growth, studies were conducted to determine whether placing COS cell aggregates posterior to the short explants can reorient axons posteriorly (FIG. 5D and FIG. 5E). It was found that Wnt4 can readily redirect the growth of the post-crossing commissural axons to turn posteriorly, whereas the COS cell transfected with vector only did not affect the behavior of the post-crossing axons in the short explants, suggesting that Wnt4 is an instructive cue rather than permissive cue. Quantification of data was carried out using the same criteria throughout the these studies. For the reorientation experiments, if all axons turned posteriorly, that injection site was counted as posterior turn and shown in the bars to the far right in FIG. 5F.

In order to test whether anterior tissue contain instructive attractant(s) for commissural axons, studies were conducted to attempt to reorient post-crossing commissural axons posteriorly by putting the ventral-posterior thalamus posterior to the "open-book" explants. It was found that in contrast to the Wnt4-overexpressing COS cells, thalamus could not reproducibly reorient axons. The expression of Wnt proteins in the thalamus may not be sufficient to allow Wnt proteins to diffuse into the "open-book" explants to redirect axons. It was found that anterior spinal cord tissue could not reorient axons, either. The spinal cord contains potent repellents to post-crossing commissural axons, such as Sema3B, Sema3F and the Slit proteins, to prevent them from re-entering the grey matter and has a net repulsive effect on post-crossing commissural axons in collagen gel assays (Zou et al., 2000). The Wnt4 protein gradient in the spinal cord is only restricted to the floor plate. The rest of the ventricular zone does not have Wnt4 expression gradient. Therefore, it is very hard to recreate a Wnt4 counter gradient in the "open-book" assay by putting a piece of spinal cord posterior to the explants.

Example 7

Frizzled 3 is Required for Anterior-Posterior Guidance of the Post-Crossing Commissural Axons In vivo Three frizzled genes, which encode receptors for Wnts, fz3, fz8 and fz9, have been found to be expressed in the spinal cord (Borello et al., 1999). This was confirmed by in situ hybridization that fz3, fz8 and fz9 are indeed expressed in the spinal cord from E9.5 to E13.5 during the time when commissural axons are making anterior turns. Among the three frizzleds, fz3 is the most relevant, because it is expressed broadly in the spinal cord, covering the area where commissural neuron cell bodies are located. Interestingly, fz3 transcripts appear to be enriched in the ventral funiculi where post-crossing commissural axons are located at a E11.5, when a large number of commissural axons have already crossed the midline. Fz8 is expressed more weakly and is not expressed in the most dorsal portion of the spinal cord. Fz9 is only expressed in the ventricular zone where non-differentiated neurons are localized but not in the dorsal mantle zone where commissural neuron cell bodies are located. Commissural axon projections in fz3 knockout embryos (Wang et al., 2002) were examined by immunohistochemistry and DiI labeling with a monoclonal antibody against TAG-1, a commissural axonal marker that only labels the pre-crossing and the midline crossing segments of the commissural axons but not the post-crossing segment of the commissural axons. It was found that the dorsal-ventral projection of pre-crossing commissural axons were normal compared to wild type control, but post-crossing commissural axons projected randomly along the anterior-posterior axis after midline crossing with 100% penetrance. From crosses between fz3 heterozygotes, four litters among which were seven homozygous mutants were examined. For three of these litters, the dissected spinal cords were analyzed without knowledge of their genotypes. In these blinded experiments, 5/5 mutant and 11/11 wild type or heterozygous spinal cords were correctly identified; the probability of this occurring by chance is $4 \times 10^{-5}$. It was found that in all injection sites, commissural axons either turned randomly along the anterior-posterior axis or stalled after midline crossing, whereas their pre-crossing trajectory was normal, consistent with the observations discussed above using explant assays, suggesting that the Wnt/Frizzled pathway is only required for anterior-posterior axon guidance after midline crossing in vivo. As previously reported, no spinal cord patterning defects were observed in the fz3 knockout mice at this stage of development as assessed by markers such as Nkx2.2, HNF-3β, Lim2, and Isl1 (Wang et al., 2002). Both the dorsal-ventral and anterior-posterior pathfinding of commissural axons are normal in LRP6−/− embryos although dramatic patterning defects were observed in these animals (Pinson et al., 2000), suggesting that the canonical Wnt/β-catenin signaling pathway is not involved in the differentiation, the dorsal-ventral pathfinding and the anterior-posterior guidance decision of commissural axons at the midline.

Example 8

Wnt Genes are Expressed in a "Half-Pipe" Gradient Along the Neonatal Spinal Cord Because corticospinal tract axons project posteriorly along the dorsal funiculus of the spinal cord, the inventor examined the expression pattern of Wnt genes around the dorsal funiculus by in situ hybridization. The inventor cloned the entire family of rodent Wnt genes (including 19 members) and performed in situ hybridization at postnatal days 0 and 3 along the anterior-posterior axis. The inventor found that five Wnt genes are expressed in the dorsal midline and dorsal funiculus. Wnt1, and Wnt5a are expressed at a higher level. The other Wnts, Wnt7b, Wnt8a, and Wnt9a, are expressed at lower levels. Along the anterior-posterior axis, all of these Wnt genes have a high-to-low gradient from the cervical and thoracic level. Intriguingly, all these Wnt genes display a reverse gradient at the lumbar level: low-to-high gradient. Therefore, multiple Wnt genes are expressed in a biphasic gradient, or "half-pipe" gradient.

The biphasic gradient along the entire spinal cord suggests that Wnts first "push" CST axons posteriorly along the cervical and thoracic cord but then act as stop signal to terminate the CST axons at the lumber cord, much like the motion in a "half-pipe".

Example 9

Wnt Proteins Repel Frontal Cortical Axons

In order to test whether Wnts can guide corticospinal tract axons, the inventor performed explant assays to evaluate the function of Wnt proteins in frontal cortical axons in collagen gel. Postnatal day 0 brains were dissected out and sliced with tissue chopper. Layer 5 cortical explants were dissected from the frontal motor cortical region and culture in collagen for 60 hours. Long axons grew out in the collagen gel and are stained positively with a corticospinal tract marker, a monoclonal antibody against N-CAM, 5A5. COS cells were transfected with Wnt expression constructs and made into cell aggregates, and the inventor positioned the cell aggregates next to the cortical explants dissected out from postnatal P0 frontal cortex. The inventor found that Wnt1 protein potently inhibits the outgrowth of axons from the frontal cortex in these assays, suggesting that corticospinal tract axons might respond to Wnt proteins as they pathfind along the spinal cord in vivo. Very few axons grew out in the collagen gel, and the axon's length is much reduced as well. A slight repulsive effect can be observed. To address the possibility that the cell aggregates may be secreting too much Wnt1 protein so that axons cannot grow out of the explants, the inventor diluted the transfected COS cells with untransfected COS cells and found that Wnt1 shows robust repulsion when diluted. The inventor tested the function of Wnt1 on E18.5 cortical axons and found Wnt1 can only weakly repel frontal cortical axons. CST axons reach the spinal cord at P0. At E18.5, the CST axons are still in the midbrain and the hindbrain. The time course of Wnt1 responsiveness is consistent with it role in CST axon pathfinding once CST axons enter the spinal cord. Wnt5a also repel postnatal motor cortical axons.

Example 10

Wnt Proteins Also Regulate the A-P Pathfinding of the CST Axons

The inventor found that several Wnt genes are expressed in a high-to-low gradient in the gray matter cupping the dorsal funiculus from the cervical to the thoracic spinal cord where corticospinal tract axons first enter the spinal cord and project posteriorly at postnatal day 0. At the lumbar spinal cord, Wnt gene expression in the gray matter displays a reversed gradient (low-to-high) forming a "half-pipe" gradient along the entire length of the spinal cord. Such gradient persists from P0 to at least P5. The functional studies showed that Wnt proteins could repel axons from frontal motor cortex in a collagen gel assay. Therefore, first gradient guides CST axons to project from the cervical cord to the thoracic cord, and the second reverse gradient helps to stop CST axons at the lumbar level.

Example 11

A Repulsive Wnt Receptor, Ryk, is Expressed in the CST Axons Along the Entire A-P Trajectory Axon guidance molecules are often bi-functional, attracting some axons while repelling others, depending on the guidance receptor composition in the responding neurons. Vertebrate commissural axons are attracted by Wnts, whereas frontal cortical axons are repelled by Wnts. In Drosophila, Wnt5 was found to play a repulsive role in the pathway selection before midline crossing (Yoshikawa et al., 2003). This repulsion is mediated by a Wnt receptor called Derailed through direct binding and is independent of Frizzled (Yoshikawa et al., 2003). The inventor found that the vertebrate Derailed, Ryk (Halford et al., 2000), is not expressed in commissural axons, although Frizzled3 is, and Frizzled3 is required for mediating Wnt attraction (Lyuksyutova et al., 2003).

Further investigating why the cortical axons are repelled by Wnts, the inventor first generated an in situ probe for Ryk and found that the Ryk gene is expressed in layers 5 and 6 of the frontal cortex. The levels of Ryk expression at E18.5 are much lower than are that of P0. The inventor obtained a published antibody against the mouse Ryk protein (Kamitori et al., 2002) and performed immunohistochemistry, and the inventor found that Ryk protein is present in layer 5 neurons and is present in the internal capsule of E18.5 brain. The inventor then generated polyclonal antibodies against the extracellular domain of Ryk and further confirmed that Ryk protein is present in the CST axons forming the pyramidal decussation and the pyramidal tracts in the dorsal funiculus of the spinal cord. Therefore, Ryk is expressed in the CST axons at the right time to mediates Wnt repulsion.

Example 12

Ryk Antibodies Can Block the Repulsion of CST Axons by Wnts

To demonstrate that Ryk is involved in mediating Wnt repulsion in vertebrate axons, the inventor used the polyclonal antibodies generated against the ectodomain of Ryk and tested whether the Ryk antibodies can block the repulsion by Wnts in collagen gel assays. The inventor found that addition of purified Ryk antibodies in collagen gel assays blocked the repulsive effects of Wnt proteins, suggesting that Ryk does mediate Wnt repulsion in vertebrates and may play important roles in CST axon guidance such as the anterior-posterior guidance of CST axons in vivo. The inventor found that in the presence of Wnt1 protein, frontal cortical axons tend to grow much shorter and away from the pointed source of Wnt1. When Ryk antibodies were included, frontal cortical axons were no longer repelled, and the outgrowth was increased.

Example 13

Intrathecal Injection of sFRP2 Protein at Cervical Level Caused Reduction of CST Fibers in the Dorsal Funiculus and Impaired Motor Function To address the in vivo function of the repulsive effects of Wnt proteins on corticospinal tract axon guidance, the inventor injected purified sFRP2 protein to postnatal cervical spinal cord at P1, P3 and then analyzed the CST axon projection in P5 spinal cord. Transverse section of the vehicle and sFRP2 injected animals were collected every 800 um along the entire A-P axis of the P5 spinal cord and stained with a CST marker 5A5. The inventor found that the dorsal funiculus areas are much reduced in injected animals, suggesting that the posterior growth of CST axons was interfered. Similar results were obtained from multiple groups of mice and rats. Some animals were raised to adulthood and their motor functions were analyzed. The inventor found that the sFRP2 injected animals display consistent weakening of grip strength throughout the entire period of the tests, suggesting the posterior growth defects caused by sFPR2 injection interfered motor system development.

These studies suggest that Wnt proteins control not only the guidance of ascending sensory axons, but also that of the descending motor pathways through a Ryk-dependent signaling pathway.

Example 14

Additional Studies Involving Injection of Wnt Inhibitors into Spinal Cords

In addition to the studies described above, the sFRP2 protein has also been injected to the lumbar and sacral spinal cord on postnatal day 5 and 7 and animals were fixed on day 9. Data obtained from these studies will indicate whether inhibiting Wnt function in the posterior portion of the spinal cord will cause overshooting of corticospinal tract axons, leading to abnormal development of the motor system, and provide further information allowing one of skill to develop appropriate regimes for spinal cord regeneration.

Additionally, Anti-Ryk antibodies have also been injected to both the cervical and lumbar spinal cord regions to allow for the analysis of anatomical defects of motor axon growth and behavioral defects. These studies, have confirmed that Ryk is an inhibitor of Wnt-mediated action on neurons and a target for therapeutics.

Example 15

In situ Hybridization Studies of Wnts Expression in Normal and Injured Spinal Cords To study patterns of Wnt expression, the inventor cloned the entire family of Wnts and performed in situ hybridization. Most of the Wnts are no longer expressed in the adult spinal cord. One Wnt gene, Wnt5a, is expressed highly in the spinal cord. Wnt8a is weakly expressed.

Researchers have found that it is possible to regenerate sensory axons by blocking inhibitors of axon growth but it is nearly impossible to regenerate corticospinal cord (Sivasankaran et al. 2004). It is possible to that the Wnt5a is expressed in the adult spinal cord and other Wnts that become induced at injured sites in the spinal cord result in inhibition of normal cord growth. Because corticospinal tract axons are repelled by Wnts and sensory axons are attracted by Wnts, abnormal Wnt production after injury can result in selective inhibition of the motor cortical axons in the spinal cord. Any injury-induced Wnts, together with Wnt5a, may cause a repulsive environment so that the adult axons fail to regenerate.

One can use the data from in situ studies of normal and injured spinal cords to study whether various Wnt genes are induced upon spinal cord injury. To obtain data from injured spinal cords, an adult mouse spinal cord can be lesioned at cervical and thoracic levels by a hemi-section injury paradigm. The animals can be fixed at day 1, 7, 14 and one month after injury and the expression patterns of Wnt genes determined by in situ hybridization and compared to data from uninjured spinal cords.

Data from the studies described in this example can be used to determine appropriate substances to use to prevent any injury-induced Wnts from preventing proper neuronal regeneration.

Example 16

Transgenic Mice Studies

In order to further demonstrate the roles of Wnts in neuronal guidance and regeneration, a variety of transgenic mice lines were created. In these lines, generally, a dominant-negative inhibitor transgene is expressed to produce an inhibitor of a Wnt inside relevant neurons. These transgenic mice are produced by methods well-known to those of skill in the art.

For example, transgenic mice lines expressing specific dominant-negative inhibitors of Wnt intracellular signaling (dominant-negative disheveled) in a subset (Neurogenin-2 expressing) of commissural neurons (which likely give rise to pain sensory pathway and are attracted by Wnts to project to the brain) showed a kangaroo gait phenotype in the hindlimb. The gait (hopping) behavior appears to depend on the texture of the surface the mice were walking on, suggesting sensory system defects in these neuron. These data demonstrate that Wnt signaling is important for the normal wiring of the nervous system and support a cell-autonomous mechanism, meaning that the Wnt signaling pathway is required in the neurons which are responding to the Wnt gradient.

One can conduct further transgenic animal studies to show the roles in which the Wnt signaling pathway in axon sensory axon guidance and provide tools for axonal regeneration inhibitors of Wnt signaling. In this regard, dominant negative transgenic animals can be created in subsets of commissural neurons to further test the role of Wnt signaling pathway in commissural neurons. Axonal projection and mouse behavior can be analyzed in these animals.

Further once transgenic mice are created, spinal cord lesion experiments as described above can be carried out and the Wnt expression pattern in the injured spinal cord analyzed. The function of Wnts in adult spinal cord axons can be tested to see whether Wnts continue to attract sensory axons and repel motor axons. If Wnt attract sensory axons, the induction of Wnts may be helpful for axon regeneration. But if Wnts repel motor axons, the induced Wnts in the spinal cord will block regenerative growth of motor axons. In this case, anti-Ryk antibody, which blocks the repulsive function of Wnt specifically will be applied to block the inhibitory effects of Wnts on motor axon regeneration. Alternatively, interference of the Ryk signaling specifically will also block the repulsion, allowing regeneration to occur. These results will provide insights to how Wnts can be used to help spinal cord axon regeneration.

Example 17

Psychoactive Drugs In Combination with Wnt Therapy

Psychoactive drugs, such as amphetamine, improve functional recovery following stroke in experimental animals, suggesting a role in promoting nerve repair and regeneration (Long and Young, 2003). In view of the teachings of this specification, those of skill will be able to determine the effects of these drugs on Wnt signaling, axon guidance, and regeneration. Those of skill will then be able to further modify such drugs and/or their treatment regimes to enhance the drug effect on regeneration and reduce side effects without losing the effect on regeneration.

It is expected, in view of the teachings of this specification, that a combination of Wnt inhibitors or psychoactive drugs will be beneficial in promoting axonal regeneration.

Example 18

Wnts Pattern Synaptic Connections

Wnts not only are axon guidance molecules controlling pathfinding of axons toward their targets but also play important roles in patterning the synaptic connections once they reach their target. This process of target selection ensures the specific neuron to neuron connection and is essential to the development of the functional circuits throughout the nervous system. The inventor has found, at least in the somatosensory system and the visual system, Wnts play critical roles in patterning these synaptic target connections to establish topographic map. For example, when, in an animal model, Wnts are mis-expressed in the synaptic neuronal target area, the tectum, there is misconnection of the axons at the tectum and a resulting disrupted target map, causing the animals to be blind. Likewise, if Ryk is inhibited in a transgenic mouse in which a dominant-negative Ryk inhibitor is expressed in retinal ganglia cell neurons, similar results occur.

These studies suggest that Wnts play a role in patterning synaptic connections and that the Wnt pathway can be modulated in manners discussed elsewhere in this specification to ensure specific synaptic reconnection in repair damaged neural circuits.

Example 19

Testing of Wnt, Wnt-like Substances, and Compounds Affecting a Wnt Signaling Pathway Based on the disclosure of the specification and the knowledge available to one of ordinary skill in the art, Wnts, Wnt-like substances, chemical compounds affecting a Wnt signaling pathway, sFRPs, sFRP-like substances, Ryk, Ryk-like substances, blockers of neuronal growth inhibitors, neuronal growth inhibitors, and/or repulsive and attractive neuronal guidance molecules can be identified. The candidate substances that have been identified can then be tested in accordance with the techniques disclosed in the specification, and evaluated for the ability to modulate neuronal growth. Testing can be conducted in vitro, such as by use of the previously disclosed explant assay, or in vivo in animal models of neuronal damage. One of ordinary skill in the art would be familiar with the numerous methods and techniques that can be employed to test candidate substances affecting a Wnt signaling pathway for ability to promote neuronal growth and regeneration.

Example 20

Clinical Trials of the Use of a Wnts, Wnt-like Substances, and/or Chemical Compounds Affecting a Wnt Signaling Pathway in the Treatment of Diseases in General This example is generally concerned with the development of human treatment protocols using Wnts, Wnt-like substances, chemical compounds affecting a Wnt signaling pathway, sFRPs, sFRP-like substances, Ryk, Ryk-like substances, blockers of neuronal growth inhibitors, neuronal growth inhibitors, and/or repulsive and attractive neuronal guidance molecules in the treatment of diseases such as those previously discussed in this specification. In particular, such drug treatment can be of use in the clinical treatment of various diseases in which neuronal dysfunction plays a role. Examples of these diseases include traumatic spinal cord injury. A more detailed example pertaining to traumatic spinal cord injury is discussed in the next example.

The various elements of conducting a clinical trial, including patient treatment and monitoring, will be known to those of skill in the art in light of the present disclosure. The following information can be used as a general guideline for use in establishing use of Wnts, Wnt-like substances, chemical compounds affecting a Wnt signaling pathway, sFRPs, sFRP-like substances, Ryk, Ryk-like substances, blockers of neuronal growth inhibitors, neuronal growth inhibitors, and/or repulsive and attractive neuronal guidance molecules in clinical trials.

Patients with the targeted disease can be newly diagnosed patients or patients with existing disease. Patients with existing disease may include those who have failed to respond to at least one course of conventional therapy.

The Wnts, Wnt-like substances, chemical compounds affecting a Wnt signaling pathway, sFRPs, sFRP-like substances, Ryk, Ryk-like substances, blockers of neuronal growth inhibitors, neuronal growth inhibitors, and/or repulsive and attractive neuronal guidance molecules may be administered alone or in combination with the another therapeutic agent. The agents may be administered intravenously, directly into the cerebrospinal fluid, or by another mechanism that is specific to the disease that is being treated. The agent may also be administered intraoperatively, such as by direct application to the spinal cord during surgery.

The starting dose may, for example, be 0.5 mg/kg body weight. Three patients may be treated at each dose level in the absence of a defined level of toxicity. Dose escalation may be done by 100% increments (e.g., 0.5 mg, 1 mg, 2 mg, 4 mg) until drug related toxicity of a specific level develops. Thereafter dose escalation may proceed by 25% increments. The administered dose may be fractionated.

The therapeutic agent may be administered over a short infusion time or at a steady rate of infusion over a period of days. The infusion may be administered alone or in combination with other agents. The infusion given at any dose level will be dependent upon the toxicity achieved after each.

Physical examination, laboratory tests, and other clinical studies specific to the disease being treated may, of course, be performed before treatment and at intervals of about 3-4 weeks later. Laboratory studies can include CBC, differential and platelet count, urinalysis, SMA-12-100 (liver and renal function tests), coagulation profile, and any other appropriate chemistry studies to determine the extent of disease, or determine the cause of existing symptoms. If necessary, appropriate biological markers in serum can be monitored.

Example 21

Clinical Trials of the Use of a Wnt or a Wnt-like Substance or Chemical Compounds Affecting a Wnt Signaling Pathways in the Treatment of Spinal Cord Injury This example is concerned with the development of human treatment protocols using a Wnts, Wnt-like substances, chemical compounds affecting a Wnt signaling pathway, sFRPs, sFRP-like substances, Ryk, Ryk-like substances, blockers of neuronal growth inhibitors, neuronal growth inhibitors, and/or repulsive and attractive neuronal guidance molecules in the treatment of spinal cord injury. The various elements of conducting a clinical trial, including patient treatment and monitoring, will be known to those of skill in the art in light of the present disclosure. The following information can be used as a general guideline for use in establishing clinical trials pertaining to spinal cord treatment.

Patients with spinal cord injury for clinical study will typically have failed to respond to at least one course of conventional therapy. Measurable disease is not required.

The therapeutic agent may be administered alone or in combination with the another chemotherapeutic agent. The administration may be intravenously, directly into or around the spinal cord, or in any other manner known to those of skill in the art. The starting dose may be 0.5 mg/kg body weight. Three patients may be treated at each dose level in the absence of grade>3 toxicity. Dose escalation may be done by 100% increments (0.5 mg, 1 mg, 2 mg, 4 mg) until toxicity is detected. Thereafter dose escalation may proceed by 25% increments.

The therapeutic agent may be administered over a short infusion time or at a steady rate of infusion over a 7 to 21 day period. The agent may be administered alone or in combination with agents for treatment of spinal cord injury. The infusion given at any dose level will be dependent upon the toxicity achieved after each. Increasing doses of the Wnts, Wnt-like substances, chemical compounds affecting a Wnt signaling pathway, sFRPs, sFRP-like substances, Ryk, Ryk-like substances, blockers of neuronal growth inhibitors, neuronal growth inhibitors, and/or repulsive and attractive neuronal guidance molecules, in combination with other therapeutic agents will be administered to groups of patients until approximately 60% of patients show unacceptable toxicity. Doses that are ⅔ of this value could be defined as the safe dose.

Physical examination, neurological function, and laboratory tests can, of course, be performed before treatment and at intervals of about 3-4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum can be monitored.

To monitor disease course and evaluate the response, it is contemplated that the patients may be examined for neurological function. Laboratory studies such as a CBC, differential and platelet count, coagulation profile, and/or SMA-12-100 shall be performed weekly. Appropriate clinical studies such as radiological studies should be performed and repeated every 8 weeks to evaluate response.

Clinical response may be defined by acceptable measure. For example, a response may be defined by improvement in neurological dysfunction, and can be graded using parameters known to those of skill in the art.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,797,368
U.S. Pat. No. 5,139,941
Aksentijevich et al., *Hum. Gene Ther.,* 7(9):1111-1122, 1996.
Altman et al., *Adv. Anat. Embryol Cell Biol.,* 85:1-164, 1984.
Augsburger et al., *Neuron,* 24:127-141, 1999.
Borello et al., *Mech. Dev.,* 89:173-177, 1999.
Boussif et al., *Proc. Natl. Acad. Sci. USA,* 92(16):7297-7301, 1995.
Bradley and Brown, *EMBO J.,* 9:1569-1575, 1990.
Bueno et al., *Int. J. Dev. Biol. Suppl.* 1:79S-80S, 1996.
Caley et al., *J. Virology,* 71(4):3031-3038, 1997.
Carbonelli et al., *FEMS Microbiol. Lett.,* 177(1):75-82, 1999.
Chen and Okayama, *Mol. Cell Biol.,* 7(8):2745-2752, 1987.
Christiansen et al., *Mech. Dev.,* 51:341-350, 1995.
Cocea, *Biotechniques,* 23(5):814-816, 1997.
Coffin, In: *Virology,* Fields et al., eds., Raven Press, NY, 1437-1500, 1990.
Couch et al., *Am. Rev. Resp. Dis.,* 88:394-403, 1963.
Davis et al, *Curr. Biol.,* 6:146-148, 1996.
Dealy et al., *Mech. Dev.,* 43:175-186, 1993.
Derossi et al., *J. Biol. Chem.,* 269:10444-10450, 1994.
Dickson, *Science,* 298:1959-1964, 2002.
Ebens et al., *Neuron,* 17:1157-1172, 1996.

Elliott and O'Hare, *Cell*, 88:223-233, 1997.
Fan et al., *Dev. Biol.*, 191:160-165, 1997.
Fechheimer et al., *Proc. Natl. Acad. Sci. USA*, 84:8463-8467, 1987.
Finch et al., *Proc. Natl .Acad. Sci. USA*, 94:6770-6775, 1997.
FitzGerald, In: *Neuroanatomy Basic and Clinical*, W. B. Sauders Company LTD, 1996.
Fraley et al., *Proc. Natl. Acad. Sci. USA*, 76:3348-3352, 1979.
Francis et al., *Development*, 120:209-218, 1994.
Fraser, In: *Methods in Cell Biology*, 147-160, Academic Press, Inc., 1996.
Gabizon et al., *Cancer Res.*, 50(19):6371-6378, 1990.
Gavin et al., *Genes Dev.*, 4:2319-2332, 1990.
Glorioso et al., *Mol. Biotechnol.*, 4(1):87-99, 1995.
Gopal, *Mol. Cell Biol.*, 5:1188-1190, 1985.
Graham and Van Der Eb, *Virology*, 52:456-467, 1973.
Grunhaus et al., *Seminar in Virology*, 200(2):535-546, 1992.
Halford et al., *Nat. Genet.*, 25:414-418, 2000.
Hall et al., *Cell*, 100:525-535, 2000.
Harland and Weintraub, *J. Cell Biol.*, 101:1094-1099, 1985.
Hofmann et al., *Dev. Genet.*, 19:43-50, 1996.
Joosten et al., *Brain Res. Dev. Brain Res.*, 94:99-105, 1996.
Kamitori et al., *Brain Res. Mol. Brain Res.*, 104:255-266, 2002.
Keino-Masu et al., *Cell*, 87:175-185, 1996.
Kennedy et al., *Cell*, 78:425-435, 1994.
Kispert et al., *Development*, 122:3627-3637, 1996.
Klein and Melton, *Proc. Natl. Acad. Sci. USA*, 93:8455-59, 1996.
Klingensmith and Nusse, *Dev. Biol.*, 166:396-414, 1994.
Kotin et al., *Proc. Natl. Acad. Sci. USA*, 87(6):2211-5, 1990.
Krylova et al., *Neuron*, 35:1043-1056, 2002.
Laughlin et al., *J. Virol.*, 60(2):515-524, 1986.
Lebkowski et al., *Mol. Cell. Biol.*, 8(10):3988-3996, 1988.
Levenson et al., *Hum Gene Ther*, 9(8):1233-6, 1998.
Liu et al., *Mech. Dev.*, 91:409-413, 2000.
Long and Young, *Qjm* 96:673-685, 2003.
Lucas and Salinas, *Dev. Bio.*, 192:31-44, 1997.
Lyuksyutova et al., *Science*, 302:1984-1988, 2003.
McCarty et al., *J. Virol.*, 65(6):2936-2945, 1991.
McLaughlin et al., *J. Virol.*, 62(6):1963-1973, 1988.
McMahon, *Trends Genet.*, 8:236-242, 1992.
McMahon and Bradley, *Cell*, 62:1073-1085, 1990.
Miller, *Genome Biology*, 3(1):3001.1-3001.15, 2001.
Morata and Lawrence, *Dev. Biol.*, 56:227-240, 1977.
Muzyczka, *Curr Top Microbiol Immunol*, 158:97-129, 1992.
Nagahara et al., *Nature Medicine*, 4:1449-1452, 1998.
Nicolau and Sene, *Biochim. Biophys. Acta*, 721:185-190, 1982.
Nusse and Varmus, *Cell*, 69:1073-1087, 1992.
Papkoff and Schryver, *Mol. Cell Biol.*, 10:2723-2730, 1990.
Parr et al., *Dev. Biol.*, 237:324-332, 2001.
Paxinos, In: *The Rat Nervous System*, 2$^{nd}$ Ed., Academic Press, 1995.
Pelletier and Sonenberg, *Nature*, 334:320-325, 1988.
Pinson et al., *Nature*, 407:535-538, 2000.
Potter et al., *Proc. Natl. Acad. Sci. USA*, 81:7161-7165, 1984.
Ramon y Cajal, *La Cellule*, 9:119-258, 1893.
Rijsenijk et al., *Cell*, 50:649-657, 1987.
Rippe et al., *Mol. Cell Biol.*, 10:689-695, 1990.
Roux et al., *Proc. Nat'l Acad. Sci. USA*, 86:9079-9083, 1989.
Samulski et al, *EMBO J.*, 10:3941-3950, 1991.
Samulski et al., *J. Virol*, 63:3822-3828, 1989.
Saulnier et al., *Dev. Biol.*, 248:13-28, 2002.
Serafini et al., *Cell*, 78:409-424, 1994.
Serafini et al., *Cell*, 87:1001-1014, 1996.
Shelling and Smith, *Gene Therapy*, 1:165-169, 1994.
Shirasaki et al., *Science*, 279:105-107, 1998.
Shu et al., *Development* ,129:4831-4842, 2002.
Sivasankaran et al., *Nat Neurosci* 7:261-268, 2004.
Solodin et al., *Biochemistry*, 34(41):13537-13544, 1995.
Tessier-Lavigne et al., *Nature*, 336:775-758, 1988.
Tessier-Lavigne et al., *Science*, 274:1123-1133, 1996.
Tessier-Lavigne, *Curr. Opin. Genet. Dev.*, 4:596-601, 1994.
Thierry et al., *Proc. Natl. Acad. Sci. USA*, 92(21):9742-9746, 1995.
Thomas and Cappechi, *Nature*, 346:847-850, 1990.
Top et al., *J. Infect. Dis.*, 124:155-160, 1971.
Tratschin et al., *Mol. Cell. Biol.*, 4:2072-2081, 1984.
Tsukamoto et al., *Nat. Genet.*, 9(3):243-248, 1995.
Tur-Kaspa et al., *Mol. Cell Biol.*, 6:716-718, 1986.
Ungar et al., *Mech. Dev.*, 52:153-164, 1995.
Vant Veer et al., *Mol. Cell Biol.*, 4:2532-2534, 1984.
Wagner et al., *Science*, 260:1510-1513, 1993.
Wang et al., *J. Neurosci.*, 22:8563-8573, 2002.
Wodarz et al., *Annu. Rev. Cell Dev. Biol.*, 14:59-88, 1998.
Wu and Wu, *Biochemistry*, 27:887-892, 1988.
Wu and Wu, *J. Biol. Chem.*, 262:4429-4432, 1987.
Yang et al., *Proc Natl. Acad Sci. USA*, 87:9568-9572, 1990.
Yoshikawa et al., *Nature*, 422(6932):583-588, 2003.
Zakany et al., *Nature*, 362:546-549, 1993.
Zhu et al., *Science*, 261(5118):209-211, 1993.
Zou et al., *Cell*, 102:363-375, 2000.
Zou, et al., *Development*, 124:793-804, 1997.

What is claimed is:

1. A method for modulating the directional growth of a mammalian neuron comprising contacting the neuron with an inhibitor of a Wnt receptor, wherein the inhibitor is an anti-Ryk antibody.

2. The method of claim 1, wherein the neuron is contacted with the inhibitor in a spinal cord.

3. The method of claim 2, wherein the inhibitor is provided as a concentration gradient.

4. The method of claim 3, wherein the concentration gradient is provided as a decreasing anterior-posterior concentration gradient along the spinal cord.

5. The method of claim 2, wherein the directional growth of the neuron occurs along the anterior-posterior axis of the spinal cord.

6. The method of claim 2, wherein the directional growth of the neuron is along the spinothalamic pathway.

7. The method of claim 2, wherein the spinal cord has been damaged.

8. The method of claim 1, wherein the neuron is further contacted with a sFRP.

9. The method of claim 8, wherein the sFRP is selected from sFRP1, sFRP2 and sFRP3.

10. The method of claim 1, wherein the neuron is a motor neuron.

11. The method of claim 1, wherein the neuron is a sensory neuron.

12. The method of claim 1, wherein the neuron is a damaged neuron.

13. The method of claim 12, wherein the directional growth of the neuron facilitates regeneration of the neuron.

14. The method of claim 1, wherein the inhibitor is provided as a pharmaceutical composition.

* * * * *